US011851680B2

(12) United States Patent
Martin et al.

(10) Patent No.: US 11,851,680 B2
(45) Date of Patent: Dec. 26, 2023

(54) GENETICALLY-MODIFIED IMMUNE CELLS COMPRISING A MICRORNA-ADAPTED SHRNA (SHRNAMIR)

(71) Applicant: Precision Biosciences, Inc., Durham, NC (US)

(72) Inventors: Aaron Martin, Carrboro, NC (US); Jon E. Chatterton, Needham, MA (US); Michelle Brenda Pires, Apex, NC (US)

(73) Assignee: Precision Biosciences, Inc., Durham, NC (US)

( * ) Notice: Subject to any disclaimer, the term of this patent is extended or adjusted under 35 U.S.C. 154(b) by 0 days.

(21) Appl. No.: 17/820,425

(22) Filed: Aug. 17, 2022

(65) Prior Publication Data

US 2023/0279349 A1  Sep. 7, 2023

Related U.S. Application Data

(63) Continuation of application No. 17/694,210, filed on Mar. 14, 2022, now Pat. No. 11,453,861, which is a continuation of application No. 17/511,022, filed on Oct. 26, 2021, now Pat. No. 11,384,335, which is a continuation of application No. 17/225,788, filed on Apr. 8, 2021, now Pat. No. 11,186,822, which is a continuation of application No. 16/908,030, filed on Jun. 22, 2020, now Pat. No. 11,008,548, which is a continuation of application No. PCT/US2020/026571, filed on Apr. 3, 2020.

(60) Provisional application No. 63/000,774, filed on Mar. 27, 2020, provisional application No. 62/930,905, filed on Nov. 5, 2019, provisional application No. 62/900,126, filed on Sep. 13, 2019, provisional application No. 62/843,804, filed on May 6, 2019, provisional application No. 62/828,794, filed on Apr. 3, 2019.

(51) Int. Cl.
| | | |
|---|---|---|
| *C07H 21/02* | (2006.01) | |
| *C12N 5/0783* | (2010.01) | |
| *C12N 15/11* | (2006.01) | |
| *C12N 15/113* | (2010.01) | |

(52) U.S. Cl.
CPC .......... *C12N 5/0636* (2013.01); *C12N 15/111* (2013.01); *C12N 15/113* (2013.01); *C12N 2310/14* (2013.01); *C12N 2310/141* (2013.01); *C12N 2310/531* (2013.01)

(58) Field of Classification Search
CPC ............ C12N 15/113; C12N 2310/141; C12N 2310/531
See application file for complete search history.

(56) References Cited

U.S. PATENT DOCUMENTS

| | | |
|---|---|---|
| 8,445,251 B2 | 5/2013 | Smith et al. |
| 8,697,359 B1 | 4/2014 | Zhang |
| 8,956,828 B2 | 2/2015 | Bonini et al. |
| 9,340,777 B2 | 5/2016 | Smith et al. |
| 9,993,502 B1 | 6/2018 | Jantz et al. |
| 10,041,053 B2 | 8/2018 | Smith et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0188987 A1 | 8/2006 | Guschin et al. |
| 2007/0036773 A1 | 2/2007 | Cooper et al. |
| 2011/0145940 A1 | 6/2011 | Voytas et al. |
| 2012/0321667 A1 | 12/2012 | Sentman |
| 2014/0301990 A1 | 10/2014 | Gregory et al. |
| 2016/0208243 A1 | 7/2016 | Zhang et al. |

FOREIGN PATENT DOCUMENTS

| | | |
|---|---|---|
| WO | WO 95/17911 A1 | 7/1995 |
| WO | WO 2007/014275 A2 | 2/2007 |
| WO | WO 2007/047859 A2 | 4/2007 |
| WO | WO 2008/102274 A2 | 8/2008 |
| WO | WO 2009/141729 A2 | 11/2009 |
| WO | WO 2010/079430 A1 | 7/2010 |
| WO | WO 2012/145384 | 10/2012 |
| WO | WO 2013/074916 A1 | 5/2013 |
| WO | WO 2013/176915 A1 | 11/2013 |
| WO | WO 2014/117050 | 7/2014 |
| WO | WO 2014/159435 A1 | 10/2014 |
| WO | WO 2014/165707 A2 | 10/2014 |
| WO | WO 2014/191527 | 12/2014 |
| WO | WO 2015/136001 A1 | 9/2015 |
| WO | WO 2016/061232 | 4/2016 |

(Continued)

OTHER PUBLICATIONS

Agarwal, V., et al., "Predicting effective microRNA target sites in mammalian mRNAs," *eLife*, 2015, 4:e05005, pp. 1-38.

(Continued)

*Primary Examiner* — Amy H Bowman

(74) *Attorney, Agent, or Firm* — Womble Bond Dickinson (US) LLP

(57) ABSTRACT

The present invention encompasses genetically-modified immune cells (and populations thereof) expressing a microRNA-adapted shRNA (shRNAmiR) that reduces the expression of a target endogenous protein. Methods for reducing the expression of an endogenous protein in an immune cell are also provided wherein the method comprises introducing a shRNAmiR that targets the endogenous protein. Using shRNAmiRs for knocking down the expression of a target protein allows for stable knockdown of expression of endogenous proteins in immune cells.

3 Claims, 51 Drawing Sheets

Specification includes a Sequence Listing.

(56) References Cited

FOREIGN PATENT DOCUMENTS

| WO | WO 2016/069283 A1 | 5/2016 |
| WO | WO 2016/196388 A1 | 12/2016 |
| WO | WO 2017/062439 | 4/2017 |
| WO | WO 2017/062451 | 4/2017 |
| WO | WO 2017/112859 | 6/2017 |
| WO | WO 2018/049471 | 3/2018 |
| WO | WO 2018/067697 A1 | 4/2018 |
| WO | WO 2018/208837 | 11/2018 |
| WO | WO 2019/032675 A1 | 2/2019 |

OTHER PUBLICATIONS

Bix, M., et al., "Rejection of class I MHC-deficient haemopoietic cells by irradiated MHC-matched mice," *Letters to Nature*, 1991, vol. 349(6307) pp. 329-331.

Boch, J., et al., "Breaking the Code of DNA Binding Specificity of TAL-Type III Effectors," *Science*, 2009, vol. 326(5959), pp. 1509-1512.

Eyquem, J., et al., "Targeting a CAR to the TRAC locus with CRISPR/Cas9 enhances tumour rejection," *Nature*, 2017, vol. 543, pp. 113-117.

Fellmann, C., et al., "An optimized microRNA backbone for effective single-copy RNAi," *Cell Reports*, 2013, vol. 5(6), pp. 1704-1713.

Gonzalez, S., et al., "Amplification of RNAi—Targeting HLA mRNAs," *Molecular Therapy*, 2005, vol. 11(5), pp. 811-818.

Hu, C., et al., "The HIV-1 Central Polypurine Tract Functions as a Second Line of Defense against APOBEC3G/F," *Journal of Viroloogy*, 2010, vol. 84(22), pp. 11981-11993.

Iglesias, C., et al., "Residual HIV-1 DNA Flap-independent nuclear import of cPPT/CTS double mutant viruses does not support spreading infection," *Retrovirology*, 2011, vol. 8(92), pp. 1-13.

Kanwar, N., et al., "IQGAP1 involvement in MTOC and granule polarization in NK-cell cytotoxicity," *Eur. J. Immunol.*, 2011, vol. 41, pp. 2763-2773.

Katkere, B., et al., "The Syk-binding Ubiquitin Ligase c-Cbl Mediates Signaling-dependent B Cell Receptor Ubiquitination and B Cell Receptor-mediated Antigen Processing and Presentation," *The Journal of Biological Chemistry*, 2012, vol. 287, pp. 16636-16644.

Knott, S.R.V., et al., "A Computational Algorithm to Predict shRNA Potency," *Molecular Cell*, 2014, vol. 56(6), pp. 796-807.

Labun, K., et al., "CHOPCHOP v2: a web tool for the next generation of CRISPR genome engineering," *Nucleic Acids Research*, 2016, vol. 44 (Web Server Issue), pp. W272-W276.

Macleod, D., et al., "Integration of a CD19 CAR into the TCR Alpha Chain Locus Streamlines Production of Allogeneic Gene-Edited CAR T Cells," *Molecular Therapy*, 2017, vol. 25(4), pp. 949-961.

Mandell, J., et anon, "Zinc Finger Tools: custom DNA-binding domains for transcription factors and nucleases," *Nucleic Acids Research*, 2006, vol. 34 (Web Server Issue), pp. W516-W523.

Montague, T., et al., "CHOPCHOP: a CRISPER/Cas9 and TALEN web tool for genome editing," *Nucleic Acids Research*, 2014, vol. 42 (Web Server Issue), pp. W401-W407.

Moscou, M., et anon, "A Simple Cipher Governs DNA Recognition by TAL Effectors," *Science*, 2009, vol. 326(5959), p. 1501.

Osborn, M.J., et al., "Evaluation of TCR Gene Editing Achieved by TALENs, CRISPR/Cas9, and megaTAL Nucleases," *Molecular Therapy*, 2016, vol. 24(3), pp. 570-581.

Poirot, L., et al., "Multiplex Genome-Edited T-cell Manufacturing Platform for "Off-the-Shelf" Adoptive T-cell Immunotherapies," *Cancer Res*, 2015, vol. 75(18), pp. 3854-3864.

Provasi, E., et al., "Editing T cell specificity towards leukemia by zinc-finger nucleases and lentiviral gene transfer," *Nat Med.*, 2012, vol. 18(5), pp. 807-815.

Ren, J., et al., "Multiplex Genome Editing to Generate Universal CAR T Cells Resistant to PD1 Inhibition," *Clin Cancer Res.*, 2017, vol. 23(9), pp. 2255-2266.

Schwartz, J. R., et al., "Glucocorticoid receptor knock down reveals a similar apoptotic threshold but differing gene regulation patterns in T-cell and pre-B-cell acute lymphoblastic leukemia," *Molecular and Cellular Endocrinology*, 2010, vol. 320, pp. 76-86.

Tissue expression of B2M—Summary, The Human Protein Atlas, pp. 1-3; https://www.proteinatlas.org/ENSG00000166710-B2M/tissue, downloaded on Jan. 13, 2020.

Zaiss, A. K., et al., "Reversible Suppression of Cyclooxygenase 2 (COX-2) Expression In Vivo by Inducible RNA Interference," *Plos One*, 2014, vol. 9(7), pp. 1-15.

FIG. 1A
shRNA vs no shRNA
FIG. 1B
CAR+ vs CAR- reference
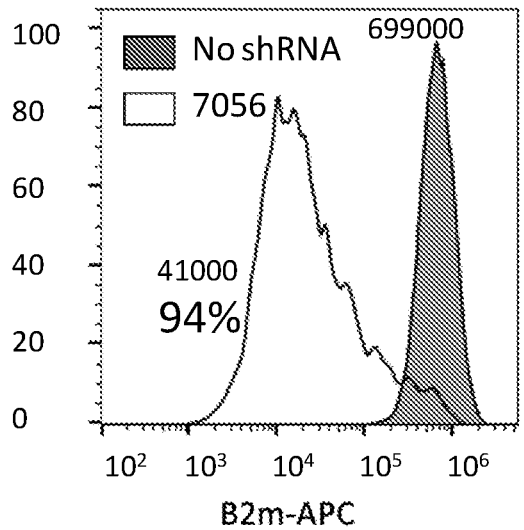
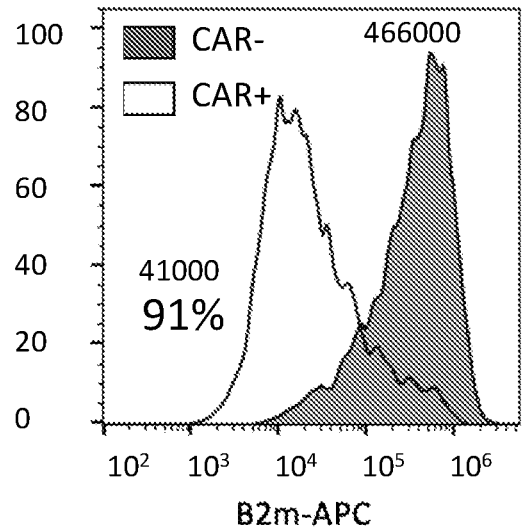
FIG. 1C
FIG. 1D
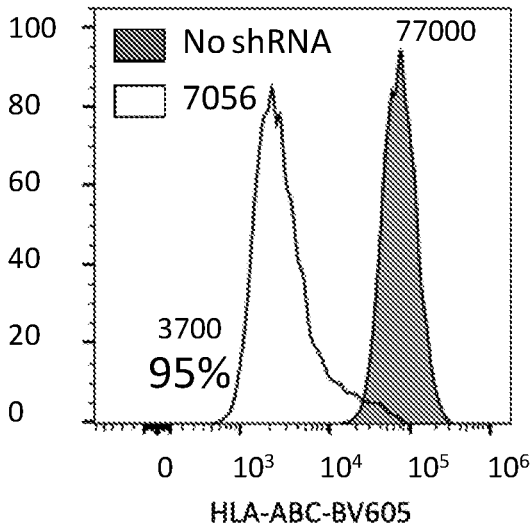
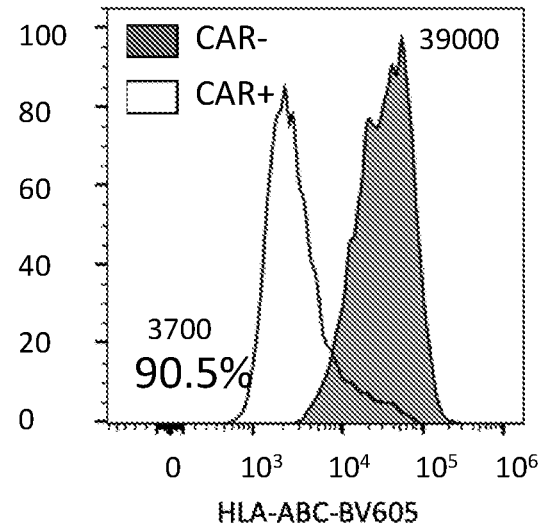
FIGURE 1

FIG. 5A 7206
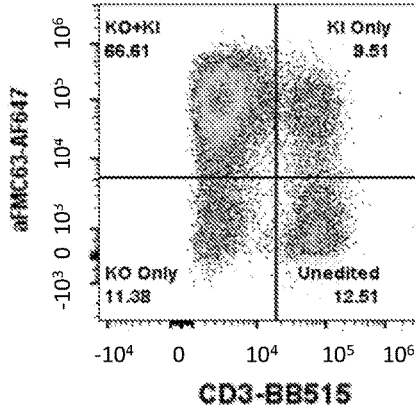
FIG. 5C 7282
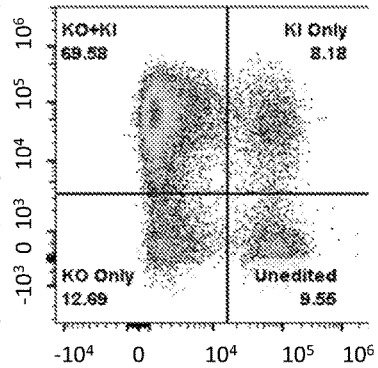
FIG. 5E 7056
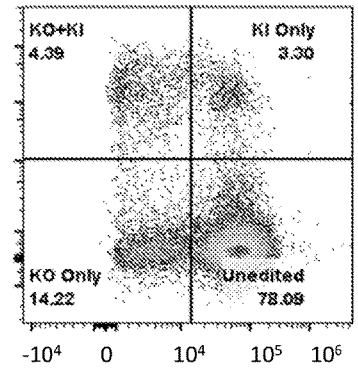
FIG. 5B
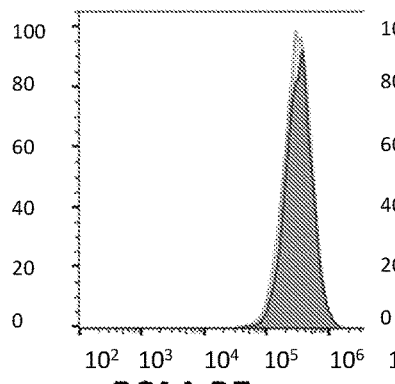
FIG. 5D
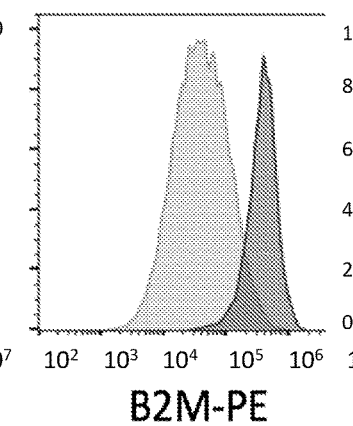
FIG. 5F
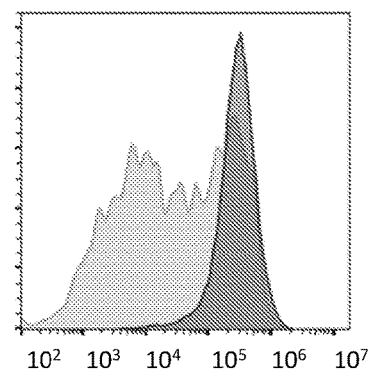
FIGURE 5

FIG. 6A
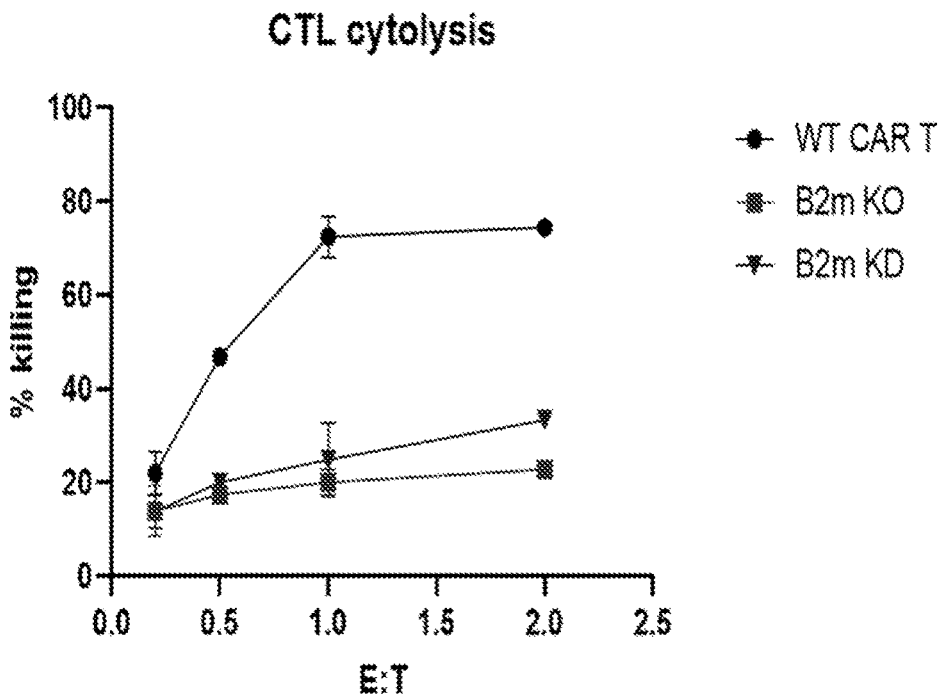
FIG. 6B
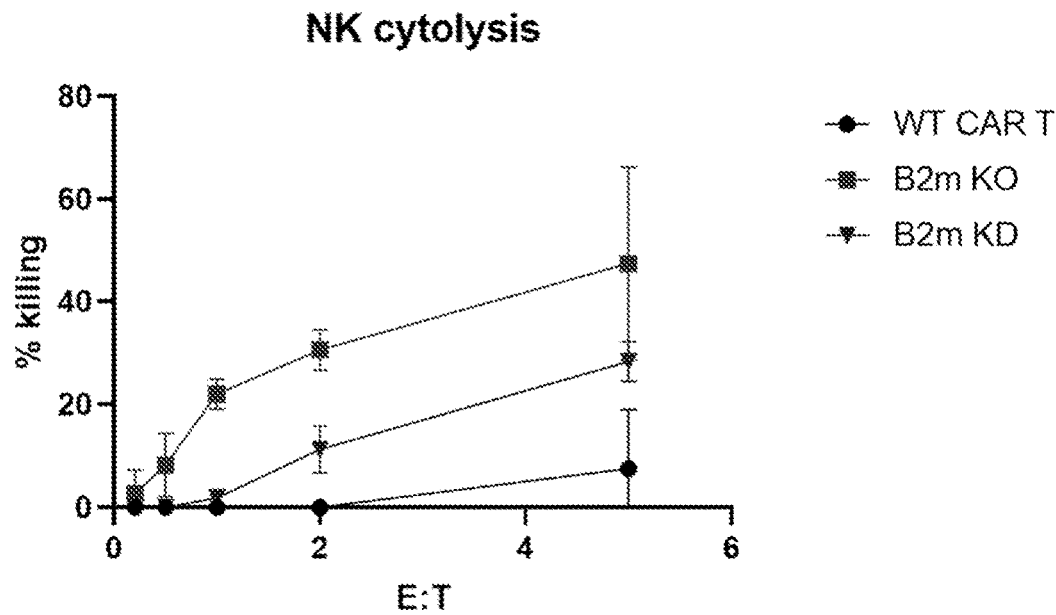
FIGURE 6

FIG. 7A
B2m13-14x479
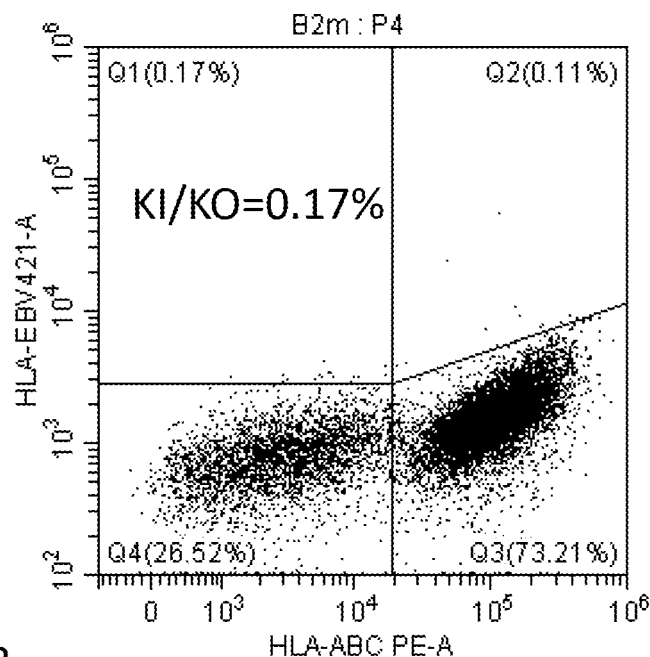
FIG. 7B
B2m13-14x479
+AAV7356
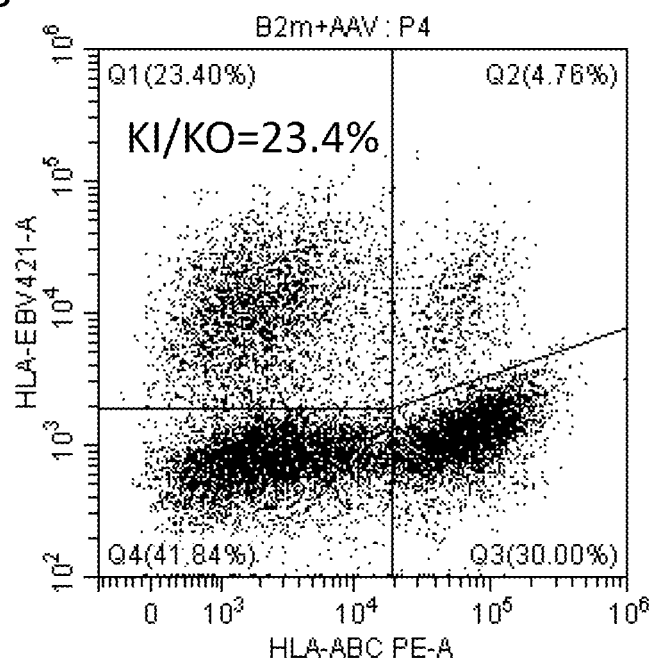
FIGURE 7

FIG. 8A
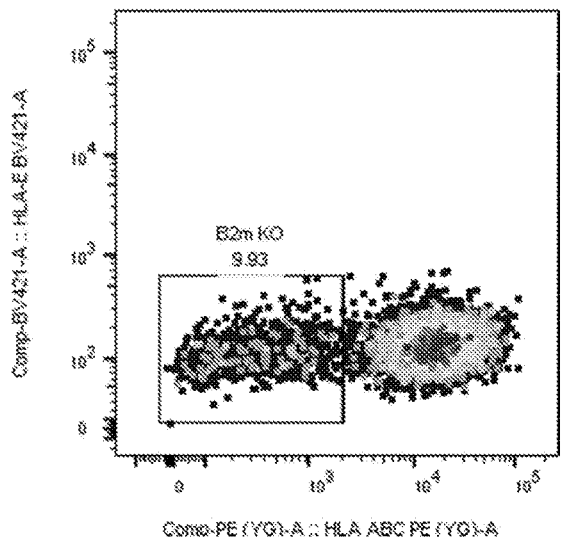
FIG. 8B
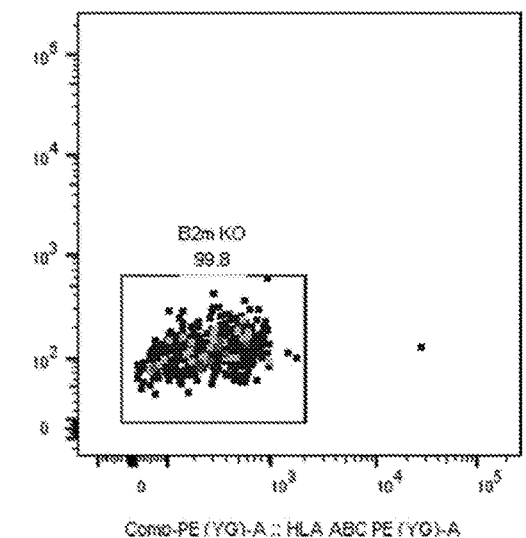
FIG. 8C
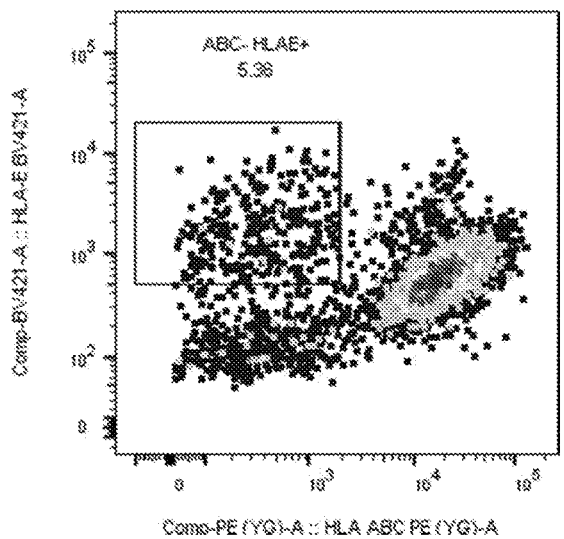
FIG. 8D
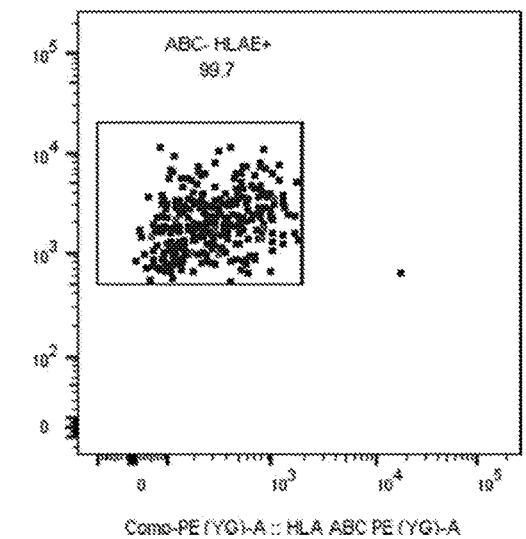
FIGURE 8

FIG. 10A
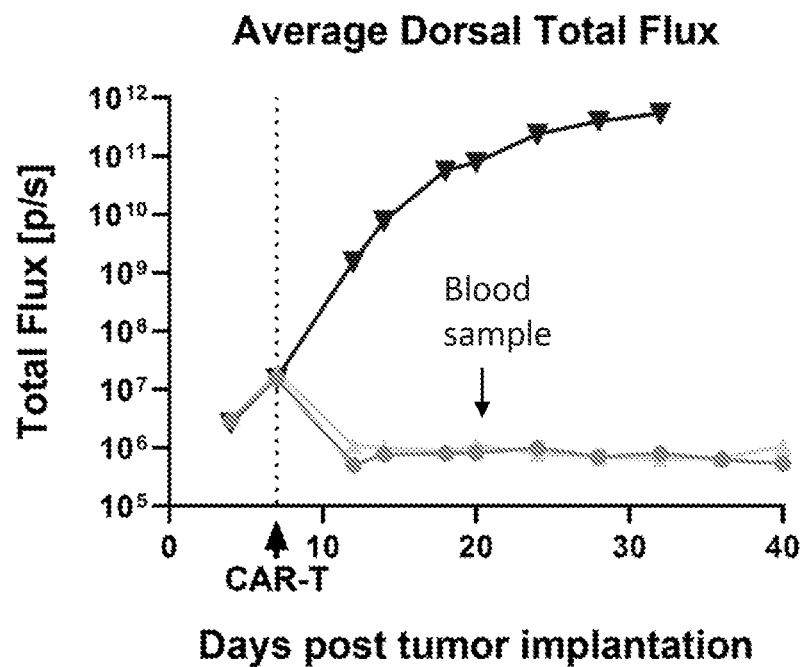
FIG. 10B
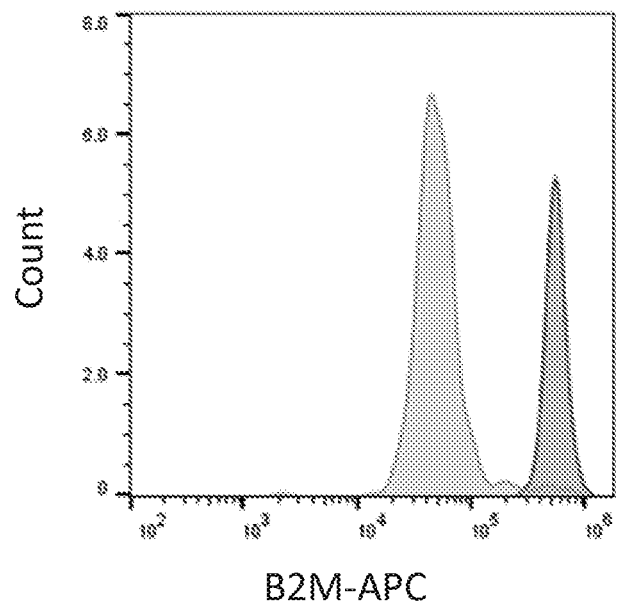
FIGURE 10

FIG. 11A — No RNAi

FIG. 11B — 72101, 26% knockdown

FIG. 11C — 72102, 30% knockdown

FIG. 11D — 72103, 36% knockdown

Mock

72110

CAR+ MFI = 1019
CAR- MFI = 2760

63% KD

72111

CAR+ MFI = 818
CAR- MFI = 2490

67% KD

72113

CAR+ MFI = 830
CAR- MFI = 2216

63% KD

72114

CAR+ MFI = 885
CAR- MFI = 1834

52% KD

FIG. 13A
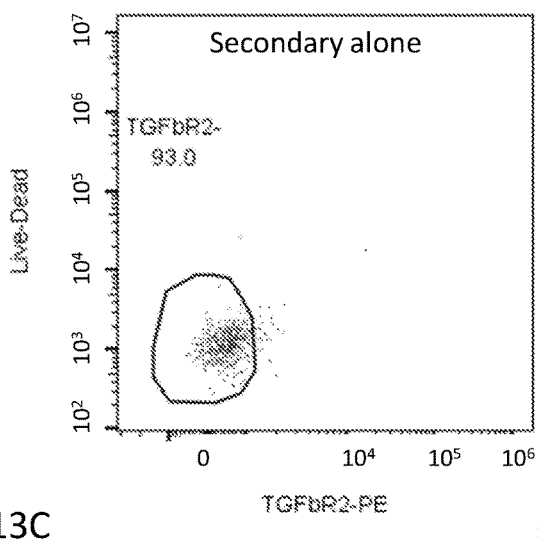
FIG. 13B
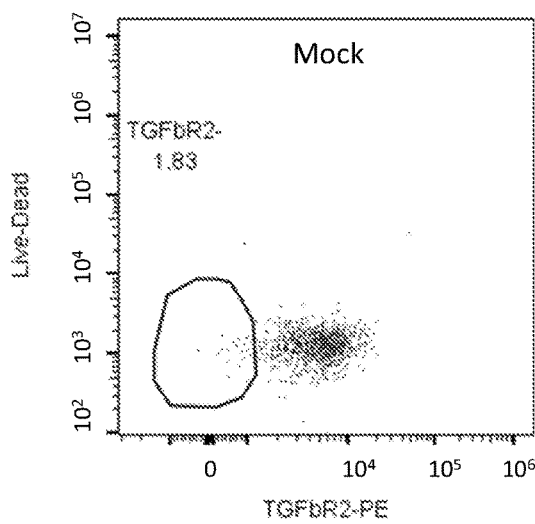
FIG. 13C
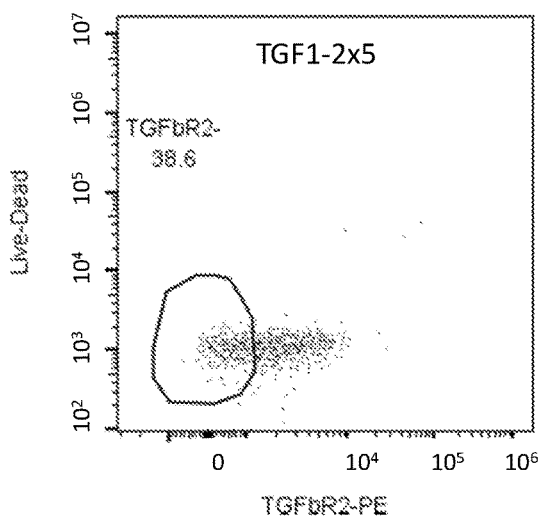
FIG. 13D
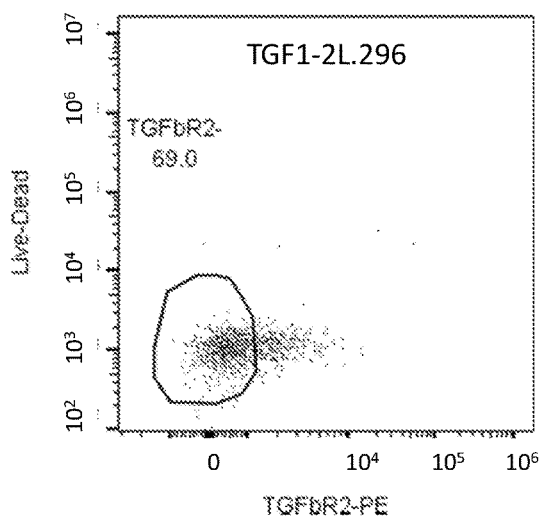
FIGURE 13

FIG. 23A
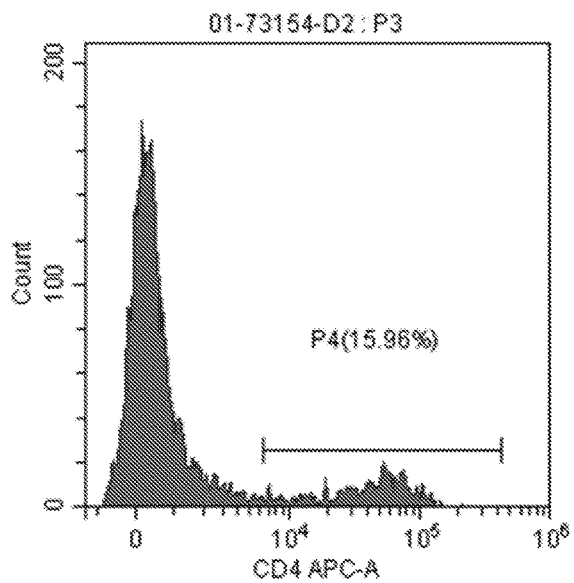
FIG. 23B
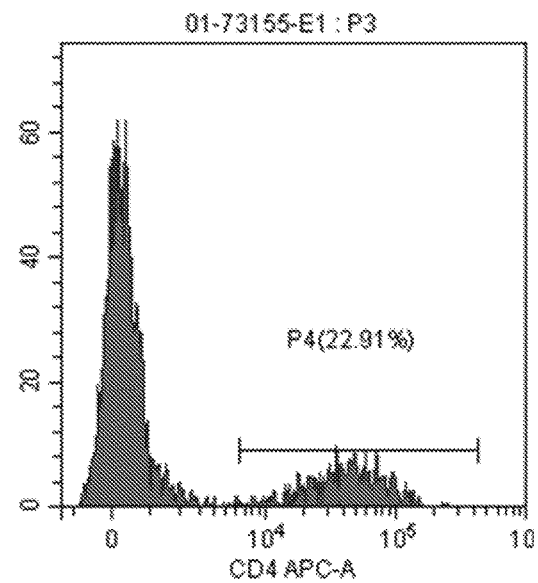
FIG. 23C
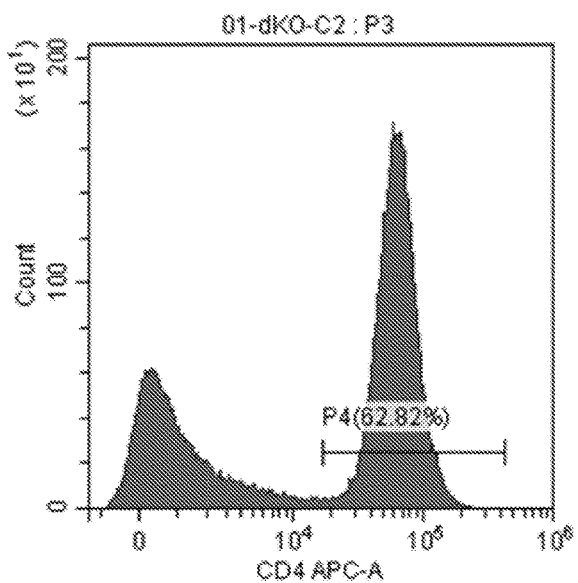
FIGURE 23

FIG. 24A
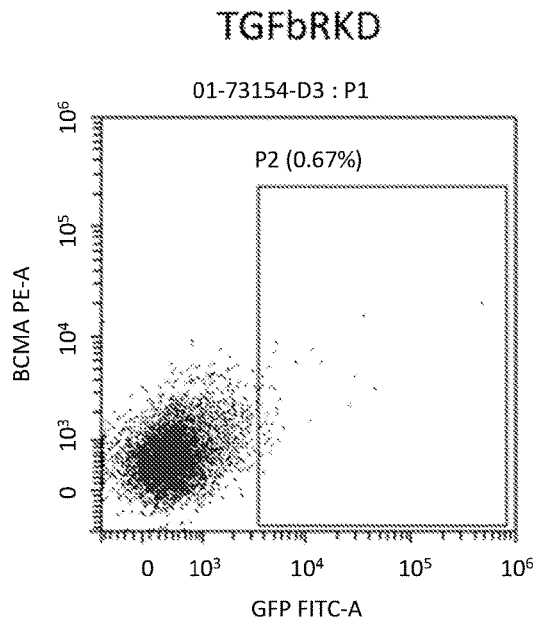
FIG. 24B
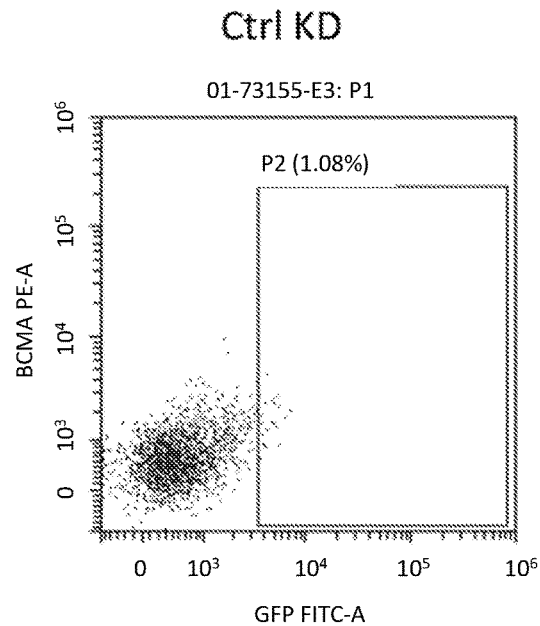
FIG. 24C
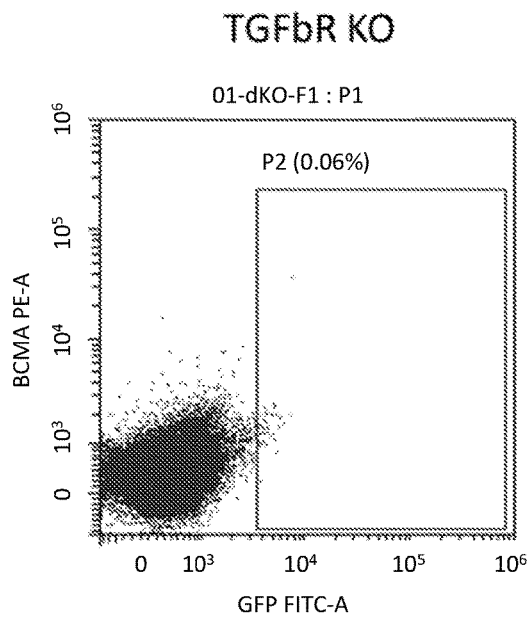
FIGURE 24

FIG. 24D
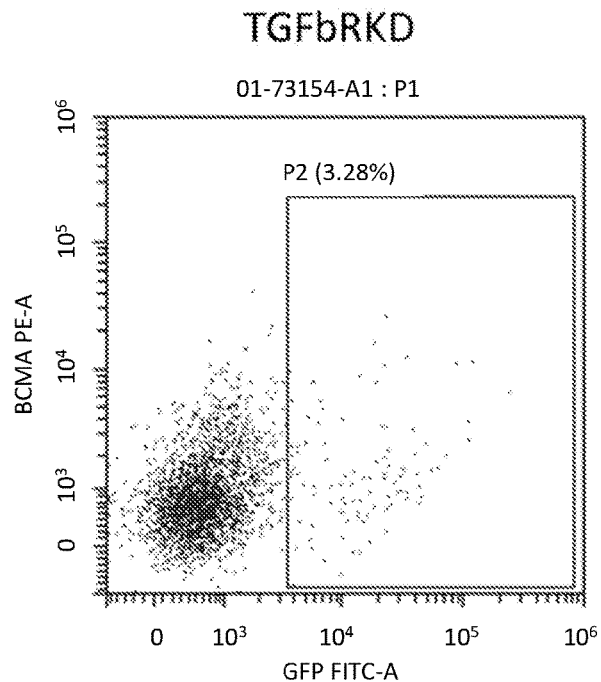
FIG. 24E
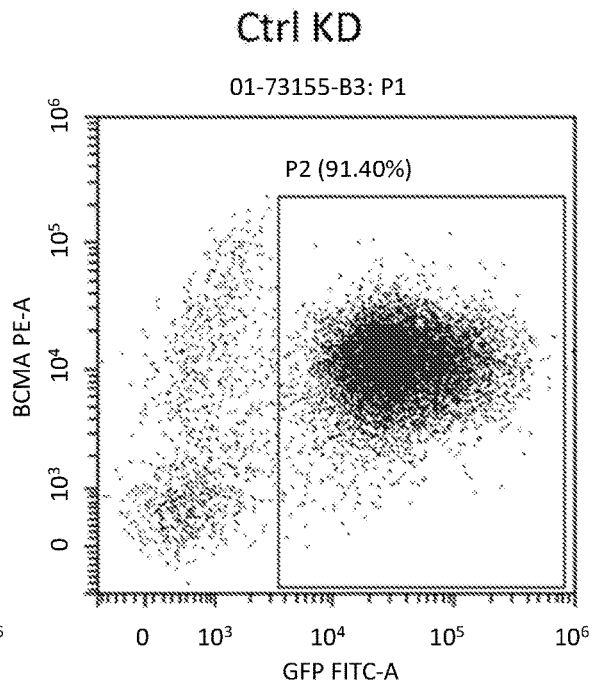
FIG. 24F
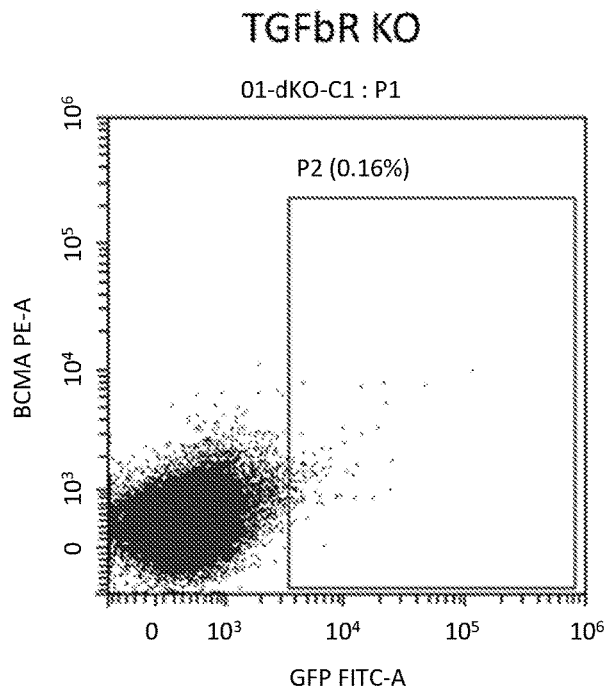
FIGURE 24 (cont.)

FIG. 25A
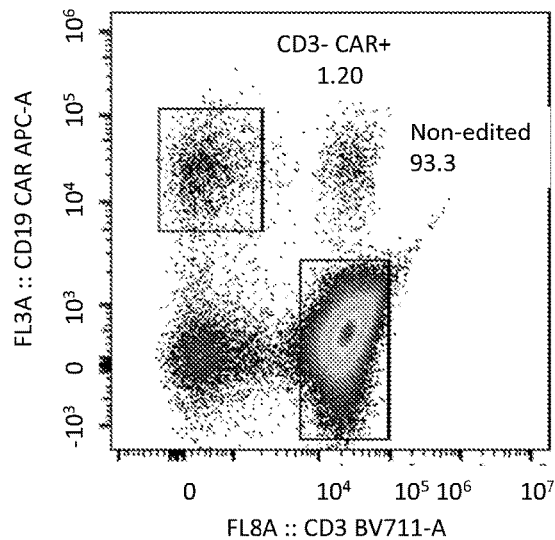
FIG. 25B 72123
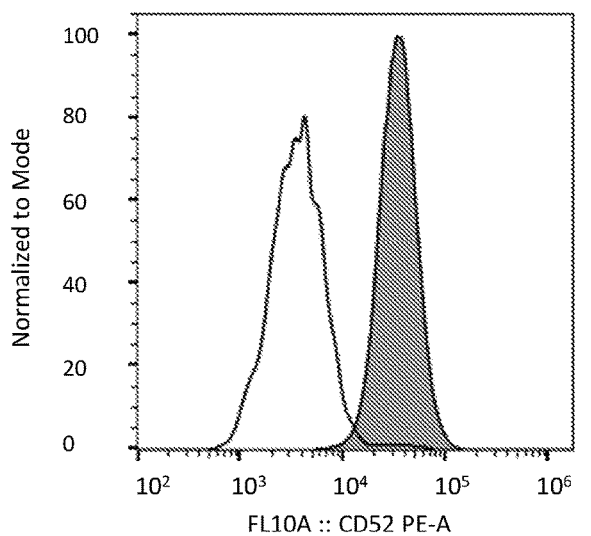
FIG. 25C 72124
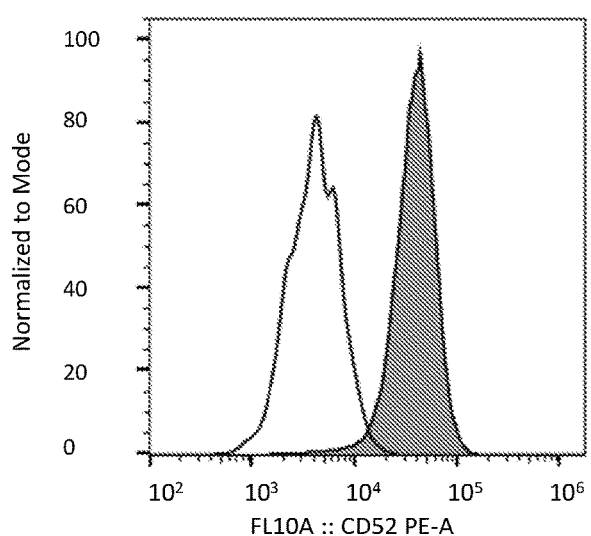
FIGURE 25

FIG. 28A
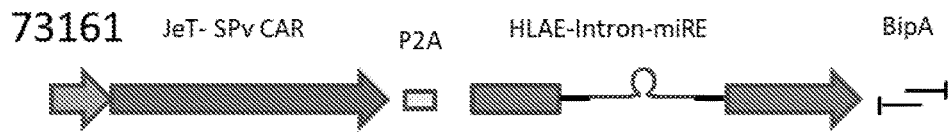
FIG. 28B
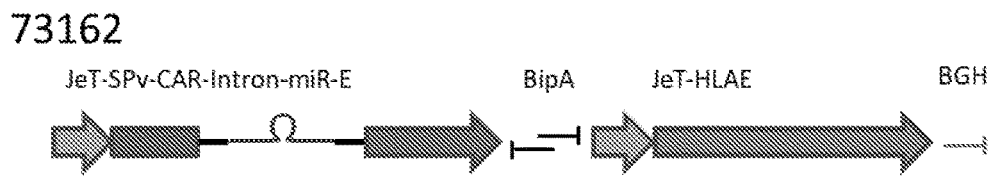
FIG. 28C
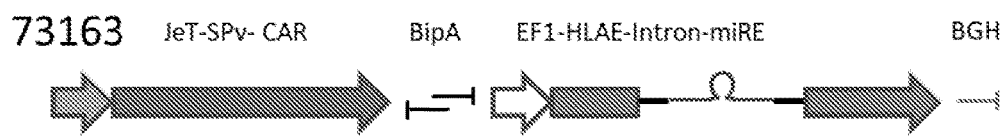
FIG. 28D
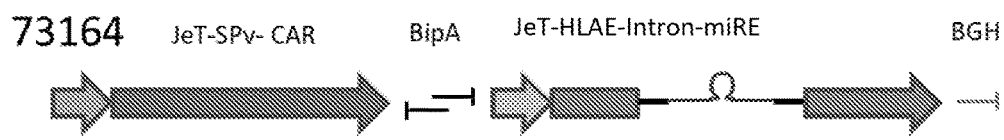
FIGURE 28

| AAV | CD3-CAR+ % | KO of KI | CAR+ MFI | MFI of 7206 |
|---|---|---|---|---|
| 7206 | 53% | 69% | 2.9e5 | 100% |
| 73161 | 48% | 64% | 5.4e5 | 186% |
| 73162 | 22% | 32% | 4.4e5 | 152% |
| 73163 | 42% | 59% | 6.6e5 | 228% |
| 73164 | 28% | 41% | 4.3e5 | 148% |
| dKO dKI | 37% | 70% | 2.3e5 | 79% |

FIGURE 29

| AAV | HLA WT% (CD3-CAR+ Population) | HLA KD (WT Gated Out) | HLA-E + (of CDE-CAR+) | HLA-E MFI | HLA-E+ of CAR- |
|---|---|---|---|---|---|
| 7206 | 99% | - | 0.9% | 6.7e3 | 0.3% |
| 73161 | 3% | 90% | 96.3% | 5.4e4 | 0.3% |
| 73162 | 7% | 90% | 86.3% | 6.6e4 | 24.3% |
| 73163 | 11% | 90% | 86.8% | 2.0e4 | 0.8% |
| 73164 | 6% | 89% | 92.8% | 1.3e5 | 20% |
| dKO dKI | 32% | - | 21.3% | 3.2e3 | 0.2% |

FIGURE 30

| AAV / Construct | CD3-CAR+ % | KO of KI | CAR+ MFI | MFI % of 7206 | HLA WT% (CD3-CAR+ Population) | HLA KD (WT Gated Out) | HLA-E+ (of CD3- CAR+) | HLA-E+ MFI |
|---|---|---|---|---|---|---|---|---|
| 7206 | 56% | 72% | 1.8e5 | 100% | 97% | - | 0.9% | 1.2e3 |
| 73161 | 52% | 72% | 4.6e5 | 256% | 0.4% | 92% | 98% | 7.7e3 |
| 73163 | 45% | 65% | 4.1e5 | 228% | 3.5% | 92% | 77% | 1.5e3 |
| dKO dKI | 39% | 72% | 1.6e5 | 89% | 46% | - | 34% | 1.2e3 |
| | | | | | | | | |
| Critical values | | >40% | >1.8e5 | >100% | | >90% | | 1.2e3 |
| Target values | ~50% | | | | ~0% | | ~100% | |

FIGURE 31

FIG. 32A
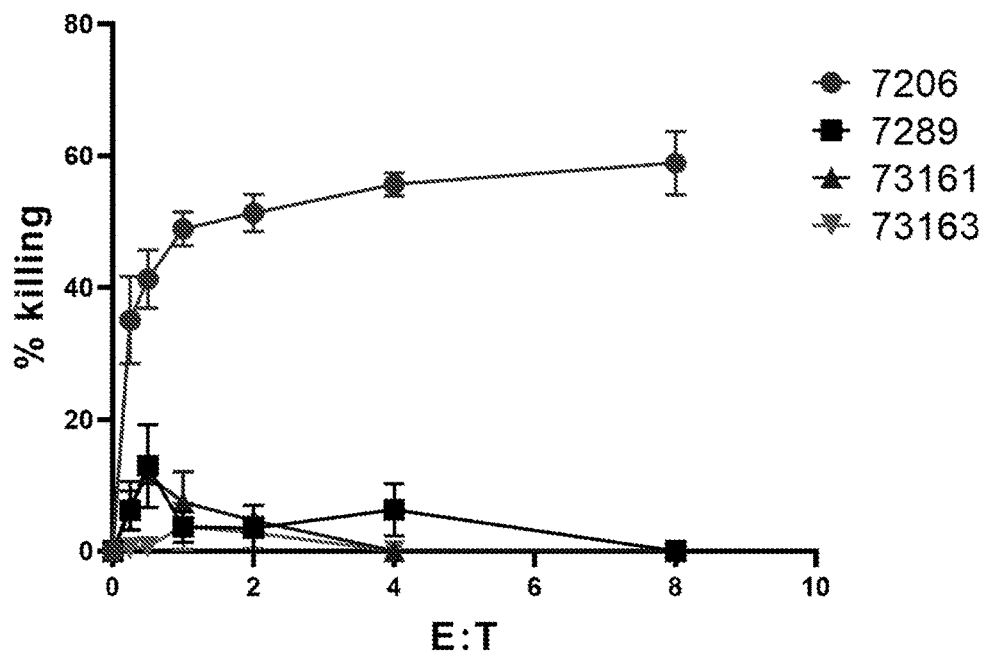
FIG. 32B
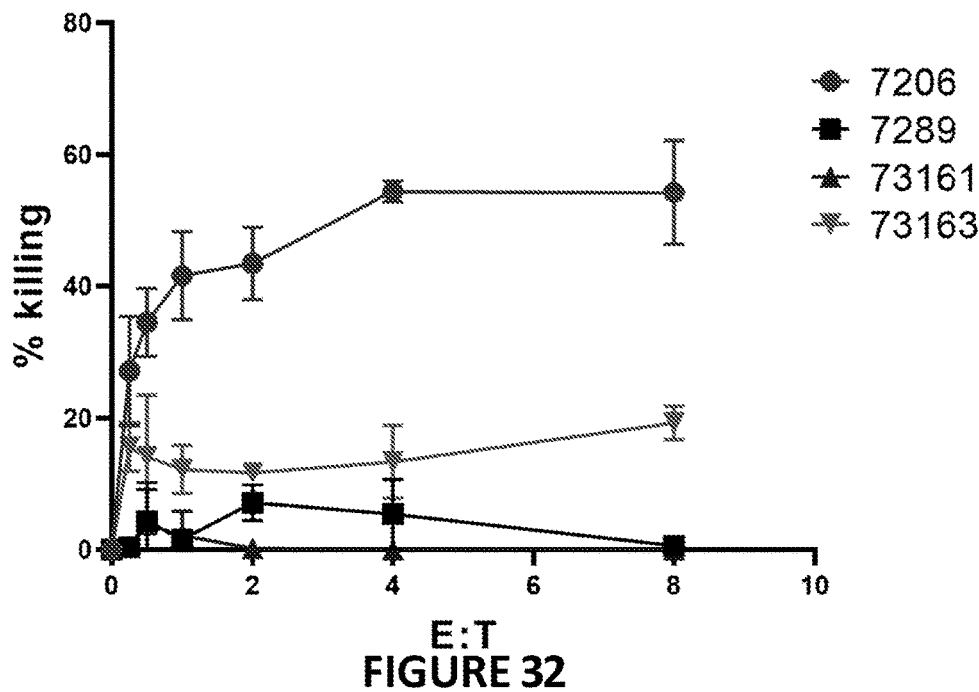
FIGURE 32

FIG. 33A
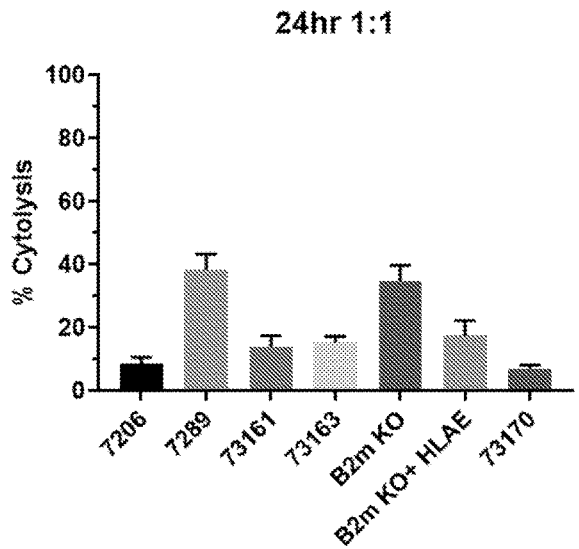
FIG. 33B
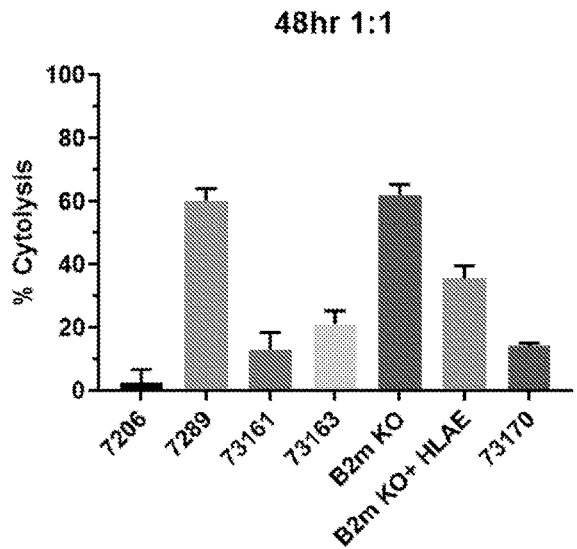
FIG. 33C
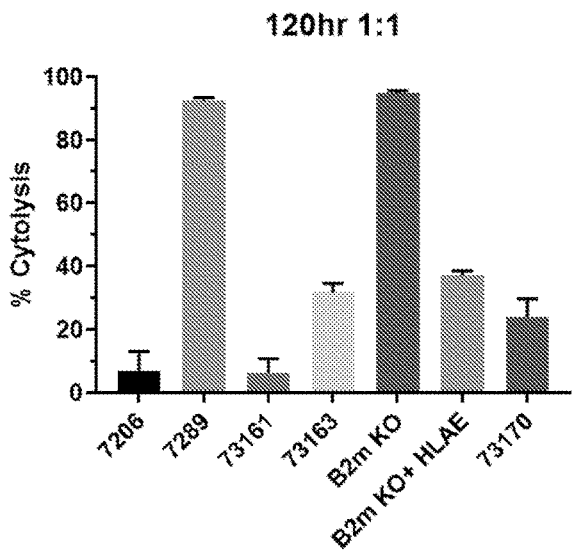
FIGURE 33

GENETICALLY-MODIFIED IMMUNE CELLS COMPRISING A MICRORNA-ADAPTED SHRNA (SHRNAMIR)

CROSS REFERENCE TO RELATED APPLICATIONS

This application is a continuation of U.S. application Ser. No. 17/694,210, filed Mar. 14, 2022, which is a continuation of U.S. application Ser. No. 17/511,022, filed Oct. 26, 2021, which is a continuation of U.S. application Ser. No. 17/225,788, filed Apr. 8, 2021, which is a continuation of U.S. application Ser. No. 16/908,030, filed Jun. 22, 2020 which is a Continuation of International Application No. PCT/US2020/026571, filed Apr. 3, 2020 which claims priority from United States Provisional Application Nos. 62/828,794, filed Apr. 3, 2019, 62/843,804, filed May 6, 2019, 62/900,126, filed Sep. 13, 2019, 62/930,905, filed Nov. 5, 2019, and 63/000,774, filed Mar. 27, 2020, which applications are hereby incorporated in their entirety by reference in this application.

FIELD OF THE INVENTION

The invention relates to the field of oncology, cancer immunotherapy, molecular biology and recombinant nucleic acid technology. In particular, the invention relates to genetically-modified immune cells comprising a microRNA-adapted shRNA (shRNAmiR) molecule that enables stable knockdown of a particular target gene. The invention further relates to the use of such genetically-modified immune cells for reducing the expression of an endogenous protein and treating a disease, including cancer, in a subject.

REFERENCE TO A SEQUENCE LISTING SUBMITTED AS A TEXT FILE VIA EFS-WEB

The instant application contains a Sequence Listing which has been submitted in ST.26 format via USPTO Patent Center and is hereby incorporated by reference in its entirety. Said ST.26 copy, created on Aug. 16, 2022 is named P89339_0143_3_Seq_List, and is 172,015 bytes in size.

BACKGROUND OF THE INVENTION

T cell adoptive immunotherapy is a promising approach for cancer treatment. The immunotherapy treatment methods disclosed herein utilize isolated human T cells that have been genetically-modified to enhance their specificity for a specific tumor associated antigen. Genetic modification may involve the expression of a chimeric antigen receptor or an exogenous T cell receptor to graft antigen specificity onto the T cell. By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. T cell adoptive immunotherapy has been utilized as a clinical therapy for a number of cancers, including B cell malignancies (e.g., acute lymphoblastic leukemia, B cell non-Hodgkin lymphoma, acute myeloid leukemia, and chronic lymphocytic leukemia), multiple myeloma, neuroblastoma, glioblastoma, advanced gliomas, ovarian cancer, mesothelioma, melanoma, prostate cancer, pancreatic cancer, and others.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CART cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, it would be advantageous to develop "off the shelf" CAR T cells, prepared using T cells from a third party, healthy donor, that have reduced expression, or have no detectable cell-surface expression, of an endogenous T cell receptor (e.g., an alpha/beta T cell receptor) and do not initiate GVHD upon administration. Such products could be generated and validated in advance of diagnosis and could be made available to patients as soon as necessary. Therefore, a need exists for the development of allogeneic CAR T cells that lack an endogenous T cell receptor in order to prevent the occurrence of GVHD.

To this end, engineered meganucleases having specificity for the beta-2 microglobulin gene have been generated in order to fully knockout the expression of the beta-2 microglobulin (B2M) protein expression (see, for example, International Publication No. WO 2017/112859). B2M is a component of the major histocompatibility complex (MHC) class I molecule, which will not assemble on the cell surface without B2M present. Thus, knockout of B2M is a means for eliminating MHC class I molecules which should reduce GVHD when CAR T cells are administered to allogeneic patients.

A consequence of fully eliminating B2M and WIC class I molecule expression on the cell surface of CAR T cells, however, is that they become more susceptible to targeting by natural killer (NK) cells which see them as non-self. In view of this phenomenon, a knockdown approach for CAR T cells was developed in order to produce an incomplete knockdown of B2M (see, for example, International Publication No. WO 2018/208837). Essentially, a cassette comprising a B2M-targeted shRNA-coding sequence was introduced into the T cell receptor alpha constant region gene of the T cell by nuclease-mediated targeted insertion. The shRNA-coding sequence was included on a cassette that also comprised a CAR coding sequence, allowing for the production of CAR T cells that were TCR-negative, CAR-positive, and had a partial knockdown of cell-surface B2M. The data in this project demonstrated that these CAR T cells were indeed less susceptible to NK cell killing than CAR T cells that exhibited a complete knockout of B2M.

As described herein, however, further experiments showed that the cassette comprising the shRNA-coding sequence was not stable, and that B2M knockdown was transient. Ultimately, the cell removed the shRNA-coding sequence from the genome, causing a return of B2M expression. Therefore, a need remains for the production of CAR T cells that can maintain a stable knockdown of endogenous proteins, such as B2M. In searching for an answer to this problem in the art, a technology was discovered herein that can be used to produce genetic knockdown of various degrees of proteins of interest in immune cells.

SUMMARY OF THE INVENTION

The present invention provides genetically-modified immune cells (and populations thereof) expressing a microRNA-adapted shRNA (shRNAmiR) that reduces the expression of a target protein. Using shRNAmiRs for knocking down the expression of a target protein allows for stable knockdown of protein expression, which is ideal for those target proteins for which knockdown, and not knockout, is preferred. For example, immune cells that express beta-2 microglobulin (B2M) at reduced levels via expression of B2M-targeted shRNAmiRs are less sensitive to cytolysis by natural killer (NK) cells than those cells in which B2M expression has been knocked out by gene inactivation. Thus, further provided are methods for reducing the expression of an endogenous protein in an immune cell by introducing a template nucleic acid comprising a nucleic acid sequence encoding a shRNAmiR that is inserted into the cell's genome and expressed in order to reduce the expression of the endogenous protein.

Thus, in one aspect, the invention provides a genetically-modified immune cell comprising in its genome a nucleic acid sequence encoding a microRNA-adapted shRNA (shRNAmiR). The shRNAmiR is expressed in the genetically-modified immune cell and reduces expression of a target protein in the genetically-modified immune cell. A reduction in target protein expression is mediated by the binding of the shRNAmiR guide sequence to mRNA encoding the target protein.

In some embodiments, the genetically-modified immune cell is a genetically-modified T cell, or a cell derived therefrom. In certain embodiments, the genetically-modified immune cell is a genetically-modified natural killer (NK) cell, or a cell derived therefrom. In other embodiments, the genetically-modified immune cell is a genetically-modified B cell, or a cell derived therefrom. In various embodiments, the genetically-modified immune cell is a genetically-modified monocyte or macrophage, or a cell derived therefrom.

In some embodiments, the shRNAmiR comprises, from 5' to 3': (a) a 5' miR scaffold domain; (b) a 5' miR basal stem domain; (c) a passenger strand; (d) a miR loop domain; (e) a guide strand; (f) a 3' miR basal stem domain; and (g) a 3' miR scaffold domain.

In some embodiments, the miR loop domain is a miR-30a loop domain, a miR-15 loop domain, a miR-16 loop domain, a miR-155 loop domain, a miR-22 loop domain, a miR-103 loop domain, or a miR-107 loop domain. In particular embodiments, the miR loop domain is a miR-30a loop domain.

In certain embodiments, the miR-30a loop domain comprises a nucleic acid sequence having at least 80%, at least 85%, at least 90%, at least 95%, or more, sequence identity to SEQ ID NO: 3. In particular embodiments, the miR-30a loop domain comprises a nucleic acid sequence of SEQ ID NO: 3.

In some embodiments, the shRNAmiR comprises a microRNA-E (miR-E) scaffold, a miR-30 (e.g., miR-30a) scaffold, a miR-15 scaffold, a miR-16 scaffold, a miR-155 scaffold, a miR-22 scaffold, a miR-103 scaffold, or a miR-107 scaffold. In certain embodiments, the shRNAmiR comprises a miR-E scaffold.

In some embodiments, the shRNAmiR comprises a structure wherein: (a) the 5' miR scaffold domain comprises a nucleic acid sequence having at least 80%, at least 85%, at least 90%, at least 95%, or more, sequence identity to SEQ ID NO: 1; (b) the 5' miR basal stem domain comprises a nucleic acid sequence having at least 80%, at least 85%, at least 90%, at least 95%, or more, sequence identity to SEQ ID NO: 2; (c) the 3' miR basal stem domain comprises a nucleic acid sequence having at least 80%, at least 85%, at least 90%, at least 95%, or more, sequence identity to SEQ ID NO: 4; and/or (d) the 3' miR scaffold domain comprises a nucleic acid sequence having at least 80%, at least 85%, at least 90%, at least 95%, or more, sequence identity to SEQ ID NO: 5.

In certain embodiments, the shRNAmiR comprises a structure wherein: (a) the 5' miR scaffold domain comprises a nucleic acid sequence of SEQ ID NO: 1; (b) the 5' miR basal stem domain comprises a nucleic acid sequence of SEQ ID NO: 2; (c) the 3' miR basal stem domain comprises a nucleic acid sequence of SEQ ID NO: 4; and (d) the 3' miR scaffold domain comprises a nucleic acid sequence of SEQ ID NO: 5.

In some embodiments, the genetically-modified immune cell comprises in its genome a nucleic acid sequence encoding a chimeric antigen receptor (CAR) or an exogenous T cell receptor (TCR), wherein the CAR or the exogenous TCR is expressed by the genetically-modified immune cell.

In some embodiments, the genetically-modified immune cell comprises in its genome a nucleic acid sequence encoding an HLA class I histocompatibility antigen, alpha chain E (HLA-E) fusion protein. In some embodiments, the HLA-E fusion protein comprises an amino acid sequence having at least 80%, at least 85%, at least 90%, at least 95%, or more, sequence identity to SEQ ID NO: 66. In some embodiments, the HLA-E fusion protein comprises an amino acid sequence of SEQ ID NO: 66.

In some embodiments, the nucleic acid sequence encoding the shRNAmiR is located within a different gene than the nucleic acid sequence encoding the CAR or the exogenous TCR. In certain embodiments, the nucleic acid sequence encoding the shRNAmiR, or the nucleic acid sequence encoding the CAR or the exogenous TCR, is located within a TCR alpha gene or a TCR alpha constant region gene. In particular embodiments, the nucleic acid sequence encoding the shRNAmiR, or the nucleic acid sequence encoding the CAR or the exogenous TCR, is located within a TCR alpha constant region gene within a sequence comprising SEQ ID NO: 58.

In some embodiments, the nucleic acid sequence encoding the shRNAmiR is located within the same gene as the nucleic acid sequence encoding the CAR or the exogenous TCR. In certain embodiments, the gene is a TCR alpha gene or TCR alpha constant region gene. In particular embodiments, the nucleic acid sequence encoding the shRNAmiR and the nucleic acid sequence encoding the CAR or the exogenous TCR is located within a TCR alpha constant region gene within a sequence comprising SEQ ID NO: 58. In certain embodiments, the nucleic acid sequence encoding the shRNAmiR and the nucleic acid encoding the CAR or the exogenous TCR are within a cassette in the gene. In some such embodiments, the nucleic acid sequence encoding the shRNAmiR and the nucleic acid sequence encoding the CAR or the exogenous TCR are operably linked to a same promoter. In some such embodiments, the genetically-modified immune cell comprises in its genome a cassette comprising, from 5' to 3': (a) the nucleic acid sequence encoding the CAR or the exogenous TCR; and (b) the nucleic acid sequence encoding the shRNAmiR. In other such embodiments, the genetically-modified immune cell comprises in its genome a cassette comprising, from 5' to 3': (a) the nucleic acid sequence encoding the shRNAmiR; and (b) the nucleic acid sequence encoding the CAR or the exogenous TCR. In some such embodiments, the nucleic acid sequence encoding the CAR or the exogenous TCR and the nucleic acid sequence encoding the shRNAmiR are separated by a 2A or IRES sequence. In certain such embodiments, the nucleic acid sequence encoding the shR- NAmiR is in the same orientation as the nucleic acid sequence encoding the CAR or the exogenous TCR. In other such embodiments, the nucleic acid sequence encoding the shRNAmiR is in a reverse orientation as the nucleic acid sequence encoding the CAR or the exogenous TCR. In some such embodiments, an intron sequence is positioned within the nucleic acid sequence encoding the CAR or the exogenous TCR, and the nucleic acid sequence encoding the shRNAmiR is positioned within the intron sequence. In some such embodiments, the cassette comprises a promoter that is operably linked to the nucleic acid sequence encoding the shRNAmiR and the nucleic acid sequence encoding the CAR or the exogenous TCR. In some such embodiments, the cassette comprises a termination signal.

In certain embodiments, the nucleic acid sequence encoding the shRNAmiR is located within the same gene as the nucleic acid sequence encoding the HLA-E fusion protein. In some embodiments, the gene is a TCR alpha gene or a TCR alpha constant region gene. In some embodiments, the nucleic acid sequence encoding the shRNAmiR and the nucleic acid sequence encoding the HLA-E fusion protein are within a cassette in the gene. In some such embodiments, the nucleic acid sequence encoding the shRNAmiR and nucleic acid sequence encoding the HLA-E fusion protein are operably linked to a same promoter. In some such embodiments, the genetically-modified immune cell comprises in its genome a cassette comprising, from 5' to 3': (a) the nucleic acid sequence encoding the HLA-E fusion protein; and (b) the nucleic acid sequence encoding the shRNAmiR. In some such embodiments, the genetically-modified immune cell comprises in its genome a cassette comprising, from 5' to 3': (a) the nucleic acid sequence encoding the shRNAmiR; and (b) the nucleic acid sequence encoding the HLA-E fusion protein. In some such embodiments, the nucleic acid sequence encoding the HLA-E fusion protein and the nucleic acid sequence encoding the shRNAmiR are separated by a 2A or IRES sequence. In certain such embodiments, an intron sequence is positioned within the nucleic acid sequence encoding the HLA-E fusion protein, wherein the nucleic acid sequence encoding the shRNAmiR is positioned within the intron sequence. In some such embodiments, the cassette comprises a promoter, wherein the nucleic acid sequence encoding the shRNAmiR and nucleic acid sequence encoding the HLA-E fusion protein are operably linked to the promoter. In some such embodiments, the cassette comprises a termination signal.

In some embodiments, the nucleic acid sequence encoding the shRNAmiR, the nucleic acid sequence encoding the CAR or the exogenous TCR, and the nucleic acid sequence encoding the HLA-E fusion protein are located within the same gene. In some embodiments, the gene is a TCR alpha gene or a TCR alpha constant region gene. In some embodiments, the nucleic acid sequence encoding the shRNAmiR, the nucleic acid sequence encoding the CAR or the exogenous TCR, and the nucleic acid sequence encoding the HLA-E fusion protein are within a cassette in the gene. In some such embodiments, the nucleic acid sequence encoding the shRNAmiR, the nucleic acid sequence encoding the CAR or the exogenous TCR, and the nucleic acid sequence encoding the HLA-E fusion protein are operably linked to a same promoter. In some such embodiments, the genetically-modified immune cell comprises within its genome a cassette comprising: (a) the nucleic acid sequence encoding the CAR or the exogenous TCR; (b) a 2A or IRES sequence; (c) the nucleic acid sequence encoding the HLA-E fusion protein; and (d) the nucleic acid sequence encoding the shRNAmiR. In some such embodiments, an intron sequence is positioned within the nucleic acid sequence encoding the CAR or the exogenous TCR, wherein the nucleic acid sequence encoding the shRNAmiR is positioned within the intron sequence. In other such embodiments, an intron sequence is positioned within the nucleic acid sequence encoding the HLA-E fusion protein, wherein the nucleic acid sequence encoding the shRNAmiR is positioned within the intron sequence. In some such embodiments, the cassette comprises a promoter that is operably linked to the nucleic acid sequence encoding the CAR or the exogenous TCR, the nucleic acid sequence encoding the HLA-E fusion protein, and the nucleic acid sequence encoding the shRNAmiR. In some such embodiments, the cassette comprises a termination signal.

In some such embodiments, the genetically-modified immune cell comprises within its genome a cassette comprising, from 5' to 3': (a) a promoter; (b) the nucleic acid sequence encoding the CAR or the exogenous TCR; (c) a 2A or IRES sequence; (d) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments, the genetically-modified immune cell comprises within its genome a cassette comprising, from 5' to 3': (a) a promoter; (b) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; (c) a 2A or IRES sequence; (d) the nucleic acid sequence encoding the CAR or the exogenous TCR; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments, the genetically-modified immune cell comprises within its genome a cassette comprising, from 5' to 3': (a) a promoter; (b) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; (c) a 2A or IRES sequence; (d) the nucleic acid sequence encoding the HLA-E fusion protein; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments, the genetically-modified immune cell comprises within its genome a cassette comprising, from 5' to 3': (a) a promoter; (b) the nucleic acid sequence encoding the HLA-E fusion protein; (c) a 2A or IRES sequence; (d) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some embodiments described above, the intron sequence is a synthetic intron sequence. In certain embodiments, the intron sequence comprises a nucleic acid sequence having at least 80%, at least 85%, at least 90%, at least 95%, or more, sequence identity to SEQ ID NO: 69. In particular embodiments, the intron sequence comprises a nucleic acid sequence of SEQ ID NO: 69.

In some embodiments described above, the termination signal is a polyA sequence or a bovine growth hormone (BGH) termination signal. In certain embodiments, the polyA sequence comprises a nucleic acid sequence having at least 80%, at least 85%, at least 90%, at least 95%, or more, sequence identity to SEQ ID NO: 68. In particular embodiments, the polyA sequence comprises a nucleic acid sequence of SEQ ID NO: 68. In certain embodiments, the BGH termination signal comprises a nucleic acid sequence having least 80%, at least 85%, at least 90%, at least 95%, or more, sequence identity to SEQ ID NO: 71. In particular embodiments, the BGH termination signal comprises a nucleic acid sequence of SEQ ID NO: 71.

In some embodiments described above, the promoter comprises a nucleic acid sequence having at least 80%, at least 85%, at least 90%, at least 95%, or more, sequence identity to SEQ ID NO: 67. In particular embodiments, the promoter comprises a nucleic acid sequence of SEQ ID NO: 67.

In some embodiments described above, the 2A sequence is a P2A/furin site comprising a nucleic acid sequence having at least 80%, at least 85%, at least 90%, at least 95%, or more, sequence identity to SEQ ID NO: 70. In particular embodiments, the 2A sequence is a P2A/furin site comprising a nucleic acid sequence of SEQ ID NO: 70.

In some embodiments described above, the CAR comprises a signal peptide comprising an amino acid sequence having at least 80%, at least 85%, at least 90%, at least 95%, or more, sequence identity to SEQ ID NO: 73. In particular embodiments, the CAR comprises a signal peptide comprising an amino acid sequence of SEQ ID NO: 73.

In particular embodiments, the genetically-modified immune cell comprises in its genome a cassette comprising, from 5' to 3': (a) a promoter comprising a nucleic acid sequence having at least 80%, at least 85%, at least 90%, at least 95%, or more, sequence identity to SEQ ID NO: 67; (b) the nucleic acid sequence encoding the CAR, wherein the CAR comprises a signal peptide comprising an amino acid sequence having at least 80%, at least 85%, at least 90%, at least 95%, or more, sequence identity to SEQ ID NO: 73; (c) a P2A/furin site comprising a nucleic acid sequence having at least 80%, at least 85%, at least 90%, at least 95%, or more, sequence identity to SEQ ID NO: 70; (d) the nucleic acid sequence encoding the HLA-E fusion protein, wherein the HLA-E fusion protein comprises an amino acid sequence having at least 80%, at least 85%, at least 90%, at least 95%, or more, sequence identity to SEQ ID NO: 66, and wherein an intron sequence is positioned within the nucleic acid sequence encoding the HLA-E fusion protein, wherein the intron sequence comprises a nucleic acid sequence having at least 80%, at least 85%, at least 90%, at least 95%, or more, sequence identity to SEQ ID NO: 69, and wherein the nucleic acid sequence encoding the shRNAmiR is positioned within the intron sequence; and (e) optionally a termination signal comprising a nucleic acid sequence having at least 80%, at least 85%, at least 90%, at least 95%, or more, sequence identity to SEQ ID NO: 68; wherein the nucleic acid sequence encoding the CAR, the nucleic acid sequence encoding the HLA-E fusion protein, and the nucleic acid sequence encoding the shRNAmiR are operably linked to the promoter.

In particular embodiments, the genetically-modified immune cell comprises in its genome a cassette comprising, from 5' to 3': (a) a promoter comprising a nucleic acid sequence of SEQ ID NO: 67; (b) the nucleic acid sequence encoding the CAR, wherein the CAR comprises a signal peptide comprising an amino acid sequence of SEQ ID NO: 73; (c) a P2A/furin site comprising a nucleic acid sequence of SEQ ID NO: 70; (d) the nucleic acid sequence encoding the HLA-E fusion protein, wherein the HLA-E fusion protein comprises an amino acid sequence of SEQ ID NO: 66, and wherein an intron sequence is positioned within the nucleic acid sequence encoding the HLA-E fusion protein, wherein the intron sequence comprises a nucleic acid sequence of SEQ ID NO: 69, and wherein the nucleic acid sequence encoding the shRNAmiR is positioned within the intron sequence; and (e) optionally a termination signal comprising a nucleic acid sequence of SEQ ID NO: 68; wherein the nucleic acid sequence encoding the CAR, the nucleic acid sequence encoding the HLA-E fusion protein, and the nucleic acid sequence encoding the shRNAmiR are operably linked to the promoter.

In particular embodiments, the genetically-modified immune cell comprises in its genome a cassette comprising a nucleic acid sequence having at least 80%, at least 85%, at least 90%, at least 95%, or more, sequence identity to SEQ ID NO: 74, wherein the cassette is positioned in the genome within a TCR alpha constant region gene. In particular embodiments, the genetically-modified immune cell comprises in its genome a cassette comprising a nucleic acid sequence of SEQ ID NO: 74, wherein the cassette is positioned in the genome within a TCR alpha constant region gene.

In some embodiments described above, the cassette comprises two or more nucleic acids encoding shRNAmiRs. In certain embodiments, the two or more nucleic acids can encode the same shRNAmiR. In some embodiments, the two or more nucleic acids can encode different shRNAmiRs that reduce the expression of the same target protein. In other embodiments, the two or more nucleic acids encode different shRNAmiRs that reduce the expression of different target proteins. In certain embodiments, the cassette can comprise two or more nucleic acids encoding different shRNAmiRs described herein. In particular embodiments, the cassette can comprise a nucleic acid sequence encoding a shRNAmiR that reduces the expression of B2M, and a nucleic acid sequence encoding a shRNAmiR that reduces the expression of CD52.

In some embodiments, the nucleic acid sequence encoding the shRNAmiR and the nucleic acid sequence encoding the CAR or the exogenous TCR are located in the same gene and are operably linked to different promoters. In some such embodiments, the genetically-modified immune cell comprises in its genome a cassette comprising, from 5' to 3': (a) a first promoter; (b) the nucleic acid sequence encoding the CAR or exogenous TCR which is operably linked to the first promoter; (c) a second promoter; and (d) the nucleic acid sequence encoding the shRNAmiR which is operably linked to the second promoter. In other such embodiments, the genetically-modified immune cell comprises in its genome a cassette comprising, from 5' to 3': (a) a first promoter; (b) the nucleic acid sequence encoding the shRNAmiR which is operably linked to the first promoter; (c) a second promoter; and (d) the nucleic acid sequence encoding the CAR or exogenous TCR which is operably linked to the second promoter. In some such embodiments, the nucleic acid sequence encoding the shRNAmiR is in the same orientation as the nucleic acid sequence encoding the CAR or exogenous TCR. In other such embodiments, the nucleic acid sequence encoding the shRNAmiR is in a reverse orientation as the nucleic acid sequence encoding the CAR or exogenous TCR. In certain such embodiments, the first promoter and the second promoter are identical. In other embodiments, the first promoter and the second promoter are different. In some such embodiments, the cassette comprises one or more termination signals.

In some embodiments, the nucleic acid sequence encoding the shRNAmiR and the nucleic acid sequence encoding the HLA-E fusion protein are operably linked to different promoters. In some such embodiments, the genetically-modified immune cell comprises in its genome a cassette comprising, from 5' to 3': (a) a first promoter; (b) the nucleic acid sequence encoding the HLA-E fusion protein which is operably linked to the first promoter; (c) a second promoter; and (d) the nucleic acid sequence encoding the shRNAmiR which is operably linked to the second promoter. In other such embodiments, the genetically-modified immune cell comprises in its genome a cassette comprising, from 5' to 3': (a) a first promoter; (b) the nucleic acid sequence encoding the shRNAmiR which is operably linked to the first promoter; (c) a second promoter; and (d) the nucleic acid sequence encoding the HLA-E fusion protein which is operably linked to the second promoter. In certain such embodiments, the first promoter and the second promoter are identical. In other such embodiments, the first promoter and the second promoter are different. In some such embodiments, the cassette comprises one or more termination signals.

In some embodiments, the genetically-modified immune cell comprises within its genome a cassette comprising: (a) the nucleic acid sequence encoding the CAR or the exogenous TCR; (b) the nucleic acid sequence encoding the HLA-E fusion protein; and (c) the nucleic acid sequence encoding the shRNAmiR; wherein the nucleic acid sequence encoding the CAR or the exogenous TCR is operably linked to a first promoter, and wherein the nucleic acid sequence encoding the HLA-E fusion protein and the nucleic acid sequence encoding the shRNAmiR are operably linked to a second promoter. In some such embodiments, an intron sequence is positioned within the nucleic acid sequence encoding the HLA-E fusion protein, wherein the nucleic acid sequence encoding the shRNAmiR is positioned within the intron sequence. In some embodiments, the genetically-modified immune cell comprises within its genome a cassette comprising: (a) the nucleic acid sequence encoding the CAR or the exogenous TCR; (b) the nucleic acid sequence encoding the HLA-E fusion protein; and (c) the nucleic acid sequence encoding the shRNAmiR; wherein the nucleic acid sequence encoding the CAR or the exogenous TCR and the nucleic acid sequence encoding the shRNAmiR are operably linked to a first promoter, and wherein the nucleic acid sequence encoding the HLA-E fusion protein is operably linked to a second promoter. In some such embodiments, an intron sequence is positioned within the nucleic acid sequence encoding the CAR or the exogenous TCR, wherein the nucleic acid sequence encoding the shRNAmiR is positioned within the intron sequence. In some such embodiments, the cassette comprises a first termination signal capable of terminating transcription of the CAR or the exogenous TCR, and a second termination signal capable of terminating transcription of the HLA-E fusion protein. In other such embodiments, the cassette comprises a first termination signal capable of terminating transcription of the HLA-E fusion protein, and a second termination signal capable of terminating transcription of the CAR or the exogenous TCR.

In some such embodiments, the genetically-modified immune cell comprises within its genome a cassette comprising, from 5' to 3': (a) a first promoter; (b) the nucleic acid sequence encoding the CAR or the exogenous TCR; (c) optionally a first termination signal; (d) a second promoter; (e) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; and (f) optionally a second termination signal; wherein the nucleic acid sequence encoding the CAR or the exogenous TCR is operably linked to the first promoter, and wherein the nucleic acid sequence encoding the HLA-E fusion protein and the nucleic acid sequence encoding the shRNAmiR are operably linked to the second promoter.

In some such embodiments, the genetically-modified immune cell comprises within its genome a cassette comprising, from 5' to 3': (a) a first promoter; (b) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; (c) optionally a first termination signal; (d) a second promoter; (e) the nucleic acid sequence encoding the CAR or the exogenous TCR; and (f) optionally a second termination signal; wherein the nucleic acid sequence encoding the HLA-E fusion protein and the nucleic acid sequence encoding the shRNAmiR are operably linked to the first promoter, and wherein the nucleic acid sequence encoding the CAR or the exogenous TCR is operably linked to the second promoter.

In some such embodiments, the genetically-modified immune cell comprises within its genome a cassette comprising, from 5' to 3': (a) a first promoter; (b) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; (c) optionally a first termination signal; (d) a second promoter; (e) the nucleic acid sequence encoding the HLA-E fusion protein; and (f) optionally a second termination signal; wherein the nucleic acid sequence encoding the CAR or the exogenous TCR and the nucleic acid sequence encoding the shRNAmiR are operably linked to the first promoter, and wherein the nucleic acid sequence encoding the HLA-E fusion protein is operably linked to the second promoter.

In some such embodiments, the genetically-modified immune cell comprises within its genome a cassette comprising, from 5' to 3': (a) a first promoter; (b) the nucleic acid sequence encoding the HLA-E fusion protein; (c) optionally a first termination signal; (d) a second promoter; (e) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; and (f) optionally a second termination signal; wherein the nucleic acid sequence encoding the HLA-E fusion protein is operably linked to the first promoter, and wherein the nucleic acid sequence encoding the CAR or the exogenous TCR and the nucleic acid sequence encoding the shRNAmiR are operably linked to the second promoter.

In some embodiments described above, the intron sequence is a synthetic intron sequence. In certain embodiments, the intron sequence comprises a nucleic acid sequence having at least 80%, at least 85%, at least 90%, at least 95%, or more, sequence identity to SEQ ID NO: 69. In particular embodiments, the intron sequence comprises a nucleic acid sequence of SEQ ID NO: 69.

In some embodiments described above, the one or more termination signals is a polyA sequence or a BGH termination signal.

In some embodiments described above, the first termination signal is identical to the second termination signal. In some such embodiments, the first termination signal and the second termination signal are a polyA sequence or a BGH termination signal.

In some embodiments described above, the first termination signal is different from the second termination signal. In some embodiments, the first termination signal is a polyA sequence and the second termination signal is a BGH termination signal. In some embodiments, the first termination signal is a BGH termination signal and the second termination signal is a polyA sequence.

In some embodiments described above, the polyA sequence comprises a nucleic acid sequence having at least 80%, at least 85%, at least 90%, at least 95%, or more, sequence identity to SEQ ID NO: 68. In certain embodiments, the polyA sequence comprises a nucleic acid sequence of SEQ ID NO: 68. In some embodiments, the BGH termination signal comprises a nucleic acid sequence having at least 80%, at least 85%, at least 90%, at least 95%, or more, sequence identity to SEQ ID NO: 71. In certain embodiments, the BGH termination signal comprises a nucleic acid sequence of SEQ ID NO: 71.

In some embodiments described above, the first promoter and the second promoter are identical. In some such embodiments, the first promoter and the second promoter are a JeT promoter or an EF1 alpha core promoter.

In some embodiments described above, the first promoter is different from the second promoter. In certain embodiments, the first promoter is a JeT promoter, and the second promoter is an EF1 alpha core promoter. In certain embodiments, the first promoter is an EF1 alpha core promoter, and the second promoter is a JeT promoter.

In certain embodiments described above, the JeT promoter comprises a nucleic acid sequence having at least 80%, at least 85%, at least 90%, at least 95%, or more, sequence identity to SEQ ID NO: 67. In particular embodiments, the JeT promoter comprises a nucleic acid sequence of SEQ ID NO: 67. In certain embodiments, the EF1 alpha core promoter comprises a nucleic acid sequence having at least 80%, at least 85%, at least 90%, at least 95%, or more, sequence identity to SEQ ID NO: 72. In some embodiments, the EF1 alpha core promoter comprises a nucleic acid sequence of SEQ ID NO: 72.

In some embodiments described above, the CAR comprises a signal peptide comprising an amino acid sequence having at least 80%, at least 85%, at least 90%, at least 95%, or more, sequence identity to SEQ ID NO: 73. In particular embodiments, the CAR comprises a signal peptide comprising an amino acid sequence of SEQ ID NO: 73.

In some embodiments, the genetically-modified immune cell comprises in its genome a cassette comprising, from 5' to 3': (a) a first promoter comprising a nucleic acid sequence having at least 80%, at least 85%, at least 90%, at least 95%, or more, sequence identity to SEQ ID NO: 67; (b) the nucleic acid sequence encoding the CAR, wherein the CAR comprises a signal peptide comprising an amino acid sequence having at least 80%, at least 85%, at least 90%, at least 95%, or more, sequence identity to SEQ ID NO: 73; (c) optionally a first termination signal comprising a nucleic acid sequence having at least 80%, at least 85%, at least 90%, at least 95%, or more, sequence identity to SEQ ID NO: 70; (d) a second promoter comprising a nucleic acid sequence having at least 80%, at least 85%, at least 90%, at least 95%, or more, sequence identity to SEQ ID NO: 72; (e) the nucleic acid sequence encoding the HLA-E fusion protein, wherein the HLA-E fusion protein comprises an amino acid sequence having at least 80%, at least 85%, at least 90%, at least 95%, or more, sequence identity to SEQ ID NO: 66, and wherein an intron sequence is positioned within the nucleic acid sequence encoding the HLA-E fusion protein, wherein the intron sequence comprises a nucleic acid sequence having at least 80%, at least 85%, at least 90%, at least 95%, or more, sequence identity to SEQ ID NO: 69, and wherein the nucleic acid sequence encoding the shRNAmiR is positioned within the intron sequence; and (f) optionally a second termination signal comprising a nucleic acid sequence having at least 80%, at least 85%, at least 90%, at least 95%, or more, sequence identity to SEQ ID NO: 71; wherein the nucleic acid sequence encoding the CAR is operably linked to the first promoter, and wherein the nucleic acid sequence encoding the HLA-E fusion protein and the nucleic acid sequence encoding the shRNAmiR are operably linked to the second promoter.

In particular embodiments, the genetically-modified immune cell comprises in its genome a cassette comprising, from 5' to 3': (a) a first promoter comprising a nucleic acid sequence of SEQ ID NO: 67; (b) the nucleic acid sequence encoding the CAR, wherein the CAR comprises a signal peptide comprising an amino acid sequence of SEQ ID NO: 73; (c) optionally a first termination signal comprising a nucleic acid sequence of SEQ ID NO: 70; (d) a second promoter comprising a nucleic acid sequence of SEQ ID NO: 72; (e) the nucleic acid sequence encoding the HLA-E fusion protein, wherein the HLA-E fusion protein comprises an amino acid sequence of SEQ ID NO: 66, and wherein an intron sequence is positioned within the nucleic acid sequence encoding the HLA-E fusion protein, wherein the intron sequence comprises a nucleic acid sequence of SEQ ID NO: 69, and wherein the nucleic acid sequence encoding the shRNAmiR is positioned within the intron sequence; and (f) optionally a second termination signal comprising a nucleic acid sequence of SEQ ID NO: 71; wherein the nucleic acid sequence encoding the CAR is operably linked to the first promoter, and wherein the nucleic acid sequence encoding the HLA-E fusion protein and the nucleic acid sequence encoding the shRNAmiR are operably linked to the second promoter.

In particular embodiments, the genetically-modified immune cell comprises in its genome a cassette comprising a nucleic acid sequence having at least 80%, at least 85%, at least 90%, at least 95%, or more, sequence identity to SEQ ID NO: 75, wherein the cassette is positioned in the genome within a TCR alpha constant region gene. In particular embodiments, the genetically-modified immune cell comprises in its genome a cassette comprising a nucleic acid sequence of SEQ ID NO: 75, wherein the cassette is positioned in the genome within a TCR alpha constant region gene.

In some embodiments described above, the cassette comprises two or more nucleic acids encoding shRNAmiRs. In certain embodiments, the two or more nucleic acids can encode the same shRNAmiR. In some embodiments, the two or more nucleic acids can encode different shRNAmiRs that reduce the expression of the same target protein. In other embodiments, the two or more nucleic acids encode different shRNAmiRs that reduce the expression of different target proteins. In certain embodiments, the cassette can comprise two or more nucleic acids encoding different shRNAmiRs described herein. In particular embodiments, the cassette can comprise a nucleic acid sequence encoding a shRNAmiR that reduces the expression of B2M, and a nucleic acid sequence encoding a shRNAmiR that reduces the expression of CD52.

In some embodiments, expression of the target protein is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell.

In some embodiments, the target protein is beta-2 microglobulin, CS1, transforming growth factor-beta receptor 2 (TGFBR2), Cbl proto-oncogene B (CBL-B), CD52, a TCR alpha gene, a TCR alpha constant region gene, CD7, glucocorticoid receptor (GR), deoxycytidine kinase (DCK), nuclear receptor subfamily 2 group F member 6 (NR2F6), cytotoxic T-lymphocyte-associated protein 4 (CTLA-4), or C—C chemokine receptor type 5 (CCR5).

In some embodiments, the target protein is beta-2 microglobulin. In some such embodiments, cell surface expression of beta-2 microglobulin is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further embodiments, expression of MHC class I molecules is reduced on the cell surface by at least about 10%, about 20%, about 30%, about 40%, about 50%, about 55%, about 60%, about 65%, about 70%, about 75%, about 80%, about 85%, about 90%, about 95%, or up to about 99% compared to a control cell. In some such embodiments, the genetically-modified immune cell has reduced allogenicity compared to a control cell.

In some such embodiments, the shRNAmiR has a structure wherein: (a) the passenger strand comprises a nucleic acid sequence of SEQ ID NO: 17 and the guide strand comprises a nucleic acid sequence of SEQ ID NO: 18; (b) the passenger strand comprises a nucleic acid sequence of SEQ ID NO: 7 and the guide strand comprises a nucleic acid sequence of SEQ ID NO: 8; (c) the passenger strand comprises a nucleic acid sequence of SEQ ID NO: 9 and the guide strand comprises a nucleic acid sequence of SEQ ID NO: 10; (d) the passenger strand comprises a nucleic acid sequence of SEQ ID NO: 11 and the guide strand comprises a nucleic acid sequence of SEQ ID NO: 12; (e) the passenger strand comprises a nucleic acid sequence of SEQ ID NO: 13 and the guide strand comprises a nucleic acid sequence of SEQ ID NO: 14; or (f) the passenger strand comprises a nucleic acid sequence of SEQ ID NO: 15 and the guide strand comprises a nucleic acid sequence of SEQ ID NO: 16. In certain such embodiments, the passenger strand comprises a nucleic acid sequence of SEQ ID NO: 17 and the guide strand comprises a nucleic acid sequence of SEQ ID NO: 18. In particular such embodiments, the nucleic acid sequence encoding the shRNAmiR comprises a sequence having at least 80%, at least 85%, at least 90%, at least 95%, or more, sequence identity to SEQ ID NO: 46. In further such embodiments, the nucleic acid sequence encoding the shRNAmiR comprises the sequence of SEQ ID NO: 46.

In some embodiments, the target protein is CS1. In some such embodiments, cell surface expression of CS1 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In some such embodiments, the genetically-modified immune cell expresses a CAR having specificity for CS1. In further such embodiments, the genetically-modified immune cell is less susceptible to fratricide by a genetically-modified immune cell expressing a CAR having specificity for CS1 compared to a control cell.

In some such embodiments, the shRNAmiR has a structure wherein: (a) the passenger strand comprises a nucleic acid sequence of SEQ ID NO: 21 and the guide strand comprises a nucleic acid sequence of SEQ ID NO: 22; (b) the passenger strand comprises a nucleic acid sequence of SEQ ID NO: 23 and the guide strand comprises a nucleic acid sequence of SEQ ID NO: 24; or (c) the passenger strand comprises a nucleic acid sequence of SEQ ID NO: 25 and the guide strand comprises a nucleic acid sequence of SEQ ID NO: 26. In certain such embodiments, the passenger strand comprises a nucleic acid sequence of SEQ ID NO: 25 and the guide strand comprises a nucleic acid sequence of SEQ ID NO: 26. In particular such embodiments, the shRNAmiR comprises a sequence having at least 80%, at least 85%, at least 90%, at least 95%, or more, sequence identity to SEQ ID NO: 50. In further such embodiments, the shRNAmiR comprises the sequence of SEQ ID NO: 50.

In some embodiments, the target protein is TGFBR2. In some such embodiments, the cell surface expression of TGFBR2 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further embodiments, the genetically-modified immune cell is less susceptible to immunosuppression by transforming growth factor B1 (TGFB1) compared to a control cell.

In some such embodiments, the shRNAmiR has a structure wherein: (a) the passenger strand comprises a nucleic acid sequence of SEQ ID NO: 27 and the guide strand comprises a nucleic acid sequence of SEQ ID NO: 28; (b) the passenger strand comprises a nucleic acid sequence of SEQ ID NO: 29 and the guide strand comprises a nucleic acid sequence of SEQ ID NO: 30; (c) the passenger strand comprises a nucleic acid sequence of SEQ ID NO: 31 and the guide strand comprises a nucleic acid sequence of SEQ ID NO: 32; (d) the passenger strand comprises a nucleic acid sequence of SEQ ID NO: 33 and the guide strand comprises a nucleic acid sequence of SEQ ID NO: 34; or (e) the passenger strand comprises a nucleic acid sequence of SEQ ID NO: 35 and the guide strand comprises a nucleic acid sequence of SEQ ID NO: 36. In certain such embodiments, the passenger strand comprises a nucleic acid sequence of SEQ ID NO: 31 and the guide strand comprises a nucleic acid sequence of SEQ ID NO: 32. In particular such embodiments, the nucleic acid sequence encoding the shRNAmiR comprises a sequence having at least 80%, at least 95%, at least 90%, at least 95%, or more, sequence identity to SEQ ID NO: 53. In further such embodiments, the nucleic acid sequence encoding the shRNAmiR comprises the sequence of SEQ ID NO: 53.

In some embodiments, the target protein is CBL-B. In some such embodiments, cell surface expression of CBL-B is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments, the immune cell is less susceptible to suppression of T cell receptor (TCR) signaling by degradation of downstream signaling proteins compared to a control cell.

In some embodiments, the target protein is CD52. In some such embodiments, cell surface expression of CD52 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further embodiments, the genetically-modified immune cell is less susceptible to CD52 antibody-induced cell death.

In some such embodiments, the shRNAmiR has a structure wherein: (a) the passenger strand comprises a nucleic acid sequence of SEQ ID NO: 37 and the guide strand comprises a nucleic acid sequence of SEQ ID NO: 38; or (b) the passenger strand comprises a nucleic acid sequence of SEQ ID NO: 39 and the guide strand comprises a nucleic acid sequence of SEQ ID NO: 40. In certain such embodiments, the passenger strand comprises a nucleic acid sequence of SEQ ID NO: 37 and the guide strand comprises a nucleic acid sequence of SEQ ID NO: 38. In particular such embodiments, the nucleic acid sequence encoding the shRNAmiR comprises a sequence having at least 80%, at least 85%, at least 90%, at least 95%, or more, sequence identity to SEQ ID NO: 56. In further such embodiments, the nucleic acid sequence encoding the shRNAmiR comprises the sequence of SEQ ID NO: 56.

In some embodiments, the target protein is DCK. In some such embodiments, cell surface expression of DCK is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments, the genetically-modified immune cell is less susceptible to effects of purine nucleoside analogs (e.g., fludarabine) on cell proliferation.

In some such embodiments, the shRNAmiR has a structure wherein: (a) the passenger strand comprises a nucleic acid sequence of SEQ ID NO: 76 and the guide strand comprises a nucleic acid sequence of SEQ ID NO: 77; (b) the passenger strand comprises a nucleic acid sequence of SEQ ID NO: 78 and the guide strand comprises a nucleic acid sequence of SEQ ID NO: 79; (c) the passenger strand comprises a nucleic acid sequence of SEQ ID NO: 80 and the guide strand comprises a nucleic acid sequence of SEQ ID NO: 81; (d) the passenger strand comprises a nucleic acid sequence of SEQ ID NO: 82 and the guide strand comprises a nucleic acid sequence of SEQ ID NO: 83; or (e) the passenger strand comprises a nucleic acid sequence of SEQ ID NO: 84 and the guide strand comprises a nucleic acid sequence of SEQ ID NO: 85. In particular such embodiments, the passenger strand comprises a nucleic acid sequence of SEQ ID NO: 76 and the guide strand comprises a nucleic acid sequence of SEQ ID NO: 77. In particular such embodiments, the nucleic acid sequence encoding the shRNAmiR comprises a sequence having at least 80%, at least 85%, at least 90%, at least 95%, or more, sequence identity to SEQ ID NO: 86. In further such embodiments, the nucleic acid sequence encoding the shRNAmiR comprises the sequence of SEQ ID NO: 86.

In some embodiments, the target protein is GR. In some such embodiments, cell surface expression of GR is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments, the genetically-modified immune cell is less susceptible to effects of glucocorticoids (e.g., dexamethasone), such as reduced proliferation.

In some such embodiments, the shRNAmiR has a structure wherein: (a) the passenger strand comprises a nucleic acid sequence of SEQ ID NO: 91 and the guide strand comprises a nucleic acid sequence of SEQ ID NO: 92; (b) the passenger strand comprises a nucleic acid sequence of SEQ ID NO: 93 and the guide strand comprises a nucleic acid sequence of SEQ ID NO: 94; (c) the passenger strand comprises a nucleic acid sequence of SEQ ID NO: 95 and the guide strand comprises a nucleic acid sequence of SEQ ID NO: 96; (d) the passenger strand comprises a nucleic acid sequence of SEQ ID NO: 97 and the guide strand comprises a nucleic acid sequence of SEQ ID NO: 98; (e) the passenger strand comprises a nucleic acid sequence of SEQ ID NO: 99 and the guide strand comprises a nucleic acid sequence of SEQ ID NO: 100; (f) the passenger strand comprises a nucleic acid sequence of SEQ ID NO: 101 and the guide strand comprises a nucleic acid sequence of SEQ ID NO: 102; (g) the passenger strand comprises a nucleic acid sequence of SEQ ID NO: 103 and the guide strand comprises a nucleic acid sequence of SEQ ID NO: 104; (h) the passenger strand comprises a nucleic acid sequence of SEQ ID NO: 105 and the guide strand comprises a nucleic acid sequence of SEQ ID NO: 106; or (i) the passenger strand comprises a nucleic acid sequence of SEQ ID NO: 107 and the guide strand comprises a nucleic acid sequence of SEQ ID NO: 108. In particular such embodiments, the passenger strand comprises a nucleic acid sequence of SEQ ID NO: 95 and the guide strand comprises a nucleic acid sequence of SEQ ID NO: 96. In particular such embodiments, the nucleic acid sequence encoding the shRNAmiR comprises a sequence having at least 80%, at least 85%, at least 90%, at least 95%, or more, sequence identity to SEQ ID NO: 111. In further such embodiments, the nucleic acid sequence encoding the shRNAmiR comprises the sequence of SEQ ID NO: 111.

In another aspect, the invention provides a method for reducing the expression of an endogenous protein in an immune cell, the method comprising introducing into the immune cell a template nucleic acid comprising a nucleic acid sequence encoding a shRNAmiR, wherein the template nucleic acid is inserted into the genome of the immune cell. The shRNAmiR is expressed in the immune cell and reduces expression of an endogenous target protein in the immune cell. A reduction in target protein expression is mediated by the binding of the shRNAmiR guide sequence to mRNA encoding the target protein.

In some embodiments of the method, the immune cell is a T cell, or a cell derived therefrom. In certain embodiments, the immune cell is a natural killer (NK) cell, or a cell derived therefrom. In other embodiments, the immune cell is a B cell, or a cell derived therefrom. In various embodiments, the immune cell is a monocyte or macrophage, or a cell derived therefrom.

In some embodiments of the method, the template nucleic acid is inserted into the genome of the immune cell by random integration. In some such embodiments of the method, the template nucleic acid is introduced into the immune cell using a viral vector (i.e., a recombinant virus), such as a lentiviral vector (i.e., a recombinant lentivirus).

In some embodiments of the method, the immune cell expresses a CAR or exogenous TCR.

In some embodiments, the method further comprises introducing into the immune cell a second nucleic acid encoding an engineered nuclease having specificity for a recognition sequence in the genome of the immune cell. The engineered nuclease is expressed in the immune cell and generates a cleavage site at the recognition sequence. The template nucleic acid comprising a nucleic acid sequence encoding the shRNAmiR is inserted into the genome of the immune cell at the cleavage site. In some such embodiments of the method, the template nucleic acid is flanked by homology arms having homology to sequences flanking the recognition sequence, and the template nucleic acid is inserted at the cleavage site by homologous recombination. In some such embodiments of the method, the template nucleic acid is introduced into the immune cell using a viral vector (i.e., a recombinant virus). In some such embodiments, the viral vector is a recombinant AAV vector (i.e., a recombinant AAV). In particular embodiments, the AAV vector has a serotype of AAV2 or AAV6. In some such embodiments of the method, the recognition sequence is within a target gene. In some such embodiments of the method, the expression of a protein encoded by the target gene is disrupted in the immune cell. In certain such embodiments of the method, the target gene is a TCR alpha gene or a TCR alpha constant region gene, and the immune cell does not have detectable cell-surface expression of an endogenous TCR (e.g., an alpha/beta TCR). In some such embodiments of the method, the engineered nuclease is an engineered meganuclease, a zinc finger nuclease, a TALEN, a compact TALEN, a CRISPR system nuclease, or a megaTAL. In particular such embodiments of the method, the engineered nuclease is an engineered meganuclease. In certain such embodiments of the method, the second nucleic acid encoding the engineered nuclease is introduced using an mRNA.

In some embodiments of the method, the immune cell into which the template nucleic acid is introduced further comprises in its genome a nucleic acid sequence encoding a CAR or exogenous TCR. In certain embodiments of the method, the immune cell into which the template nucleic acid is introduced further comprises in its genome a nucleic acid sequence encoding an HLA-E fusion protein.

In some embodiments of the method, the template nucleic acid further comprises a nucleic acid sequence encoding a CAR or an exogenous TCR, wherein the CAR or the exogenous TCR is expressed by the immune cell. In some such embodiments, the nucleic acid sequence encoding the shRNAmiR and the nucleic acid sequence encoding the CAR or the exogenous TCR are operably linked to a same promoter in the immune cell following introduction of the template nucleic acid at the cleavage site. In some such embodiments of the method, the template nucleic acid comprises, from 5' to 3': (a) the nucleic acid sequence encoding the CAR or the exogenous TCR; and (b) the nucleic acid sequence encoding the shRNAmiR. In other such embodiments of the method, the template nucleic acid comprises, from 5' to 3': (a) the nucleic acid sequence encoding the shRNAmiR; and (b) the nucleic acid sequence encoding the CAR or the exogenous TCR. In certain such embodiments of the method, the nucleic acid sequence encoding the CAR or the exogenous TCR and the nucleic acid sequence encoding the shRNAmiR are separated by a 2A or IRES sequence. In some such embodiments of the method, the nucleic acid sequence encoding the shRNAmiR is in the same orientation as the nucleic acid sequence encoding the CAR or the exogenous TCR. In other such embodiments of the method, the nucleic acid sequence encoding the shRNAmiR is in a reverse orientation as the nucleic acid sequence encoding the CAR or the exogenous TCR. In some such embodiments of the method, an intron sequence is positioned within the nucleic acid sequence encoding the CAR or the exogenous TCR, wherein the nucleic acid sequence encoding the shRNAmiR is positioned within the intron sequence. In certain such embodiments of the method, the template nucleic acid comprises a promoter, wherein the promoter is operably linked to the nucleic acid sequence encoding the CAR or the exogenous TCR and to the nucleic acid sequence encoding the shRNAmiR. In some such embodiments of the method, the template nucleic acid comprises a termination signal.

In some embodiments of the method, the template nucleic acid comprises a nucleic acid sequence encoding an HLA-E fusion protein, wherein the HLA-E fusion protein is expressed by the immune cell. In some such embodiments of the method, the shRNAmiR and the nucleic acid sequence encoding the HLA-E fusion protein are operably linked to a same promoter in the immune cell following introduction of the template nucleic acid at the cleavage site. In certain such embodiments of the method, the template nucleic acid comprises, from 5' to 3': (a) the nucleic acid sequence encoding the HLA-E fusion protein; and (b) the nucleic acid sequence encoding the shRNAmiR. In other such embodiments of the method, the template nucleic acid comprises, from 5' to 3': (a) the nucleic acid sequence encoding the shRNAmiR; and (b) the nucleic acid sequence encoding the HLA-E fusion protein. In some such embodiments of the method, the nucleic acid sequence encoding the HLA-E fusion protein and the nucleic acid sequence encoding the shRNAmiR are separated by a 2A or IRES sequence. In certain such embodiments, of the method, an intron sequence is positioned within the nucleic acid sequence encoding the HLA-E fusion protein, wherein the nucleic acid sequence encoding the shRNAmiR is positioned within the intron sequence. In some such embodiments of the method, the template nucleic acid comprises a promoter, wherein the promoter is operably linked to the nucleic acid sequence encoding the HLA-E fusion protein and to the nucleic acid sequence encoding the shRNAmiR. In certain such embodiments of the method, the template nucleic acid comprises a termination signal.

In some embodiments of the method, the template nucleic acid comprises a nucleic acid sequence encoding a CAR or an exogenous TCR and a nucleic acid sequence encoding an HLA-E fusion protein, wherein the CAR or the exogenous TCR and the HLA-E fusion protein are expressed by the immune cell. In some embodiments of the method, the nucleic acid sequence encoding the shRNAmiR, the nucleic acid sequence encoding the CAR or the exogenous TCR, and the nucleic acid sequence encoding the HLA-E fusion protein are operably linked to a same promoter following introduction of the template nucleic acid at the cleavage site. In some such embodiments of the method, the template nucleic acid comprises: (a) the nucleic acid sequence encoding the CAR or the exogenous TCR; (b) a 2A or IRES sequence; (c) the nucleic acid sequence encoding the HLA-E fusion protein; and (d) the nucleic acid sequence encoding the shRNAmiR. In certain such embodiments of the method, an intron sequence is positioned within the nucleic acid sequence encoding the HLA-E fusion protein, and wherein the nucleic acid sequence encoding the shRNAmiR is positioned within the intron sequence. In other such embodiments of the method, an intron sequence is positioned within the nucleic acid sequence encoding the CAR or the exogenous TCR, and wherein the nucleic acid sequence encoding the shRNAmiR is positioned within the intron sequence. In some such embodiments of the method, the template nucleic acid comprises a promoter that is operably linked to the nucleic acid sequence encoding the CAR or the exogenous TCR, the nucleic acid sequence encoding the HLA-E fusion protein, and the nucleic acid sequence encoding the shRNAmiR. In certain such embodiments of the method, the template nucleic acid comprises a termination signal.

In some such embodiments of the method, the template nucleic acid comprises, from 5' to 3': (a) a promoter; (b) the nucleic acid sequence encoding the CAR or the exogenous TCR; (c) a 2A or IRES sequence; (d) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments of the method, the template nucleic acid comprises, from 5' to 3': (a) a promoter; (b) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; (c) a 2A or IRES sequence; (d) the nucleic acid sequence encoding the CAR or the exogenous TCR; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments of the method, the template nucleic acid comprises, from 5' to 3': (a) a promoter; (b) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; (c) a 2A or IRES sequence; (d) the nucleic acid sequence encoding the HLA-E fusion protein; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some such embodiments of the method, the template nucleic acid comprises, from 5' to 3': (a) a promoter; (b) the nucleic acid sequence encoding the HLA-E fusion protein; (c) a 2A or IRES sequence; (d) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; and (e) optionally a termination signal; wherein the nucleic acid sequence encoding the CAR or the exogenous TCR, the nucleic acid sequence encoding the HLA-E fusion protein, and the nucleic acid sequence encoding the shRNAmiR are operably linked to the promoter.

In some embodiments of the method described above, the intron sequence is a synthetic intron sequence. In certain embodiments of the method, the intron sequence comprises a nucleic acid sequence having at least 80%, at least 85%, at least 90%, at least 95%, or more, sequence identity to SEQ ID NO: 69. In particular embodiments of the method, the intron sequence comprises a nucleic acid sequence of SEQ ID NO: 69.

In some embodiments of the method described above, the termination signal is a polyA sequence or a bovine growth hormone (BGH) termination signal. In certain embodiments of the method, the polyA sequence comprises a nucleic acid sequence having at least 80%, at least 85%, at least 90%, at least 95%, or more, sequence identity to SEQ ID NO: 68. In particular embodiments of the method, the polyA sequence comprises a nucleic acid sequence of SEQ ID NO: 68. In certain embodiments of the method, the BGH termination signal comprises a nucleic acid sequence having at least 80%, at least 85%, at least 90%, at least 95%, or more, sequence identity to SEQ ID NO: 71. In particular embodiments of the method, the BGH termination signal comprises a nucleic acid sequence of SEQ ID NO: 71.

In certain embodiments of the method described above, the promoter comprises a nucleic acid sequence having at least 80%, at least 85%, at least 90%, at least 95%, or more, sequence identity to SEQ ID NO: 67. In particular embodiments of the method, the promoter comprises a nucleic acid sequence of SEQ ID NO: 67.

In certain embodiments of the method described above, the 2A sequence is a P2A/furin site comprising a nucleic acid sequence having at least 80%, at least 85%, at least 90%, at least 95%, or more, sequence identity to SEQ ID NO: 70. In particular embodiments of the method, the 2A sequence is a P2A/furin site comprising a nucleic acid sequence of SEQ ID NO: 70.

In certain embodiments of the method described above, the HLA-E fusion protein comprises an amino acid sequence having at least 80%, at least 85%, at least 90%, at least 95%, or more, sequence identity to SEQ ID NO: 66. In particular embodiments of the method, the HLA-E fusion protein comprises an amino acid sequence of SEQ ID NO: 66.

In certain embodiments of the method described above, the CAR comprises a signal peptide comprising an amino acid sequence having at least 80%, at least 85%, at least 90%, at least 95%, or more, sequence identity to SEQ ID NO: 73. In particular embodiments of the method, the CAR comprises a signal peptide comprising an amino acid sequence of SEQ ID NO: 73.

In particular embodiments of the method, the template nucleic acid comprises, from 5' to 3': (a) a promoter comprising a nucleic acid sequence having at least 80%, at least 85%, at least 90%, at least 95%, or more, sequence identity to SEQ ID NO: 67; (b) the nucleic acid sequence encoding the CAR, wherein the CAR comprises a signal peptide comprising an amino acid sequence having at least 80%, at least 85%, at least 90%, at least 95%, or more, sequence identity to SEQ ID NO: 73; (c) a P2A/furin site comprising a nucleic acid sequence having at least 80%, at least 85%, at least 90%, at least 95%, or more, sequence identity to SEQ ID NO: 70; (d) the nucleic acid sequence encoding the HLA-E fusion protein, wherein the HLA-E fusion protein comprises an amino acid sequence having at least 80%, at least 85%, at least 90%, at least 95%, or more, sequence identity to SEQ ID NO: 66, and wherein an intron sequence is positioned within the nucleic acid sequence encoding the HLA-E fusion protein, wherein the intron sequence comprises a nucleic acid sequence having at least 80%, at least 85%, at least 90%, at least 95%, or more, sequence identity to SEQ ID NO: 69, and wherein the nucleic acid sequence encoding the shRNAmiR is positioned within the intron sequence; and (e) optionally a termination signal comprising a nucleic acid sequence having at least 80%, at least 85%, at least 90%, at least 95%, or more, sequence identity to SEQ ID NO: 68; wherein the nucleic acid sequence encoding the CAR, the nucleic acid sequence encoding the HLA-E fusion protein, and the nucleic acid sequence encoding the shRNAmiR are operably linked to the promoter.

In particular embodiments of the method, the template nucleic acid comprises, from 5' to 3': (a) a promoter comprising a nucleic acid sequence of SEQ ID NO: 67; (b) the nucleic acid sequence encoding the CAR, wherein the CAR comprises a signal peptide comprising an amino acid sequence of SEQ ID NO: 73; (c) a P2A/furin site comprising a nucleic acid sequence of SEQ ID NO: 70; (d) the nucleic acid sequence encoding the HLA-E fusion protein, wherein the HLA-E fusion protein comprises an amino acid sequence of SEQ ID NO: 66, and wherein an intron sequence is positioned within the nucleic acid sequence encoding the HLA-E fusion protein, wherein the intron sequence comprises a nucleic acid sequence of SEQ ID NO: 69, and wherein the nucleic acid sequence encoding the shRNAmiR is positioned within the intron sequence; and (e) optionally a termination signal comprising a nucleic acid sequence of SEQ ID NO: 68; wherein the nucleic acid sequence encoding the CAR, the nucleic acid sequence encoding the HLA-E fusion protein, and the nucleic acid sequence encoding the shRNAmiR are operably linked to the promoter.

In particular embodiments of the method, the template nucleic acid comprises a nucleic acid sequence having at least 80%, at least 85%, at least 90%, at least 95%, or more, sequence identity to SEQ ID NO: 74, wherein the template nucleic acid is inserted in the genome within a TCR alpha constant region gene. In particular embodiments of the method, the template nucleic acid comprises a nucleic acid sequence of SEQ ID NO: 74, wherein the template nucleic acid is inserted in the genome within a TCR alpha constant region gene.

In some embodiments of the method described above, the template nucleic acid comprises two or more nucleic acids encoding shRNAmiRs. In certain embodiments of the method, the two or more nucleic acids can encode the same shRNAmiR. In some embodiments of the method, the two or more nucleic acids can encode different shRNAmiRs that reduce the expression of the same target protein. In other embodiments of the method, the two or more nucleic acids encode different shRNAmiRs that reduce the expression of different target proteins. In certain embodiments of the method, the template nucleic acid can comprise two or more nucleic acids encoding different shRNAmiRs described herein. In particular embodiments of the method, the template nucleic acid can comprise a nucleic acid sequence encoding a shRNAmiR that reduces the expression of B2M, and a nucleic acid sequence encoding a shRNAmiR that reduces the expression of CD52.

In some embodiments of the method, the nucleic acid sequence encoding the shRNAmiR and the nucleic acid sequence encoding the CAR or the exogenous TCR are operably linked to different promoters in the immune cell following introduction of the template nucleic acid at the cleavage site. In some such embodiments of the method, the template nucleic acid comprises, from 5' to 3': (a) a first promoter; (b) the nucleic acid sequence encoding the CAR or exogenous TCR which is operably linked to the first promoter; (c) a second promoter; and (d) the nucleic acid sequence encoding the shRNAmiR which is operably linked to the second promoter. In other such embodiments of the method, the template nucleic acid comprises, from 5' to 3': (a) a first promoter; (b) the nucleic acid sequence encoding the shRNAmiR which is operably linked to the first promoter; (c) a second promoter; and (d) the nucleic acid sequence encoding the CAR or exogenous TCR which is operably linked to the second promoter. In certain such embodiments of the method, the nucleic acid sequence encoding the shRNAmiR is in the same orientation as the nucleic acid sequence encoding the CAR or exogenous TCR. In other such embodiments of the method, the nucleic acid sequence encoding the shRNAmiR is in a reverse orientation as the nucleic acid sequence encoding the CAR or exogenous TCR. In particular such embodiments of the method, the first promoter and the second promoter are identical. In other such embodiments of the method, the first promoter and the second promoter are different. In some such embodiments of the method, the template nucleic acid comprises one or more termination signals.

In some embodiments of the method, the nucleic acid sequence encoding the shRNAmiR and the nucleic acid sequence encoding the HLA-E fusion protein are operably linked to different promoters in the immune cell following introduction of the template nucleic acid at the cleavage site. In certain such embodiments of the method, the template nucleic acid comprises, from 5' to 3': (a) a first promoter; (b) the nucleic acid sequence encoding the HLA-E fusion protein which is operably linked to the first promoter; (c) a second promoter; and (d) the nucleic acid sequence encoding the shRNAmiR which is operably linked to the second promoter. In some such embodiments of the method, the template nucleic acid comprises, from 5' to 3': (a) a first promoter; (b) the nucleic acid sequence encoding the shRNAmiR which is operably linked to the first promoter; (c) a second promoter; and (d) the nucleic acid sequence encoding the HLA-E fusion protein which is operably linked to the second promoter. In certain such embodiments of the method, the first promoter and the second promoter are identical. In other such embodiments of the method, the first promoter and the second promoter are different. In some such embodiments of the method, the template nucleic acid comprises one or more termination signals.

In some embodiments of the method, the template nucleic acid comprises: (a) the nucleic acid sequence encoding the CAR or the exogenous TCR; (b) the nucleic acid sequence encoding the HLA-E fusion protein; and (c) the nucleic acid sequence encoding the shRNAmiR; wherein the nucleic acid sequence encoding the CAR or the exogenous TCR is operably linked to a first promoter, and wherein the nucleic acid sequence encoding the HLA-E fusion protein and the nucleic acid sequence encoding the shRNAmiR are operably linked to a second promoter. In some embodiments of the method, an intron sequence is positioned within the nucleic acid sequence encoding the HLA-E fusion protein, wherein the nucleic acid sequence encoding the shRNAmiR is positioned within the intron sequence. In some embodiments of the method, the template nucleic acid comprises: (a) the nucleic acid sequence encoding the CAR or the exogenous TCR; (b) the nucleic acid sequence encoding the HLA-E fusion protein; and (c) the nucleic acid sequence encoding the shRNAmiR; wherein the nucleic acid sequence encoding the CAR or the exogenous TCR and the nucleic acid sequence encoding the shRNAmiR are operably linked to a first promoter, and wherein the nucleic acid sequence encoding the HLA-E fusion protein is operably linked to a second promoter. In some embodiments of the method, an intron sequence is positioned within the nucleic acid sequence encoding the CAR or the exogenous TCR, wherein the nucleic acid sequence encoding the shRNAmiR is positioned within the intron sequence.

In some such embodiments of the method, the template nucleic acid comprises a first termination signal capable of terminating transcription of the CAR or the exogenous TCR, and a second termination signal capable of terminating transcription of the HLA-E fusion protein. In some such embodiments of the method, the template nucleic acid comprises a first termination signal capable of terminating transcription of the HLA-E fusion protein, and a second termination signal capable of terminating transcription of the CAR or the exogenous TCR.

In some such embodiments of the method, the template nucleic acid comprises, from 5' to 3': (a) a first promoter; (b) the nucleic acid sequence encoding the CAR or the exogenous TCR; (c) optionally a first termination signal; (d) a second promoter; (e) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; and (f) optionally a second termination signal; wherein the nucleic acid sequence encoding the CAR or the exogenous TCR is operably linked to the first promoter, and wherein the nucleic acid sequence encoding the HLA-E fusion protein and the nucleic acid sequence encoding the shRNAmiR are operably linked to the second promoter.

In some such embodiments of the method, the template nucleic acid comprises, from 5' to 3': (a) a first promoter; (b) the nucleic acid sequence encoding the HLA-E fusion protein, wherein an intron sequence is positioned within the nucleic acid sequence encoding the HLA-E fusion protein, and wherein the nucleic acid sequence encoding the shRNAmiR is positioned within the intron sequence; (c) optionally a first termination signal; (d) a second promoter; (e) the nucleic acid sequence encoding the CAR or the exogenous TCR; and (f) optionally a second termination signal; wherein the nucleic acid sequence encoding the HLA-E fusion protein and the nucleic acid sequence encoding the shRNAmiR are operably linked to the first promoter, and wherein the nucleic acid sequence encoding the CAR or the exogenous TCR is operably linked to the second promoter.

In some such embodiments of the method, the template nucleic acid comprises, from 5' to 3': (a) a first promoter; (b) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; (c) optionally a first termination signal; (d) a second promoter; (e) the nucleic acid sequence encoding the HLA-E fusion protein; and (f) optionally a second termination signal; wherein the nucleic acid sequence encoding the CAR or the exogenous TCR and the nucleic acid sequence encoding the shRNAmiR are operably linked to the first promoter, and wherein the nucleic acid sequence encoding the HLA-E fusion protein is operably linked to the second promoter.

In some such embodiments of the method, the template nucleic acid comprises, from 5' to 3': (a) a first promoter; (b) the nucleic acid sequence encoding the HLA-E fusion protein; (c) optionally a first termination signal; (d) a second promoter; (e) the nucleic acid sequence encoding the CAR or the exogenous TCR, wherein an intron sequence is positioned within the nucleic acid sequence encoding the CAR or the exogenous TCR, and wherein the nucleic acid sequence encoding the shRNAmiR is positioned within the intron sequence; and (f) optionally a second termination signal; wherein the nucleic acid sequence encoding the HLA-E fusion protein is operably linked to the first promoter, and wherein the nucleic acid sequence encoding the CAR or the exogenous TCR and the nucleic acid sequence encoding the shRNAmiR are operably linked to the second promoter.

In some embodiments of the method described above, the intron sequence is a synthetic intron sequence. In certain embodiments of the method, the intron sequence comprises a nucleic acid sequence having at least 80%, at least 85%, at least 90%, at least 95%, or more, sequence identity to SEQ ID NO: 69. In particular embodiments of the method, the intron sequence comprises a nucleic acid sequence of SEQ ID NO: 69.

In some embodiments of the method described above, the one or more termination signals are a polyA sequence or a BGH termination signal.

In some embodiments of the method described above, the first termination signal is identical to the second termination signal. In other embodiments of the method, the first termination signal is different from the second termination signal. In certain embodiments of the method, the first termination signal is a polyA sequence and the second termination signal is a BGH termination signal. In certain embodiments of the method, the first termination signal is a BGH termination signal and the second termination signal is a polyA sequence.

In certain embodiments of the method described above, the polyA sequence comprises a nucleic acid sequence having at least 80%, at least 85%, at least 90%, at least 95%, or more, sequence identity to SEQ ID NO: 68. In particular embodiments of the method, the polyA sequence comprises a nucleic acid sequence of SEQ ID NO: 68. In certain embodiments of the method, the BGH termination signal comprises a nucleic acid sequence having at least 80%, at least 85%, at least 90%, at least 95%, or more, sequence identity to SEQ ID NO: 71. In particular embodiments of the method, the BGH termination signal comprises a nucleic acid sequence of SEQ ID NO: 71.

In some embodiments of the method described above, the first promoter and the second promoter are identical. In other embodiments of the method, the first promoter is different from the second promoter. In certain embodiments of the method, the first promoter is a JeT promoter, and the second promoter is an EF1 alpha core promoter. In certain embodiments of the method, the first promoter is an EF1 alpha core promoter, and the second promoter is a JeT promoter.

In certain embodiments of the method described above, the JeT promoter comprises a nucleic acid sequence having at least 80%, at least 85%, at least 90%, at least 95%, or more, sequence identity to SEQ ID NO: 67. In particular embodiments of the method, the JeT promoter comprises a nucleic acid sequence of SEQ ID NO: 67. In certain embodiments of the method, the EF1 alpha core promoter comprises a nucleic acid sequence having at least 80%, at least 85%, at least 90%, at least 95%, or more, sequence identity to SEQ ID NO: 72. In particular embodiments, the EF1 alpha core promoter comprises a nucleic acid sequence of SEQ ID NO: 72.

In some embodiments of the method described above, the HLA-E fusion protein comprises an amino acid sequence having at least 80%, at least 85%, at least 90%, at least 95%, or more, sequence identity to SEQ ID NO: 66. In particular embodiments of the method, the HLA-E fusion protein comprises an amino acid sequence of SEQ ID NO: 66.

In some embodiments of the method described above, the CAR comprises a signal peptide comprising an amino acid sequence having at least 80%, at least 85%, at least 90%, at least 95%, or more, sequence identity to SEQ ID NO: 73. In particular embodiments of the method, the CAR comprises a signal peptide comprising an amino acid sequence of SEQ ID NO: 73.

In particular embodiments of the method, the template nucleic acid comprises, from 5' to 3': (a) a first promoter comprising a nucleic acid sequence having at least 80%, at least 85%, at least 90%, at least 95%, or more, sequence identity to SEQ ID NO: 67; (b) the nucleic acid sequence encoding the CAR, wherein the CAR comprises a signal peptide comprising an amino acid sequence having at least 80%, at least 85%, at least 90%, at least 95%, or more, sequence identity to SEQ ID NO: 73; (c) optionally a first termination signal comprising a nucleic acid sequence having at least 80%, at least 85%, at least 90%, at least 95%, or more, sequence identity to SEQ ID NO: 70; (d) a second promoter comprising a nucleic acid sequence having at least 80%, at least 85%, at least 90%, at least 95%, or more, sequence identity to SEQ ID NO: 72; (e) the nucleic acid sequence encoding the HLA-E fusion protein, wherein the HLA-E fusion protein comprises an amino acid sequence having at least 80%, at least 85%, at least 90%, at least 95%, or more, sequence identity to SEQ ID NO: 66, and wherein an intron sequence is positioned within the nucleic acid sequence encoding the HLA-E fusion protein, wherein the intron sequence comprises a nucleic acid sequence having at least 80%, at least 85%, at least 90%, at least 95%, or more, sequence identity to SEQ ID NO: 69, and wherein the nucleic acid sequence encoding the shRNAmiR is positioned within the intron sequence; and (f) optionally a second termination signal comprising a nucleic acid sequence having at least 80%, at least 85%, at least 90%, at least 95%, or more, sequence identity to SEQ ID NO: 71; wherein the nucleic acid sequence encoding the CAR is operably linked to the first promoter, and wherein the nucleic acid sequence encoding the HLA-E fusion protein and the nucleic acid sequence encoding the shRNAmiR are operably linked to the second promoter.

In particular embodiments of the method, the template nucleic acid comprises, from 5' to 3': (a) a first promoter comprising a nucleic acid sequence of SEQ ID NO: 67; (b) the nucleic acid sequence encoding the CAR, wherein the CAR comprises a signal peptide comprising an amino acid sequence of SEQ ID NO: 73; (c) optionally a first termination signal comprising a nucleic acid sequence of SEQ ID NO: 70; (d) a second promoter comprising a nucleic acid sequence of SEQ ID NO: 72; (e) the nucleic acid sequence encoding the HLA-E fusion protein, wherein the HLA-E fusion protein comprises an amino acid sequence of SEQ ID NO: 66, and wherein an intron sequence is positioned within the nucleic acid sequence encoding the HLA-E fusion protein, wherein the intron sequence comprises a nucleic acid sequence of SEQ ID NO: 69, and wherein the nucleic acid sequence encoding the shRNAmiR is positioned within the intron sequence; and (f) optionally a second termination signal comprising a nucleic acid sequence of SEQ ID NO: 71; wherein the nucleic acid sequence encoding the CAR is operably linked to the first promoter, and wherein the nucleic acid sequence encoding the HLA-E fusion protein and the nucleic acid sequence encoding the shRNAmiR are operably linked to the second promoter.

In particular embodiments of the method, the template nucleic acid comprises a nucleic acid sequence having at least 80%, at least 85%, at least 90%, at least 95%, or more, sequence identity to SEQ ID NO: 75, wherein the cassette is inserted in the genome within a TCR alpha constant region gene. In particular embodiments of the method, the template nucleic acid comprises a nucleic acid sequence of SEQ ID NO: 75, wherein the cassette is inserted in the genome within a TCR alpha constant region gene.

In some embodiments of the method described above, the template nucleic acid comprises two or more nucleic acids encoding shRNAmiRs. In certain embodiments of the method, the two or more nucleic acids can encode the same shRNAmiR. In some embodiments of the method, the two or more nucleic acids can encode different shRNAmiRs that reduce the expression of the same target protein. In other embodiments of the method, the two or more nucleic acids encode different shRNAmiRs that reduce the expression of different target proteins. In certain embodiments of the method, the template nucleic acid can comprise two or more nucleic acids encoding different shRNAmiRs described herein. In particular embodiments of the method, the template nucleic acid can comprise a nucleic acid sequence encoding a shRNAmiR that reduces the expression of B2M, and a nucleic acid sequence encoding a shRNAmiR that reduces the expression of CD52.

In some embodiments of the method, the shRNAmiR comprises, from 5' to 3': (a) a 5' miR scaffold domain; (b) a 5' miR basal stem domain; (c) a passenger strand; (d) a miR loop domain; (e) a guide strand; (f) a 3' miR basal stem domain; and (g) a 3' miR scaffold domain.

In some embodiments of the method, the miR loop domain is a miR-30a loop domain, a miR-15 loop domain, a miR-16 loop domain, a miR-155 loop domain, a miR-22 loop domain, a miR-103 loop domain, or a miR-107 loop domain. In particular embodiments of the method, the miR loop domain is a miR-30a loop domain.

In certain embodiments of the method, the miR-30a loop domain comprises a nucleic acid sequence having at least 80%, at least 85%, at least 90%, at least 95%, or more, sequence identity to SEQ ID NO: 3. In particular embodiments of the method, the miR-30a loop domain comprises a nucleic acid sequence of SEQ ID NO: 3.

In some embodiments of the method, the shRNAmiR comprises a microRNA-E (miR-E) scaffold, a miR-30 (e.g., miR-30a) scaffold, a miR-15 scaffold, a miR-16 scaffold, a miR-155 scaffold, a miR-22 scaffold, a miR-103 scaffold, or a miR-107 scaffold. In certain embodiments of the method, the shRNAmiR comprises a miR-E scaffold.

In some embodiments of the method, the shRNAmiR comprises a structure wherein: (a) the 5' miR scaffold domain comprises a nucleic acid sequence having at least 80%, at least 85%, at least 90%, at least 95%, or more, sequence identity to SEQ ID NO: 1; (b) the 5' miR basal stem domain comprises a nucleic acid sequence having at least 80%, at least 85%, at least 90%, at least 95%, or more, sequence identity to SEQ ID NO: 2; (c) the 3' miR basal stem domain comprises a nucleic acid sequence having at least 80%, at least 85%, at least 90%, at least 95%, or more, sequence identity to SEQ ID NO: 4; and/or (d) the 3' miR scaffold domain comprises a nucleic acid sequence having at least 80%, at least 85%, at least 90%, at least 95%, or more, sequence identity to SEQ ID NO: 5.

In certain embodiments of the method, the shRNAmiR comprises a structure wherein: (a) the 5' miR scaffold domain comprises a nucleic acid sequence of SEQ ID NO: 1; (b) the 5' miR basal stem domain comprises a nucleic acid sequence of SEQ ID NO: 2; (c) the 3' miR basal stem domain comprises a nucleic acid sequence of SEQ ID NO:

4; and (d) the 3' miR scaffold domain comprises a nucleic acid sequence of SEQ ID NO: 5.

In some embodiments of the method, expression of the target protein is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell.

In some embodiments of the method, the target protein is beta-2 microglobulin, CS1, transforming growth factor-beta receptor 2 (TGFBR2), Cbl proto-oncogene B (CBL-B), CD52, a TCR alpha gene, a TCR alpha constant region gene, CD7, glucocorticoid receptor (GR), deoxycytidine kinase (DCK), nuclear receptor subfamily 2 group F member 6 (NR2F6), cytotoxic T-lymphocyte-associated protein 4 (CTLA-4), or C—C chemokine receptor type 5 (CCR5).

In some embodiments of the method, the target protein is beta-2 microglobulin. In some such embodiments of the method, cell surface expression of beta-2 microglobulin is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments of the method, expression of MHC class I molecules is reduced on the cell surface by at least about 10%, about 20%, about 30%, about 40%, about 50%, about 55%, about 60%, about 65%, about 70%, about 75%, about 80%, about 85%, about 90%, about 95%, or up to about 99% compared to a control cell. In some such embodiments of the method, the immune cell has reduced allogenicity compared to a control cell.

In some such embodiments of the method, the shRNAmiR has a structure wherein: (a) the passenger strand comprises a nucleic acid sequence of SEQ ID NO: 17 and the guide strand comprises a nucleic acid sequence of SEQ ID NO: 18; (b) the passenger strand comprises a nucleic acid sequence of SEQ ID NO: 7 and the guide strand comprises a nucleic acid sequence of SEQ ID NO: 8; (c) the passenger strand comprises a nucleic acid sequence of SEQ ID NO: 9 and the guide strand comprises a nucleic acid sequence of SEQ ID NO: 10; (d) the passenger strand comprises a nucleic acid sequence of SEQ ID NO: 11 and the guide strand comprises a nucleic acid sequence of SEQ ID NO: 12; (e) the passenger strand comprises a nucleic acid sequence of SEQ ID NO: 13 and the guide strand comprises a nucleic acid sequence of SEQ ID NO: 14; or (f) the passenger strand comprises a nucleic acid sequence of SEQ ID NO: 15 and the guide strand comprises a nucleic acid sequence of SEQ ID NO: 16. In certain such embodiments of the method, the passenger strand comprises a nucleic acid sequence of SEQ ID NO: 17 and the guide strand comprises a nucleic acid sequence of SEQ ID NO: 18. In particular such embodiments of the method, the nucleic acid sequence encoding the shRNAmiR comprises a sequence having at least 80%, at least 85%, at least 90%, at least 95%, or more, sequence identity to SEQ ID NO: 46. In further such embodiments of the method, the nucleic acid sequence encoding the shRNAmiR comprises the sequence of SEQ ID NO: 46.

In some embodiments of the method, the target protein is CS1. In some such embodiments of the method, cell surface expression of CS1 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In some such embodiments of the method, the immune cell expresses a CAR having specificity for CS1. In further such embodiments of the method, the immune cell is less susceptible to fratricide by a immune cell expressing a CAR having specificity for CS1 compared to a control cell.

In some such embodiments of the method, the shRNAmiR has a structure wherein: (a) the passenger strand comprises a nucleic acid sequence of SEQ ID NO: 21 and the guide strand comprises a nucleic acid sequence of SEQ ID NO: 22; (b) the passenger strand comprises a nucleic acid sequence of SEQ ID NO: 23 and the guide strand comprises a nucleic acid sequence of SEQ ID NO: 24; or (c) the passenger strand comprises a nucleic acid sequence of SEQ ID NO: 25 and the guide strand comprises a nucleic acid sequence of SEQ ID NO: 26. In certain such embodiments of the method, the passenger strand comprises a nucleic acid sequence of SEQ ID NO: 25 and the guide strand comprises a nucleic acid sequence of SEQ ID NO: 26. In particular such embodiments of the method, the shRNAmiR comprises a sequence having at least 80%, at least 85%, at least 90%, at least 95%, or more, sequence identity to SEQ ID NO: 50. In further such embodiments of the method, the shRNAmiR comprises the sequence of SEQ ID NO: 50.

In some embodiments of the method, the target protein is TGFBR2. In some such embodiments of the method, the cell surface expression of TGFBR2 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments of the method, the immune cell is less susceptible to immunosuppression by transforming growth factor B1 (TGFB1) compared to a control cell.

In some such embodiments of the method, the shRNAmiR has a structure wherein: (a) the passenger strand comprises a nucleic acid sequence of SEQ ID NO: 27 and the guide strand comprises a nucleic acid sequence of SEQ ID NO: 28; (b) the passenger strand comprises a nucleic acid sequence of SEQ ID NO: 29 and the guide strand comprises a nucleic acid sequence of SEQ ID NO: 30; (c) the passenger strand comprises a nucleic acid sequence of SEQ ID NO: 31 and the guide strand comprises a nucleic acid sequence of SEQ ID NO: 32; (d) the passenger strand comprises a nucleic acid sequence of SEQ ID NO: 33 and the guide strand comprises a nucleic acid sequence of SEQ ID NO: 34; or (e) the passenger strand comprises a nucleic acid sequence of SEQ ID NO: 35 and the guide strand comprises a nucleic acid sequence of SEQ ID NO: 36. In certain such embodiments of the method, the passenger strand comprises a nucleic acid sequence of SEQ ID NO: 31 and the guide strand comprises a nucleic acid sequence of SEQ ID NO: 32. In particular such embodiments of the method, the nucleic acid sequence encoding the shRNAmiR comprises a sequence having at least 80%, at least 95%, at least 90%, at least 95%, or more, sequence identity to SEQ ID NO: 53. In further such embodiments of the method, the nucleic acid sequence encoding the shRNAmiR comprises the sequence of SEQ ID NO: 53.

In some embodiments of the method, the target protein is CBL-B. In some such embodiments of the method, cell surface expression of CBL-B is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments of the method, the immune cell is less susceptible to suppression of T cell receptor (TCR) signaling by degradation of downstream signaling proteins compared to a control cell.

In some embodiments of the method, the target protein is CD52. In some such embodiments of the method, cell surface expression of CD52 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments of the method, the immune cell is less susceptible to CD52 antibody-induced cell death.

In some such embodiments of the method, the shRNAmiR has a structure wherein: (a) the passenger strand comprises a nucleic acid sequence of SEQ ID NO: 37 and the guide strand comprises a nucleic acid sequence of SEQ ID NO: 38; or (b) the passenger strand comprises a nucleic acid sequence of SEQ ID NO: 39 and the guide strand comprises a nucleic acid sequence of SEQ ID NO: 40. In certain such embodiments of the method, the passenger strand comprises a nucleic acid sequence of SEQ ID NO: 37 and the guide strand comprises a nucleic acid sequence of SEQ ID NO: 38. In particular such embodiments of the method, the nucleic acid sequence encoding the shRNAmiR comprises a sequence having at least 80%, at least 85%, at least 90%, at least 95%, or more, sequence identity to SEQ ID NO: 56. In further such embodiments of the method, the nucleic acid sequence encoding the shRNAmiR comprises the sequence of SEQ ID NO: 56.

In some embodiments of the method, the target protein is DCK. In some such embodiments, cell surface expression of DCK is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments of the method, the immune cell is less susceptible to effects of purine nucleoside analogs (e.g., fludarabine) on cell proliferation.

In some such embodiments of the method, the shRNAmiR has a structure wherein: (a) the passenger strand comprises a nucleic acid sequence of SEQ ID NO: 76 and the guide strand comprises a nucleic acid sequence of SEQ ID NO: 77; (b) the passenger strand comprises a nucleic acid sequence of SEQ ID NO: 78 and the guide strand comprises a nucleic acid sequence of SEQ ID NO: 79; (c) the passenger strand comprises a nucleic acid sequence of SEQ ID NO: 80 and the guide strand comprises a nucleic acid sequence of SEQ ID NO: 81; (d) the passenger strand comprises a nucleic acid sequence of SEQ ID NO: 82 and the guide strand comprises a nucleic acid sequence of SEQ ID NO: 83; or (e) the passenger strand comprises a nucleic acid sequence of SEQ ID NO: 84 and the guide strand comprises a nucleic acid sequence of SEQ ID NO: 85. In particular such embodiments of the method, the passenger strand comprises a nucleic acid sequence of SEQ ID NO: 76 and the guide strand comprises a nucleic acid sequence of SEQ ID NO: 77. In particular such embodiments of the method, the nucleic acid sequence encoding the shRNAmiR comprises a sequence having at least 80%, at least 85%, at least 90%, at least 95%, or more, sequence identity to SEQ ID NO: 86. In further such embodiments of the method, the nucleic acid sequence encoding the shRNAmiR comprises the sequence of SEQ ID NO: 86.

In some embodiments of the method, the target protein is GR. In some such embodiments of the method, cell surface expression of GR is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell. In further such embodiments, the immune cell is less susceptible to effects of glucocorticoids (e.g., dexamethasone), such as reduced proliferation.

In some such embodiments of the method, the shRNAmiR has a structure wherein: (a) the passenger strand comprises a nucleic acid sequence of SEQ ID NO: 91 and the guide strand comprises a nucleic acid sequence of SEQ ID NO: 92; (b) the passenger strand comprises a nucleic acid sequence of SEQ ID NO: 93 and the guide strand comprises a nucleic acid sequence of SEQ ID NO: 94; (c) the passenger strand comprises a nucleic acid sequence of SEQ ID NO: 95 and the guide strand comprises a nucleic acid sequence of SEQ ID NO: 96; (d) the passenger strand comprises a nucleic acid sequence of SEQ ID NO: 97 and the guide strand comprises a nucleic acid sequence of SEQ ID NO: 98; (e) the passenger strand comprises a nucleic acid sequence of SEQ ID NO: 99 and the guide strand comprises a nucleic acid sequence of SEQ ID NO: 100; (f) the passenger strand comprises a nucleic acid sequence of SEQ ID NO: 101 and the guide strand comprises a nucleic acid sequence of SEQ ID NO: 102; (g) the passenger strand comprises a nucleic acid sequence of SEQ ID NO: 103 and the guide strand comprises a nucleic acid sequence of SEQ ID NO: 104; (h) the passenger strand comprises a nucleic acid sequence of SEQ ID NO: 105 and the guide strand comprises a nucleic acid sequence of SEQ ID NO: 106; or (i) the passenger strand comprises a nucleic acid sequence of SEQ ID NO: 107 and the guide strand comprises a nucleic acid sequence of SEQ ID NO: 108. In particular such embodiments of the method, the passenger strand comprises a nucleic acid sequence of SEQ ID NO: 95 and the guide strand comprises a nucleic acid sequence of SEQ ID NO: 96. In particular such embodiments of the method, the nucleic acid sequence encoding the shRNAmiR comprises a sequence having at least 80%, at least 85%, at least 90%, at least 95%, or more, sequence identity to SEQ ID NO: 111. In further such embodiments of the method, the nucleic acid sequence encoding the shRNAmiR comprises the sequence of SEQ ID NO: 111.

In another aspect, the invention provides an immune cell made by any of the methods described herein. In some embodiments, the target protein is beta-2 microglobulin and the immune cell made by the method has reduced cell-surface expression of beta-2 microglobulin and/or MHC class I proteins. In some embodiments, the target protein is CS1 and the immune cell made by the method has reduced cell-surface expression of CS1. In some embodiments, the target protein is TGFRB2, and the immune cell made by the method has reduced expression of TGFBR2. In some embodiments, the target protein is CBL-B, and the immune cell made by the method has reduced expression of CBL-B. In some embodiments, the target protein is CD52, and the immune cell made by the method has reduced cell-surface expression of CD52. In some embodiments, the target protein is DCK, and the immune cell made by the method has reduced expression of DCK. In some embodiments, the target protein is GR, and the immune cell made by the method has reduced expression of GR.

In another aspect, the invention provides a population of cells comprising a plurality of the genetically-modified immune cells, or a plurality of the immune cells, described herein. In some embodiments, at least about 20%, about 30%, about 40%, about 50%, about 55%, about 60%, about 65%, about 70%, about 75%, about 80%, about 85%, about 90%, about 95%, or up to 100% of cells in the population are the genetically-modified immune cells described herein, or the immune cells described herein.

In another aspect, the invention provides a pharmaceutical composition comprising a pharmaceutically-acceptable carrier and a plurality of genetically-modified immune cells described herein, or a plurality of the immune cells described herein. In some embodiments, the pharmaceutical composition comprises a population of cells described herein.

In another aspect, the invention provides a method of immunotherapy for treating a disease in a subject in need thereof, the method comprising administering to the subject an effective amount of a pharmaceutical composition described herein. In some embodiments, the method is an immunotherapy for the treatment of a cancer in a subject in need thereof, wherein the genetically-modified immune cell, or immune cell, is a genetically-modified human T cell, or a cell derived therefrom, or a genetically-modified NK cell, or a cell derived therefrom, and wherein the genetically-modified immune cell, or immune cell, comprises a CAR or exogenous TCR, wherein the CAR or the exogenous TCR comprises an extracellular ligand-binding domain having specificity for a tumor-specific antigen. In some embodiments of the method, the genetically-modified immune cell or the immune cell comprises an inactivated TCR alpha gene or an inactivated TCR alpha constant region gene. In further embodiments of the method, the genetically-modified immune cell, or the immune cell, has no detectable cell-surface expression of an endogenous TCR (e.g., an alpha/beta TCR). In some embodiments of the method, the cancer is selected from the group consisting of a cancer of carcinoma, lymphoma, sarcoma, blastomas, and leukemia. In certain embodiments of the method, the cancer is selected from the group consisting of a cancer of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin lymphoma. In particular embodiments of the method, the cancer of B cell origin is selected from the group consisting of B-lineage acute lymphoblastic leukemia, B cell chronic lymphocytic leukemia, B cell non-Hodgkin lymphoma, and multiple myeloma.

In particular embodiments of the method, the subject can be a mammal, such as a human.

In another aspect, the invention provides a method for treating a disease, such as cancer, in a subject in need thereof, wherein the method comprises administering to the subject a therapeutically effective amount of a population of any genetically-modified immune cells described herein (e.g., a genetically-modified human T cell or NK cell expressing a CAR or exogenous TCR) that comprise in their genome a nucleic acid sequence encoding a shRNAmiR that reduces the expression of endogenous deoxycytidine kinase (DCK), wherein the population of genetically-modified immune cells is administered to the subject before, during, or after administration of a purine nucleoside. Reduction of DCK expression by the shRNAmiR reduces the effect of the purine nucleoside on proliferation or in vivo persistence of the genetically-modified immune cells.

In particular embodiments of the method, the population of genetically-modified immune cells and the purine nucleoside are administered such that the genetically-modified immune cells are present in the subject (i.e., have not been eliminated by the host) when the purine nucleoside is administered, or while the purine nucleoside is present in the subject at an effective level. In some embodiments of the method, the purine nucleoside is fludarabine. In some such embodiments of the method, fludarabine is administered alone or in combination with another chemotherapeutic compound as part of a lymphodepletion regimen for immunotherapy.

In particular embodiments of the method, the genetically-modified immune cells are genetically-modified human T cells or genetically-modified NK cells expressing a CAR or exogenous TCR having specificity for an antigen on the targeted cancer cells.

In another aspect, the invention provides a method for treating a disease, such as cancer, in a subject in need thereof, wherein the method comprises administering to the subject a therapeutically effective amount of a population of any genetically-modified immune cells described herein (e.g., a genetically-modified human T cell or NK cell expressing a CAR or exogenous TCR) that comprise in their genome a nucleic acid sequence encoding a shRNAmiR that reduces the expression of endogenous glucocorticoid receptor (GR), wherein the population of genetically-modified immune cells is administered to the subject before, during, or after administration of a corticosteroid. Reduction of GR expression by the shRNAmiR reduces the effect of the corticosteroid on proliferation or in vivo persistence of the genetically-modified immune cells.

In particular embodiments of the method, the population of genetically-modified immune cells and the corticosteroid are administered such that the genetically-modified immune cells are present in the subject (i.e., have not been eliminated by the host) when the corticosteroid is administered, or while the corticosteroid is present in the subject at an effective level. In some embodiments of the method, the corticosteroid is dexamethasone or methylprednisolone. In some such embodiments of the method, the corticosteroid is administered alone or in combination with another compound as part of a treatment for reducing cytokine release syndrome during immunotherapy.

In particular embodiments of the method, the genetically-modified immune cells are genetically-modified human T cells or genetically-modified NK cells expressing a CAR or exogenous TCR having specificity for an antigen on the targeted cancer cells.

In another aspect, the invention provides a genetically-modified immune cell or a population thereof, as described herein, or an immune cell or a population thereof, as described herein, for use as a medicament. The invention further provides the use of a genetically-modified immune cell or a population thereof, as described herein, or an immune cell or a population thereof, as described herein, in the manufacture of a medicament for treating a disease in a subject in need thereof. In one such aspect, the medicament is useful in the treatment of a cancer.

In another aspect, the invention provides a genetically-modified cell or population thereof, as described herein, or an immune cell or a population thereof, as described herein, for use in treatment of a disease, and preferably in the treatment of a cancer.

BRIEF DESCRIPTION OF THE FIGURES

FIG. 1 shows beta-2 microglobulin expression or HLA-A, B, and C expression (i.e., MHC class I molecule expression) on T cells transduced with an AAV comprising construct 7056 which expresses a single copy of the shRNA472 in a 3' to 5' head-to-tail configuration with the CAR.

FIG. 1A shows the B2M surface levels in CD3−/CAR+ cells compared to meganuclease-edited cells expressing no shRNA from a control culture. FIG. 1B shows B2M levels on CD3−/CAR+ versus CD3+/CAR− populations in the same culture. FIG. 1C shows HLA-ABC (i.e., MHC class I molecule) surface levels in CD3−/CAR+ cells compared to meganuclease-edited cells expressing no shRNA from a control culture. FIG. 1D shows HLA-ABC levels on CD3−/CAR+ versus CD3+/CAR− populations in the same culture.

FIG. 2A shows the frequency of CD3−/CAR+ cells at day 4. FIG. 2B shows knockdown of B2M at day 4. FIG. 2C shows the frequency of CD3−/CAR+ cells at day 7. FIG. 2D shows knockdown of B2M at day 7. FIG. 2E shows the frequency of CD3−/CAR+ cells at day 10. FIG. 2F shows knockdown of B2M at day 10.

FIG. 3A shows the frequency of CD3−/CAR+ cells in 7206-tranduced cells. FIG. 3B shows knockdown of B2M in 7206-tranduced cells. FIG. 3C shows the frequency of CD3−/CAR+ cells in 7282-tranduced cells. FIG. 3D shows knockdown of B2M in 7282-tranduced cells. FIG. 3E shows the frequency of CD3−/CAR+ cells in 7056-tranduced cells. FIG. 3F shows knockdown of B2M in 7056-tranduced cells.

FIG. 4A shows the frequency of CD3−/CAR+ cells in 7206-tranduced cells. FIG. 4B shows knockdown of B2M in 7206-tranduced cells. FIG. 4C shows the frequency of CD3−/CAR+ cells in 7282-tranduced cells. FIG. 4D shows knockdown of B2M in 7282-tranduced cells. FIG. 4E shows the frequency of CD3−/CAR+ cells in 7056-tranduced cells. FIG. 4F shows knockdown of B2M in 7056-tranduced cells.

FIG. 5 shows the frequency of CD3−/CAR+ cells, and the knockdown of B2M, in cultures produced with AAV 7206, AAV 7056, or AAV 7282 eleven days post-transduction. FIG. 5A shows the frequency of CD3−/CAR+ cells in 7206-tranduced cells. FIG. 5B shows knockdown of B2M in 7206-tranduced cells. FIG. 5C shows the frequency of CD3−/CAR+ cells in 7282-tranduced cells. FIG. 5D shows knockdown of B2M in 7282-tranduced cells. FIG. 5E shows the frequency of CD3−/CAR+ cells in 7056-tranduced cells. FIG. 5F shows knockdown of B2M in 7056-tranduced cells.

FIG. 6 shows the effects of B2M knockout or knockdown on the sensitivity of CAR T cells to cytolysis by alloantigen-specific cytotoxic lymphocytes (CTLs) or NK cells. FIG. 6A shows the cytolytic activity of primed alloantigen-specific CTLs against B2M knockout and B2M knockdown CAR T cell populations. FIG. 6B shows the cytolytic activity of NK cells against B2M knockout and B2M knockdown CAR T cell populations.

FIG. 7 shows knockout of B2M using an engineered meganuclease and targeted insertion of a donor template comprising a coding sequence for an HLA-E polypeptide. FIG. 7A shows B2M knockout without targeted insertion. FIG. 7B shows B2M knockout and targeted insertion of the donor template using AAV7346.

FIG. 8 shows purification of T cell populations with B2M knockout and cell surface expression of HLA-E encoded by the inserted donor template. FIG. 8A shows the cell population that is B2M-negative. FIG. 8B shows the purified B2M-negative population. FIG. 8C shows the cell population that is HLA-E-positive. FIG. 8D shows the purified HLA-E-positive cell population.

FIG. 10 shows in vivo efficacy and stability of shRNAmiR-induced knockdown of B2M in CAR T cells. FIG. 10A shows bioluminescence imaging of total flux over time in mice engrafted with NALM-6 cells and treated with vehicle (shown as black line with triangles), mice treated with CD19-directed CAR T cells (shown as dark gray line with circles), or mice treated with CD19-directed CAR T cells with an integrated B2M-targeting shRNAmiR (shown as light gray line with triangles). FIG. 10B shows flow cytometry staining for B2M expression on human CD45+ cells 14 days after administration of either CD19-directed CART cells with an integrated B2M-targeting shRNAmiR (shown as light gray histogram) or control CD19-directed CAR T cells (shown as dark gray histogram).

FIG. 11A shows CAR and CS1 staining seven days after transduction with an AAV encoding a BCMA CAR but no shRNAmiR construct. FIG. 11B shows CAR and CS1 staining seven days after transduction with AAV 72101. FIG. 11C shows CAR and CS1 staining seven days after transduction with AAV 72102. FIG. 11D shows CAR and CS1 staining seven days after transduction with AAV 72103.

FIG. 13 shows flow cytometry detecting knockout of TGFBR2 in T cells using two engineered meganucleases. FIG. 13A shows a negative staining control. FIG. 13B shows mock-transfected T cells. FIG. 13C shows T cells transfected with mRNA encoding the TGF 1-2x.5 meganuclease. FIG. 13D shows T cells transfected with mRNA encoding the TGF 1-2L.296 meganuclease.

FIG. 23 shows flow cytometry plots of the number of CD4+ CAR T cells at different time points in co-culture with U266 cells. FIG. 23A shows CAR T cells incorporating the 72154 construct. FIG. 23B shows CAR T cells incorporating the 72155 construct. FIG. 23C shows CAR T cells having an HLA-E fusion protein knocked into the B2M gene.

FIG. 24 shows flow cytometry plots of live versus dead U266 cells after co-culture with BCMA CAR T cell variants for 16 days. FIG. 24A shows co-culture of U266 cells with BCMA CAR T cells modified to knock down TGFBR2 using a shRNAmiR (TGFbRKD). FIG. 24B shows co-culture of U266 cells with BCMA CAR T cells modified to knock down B2M using a shRNAmiR (Ctrl KD). FIG. 24C shows co-culture of U266 cells with BCMA CAR T cells modified to knockout TGFBR2 with an engineered meganuclease (TGFbR KO). FIG. 24D shows co-culture of U266 cells secreting active TGFβ1 with BCMA CAR T cells modified to knock down TGFBR2 using a shRNAmiR (TGFbRKD). FIG. 24E shows co-culture of U266 cells secreting active TGFβ1 with BCMA CAR T cells modified to knock down B2M using a shRNAmiR (Ctrl KD). FIG. 24F shows co-culture of U266 cells secreting active TGFβ1 with BCMA CAR T cells modified to knockout TGFBR2 with an engineered meganuclease (TGFbR KO).

FIG. 25 shows shRNAmiR-induced stable knockdown of CD52 in CAR T cells. Multiple candidate guide and passenger strand sequences for a CD52 shRNAmiR were built into a miR-E scaffold and positioned after the stop codon of a CD19-specific CAR. Constructs were designated AAV 72123 and AAV 72124 and were used for transduction of donor T cells. FIG. 25A shows staining of CD3−/CAR+ T cell populations following AAV transduction. FIG. 25B shows knockdown of CD52 in CD3−/CAR+ T cells 10 days after transduction with AAV 72123. FIG. 25C shows knockdown of CD52 in CD3−/CAR+ T cells 10 days after transduction with AAV 72124.

FIG. 28 shows diagrams of constructs 73161, 73162, 73163, and 73164. FIG. 28A shows construct 73161 which comprises a JeT promoter, a CD19 CAR gene, P2A/furin site, an HLA-E gene comprising a synthetic intron which comprises a B2M-targeting shRNAmiR, and an SV40 bi-directional polyA sequence. FIG. 28B shows construct 73162 which comprises a JeT promoter, a CD19 CAR gene comprising a synthetic intron which comprises a B2M-targeting shRNAmiR, an SV40 bi-directional polyA sequence, a second JeT promoter, an HLA-E gene, and a bovine growth hormone (BGH) termination signal. FIG. 28C shows construct 73163 which comprises a JeT promoter, a CD19 CAR gene, an SV40 bi-directional polyA sequence, an EF1 alpha core promoter, an HLA-E gene comprising a synthetic intron which comprises a B2M-targeting shRNAmiR, and a BGH termination signal. FIG. 28D shows the 73164 construct which comprises a JeT promoter, a CD19 CAR gene, an SV40 bi-directional polyA sequence, a second JeT promoter, an HLA-E gene comprising a synthetic intron which comprises a B2M-targeting shRNAmiR, and a BGH termination signal.

FIG. 29 shows a table summarizing the CAR phenotype of T cells in which the identified constructs were introduced by AAV and inserted into the TRAC locus only (7206 and 73161-73164), or cells in which a CAR gene was inserted in the TRAC locus and an HLA-E gene was inserted in the B2M locus (dKO dKI). The table provides the percentage of cells that were CD3-/CAR+, percentage of CD3 knockout cells that had a CAR knock-in, mean fluorescence intensity (MFI) of the expressed CAR, and comparison of the MFI of each CAR when compared to the CAR introduced using the 7206 construct.

FIG. 30 shows a table summarizing the HLA-ABC and HLA-E phenotypes of T cells in which the identified constructs were introduced by AAV and inserted into the TRAC locus only (7206 and 73161-73164), or cells in which a CAR gene was inserted in the TRAC locus and an HLA-E gene was inserted in the B2M locus (dKO dKI). The table provides the percentage of HLA-ABC expression compared to wild-type in the CD3−/CAR+ population, the percentage of HLA-ABC knockdown with the wild-type gated out, the percentage of cells expressing HLA-E in the CD3-/CAR+ population, the MFI of HLA-E expression in such cells, and the percentage of cells in the CAR− population that were HLA-E+.

FIG. 31 shows a table summarizing characteristics of CAR T cells in which the identified constructs were introduced by AAV and inserted into the TRAC locus only (7206 and 73161-73164), or cells in which a CAR gene was inserted in the TRAC locus and an HLA-E gene was inserted in the B2M locus (dKO dKI).

FIG. 32 shows cytolysis of CD19 CAR T variants prepared with T cells from a first donor (HC6366) when co-cultured with alloantigen-primed CTLs from two different donors (K3212 or K2916). FIG. 32A shows killing of CART cells by K3212 alloantigen-primed CTLs. FIG. 32B shows killing of CART cells by K2916 alloantigen-primed CTLs.

FIG. 33 shows natural killer (NK) cell cytolysis of CD19 CAR T variants in co-culture at multiple time points at a 1:1 ratio. FIG. 33A shows cytolysis at 24 hours. FIG. 33B shows cytolysis at 48 hours. FIG. 33C shows cytolysis at 120 hours.

Figure 34:
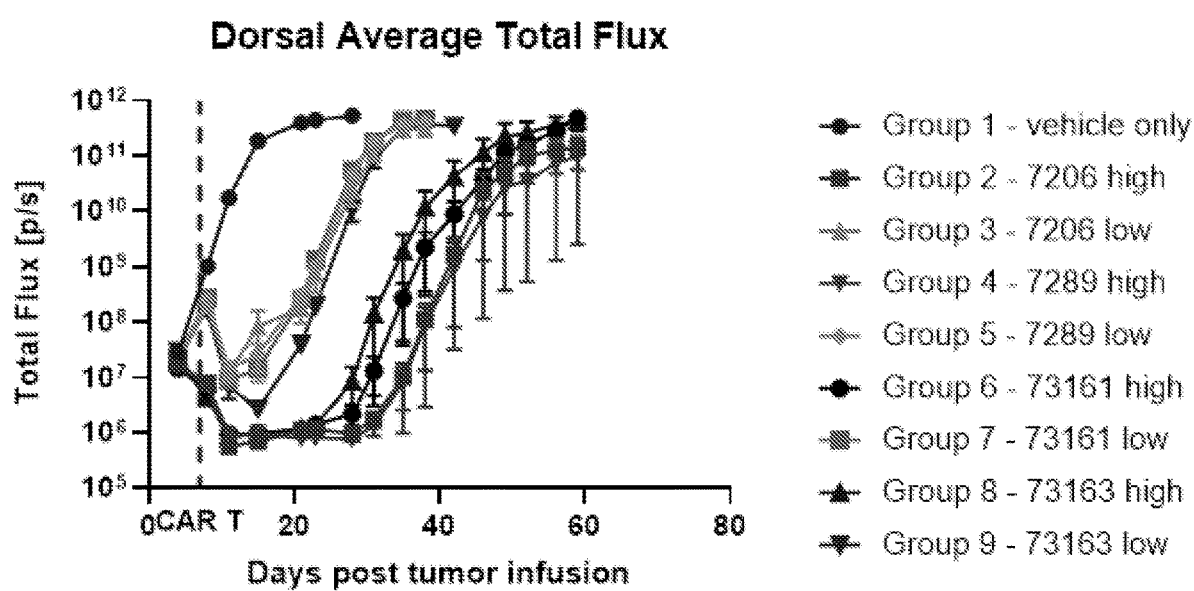

FIG. 34 shows luminescence measurements demonstrating in vivo efficacy of CD19 CAR T variants in immunodeficient mice engrafted with NALM/6 leukemia cells.

Figure 35:
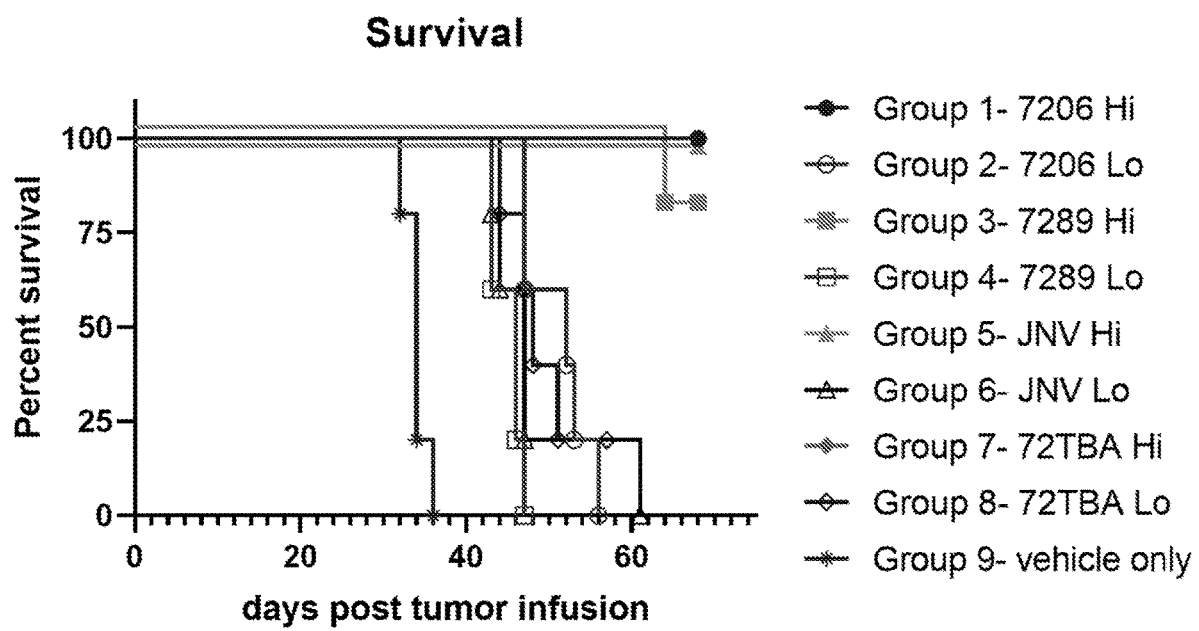

FIG. 35 shows survival of immunodeficient mice engrafted with NALM/6 leukemia cells treated with CD19 CAR T variants.

Figure 36:
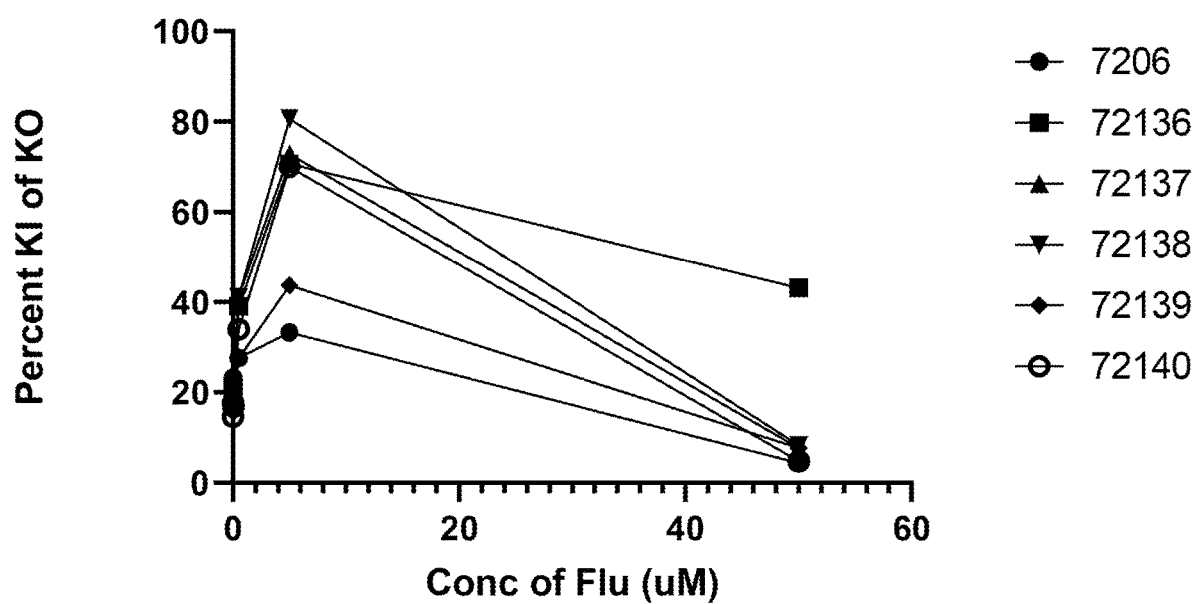

FIG. 36 shows changes in the percent knock in of a CD19 CAR sequence, with or without a DCK shRNAmiR, in CD3 knockout T cells following incubation with different concentrations of fludarabine.

Figure 37:
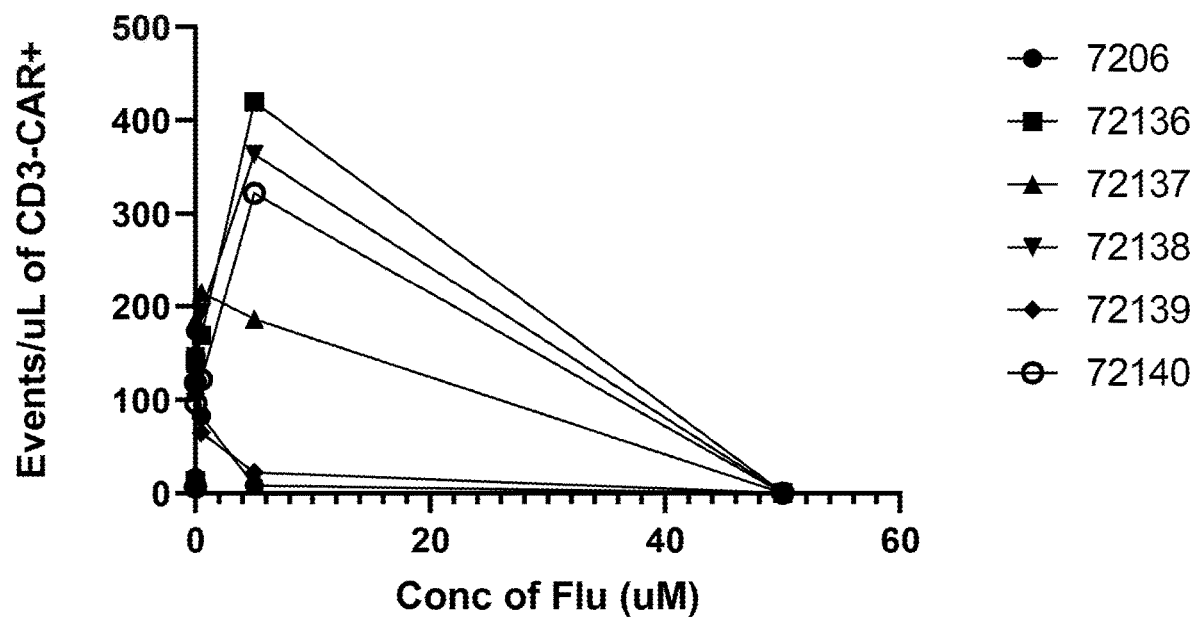

FIG. 37 shows events/uL of CD3−/CAR+ population versus the concentration of fludarabine incubated with CD19 CAR T cell variants that include, or do not include, a DCK shRNAmiR.

Figure 38:
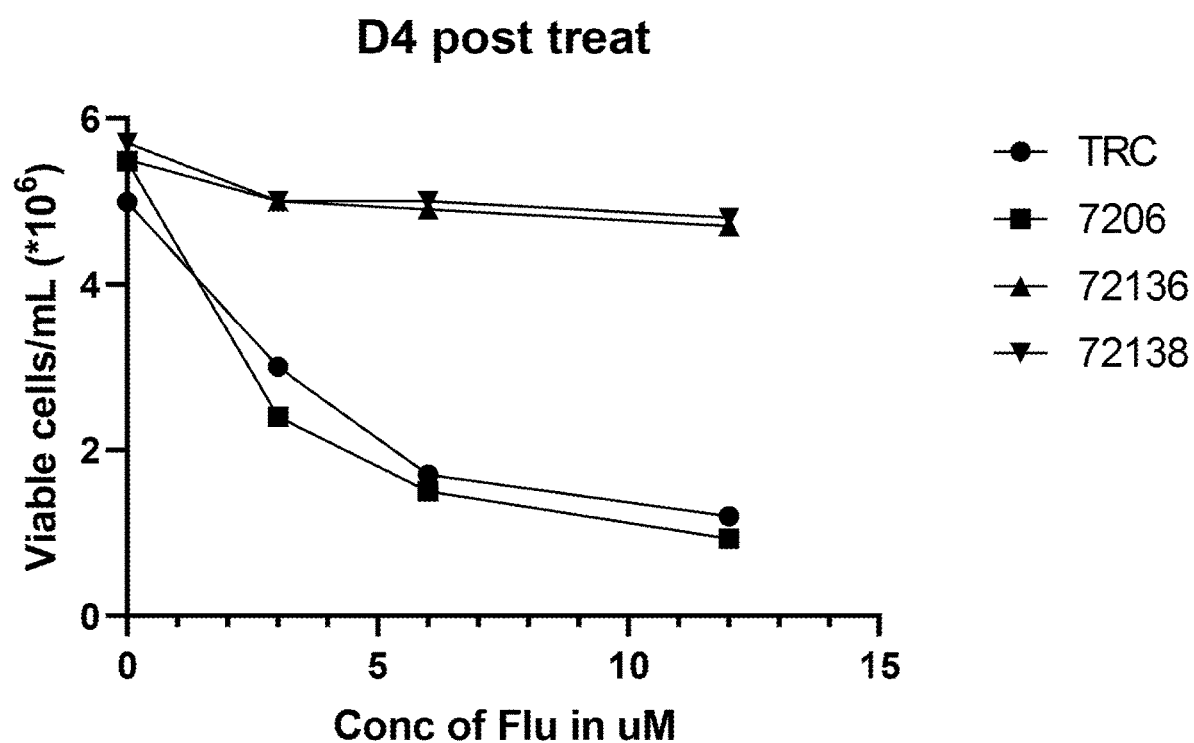

FIG. 38 shows the number of viable cells/mL on day 4 following post-treatment of different CD19 CAR T cell variants that include, or do not include, a DCK shRNAmiR, with different concentrations of fludarabine.

Figure 39:
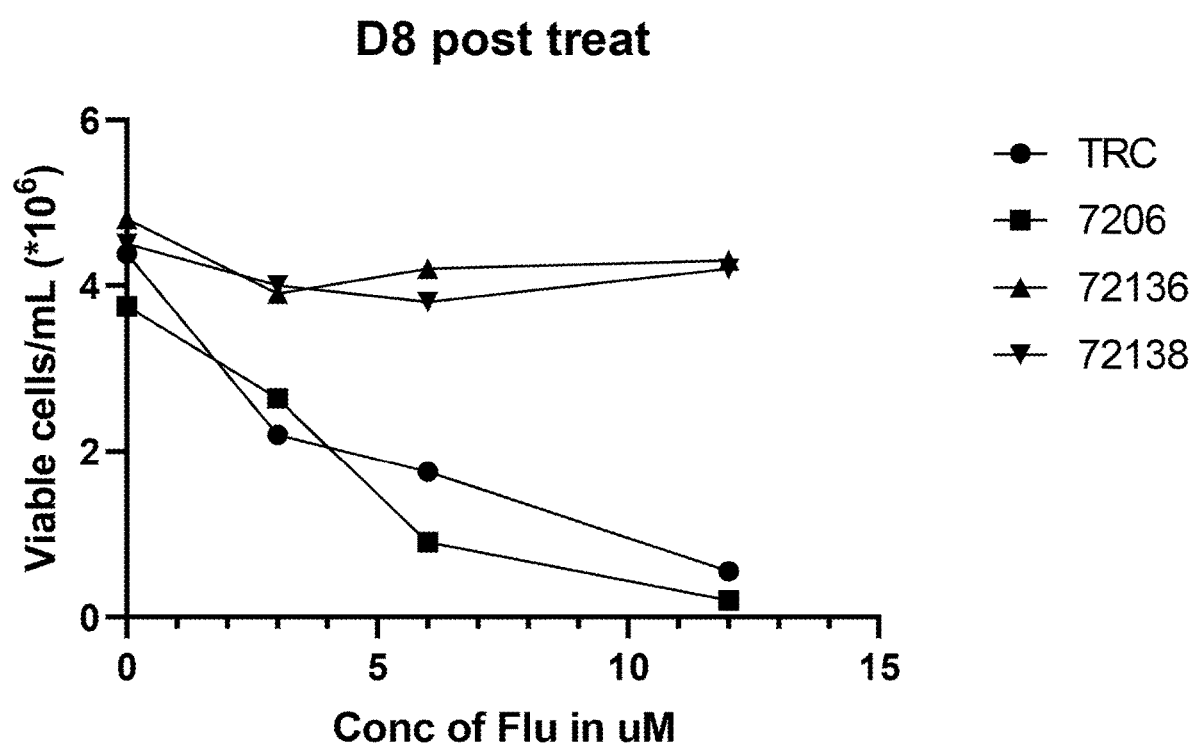

FIG. 39 shows the number of viable cells/mL on day 8 following post-treatment of different CD19 CAR T cell variants that include, or do not include, a DCK shRNAmiR, with different concentrations of fludarabine.

Figure 40:
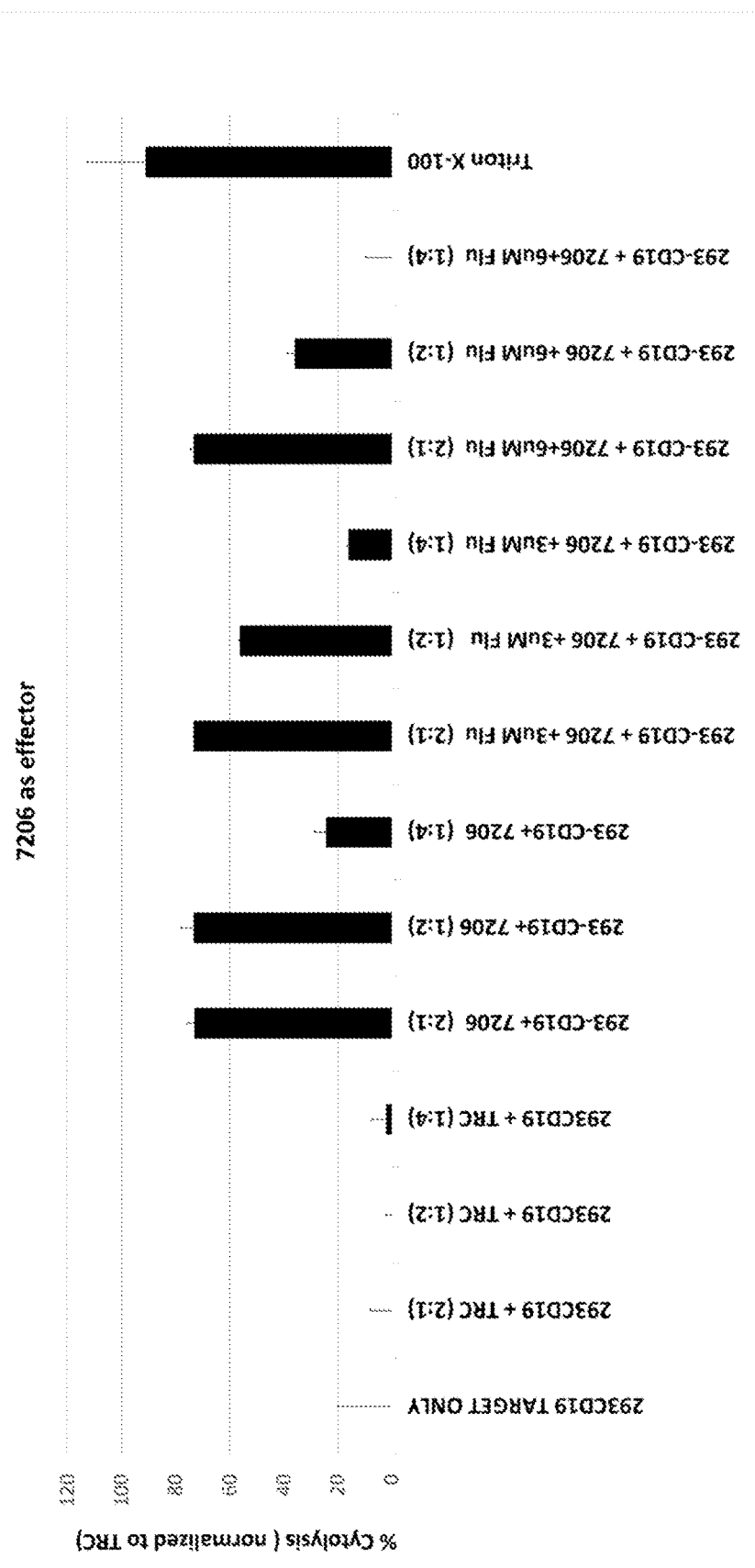

FIG. 40 shows the percent cytolysis of CD19-expressing HEK293 cells (targets) co-cultured with CD19 CAR T cells (effectors) lacking a DCK shRNAmiR in the presence of different concentrations of fludarabine. Cells were co-cultured at E:T ratios of 2:1, 1:2, and 1:4.

Figure 41:
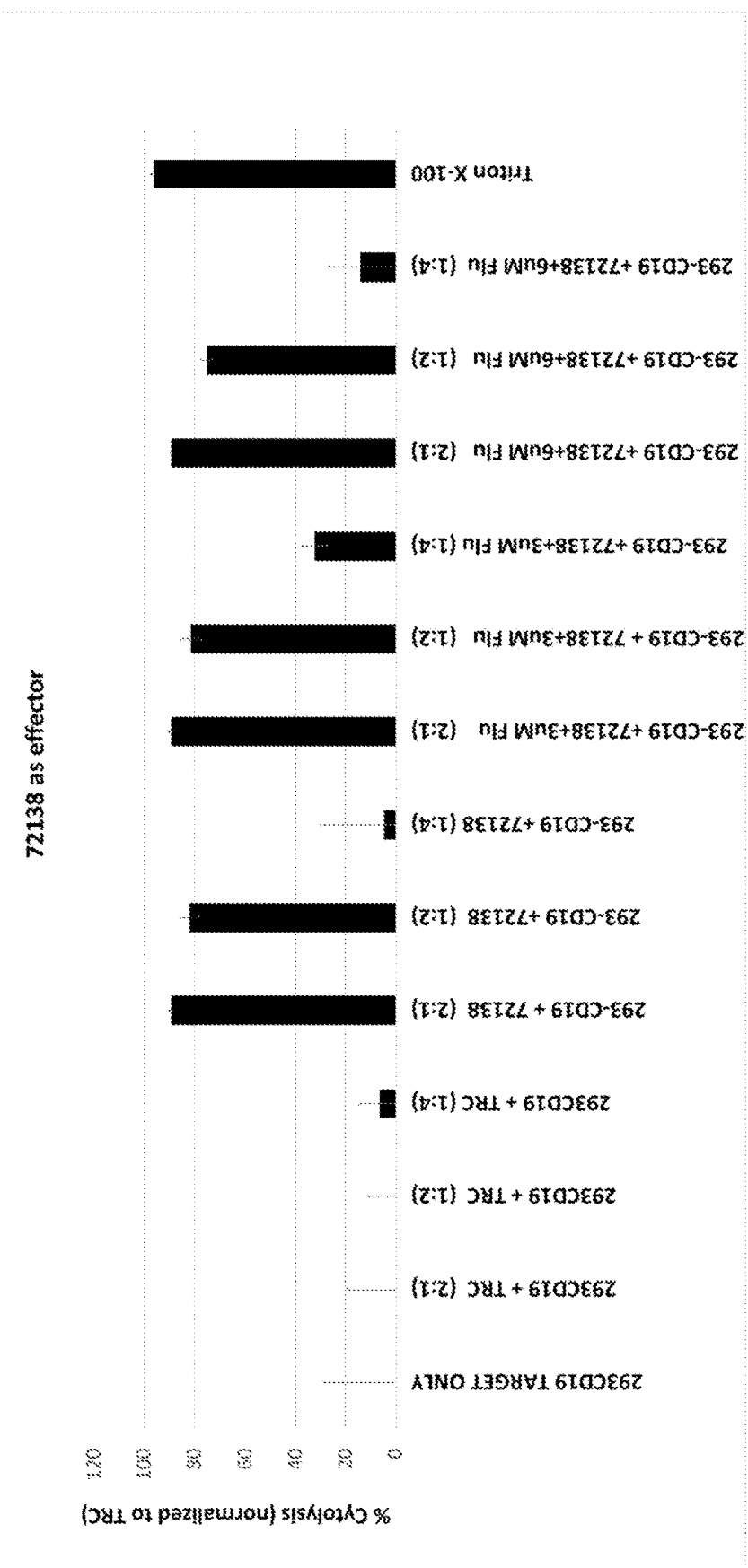

FIG. 41 shows the percent cytolysis of CD19-expressing HEK293 cells (targets) co-cultured with CD19 CAR T cells (effectors) comprising a DCK shRNAmiR (72138) in the presence of different concentrations of fludarabine. Cells were co-cultured at E:T ratios of 2:1, 1:2, and 1:4.

Figure 42:
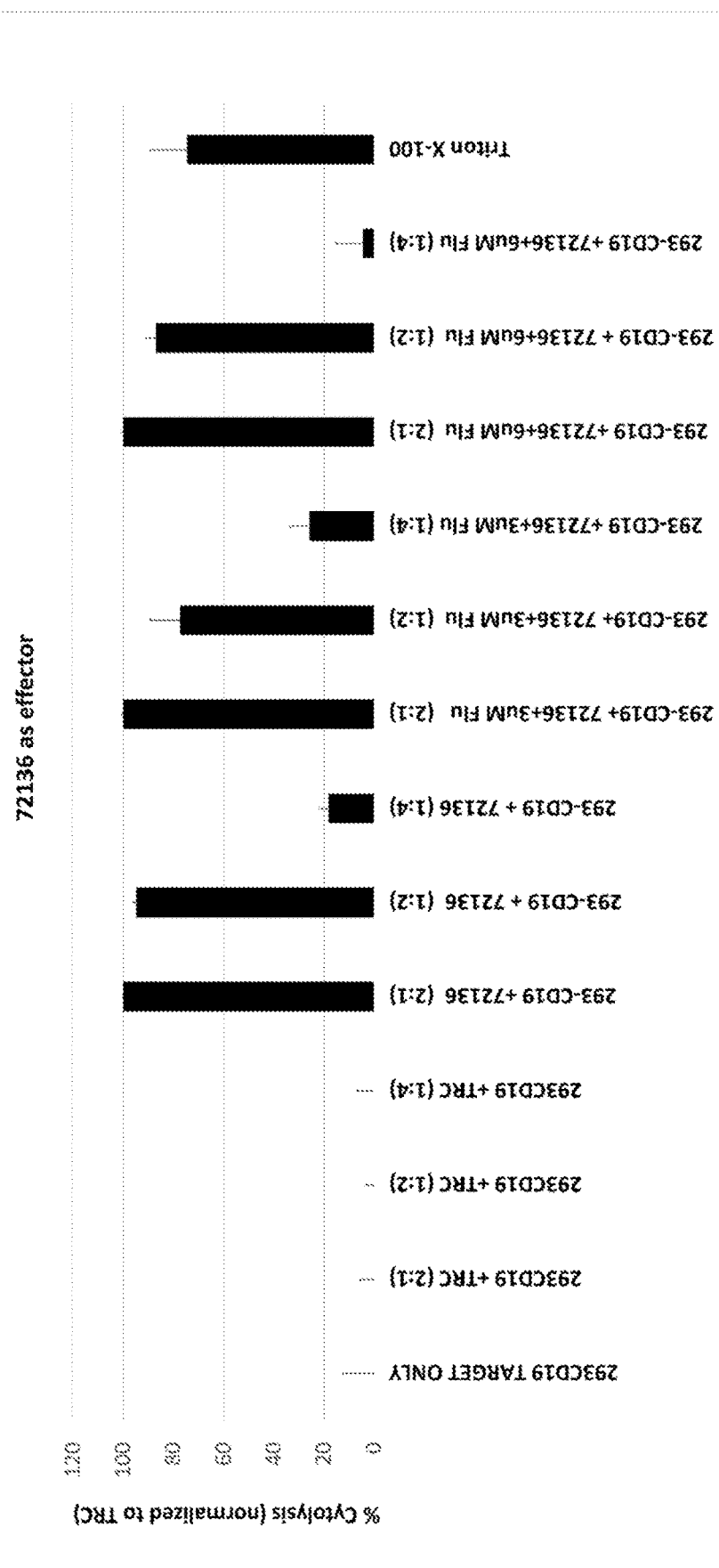

FIG. 42 shows the percent cytolysis of CD19-expressing HEK293 cells (targets) co-cultured with CD19 CAR T cells (effectors) comprising a DCK shRNAmiR (72136) in the presence of different concentrations of fludarabine. Cells were co-cultured at E:T ratios of 2:1, 1:2, and 1:4.

Figure 43:
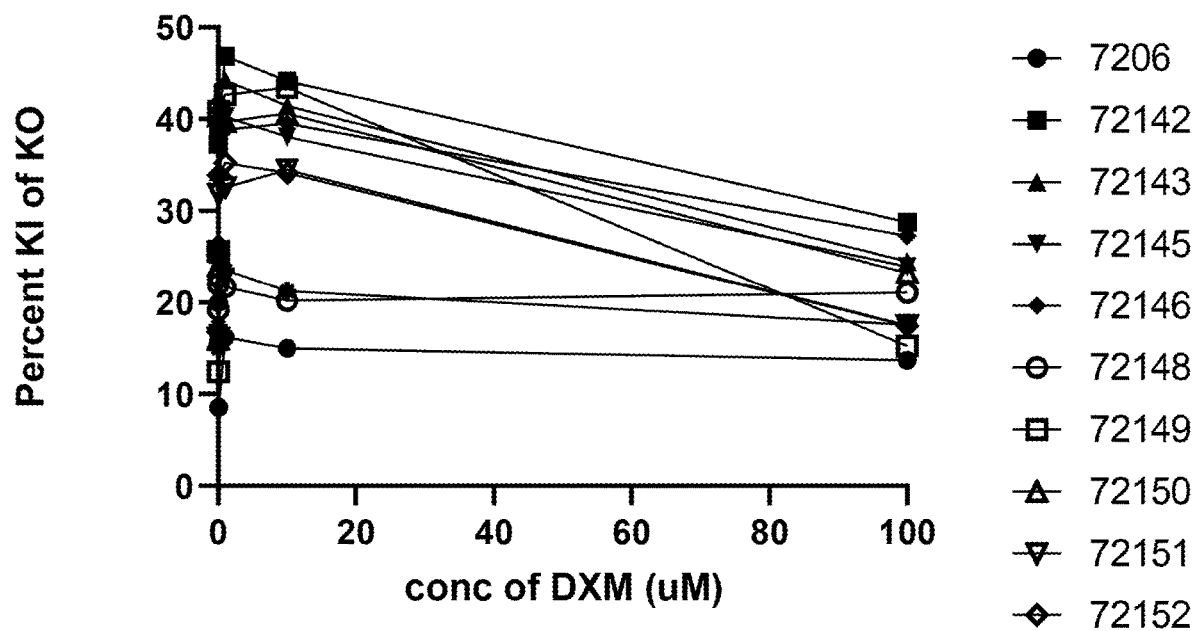

FIG. 43 shows changes in the percent knock in of a CD19 CAR sequence, with or without a GR shRNAmiR, in CD3 knockout T cells following incubation with different concentrations of dexamethasone.

Figure 44:
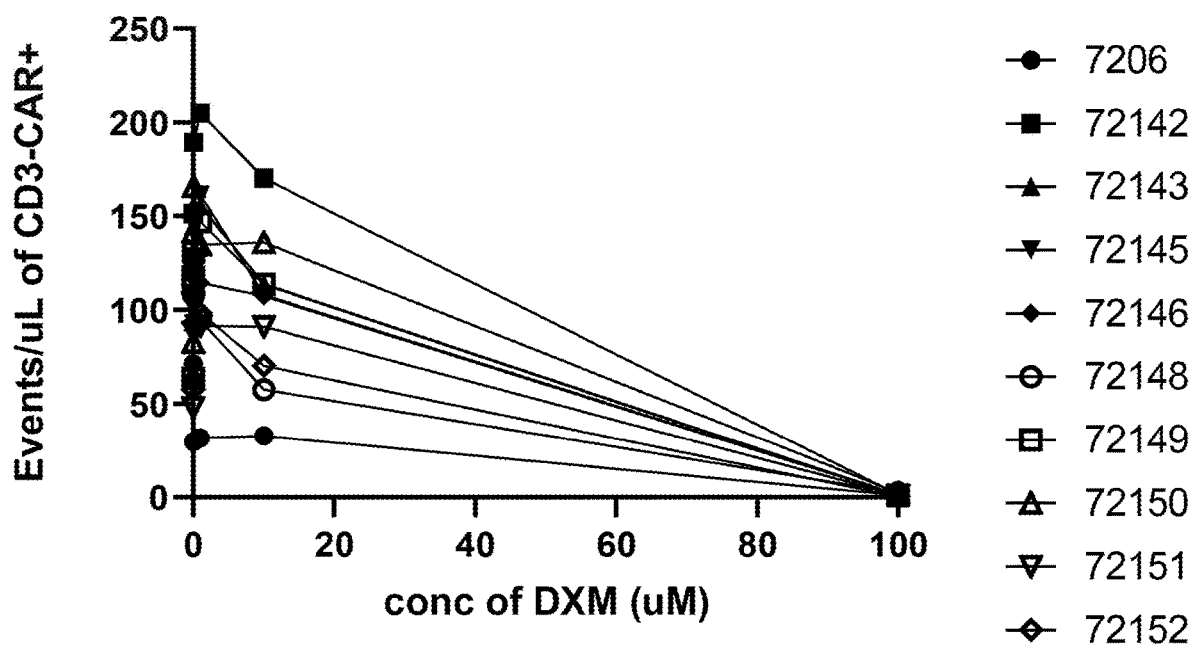

FIG. 44 shows events/uL of CD3−/CAR+ population versus the concentration of dexamethasone incubated with CD19 CAR T cell variants that include, or do not include, a GR shRNAmiR.

BRIEF DESCRIPTION OF THE SEQUENCES

SEQ ID NO: 1 sets forth the nucleic acid sequence of the 5' miR-E scaffold domain coding sequence.

SEQ ID NO: 2 sets forth the nucleic acid sequence of the 5' mir-E basal stem domain coding sequence.

SEQ ID NO: 3 sets forth the nucleic acid sequence of the miR-30a loop domain coding sequence.

SEQ ID NO: 4 sets forth the nucleic acid sequence of the 3' miR-E basal stem domain coding sequence.

SEQ ID NO: 5 sets forth the nucleic acid sequence of the 3' miR-E scaffold domain coding sequence.

SEQ ID NO: 6 sets forth the nucleic acid sequence encoding the shRNA 472.

SEQ ID NO: 7 sets forth the nucleic acid sequence encoding the passenger strand of the 7282 beta-2 microglobulin (B2M) shRNAmiR.

SEQ ID NO: 8 sets forth the nucleic acid sequence encoding the guide strand of the 7282 B2M shRNAmiR.

SEQ ID NO: 9 sets forth the nucleic acid sequence encoding the passenger strand of the 7285 B2M shRNAmiR.

SEQ ID NO: 10 sets forth the nucleic acid sequence encoding the guide strand of the 7285 B2M shRNAmiR.

SEQ ID NO: 11 sets forth the nucleic acid sequence encoding the passenger strand of the 7286 B2M shRNAmiR.

SEQ ID NO: 12 sets forth the nucleic acid sequence encoding the guide strand of the 7286 B2M shRNAmiR.

SEQ ID NO: 13 sets forth the nucleic acid sequence encoding the passenger strand of the 7287 B2M shRNAmiR.

SEQ ID NO: 14 sets forth the nucleic acid sequence encoding the guide strand of the 7287 B2M shRNAmiR.

SEQ ID NO: 15 sets forth the nucleic acid sequence encoding the passenger strand of the 7288 B2M shRNAmiR.

SEQ ID NO: 16 sets forth the nucleic acid sequence encoding the guide strand of the 7288 B2M shRNAmiR.

SEQ ID NO: 17 sets forth the nucleic acid sequence encoding the passenger strand of the 7289 B2M shRNAmiR.

SEQ ID NO: 18 sets forth the nucleic acid sequence encoding the guide strand of the 7289 B2M shRNAmiR.

SEQ ID NO: 19 sets forth the nucleic acid sequence encoding the passenger strand of the 7290 B2M shRNAmiR.

SEQ ID NO: 20 sets forth the nucleic acid sequence encoding the guide strand of the 7290 B2M shRNAmiR.

SEQ ID NO: 21 sets forth the nucleic acid sequence encoding the passenger strand of the 72101 CS1 shRNAmiR.

SEQ ID NO: 22 sets forth the nucleic acid sequence encoding the guide strand of the 72101 CS1 shRNAmiR.

SEQ ID NO: 23 sets for the nucleic acid sequence encoding the passenger strand of the 72102 CS1 shRNAmiR.

SEQ ID NO: 24 sets for the nucleic acid sequence encoding the guide strand of the 72102 CS1 shRNAmiR.

SEQ ID NO: 25 sets for the nucleic acid sequence encoding the passenger strand of the 72103 CS1 shRNAmiR.

SEQ ID NO: 26 sets forth the nucleic acid sequence encoding the guide strand of the 72103 CS1 shRNAmiR.

SEQ ID NO: 27 sets forth the nucleic acid sequence encoding the passenger strand of the 72110 transforming growth factor beta receptor 2 (TGFBR2) shRNAmiR.

SEQ ID NO: 28 sets forth the nucleic acid sequence encoding the guide strand of the 72110 TGFBR2 shRNAmiR.

SEQ ID NO: 29 sets forth the nucleic acid sequence encoding the passenger strand of the 72111 TGFBR2 shRNAmiR.

SEQ ID NO: 30 sets forth the nucleic acid sequence encoding the guide strand of the 72111 TGFBR2 shRNAmiR.

SEQ ID NO: 31 sets forth the nucleic acid sequence encoding the passenger strand of the 72112 TGFBR2 shRNAmiR.

SEQ ID NO: 32 sets forth the nucleic acid sequence encoding the guide strand of the 72112 TGFBR2 shRNAmiR.

SEQ ID NO: 33 sets forth the nucleic acid sequence encoding the passenger strand of the 72113 TGFBR2 shRNAmiR.

SEQ ID NO: 34 sets forth the nucleic acid sequence encoding the guide strand of the 72113 TGFBR2 shRNAmiR.

SEQ ID NO: 35 sets forth the nucleic acid sequence encoding the passenger strand of the 72114 TGFBR2 shRNAmiR.

SEQ ID NO: 36 sets forth the nucleic acid sequence encoding the guide strand of the 72114 TGFBR2 shRNAmiR.

SEQ ID NO: 37 sets forth the nucleic acid sequence encoding the passenger strand of the 72123 CD52 shRNAmiR.

SEQ ID NO: 38 sets forth the nucleic acid sequence encoding the guide strand of the 72123 CD52 shRNAmiR.

SEQ ID NO: 39 sets forth the nucleic acid sequence encoding the passenger strand of the 72124 CD52 shRNAmiR.

SEQ ID NO: 40 sets forth the nucleic acid sequence encoding the guide strand of the 72124 CD52 shRNAmiR.

SEQ ID NO: 41 sets forth the nucleic acid sequence encoding the 7282 B2M shRNAmiR.

SEQ ID NO: 42 sets forth the nucleic acid sequence encoding the 7285 B2M shRNAmiR.

SEQ ID NO: 43 sets forth the nucleic acid sequence encoding the 7286 B2M shRNAmiR.

SEQ ID NO: 44 sets forth the nucleic acid sequence encoding the 7287 B2M shRNAmiR.

SEQ ID NO: 45 sets forth the nucleic acid sequence encoding the 7288 B2M shRNAmiR.

SEQ ID NO: 46 sets forth the nucleic acid sequence encoding the 7289 B2M shRNAmiR.

SEQ ID NO: 47 sets forth the nucleic acid sequence encoding the 7290 B2M shRNAmiR.

SEQ ID NO: 48 sets forth the nucleic acid sequence encoding the 72101 CS1 shRNAmiR.

SEQ ID NO: 49 sets forth the nucleic acid sequence encoding the 72102 CS1 shRNAmiR.

SEQ ID NO: 50 sets forth the nucleic acid sequence encoding the 72103 CS1 shRNAmiR.

SEQ ID NO: 51 sets forth the nucleic acid sequence encoding the 72110 TGFBR2 shRNAmiR.

SEQ ID NO: 52 sets forth the nucleic acid sequence encoding the 72111 TGFBR2 shRNAmiR.

SEQ ID NO: 53 sets forth the nucleic acid sequence encoding the 72112 TGFBR2 shRNAmiR.

SEQ ID NO: 54 sets forth the nucleic acid sequence encoding the 72113 TGFBR2 shRNAmiR.

SEQ ID NO: 55 sets forth the nucleic acid sequence encoding the 72114 TGFBR2 shRNAmiR.

SEQ ID NO: 56 sets forth the nucleic acid sequence encoding the 72123 CD52 shRNAmiR.

SEQ ID NO: 57 sets forth the nucleic acid sequence encoding the 72124 CD52 shRNAmiR.

SEQ ID NO: 58 sets forth the nucleic acid sequence of the TRC 1-2 recognition sequence (sense).

SEQ ID NO: 59 sets forth the nucleic acid sequence of the TRC 1-2 recognition sequence (antisense).

SEQ ID NO: 60 sets forth the nucleic acid sequence of the B2M 13-14 recognition sequence (sense).

SEQ ID NO: 61 sets forth the nucleic acid sequence of the B2M 13-14 recognition sequence (antisense).

SEQ ID NO: 62 sets forth the nucleic acid sequence of the TGF 1-2 recognition sequence (sense).

SEQ ID NO: 63 sets forth the nucleic acid sequence of the TGF 1-2 recognition sequence (antisense).

SEQ ID NO: 64 sets forth the amino acid sequence of the TGF 1-2x.5 meganuclease.

SEQ ID NO: 65 sets forth the amino acid sequence of the TGF 1-2L.296 meganuclease.

SEQ ID NO: 66 sets forth the amino acid sequence of an HLA class I histocompatibility antigen, alpha chain E (HLA-E) fusion polypeptide.

SEQ ID NO: 67 sets forth the nucleic acid sequence of a JeT promoter.

SEQ ID NO: 68 sets forth the nucleic acid sequence of a bidirectional SV40 polyA signal.

SEQ ID NO: 69 sets forth the nucleic acid sequence of a synthetic intron.

SEQ ID NO: 70 sets forth the nucleic acid sequence of a P2A/furin site.

SEQ ID NO: 71 sets forth the nucleic acid sequence of a bovine growth hormone termination signal.

SEQ ID NO: 72 sets forth the nucleic acid sequence of an EF1 alpha core promoter.

SEQ ID NO: 73 sets forth the amino acid sequence of a signal peptide.

SEQ ID NO: 74 sets forth the nucleic acid sequence of a cassette comprised by construct 73161.

SEQ ID NO: 75 sets forth the nucleic acid sequence of a cassette comprised by construct 73163.

SEQ ID NO: 76 sets forth the nucleic acid sequence encoding the passenger strand of the 72136 DCK shRNAmiR.

SEQ ID NO: 77 sets forth the nucleic acid sequence encoding the guide strand of the 72136 DCK shRNAmiR.

SEQ ID NO: 78 sets forth the nucleic acid sequence encoding the passenger strand of the 72137 DCK shRNAmiR.

SEQ ID NO: 79 sets forth the nucleic acid sequence encoding the guide strand of the 72137 DCK shRNAmiR.

SEQ ID NO: 80 sets forth the nucleic acid sequence encoding the passenger strand of the 72138 DCK shRNAmiR.

SEQ ID NO: 81 sets forth the nucleic acid sequence encoding the guide strand of the 72138 DCK shRNAmiR.

SEQ ID NO: 82 sets forth the nucleic acid sequence encoding the passenger strand of the 72139 DCK shRNAmiR.

SEQ ID NO: 83 sets forth the nucleic acid sequence encoding the guide strand of the 72139 DCK shRNAmiR.

SEQ ID NO: 84 sets forth the nucleic acid sequence encoding the passenger strand of the 72140 DCK shRNAmiR.

SEQ ID NO: 85 sets forth the nucleic acid sequence encoding the guide strand of the 72140 DCK shRNAmiR.

SEQ ID NO: 86 sets forth the nucleic acid sequence encoding the 72136 DCK shRNAmiR.

SEQ ID NO: 87 sets forth the nucleic acid sequence encoding the 72137 DCK shRNAmiR.

SEQ ID NO: 88 sets forth the nucleic acid sequence encoding the 72138 DCK shRNAmiR.

SEQ ID NO: 89 sets forth the nucleic acid sequence encoding the 72139 DCK shRNAmiR.

SEQ ID NO: 90 sets forth the nucleic acid sequence encoding the 72140 DCK shRNAmiR.

SEQ ID NO: 91 sets forth the nucleic acid sequence encoding the passenger strand of the 72142 GR shRNAmiR.

SEQ ID NO: 92 sets forth the nucleic acid sequence encoding the guide strand of the 72142 GR shRNAmiR.

SEQ ID NO: 93 sets forth the nucleic acid sequence encoding the passenger strand of the 72143 GR shRNAmiR.

SEQ ID NO: 94 sets forth the nucleic acid sequence encoding the guide strand of the 72143 GR shRNAmiR.

SEQ ID NO: 95 sets forth the nucleic acid sequence encoding the passenger strand of the 72145 GR shRNAmiR.

SEQ ID NO: 96 sets forth the nucleic acid sequence encoding the guide strand of the 72145 GR shRNAmiR.

SEQ ID NO: 97 sets forth the nucleic acid sequence encoding the passenger strand of the 72146 GR shRNAmiR.

SEQ ID NO: 98 sets forth the nucleic acid sequence encoding the guide strand of the 72146 GR shRNAmiR.

SEQ ID NO: 99 sets forth the nucleic acid sequence encoding the passenger strand of the 72148 GR shRNAmiR.

SEQ ID NO: 100 sets forth the nucleic acid sequence encoding the guide strand of the 72148 GR shRNAmiR.

SEQ ID NO: 101 sets forth the nucleic acid sequence encoding the passenger strand of the 72149 GR shRNAmiR.

SEQ ID NO: 102 sets forth the nucleic acid sequence encoding the guide strand of the 72149 GR shRNAmiR.

SEQ ID NO: 103 sets forth the nucleic acid sequence encoding the passenger strand of the 72150 GR shRNAmiR.

SEQ ID NO: 104 sets forth the nucleic acid sequence encoding the guide strand of the 72150 GR shRNAmiR.

SEQ ID NO: 105 sets forth the nucleic acid sequence encoding the passenger strand of the 72151 GR shRNAmiR.

SEQ ID NO: 106 sets forth the nucleic acid sequence encoding the guide strand of the 72151 GR shRNAmiR.

SEQ ID NO: 107 sets forth the nucleic acid sequence encoding the passenger strand of the 72152 GR shRNAmiR.

SEQ ID NO: 108 sets forth the nucleic acid sequence encoding the guide strand of the 72152 GR shRNAmiR.

SEQ ID NO: 109 sets forth the nucleic acid sequence encoding the 72142 GR shRNAmiR.

SEQ ID NO: 110 sets forth the nucleic acid sequence encoding the 72143 GR shRNAmiR.

SEQ ID NO: 111 sets forth the nucleic acid sequence encoding the 72145 GR shRNAmiR.

SEQ ID NO: 112 sets forth the nucleic acid sequence encoding the 72146 GR shRNAmiR.

SEQ ID NO: 113 sets forth the nucleic acid sequence encoding the 72148 GR shRNAmiR.

SEQ ID NO: 114 sets forth the nucleic acid sequence encoding the 72149 GR shRNAmiR.

SEQ ID NO: 115 sets forth the nucleic acid sequence encoding the 72150 GR shRNAmiR.

SEQ ID NO: 116 sets forth the nucleic acid sequence encoding the 72151 GR shRNAmiR.

SEQ ID NO: 117 sets forth the nucleic acid sequence encoding the 72152 GR shRNAmiR.

SEQ ID NO: 118 sets forth the amino acid sequence of an HLA-E-01:03 protein.

SEQ ID NO: 119 sets forth the amino acid sequence of a beta-2 microglobulin protein.

SEQ ID NO: 120 sets forth the amino acid sequence of an HLA-G leader peptide.

SEQ ID NO: 121 sets forth the amino acid sequence of a (GGGGS)3 linker peptide.

SEQ ID NO: 122 sets forth the amino acid sequence of a (GGGGS)4 linker peptide.

SEQ ID NO: 123 sets forth the amino acid sequence of a wild-type I-CreI homing endonuclease from *Chlamydomonas reinhardtii*.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "exogenous" or "heterologous" in reference to a nucleotide sequence or amino acid sequence are intended to mean a sequence that is purely synthetic, that originates from a foreign species, or, if from the same species, is substantially modified from its native form in composition and/or genomic locus by deliberate human intervention.

As used herein, the term "endogenous" in reference to a nucleotide sequence or protein is intended to mean a sequence or protein that is naturally comprised within or expressed by a cell.

As used herein, the terms "nuclease" and "endonuclease" are used interchangeably to refer to naturally-occurring or engineered enzymes which cleave a phosphodiester bond within a polynucleotide chain.

As used herein, the term "shRNA" or "short hairpin RNA" refers to an artificial RNA molecule comprising a hairpin that can be used to silence gene expression via RNA interference.

As used herein, the term "miRNA" or "microRNA" or "miR" refers to mature microRNAs (miRNAs) that are endogenously encoded ~22 nt long RNAs that post-transcriptionally reduce the expression of target genes. miRNAs are found in plants, animals, and some viruses and are generally expressed in a highly tissue- or developmental-stage-specific fashion.

A "stem-loop structure" refers to a nucleic acid having a secondary structure that includes a region of nucleotides which are known or predicted to form a double strand (stem portion) that is linked on one side by a region of predominantly single-stranded nucleotides (loop portion), in some cases, the loop may also be very short and thereby not be recognized by Dicer, leading to Dicer-independent s RNAs (comparable to the endogenous miR0431). The term "hairpin" is also used herein to refer to stem-loop structures. The actual primary sequence of nucleotides within the stem-loop structure is not critical to the practice of the description as long as the secondary structure is present. As is known in the art, the secondary structure does not require exact base-pairing. Thus, the stem may include one or more base mismatches. Alternatively, the base-pairing may be exact (i.e., not include any mismatches).

As used herein, the terms "shRNAmiR" and "microRNA-adapted shRNA" refer to shRNA sequences embedded within a microRNA scaffold. A shRNAmiR molecule mimics naturally-occurring pri-miRNA molecules in that they comprise a hairpin flanked by sequences necessary for efficient processing and can be processed by the Drosha enzyme into pre-miRNAs, exported into the cytoplasm, and cleaved by Dicer, after which the mature miRNA can enter the RISC. The microRNA scaffold can be derived from naturally-occurring microRNA, pre-miRNAs, or pri-miRNAs or variants thereof. In some embodiments, the shRNA sequences which the shRNAmiR is based upon is of a different length from miRNAs (which are 22 nucleotides long) and the miRNA scaffold must therefore be modified in order to accommodate the longer or shorter shRNA sequence length.

As used herein, the term "microRNA flanking sequences" refers to nucleotide sequences comprising microRNA processing elements. MicroRNA processing elements are the minimal nucleic acid sequences which contribute to the production of mature microRNA from primary-microRNA or precursor microRNA. Often these elements are located within a 40 nucleotide sequence that flanks a microRNA stem-loop structure. In some instances, the microRNA processing elements are found within a stretch of nucleotide sequences of between 5 and 4,000 nucleotides in length that flank a microRNA stem-loop structure. MicroRNA flanking sequences used in the shRNAmiR molecules can be naturally-occurring sequences flanking naturally-occurring microRNA or can be variants thereof. MicroRNA flanking sequences include miR scaffold domains and miR basal stem domains.

shRNAmiR molecules used in the presently disclosed compositions and methods can comprise in the 5' to 3' direction: (a) a 5' miR scaffold domain; (b) a 5' miR basal stem domain; (c) a passenger strand; (d) a miR loop domain; (e) a guide strand; (f) a 3' miR basal stem domain; and (g) a 3' miR scaffold domain.

As used herein, the term "miR scaffold domain" as it relates to a shRNAmiR refers to a nucleotide sequence that can flank either the 5' or 3' end of a microRNA or shRNA in a shRNAmiR molecule and can be derived from a naturally-occurring microRNA flanking sequence or a variant thereof. In general, the miR basal stem domain sequence separates the shRNA sequence (passenger and guide strand, and miR loop domain) and the scaffold domains. The 5' miR scaffold domain can comprise a restriction enzyme (e.g., type IIS restriction enzyme) recognition sequence at or near its 3' end and the 3' miR scaffold domain can comprise a restriction enzyme recognition sequence at or near its 5' end, thus facilitating the insertion of a shRNA sequence. In some embodiments, the secondary structure of the miR scaffold domain is more important than the actual sequence thereof.

As used herein, the term "miR basal stem domain" as it relates to a shRNAmiR refers to sequences immediately flanking the passenger and guide strand sequences that comprise the base of the hairpin stem below the passenger: guide duplex. Thus, the 5' and 3' miR basal stem domains are complementary (fully or partially) in sequence to one another. In some embodiments, the 5' and 3' miR basal stem domains comprise sequences that when hybridized together, form two mismatch bubbles, each comprising one or two mismatched base pairs.

As used herein, the term "passenger strand" as it relates to a shRNAmiR refers to the sequence of the shRNAmiR, which is complementary (fully or partially) to the guide sequence.

As used herein, the term "guide strand" as it relates to a shRNAmiR refers to the sequence of the shRNAmiR that has complementarity (full or partial) with the target mRNA sequence for which a reduction in expression is desired.

As used herein, a "miR loop domain" as it relates to a shRNAmiR refers to the single-stranded loop sequence at one end of the passenger:guide duplex of the shRNAmiR. The miR loop domain can be derived from a naturally-occurring pre-microRNA loop sequence or a variant thereof.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 123), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in cells, particularly in human immune cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445, 251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or more, sequence identity to residues 154-195 of SEQ ID NO: 65. In some embodiments, a linker may have an amino acid sequence comprising residues 154-195 of SEQ ID NO: 65.

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, 51 nuclease, mung bean nuclease, pancreatic DNAse I, micrococcal nuclease, and yeast HO endonuclease. See, for example, Christian et al. (2010) Genetics 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRI, BglI, and AlwI. Additional Type IIs restriction endonucleases are described in International Publication No. WO 2007/014275, which is incorporated by reference in its entirety. In some embodiments, the nuclease domain of the TALEN is a FokI nuclease domain or an active portion thereof. TAL domain repeats can be derived from the TALE (transcription activator-like effector) family of proteins used in the infection process by plant pathogens of the *Xanthomonas* genus. TAL domain repeats are 33-34 amino acid sequences with divergent 12th and 13th amino acids. These two positions, referred to as the repeat variable dipeptide (RVD), are highly variable and show a strong correlation with specific nucleotide recognition. Each base pair in the DNA target sequence is contacted by a single TAL repeat with the specificity resulting from the RVD. In some embodiments, the TALEN comprises 16-22 TAL domain repeats. DNA cleavage by a TALEN requires two DNA recognition regions (i.e., "half-sites") flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally-occurring TALE protein or can be redesigned through rational or experimental means to produce a protein that binds to a pre-determined DNA sequence (see, for example, Boch et al. (2009) Science 326(5959):1509-1512 and Moscou and Bogdanove (2009) Science 326 (5959):1501, each of which is incorporated by reference in its entirety). See also, U.S. Publication No. 20110145940 and International Publication No. WO 2010/079430 for methods for engineering a TALEN to recognize and bind a specific sequence and examples of RVDs and their corresponding target nucleotides. In some embodiments, each nuclease (e.g., FokI) monomer can be fused to a TAL effector sequence that recognizes and binds a different DNA sequence, and only when the two recognition sites are in close proximity do the inactive monomers come together to create a functional enzyme. It is understood that the term "TALEN" can refer to a single TALEN protein or, alternatively, a pair of TALEN proteins (i.e., a left TALEN protein and a right TALEN protein) which bind to the upstream and downstream half-sites adjacent to the TALEN spacer sequence and work in concert to generate a cleavage site within the spacer sequence. Given a predetermined DNA locus or spacer sequence, upstream and downstream half-sites can be identified using a number of programs known in the art (Kornel Labun; Tessa G. Montague; James A. Gagnon; Summer B. Thyme; Eivind Valen. (2016). CHOPCHOP v2: a web tool for the next generation of CRISPR genome engineering. Nucleic Acids Research; doi: 10.1093/nar/gkw398; Tessa G. Montague; Jose M. Cruz; James A. Gagnon; George M. Church; Eivind Valen. (2014). CHOPCHOP: a CRISPR/Cas9 and TALEN web tool for genome editing. Nucleic Acids Res. 42. W401-W407). It is also understood that a TALEN recognition sequence can be defined as the DNA binding sequence (i.e., half-site) of a single TALEN protein or, alternatively, a DNA sequence comprising the upstream half-site, the spacer sequence, and the downstream half-site.

As used herein, the term "compact TALEN" refers to an endonuclease comprising a DNA-binding domain with one or more TAL domain repeats fused in any orientation to any portion of the I-TeeI homing endonuclease or any of the endonucleases listed in Table 2 in U.S. Application No. 20130117869 (which is incorporated by reference in its entirety), including but not limited to MmeI, EndA, EndI, I-BasI, I-TevII, I-TevIII, I-TwoI, MspI, MvaI, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the term "megaTAL" refers to a single-chain endonuclease comprising a transcription activator-like effector (TALE) DNA binding domain with an engineered, sequence-specific homing endonuclease.

As used herein, the terms "zinc finger nuclease" or "ZFN" refers to a chimeric protein comprising a zinc finger DNA-binding domain fused to a nuclease domain from an endonuclease or exonuclease, including but not limited to a restriction endonuclease, homing endonuclease, 51 nuclease, mung bean nuclease, pancreatic DNAse I, micrococcal nuclease, and yeast HO endonuclease. Nuclease domains useful for the design of zinc finger nucleases include those from a Type IIs restriction endonuclease, including but not limited to FokI, FoM, and StsI restriction enzyme. Additional Type IIs restriction endonucleases are described in International Publication No. WO 2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 basepairs in length, comprising a pair of nine basepair half-sites separated by 2-10 basepairs. See, for example, U.S. Pat. Nos. 5,789,538, 5,925,523, 6,007,988, 6,013,453, 6,200,759, and International Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in U.S. Publications Nos. 20030232410, 20050208489, 2005064474, 20050026157, 20060188987 and International Publication No. WO 07/014275, each of which is incorporated by reference in its entirety. In the case of a zinc finger, the DNA binding domains typically recognize an 18-bp recognition sequence comprising a pair of nine basepair "half-sites" separated by a 2-10 basepair "spacer sequence", and cleavage by the nuclease creates a blunt end or a 5' overhang of variable length (frequently four basepairs). It is understood that the term "zinc finger nuclease" can refer to a single zinc finger protein or, alternatively, a pair of zinc finger proteins (i.e., a left ZFN protein and a right ZFN protein) that bind to the upstream and downstream half-sites adjacent to the zinc finger nuclease spacer sequence and work in concert to generate a cleavage site within the spacer sequence. Given a predetermined DNA locus or spacer sequence, upstream and downstream half-sites can be identified using a number of programs known in the art (Mandell J G, Barbas C F 3rd. Zinc Finger Tools: custom DNA-binding domains for transcription factors and nucleases. Nucleic Acids Res. 2006 Jul. 1; 34 (Web Server issue): W516-23). It is also understood that a zinc finger nuclease recognition sequence can be defined as the DNA binding sequence (i.e., half-site) of a single zinc finger nuclease protein or, alternatively, a DNA sequence comprising the upstream half-site, the spacer sequence, and the downstream half-site.

As used herein, the terms "CRISPR nuclease" or "CRISPR system nuclease" refers to a CRISPR (clustered regularly interspaced short palindromic repeats)-associated (Cas) endonuclease or a variant thereof, such as Cas9, that associates with a guide RNA that directs nucleic acid cleavage by the associated endonuclease by hybridizing to a recognition site in a polynucleotide. In certain embodiments, the CRISPR nuclease is a class 2 CRISPR enzyme. In some of these embodiments, the CRISPR nuclease is a class 2, type II enzyme, such as Cas9. In other embodiments, the CRISPR nuclease is a class 2, type V enzyme, such as Cpf1. The guide RNA comprises a direct repeat and a guide sequence (often referred to as a spacer in the context of an endogenous CRISPR system), which is complementary to the target recognition site. In certain embodiments, the CRISPR system further comprises a tracrRNA (trans-activating CRISPR RNA) that is complementary (fully or partially) to the direct repeat sequence (sometimes referred to as a tracr-mate sequence) present on the guide RNA. In particular embodiments, the CRISPR nuclease can be mutated with respect to a corresponding wild-type enzyme such that the enzyme lacks the ability to cleave one strand of a target polynucleotide, functioning as a nickase, cleaving only a single strand of the target DNA. Non-limiting examples of CRISPR enzymes that function as a nickase include Cas9 enzymes with a D10A mutation within the RuvC I catalytic domain, or with a H840A, N854A, or N863A mutation. Given a predetermined DNA locus, rec- ognition sequences can be identified using a number of programs known in the art (Kornel Labun; Tessa G. Montague; James A. Gagnon; Summer B. Thyme; Eivind Valen. (2016). CHOPCHOP v2: a web tool for the next generation of CRISPR genome engineering. Nucleic Acids Research; doi:10.1093/nar/gkw398; Tessa G. Montague; Jose M. Cruz; James A. Gagnon; George M. Church; Eivind Valen. (2014). CHOPCHOP: a CRISPR/Cas9 and TALEN web tool for genome editing. Nucleic Acids Res. 42. W401-W407).

As used herein, a "template nucleic acid" refers to a nucleic acid (i.e., a polynucleotide) that is desired to be inserted into a cleavage site within a cell's genome.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a compact TALEN, the recognition sequence comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a compact TALEN produces two basepair 3' overhangs. In the case of a CRISPR nuclease, the recognition sequence is the sequence, typically 16-24 basepairs, to which the guide RNA binds to direct cleavage. Full complementarity between the guide sequence and the recognition sequence is not necessarily required to effect cleavage. Cleavage by a CRISPR nuclease can produce blunt ends (such as by a class 2, type II CRISPR nuclease) or overhanging ends (such as by a class 2, type V CRISPR nuclease), depending on the CRISPR nuclease. In those embodiments wherein a CpfI CRISPR nuclease is utilized, cleavage by the CRISPR complex comprising the same will result in 5' overhangs and in certain embodiments, 5 nucleotide 5' overhangs. Each CRISPR nuclease enzyme also requires the recognition of a PAM (protospacer adjacent motif) sequence that is near the recognition sequence complementary to the guide RNA. The precise sequence, length requirements for the PAM, and distance from the target sequence differ depending on the CRISPR nuclease enzyme, but PAMs are typically 2-5 base pair sequences adjacent to the target/recognition sequence. PAM sequences for particular CRISPR nuclease enzymes are known in the art (see, for example, U.S. Pat. No. 8,697,359 and U.S. Publication No. 20160208243, each of which is incorporated by reference in its entirety) and PAM sequences for novel or engineered CRISPR nuclease enzymes can be identified using methods known in the art, such as a PAM depletion assay (see, for example, Karvelis et al. (2017) Methods 121-122:3-8, which is incorporated herein in its entirety). In the case of a zinc finger, the DNA binding domains typically recognize an 18-bp recognition sequence comprising a pair of nine basepair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a nuclease.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" means the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs but may be degenerate at one or more positions. A highly-specific nuclease is capable of cleaving only one or a very few recognition sequences. Specificity can be determined by any method known in the art.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, the term "disrupted" or "disrupts" or "disrupts expression" or "disrupting a target sequence" refers to the introduction of a mutation (e.g., frameshift mutation) that interferes with the gene function and prevents expression and/or function of the polypeptide/expression product encoded thereby. For example, nuclease-mediated disruption of a gene can result in the expression of a truncated protein and/or expression of a protein that does not retain its wild-type function. Additionally, introduction of a template nucleic acid into a gene can result in no expression of an encoded protein, expression of a truncated protein, and/or expression of a protein that does not retain its wild-type function.

As used herein, the term "chimeric antigen receptor" or "CAR" refers to an engineered receptor that confers or grafts specificity for an antigen onto an immune effector cell (e.g., a human T cell). A chimeric antigen receptor comprises at least an extracellular ligand-binding domain or moiety, a transmembrane domain, and an intracellular domain that comprises one or more signaling domains and/or co-stimulatory domains.

In some embodiments, the extracellular ligand-binding domain or moiety is an antibody, or antibody fragment. In this context, the term "antibody fragment" can refer to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some embodiments, the scFv is attached via a linker sequence. In some embodiments, the scFv is murine, humanized, or fully human.

The extracellular ligand-binding domain of a chimeric antigen receptor can also comprise an autoantigen (see, Payne et al. (2016), Science 353 (6295): 179-184), that can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention. The extracellular ligand-binding domain of a chimeric antigen receptor can also comprise a naturally-occurring ligand for an antigen of interest, or a fragment of a naturally-occurring ligand which retains the ability to bind the antigen of interest.

The intracellular stimulatory domain can include one or more cytoplasmic signaling domains that transmit an activation signal to the T cell following antigen binding. Such cytoplasmic signaling domains can include, without limitation, a CD3 zeta signaling domain.

The intracellular stimulatory domain can also include one or more intracellular co-stimulatory domains that transmit a proliferative and/or cell-survival signal after ligand binding. Such intracellular co-stimulatory domains can be any of those known in the art and can include, without limitation, those co-stimulatory domains disclosed in WO 2018/067697 including, for example, Novel 6. Further examples of co-stimulatory domains can include 4-1BB (CD137), CD27, CD28, CD8, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof.

A chimeric antigen receptor further includes additional structural elements, including a transmembrane domain that is attached to the extracellular ligand-binding domain via a hinge or spacer sequence. The transmembrane domain can be derived from any membrane-bound or transmembrane protein. For example, the transmembrane polypeptide can be a subunit of the T-cell receptor (e.g., an α, β, γ or ζ, polypeptide constituting CD3 complex), IL2 receptor p55 (a chain), p75 (β chain) or γ chain, subunit chain of Fc receptors (e.g., Fcγ receptor III) or CD proteins such as the CD8 alpha chain. In certain examples, the transmembrane domain is a CD8 alpha domain. Alternatively, the transmembrane domain can be synthetic and can comprise predominantly hydrophobic residues such as leucine and valine.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence or may be an entirely synthetic hinge sequence. In particular examples, a hinge domain can comprise a part of a human CD8 alpha chain, FcγRIIIa receptor or IgG1. In certain examples, the hinge region can be a CD8 alpha domain.

As used herein, the terms "exogenous T cell receptor" or "exogenous TCR" refer to a TCR whose sequence is introduced into the genome of an immune cell (e.g., a human T cell) that may or may not endogenously express the TCR. Expression of an exogenous TCR on an immune cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, the term "HLA class I histocompatibility antigen, alpha chain E fusion protein" or "HLA-E fusion protein" refers to a protein comprising an HLA-E protein fused to at least one additional protein that enables expression of the HLA-E protein on the cell-surface. HLA-E proteins can include, for example, an HLA-E-01:01 or HLA-E-01:03 protein (e.g., SEQ ID NO: 118). An HLA-E fusion protein can comprise, for example, an HLA-E protein fused to a beta-2 microglobulin protein (e.g., SEQ ID NO: 119) that enables expression of the HLA-E protein on the cell-surface. In further examples, the HLA-E fusion protein can comprise an HLA-E protein fused to both a beta-2 microglobulin protein and an additional protein that is loaded into the HLA-E protein for presentation such as, for example, an HLA-G leader peptide (e.g., SEQ ID NO: 120) and others known in the art. The proteins of the HLA-E fusion protein can be fused by polypeptide linkers such as, for example, a linker comprising SEQ ID NO: 121 (i.e., a (GGGGS)3 linker) or SEQ ID NO: 122 (i.e., a (GGGGS)4 linker).

As used herein, the term "reduced expression" in reference to a target protein (i.e., an endogenously expressed protein) refers to any reduction in the expression of the endogenous protein by a genetically-modified cell when compared to a control cell. The term reduced can also refer to a reduction in the percentage of cells in a population of cells that express wild-type levels of an endogenous protein targeted by a shRNAmiR of the disclosure when compared to a population of control cells. Such a reduction in the percentage of cells in a population that fully express the targeted endogenous protein may be up to 5%, 10%, 20%, 30%, 40%, 50%, 60%, 70%, 80%, 90%, 95%, 96%, 97%, 98%, 99%, or up to 100%. It is understood in the context of this disclosure that the term "reduced" encompasses a partial or incomplete knockdown of a target or endogenous protein, and is distinguished from a complete knockdown, such as that achieved by gene inactivation by a nuclease.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (see, the website at ncbi.nlm.nih.gov), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "T cell receptor alpha gene" or "TCR alpha gene" refer to the locus in a T cell which encodes the T cell receptor alpha subunit. The T cell receptor alpha gene can refer to NCBI Gene ID number 6955, before or after rearrangement. Following rearrangement, the T cell receptor alpha gene comprises an endogenous promoter, rearranged V and J segments, the endogenous splice donor site, an intron, the endogenous splice acceptor site, and the T cell receptor alpha constant region locus, which comprises the subunit coding exons.

As used herein, the term "T cell receptor alpha constant region" or "TCR alpha constant region" refers to the coding sequence of the T cell receptor alpha gene. The TCR alpha constant region includes the wild-type sequence, and functional variants thereof, identified by NCBI Gene ID NO. 28755.

As used herein, the term "T cell receptor beta gene" or "TCR beta gene" refers to the locus in a T cell which encodes the T cell receptor beta subunit. The T cell receptor beta gene can refer to NCBI Gene ID number 6957.

As used herein, the term "recombinant DNA construct," "recombinant construct," "cassette," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector (i.e., a recombinant virus). Viral vectors can include, without limitation, retroviral vectors (i.e., recombinant retroviruses), lentiviral vectors (i.e., recombinant lentiviruses), adenoviral vectors (i.e., recombinant adenoviruses), and adeno-associated viral vectors (AAV) (i.e., recombinant AAVs).

As used herein, the term "immune cell" refers to any cell that is part of the immune system (innate and/or adaptive) and is of hematopoietic origin. Non-limiting examples of immune cells include lymphocytes, B cells, T cells, monocytes, macrophages, dendritic cells, granulocytes, megakaryocytes, monocytes, macrophages, natural killer cells, myeloid-derived suppressor cells, innate lymphoid cells, platelets, red blood cells, thymocytes, leukocytes, neutrophils, mast cells, eosinophils, basophils, and granulocytes.

As used herein, a "human T cell" or "T cell" or "isolated human T cell" refers to a T cell isolated from a donor, particularly a human donor. T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "human NK cell" or "NK cell" refers to a NK cell isolated from a donor, particularly a human donor. NK cells, and cells derived therefrom, include isolated NK cells that have not been passaged in culture, NK cells that have been passaged and maintained under cell culture conditions without immortalization, and NK cells that have been immortalized and can be maintained under cell culture conditions indefinitely.

As used herein, a "human B cell" or "B cell" refers to a B cell isolated from a donor, particularly a human donor. B cells, and cells derived therefrom, include isolated T cells that have not been passaged in culture, B cells that have been passaged and maintained under cell culture conditions without immortalization, and B cells that have been immortalized and can be maintained under cell culture conditions indefinitely.

As used herein, the term "a control" or "a control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, the terms "treatment" or "treating a subject" refers to the administration of a genetically-modified immune cell or population of genetically-modified immune cells of the invention to a subject having a disease. For example, the subject can have a disease such as cancer, and treatment can represent immunotherapy for the treatment of the disease. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some aspects, a genetically-modified immune cell or population of genetically-modified immune cells described herein is administered during treatment in the form of a pharmaceutical composition of the invention.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of a genetically-modified immune cell or population of genetically-modified immune cells of the invention, or pharmaceutical compositions disclosed herein, reduces at least one symptom of a disease in a subject. In those embodiments wherein the disease is a cancer, an effective amount of the pharmaceutical compositions disclosed herein reduces the level of proliferation or metastasis of cancer, causes a partial or full response or remission of cancer, or reduces at least one symptom of cancer in a subject.

As used herein, the term "cancer" should be understood to encompass any neoplastic disease (whether invasive or metastatic) which is characterized by abnormal and uncontrolled cell division causing malignant growth or tumor.

As used herein, the term "carcinoma" refers to a malignant growth made up of epithelial cells.

As used herein, the term "leukemia" refers to malignancies of the hematopoietic organs/systems and is generally characterized by an abnormal proliferation and development of leukocytes and their precursors in the blood and bone marrow.

As used herein, the term "sarcoma" refers to a tumor which is made up of a substance like the embryonic connective tissue and is generally composed of closely packed cells embedded in a fibrillary, heterogeneous, or homogeneous substance.

As used herein, the term "melanoma" refers to a tumor arising from the melanocytic system of the skin and other organs.

As used herein, the term "lymphoma" refers to a group of blood cell tumors that develop from lymphocytes.

As used herein, the term "blastoma" refers to a type of cancer that is caused by malignancies in precursor cells or blasts (immature or embryonic tissue).

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values and if the variable is inherently continuous.

2.1 Principle of the Invention

The present invention is based, in part, on the discovery that microRNA-adapted shRNA (shRNAmiR) molecules can be used to generate genetically-modified immune cells having a stable reduction in expression of an endogenous protein. It is demonstrated herein that the insertion of a nucleic acid sequence encoding a shRNAmiR into the genome of a T cell provides stable knockdown of a spectrum of endogenous proteins including, for example, the stable and effective knockdown of beta-2 microglobulin (B2M), CS1, transforming growth factor beta receptor II (TGFBR2), Cbl proto-oncogene B (CBL-B), deoxycytidine kinase (DCK), glucocorticoid (GR), and cluster of differentiation 52 (CD52). Knockdown of endogenous proteins can confer properties that, in some instances, can be advantageous compared to knockout by gene inactivation. For example, B2M knockdown by shRNAmiR produces CAR T cells that are less allogeneic and less susceptible to natural killer (NK) cell killing than CAR T cells exhibiting a complete knockout of B2M. Further, it is demonstrated that the incorporation of a shRNAmiR molecule into the genome of an immune cell solves the stability and toxicity problems observed with the insertion of a cassette encoding an shRNA molecule.

Given the demonstration that shRNAmiR molecules can be used to reduce the expression of multiple endogenous proteins, the presently disclosed compositions and methods can be used to stably knockdown the expression at various degrees of not only the B2M protein, but any endogenous protein of interest, within an immune cell.

2.2 MicroRNA-Adapted shRNA (shRNAmiR)

RNA interference (RNAi) or RNA silencing refers to a process by which gene expression is negatively regulated by non-coding RNAs such as microRNAs. The negative regulation can result from one or more of three possible mechanisms: (1) by repressing the translation of target mRNAs, (2) through deadenylation and destabilization of transcripts, and (3) through cleavage and degradation of mRNAs. RNAi is normally triggered by double-stranded RNA (dsRNA) or endogenous microRNA precursors (pri-miRNAs/pre-miRNAs).

The production of endogenous microRNA molecules begins with the transcription of a primary miRNA (pri-mRNA) from an RNA polymerase II (Pol II) promoter. Each pri-miRNA can contain from one to six pre-miRNAs. Pre-miRNAs are hairpin loop structures composed of about 70 nucleotides, with each hairpin being flanked by sequences necessary for efficient processing. The enzyme Drosha liberates hairpins from the pri-miRNAs by cleaving RNA about 11 nucleotides from the hairpin base. Pre-miRNAs that are generated by Drosha cleavage comprise a 2 nucleotide overhang at the 3' end. This 2 nucleotide overhang is bound by the Exportin-5 protein, which mediates export of the pre-miRNA from the nucleus into the cytoplasm. In the cytoplasm, pre-miRNA hairpins are cleaved by Dicer through interactions with the 5' and 3' ends of the hairpin. Dicer cleaves the pre-miRNA hairpin in the loop region to produce an imperfect miRNA:miRNA duplex, which is about 22 nucleotides in length. A single strand of the miRNA:miRNA duplex (mature miRNA) is incorporated into the RNA-induced silencing complex (RISC) where the miRNA and its mRNA target interact.

Since its discovery, RNAi has emerged as a powerful genetic tool for suppressing gene expression in mammalian cells. Gene knockdown can be achieved by expression of synthetic short hairpin RNAs (shRNAs) that mimic pre-miRNAs and are processed by Dicer and fed into the RISC. However, as described herein, shRNAs may not allow for prolonged reduction of protein expression in immune cells. In contrast, expression of the microRNA-adapted shRNA (shRNAmiR) molecules of the present invention result in persistent reduction of protein expression and reduced toxicity effects. The shRNAmiR molecules mimic pri-miRNA molecules in that they comprise a hairpin flanked by sequences necessary for efficient processing, and can be processed by the Drosha enzyme into pri-miRNAs, exported into the cytoplasm, and cleaved by Dicer, after which the mature miRNA can enter the RISC.

The present invention provides genetically-modified immune cells expressing a shRNAmiR molecule that reduces the abundance of an endogenous protein.

The shRNAmiR molecule can comprise a microRNA scaffold in that the structure of the shRNAmiR molecule can mimic that of a naturally-occurring microRNA (or pri-miRNA or pre-miRNA) or a variant thereof. Sequences of microRNAs (and pri-miRNAs and pre-miRNAs) are known in the art. Non-limiting examples of suitable miR scaffolds for the presently disclosed shRNAmiRs include miR-E, miR-30 (e.g., miR-30a), miR-15, miR-16, miR-155, miR-22, miR-103, and miR-107. In particular embodiments, the shRNAmiR used in the presently disclosed compositions and methods comprises a mir-E scaffold. The mir-E scaffold is a synthetically-derived variant of miR-30a and its genesis is described in International Publication No. WO 2014/117050, which is incorporated by reference in its entirety.

The presently disclosed shRNAmiR molecules can comprise the following domains in the 5' to 3' direction: (a) a 5' miR scaffold domain; (b) a 5' miR basal stem domain; (c) a passenger strand; (d) a miR loop domain; (e) a guide strand; (f) a 3' miR basal stem domain; and (g) a 3' miR scaffold domain. The miR scaffold domains and basal stem domains flank the miRNA stem-loop and are referred to herein as microRNA flanking sequences that comprise the microRNA processing elements (the minimal nucleic acid sequences which contribute to the production of mature microRNA from primary microRNA or precursor microRNA). Often these elements are located within a 40 nucleotide sequence that flanks a microRNA stem-loop structure. In some instances, the microRNA processing elements are found within a stretch of nucleotide sequences of between 5 and 4,000 nucleotides in length that flank a microRNA stem-loop structure.

In some embodiments, the miRNA flanking sequences are about 3 to about 4,000 nt in length and can be present on either or both the 5' and 3' ends of the shRNAmiR molecule. In other embodiments, the minimal length of the microRNA flanking sequence of the shRNAmiR molecule is about 10, about 20, about 30, about 40, about 50, about 60, about 70, about 80, about 90, about 100, about 125, about 126, about 127, about 128, about 129, about 130, about 131, about 132, about 133, about 134, about 135, about 136, about 137, about 138, about 139, about 140, about 150, about 200, and any integer therein between. In other embodiments the maximal length of the microRNA flanking sequence of the shRNAmiR molecule is about 2,000, about 2,100, about 2,200, about 2,300, about 2,400, about 2,500, about 2,600, about 2,700, about 2,800, about 2,900, about 3,000, about 3,100, about 3,200, about 3,300, about 3,400, about 3,500, about 3,600, about 3,700, about 3,800, about 3,900, about 4,000, and any integer therein between.

The microRNA flanking sequences may be native microRNA flanking sequences or artificial microRNA flanking sequences. A native microRNA flanking sequence is a nucleotide sequence that is ordinarily comprised within naturally existing systems with microRNA sequences (i.e., these sequences are found within the genomic sequences surrounding the minimal microRNA hairpin in vivo). Artificial microRNA flanking sequences are nucleotides sequences that are not found to be flanking microRNA sequences in naturally existing systems. The artificial microRNA flanking sequences may be flanking sequences found naturally in the context of other microRNA sequences. Alternatively, they may be composed of minimal microRNA processing elements which are found within naturally occurring flanking sequences and inserted into other random nucleic acid sequences that do not naturally occur as flanking sequences or only partially occur as natural flanking sequences.

In some embodiments, the 5' miR scaffold domain is about 10 to about 150 nucleotides in length, including but not limited to about 10, about 20, about 30, about 40, about 50, about 60, about 70, about 80, about 90, about 100, about 110, about 120, about 130, about 140, and about 150 nucleotides long. In some of these embodiments, the 5' miR scaffold domain is about 111 nucleotides in length. The 5' miR scaffold domain may comprise a 3' sequence that is a recognition sequence for a type IIS restriction enzyme. In some of these embodiments, the 5' miR scaffold domain comprises a XhoI recognition sequence on its 3' end. In particular embodiments, the 5' miR scaffold domain has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more sequence identity to the sequence set forth as SEQ ID NO: 1. In certain embodiments, the 5' miR scaffold domain has the sequence set forth as SEQ ID NO: 1.

The 5' miR basal stem domain of the shRNAmiR can be about 5 to about 30 nucleotides in length in some embodiments, including but not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, and about 30 nucleotides long. In some of these embodiments, the 5' miR basal stem domain is about 20 nucleotides in length. In particular embodiments, the 5' miR basal stem domain has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more sequence identity to the sequence set forth as SEQ ID NO: 2. In certain embodiments, the 5' miR basal stem domain has the sequence set forth as SEQ ID NO: 2.

The shRNAmiR molecules of the presently disclosed compositions and methods comprise a stem-loop structure, wherein the stem is comprised of the hybridized passenger and guide strands and the loop is single-stranded. The miR loop domain can be derived from a naturally-occurring pre-microRNA or pri-microRNA loop sequence or a variant thereof. In some embodiments, the miR loop domain has the sequence of a loop domain from any one of miR-30 (e.g., miR-30a), miR-15, miR-16, miR-155, miR-22, miR-103, and miR-107. In particular embodiments, the shRNAmiR comprises a miR-30a loop domain, the sequence of which is set forth as SEQ ID NO: 3.

In certain embodiments, the miR loop domain is about 5 to about 30 nucleotides in length, including but not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, and about 30 nucleotides long. In some of these embodiments, the miR loop domain is about 15 nucleotides in length. In particular embodiments, the miR loop domain has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more sequence identity to the sequence set forth as SEQ ID NO: 3. In certain embodiments, the miR loop domain has the sequence set forth as SEQ ID NO: 3.

The 3' miR basal stem domain of the shRNAmiR can be about 5 to about 30 nucleotides in length in some embodiments, including but not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, and about 30 nucleotides long. In some of these embodiments, the 3' miR basal stem domain is about 18 nucleotides in length. In particular embodiments, the 3' miR basal stem domain has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more sequence identity to the sequence set forth as SEQ ID NO: 4. In certain embodiments, the 3' miR basal stem domain has the sequence set forth as SEQ ID NO: 4.

In some embodiments, the 3' miR scaffold domain is about 50 to about 150 nucleotides in length, including but not limited to about 10, about 20, about 30, about 40, about 50, about 60, about 70, about 80, about 90, about 100, about 110, about 120, about 130, about 140, or about 150 nucleotides long. In some of these embodiments, the 3' miR scaffold domain is about 116 nucleotides in length. In particular embodiments, the 3' miR scaffold domain has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more sequence identity to the sequence set forth as SEQ ID NO: 5. In certain embodiments, the 3' miR scaffold domain has the sequence set forth as SEQ ID NO: 5.

The guide strand of the shRNAmiR is the sequence that targets the mRNA, leading to reduction in abundance of the protein encoded by the mRNA. After the guide strand binds to its target mRNA, RISC either degrades the target transcript and/or prevents the target transcript from being loaded into the ribosome for translation. The guide strand is of sufficient complementarity with the target mRNA in order to lead to reduced expression of the target mRNA. In some embodiments, the guide strand is at least about 50%, at least about 60%, at least about 70%, at least about 80%, at least about 90%, at least about 95%, at least about 97%, at least about 98%, at least about 99% or 100% complementary to the target mRNA sequence. In certain embodiments, the guide strand hybridizes with the target mRNA within a coding sequence. The guide strand can comprise 1, 2, 3, 4, 5, or more mismatching nucleotides with the target mRNA sequence. In other embodiments, the guide strand hybridizes with the target mRNA in a non-coding region, such as a 5' or 3' untranslated region (UTR). In some embodiments, the guide strand is about 15 to about 25 nucleotides in length, including but not limited to about 15, about 16, about 17, about 18, about 19, about 20, about 21, about 22, about 23, about 24, and about 25 nucleotides long. In some of these embodiments, the guide strand is about 22 nucleotides in length. In particular embodiments wherein the shRNA sequence from which the shRNAmiR is derived is less than 22 nucleotides in length, which is the length of most naturally-occurring microRNAs, an additional nucleotide is added to the shRNA sequence and in certain embodiments, this additional nucleotide is one that is complementary with the corresponding position within the target mRNA.

The passenger strand of the shRNAmiR is the sequence that is fully or partially complementary with the guide strand sequence. In some embodiments, the passenger strand is about 15 to about 25 nucleotides in length, including but not limited to about 15 to about 25 nucleotides in length, including but not limited to about 15, about 16, about 17, about 18, about 19, about 20, about 21, about 22, about 23, about 24, and about 25 nucleotides long. In some of these embodiments, the passenger strand is about 22 nucleotides in length. The passenger strand can be at least about 50%, at least about 60%, at least about 70%, at least about 80%, at least about 90%, at least about 95%, at least about 97%, at least about 98%, at least about 99% or 100% complementary to the guide strand sequence. The passenger strand can comprise 1, 2, 3, 4, 5, or more mismatching nucleotides with the guide strand. In certain embodiments, however, the guide:passenger strand duplex does not comprise any mismatching nucleotides. In general, guide/passenger strand sequences should be selected that do not form any secondary structures within themselves. Further, the use of guide/passenger strand sequences that target sites within an mRNA that comprise single-nucleotide polymorphisms should be avoided. Guide/passenger strand sequences that are specific for the target mRNA are preferred to avoid any off-target effects (i.e., reduction in expression of non-target mRNAs).

In order to aid in the selection of suitable shRNAmiR guide/passenger strands, or sequences for other shRNAmiR domains, any program known in the art that models the predicted secondary structure of a RNA molecule can be used, including but not limited to Mfold, RNAfold, and UNAFold. Any program known in the art that can predict the efficiency of a shRNA or miRNA guide/passenger sequence to target a particular mRNA can be used to select suitable guide/passenger strand sequences, including but not limited to those disclosed in Agarwal et al. (2015) eLife 4:e05005; and Knott et al. (2014) Mol Cell 56(6):796-807, each of which is incorporated herein in its entirety.

2.3 Genetically-Modified Immune Cells

The invention provides genetically-modified immune cells and populations thereof and methods for producing the same. In some embodiments, the genetically-modified immune cells of the presently disclosed compositions and methods are human immune cells. In some embodiments, the immune cells are T cells, or cells derived therefrom. In other embodiments, the immune cells are natural killer (NK) cells, or cells derived therefrom. In still other embodiments, the immune cells are B cells, or cells derived therefrom. In yet other embodiments, the immune cells are monocyte or macrophage cells or cells derived therefrom.

Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines, NK cell lines, B cell lines, monocyte cells lines, or macrophage cell lines available in the art may be used. In some embodiments of the present disclosure, immune cells (e.g., T cells) are obtained from a unit of blood collected from a subject using any number of techniques known to the skilled artisan. In one embodiment, cells from the circulating blood of an individual are obtained by apheresis. Immune cells of the invention can also be induced pluripotent stem cell (iPSC)-derived cells that have been differentiated into functional immune cells (e.g., T cells, NK cell, B cells).

The genetically-modified immune cells of the presently disclosed compositions and methods comprise in the cells' genome a nucleic acid sequence encoding a shRNAmiR, leading to the reduction of expression of a target protein.

In some of those embodiments wherein the expression of an endogenous protein is reduced by a shRNAmiR, the expression of the endogenous protein is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a shRNAmiR). Any method known in the art can be used to determine the expression level of an endogenous protein targeted by a shRNAmiR, including but not limited to, ELISA, flow cytometry, Western blot, immunocytochemistry, and immunoprecipitation.

Expressing a shRNAmiR by cells within a population can lead to a reduction in the percentage of cells in the population of cells that fully express the endogenous protein to which the shRNAmiR is targeted when compared to a population of control cells. Such a reduction may be up to 5%, 10%, 20%, 30%, 40%, 50%, 60%, 70%, 80%, 90%, 95%, 96%, 97%, 98%, 99%, or up to 100% of cells in the population.

A nucleic acid sequence encoding a shRNAmiR can be present in the genome of the genetically-modified immune cell, for example, in a cassette. Such cassettes can be inserted into the genome, for example, by introducing a template nucleic acid of the invention either by random integration (e.g., lentiviral transduction) or by targeted insertion into a selected site (e.g., by nuclease-mediated targeted insertion). Cassettes comprising the shRNAmiR-encoding sequence can include, for example, nucleic acid sequences encoding additional proteins, such as those described herein (e.g., CARs, exogenous TCRs, fusion proteins), and may also include control sequences such as promoters and termination sequences. The nucleic acid sequence encoding the shRNAmiR can be positioned at any number of locations within the cassette or template nucleic acid that allow for expression of the shRNAmiR. In some examples, a nucleic acid sequence encoding a shRNAmiR is positioned between the stop codon of another transgene (e.g., a nucleic acid sequence encoding a CAR, exogenous TCR, or fusion protein) and a termination signal. In other examples, another transgene present in the cassette or template nucleic acid (e.g., a nucleic acid sequence encoding a CAR, exogenous TCR, or fusion protein) comprises an intron that is positioned within the transgene sequence. Here, "positioned" is intended to mean that the intron sequence is inserted into the transgene sequence, such that the resulting sequence comprises a 5' portion of the transgene, the intron sequence, and a 3' portion of the transgene. In some such examples, the nucleic acid sequence encoding the shRNAmiR can be positioned within such an intron. Here, "positioned" is intended to mean that the shRNAmiR-encoding sequence is inserted into the intron sequence, such that the resulting sequence comprises a 5' portion of the intron sequence, the shRNAmiR-encoding sequence, and a 3' portion of the intron sequence. In such cases, the shRNAmiR is expressed and the intron sequence is spliced out by the cell when the transgene is expressed. Introns that can be included in this manner can be naturally-occurring introns or, alternatively, synthetic introns. A particular example of a synthetic intron useful for the invention is encoded by SEQ ID NO: 69.

In certain embodiments, the genetically-modified immune cell can further comprise in its genome a nucleic acid sequence encoding a CAR or an exogenous TCR. In some embodiments, the genetically-modified immune cell can further comprise in its genome a nucleic acid sequence encoding an HLA-E fusion protein capable of being expressed on the immune cell surface.

The CAR/TCR-encoding nucleic acid sequence and/or the nucleic acid sequence encoding the HLA-E fusion protein can be located within the same gene as the shRNAmiR-encoding sequence. Alternatively, the CAR/TCR-encoding nucleic acid sequence and/or the nucleic acid sequence encoding the HLA-E fusion protein can be located within a different gene as the shRNAmiR-encoding sequence.

Each of the coding sequences can be operably linked to different promoters. In other embodiments, the shRNAmiR-encoding sequence is operably linked to the same promoter as the nucleic acid sequence encoding the CAR or exogenous TCR and/or the nucleic acid sequence encoding the HLA-E fusion protein. In some specific examples, where a nucleic acid sequence encoding a shRNAmiR, a nucleic acid sequence encoding a CAR or exogenous TCR, and a nucleic acid sequence encoding an HLA-E fusion protein are all located within the same gene, two of the nucleic acid sequences are operably linked to a first promoter, and the third nucleic acid sequence is operably linked to a second promoter. In other specific examples, where a nucleic acid sequence encoding a shRNAmiR, a nucleic acid sequence encoding a CAR or exogenous TCR, and a nucleic acid sequence encoding an HLA-E fusion protein are all located within the same gene, all three of the nucleic acid sequences are operably linked to the same promoter. In various embodiments, the nucleic acid sequences can be operably linked to an endogenous promoter following insertion into the genome. In some such cases, the cassettes or template nucleic acids of the invention may not require an exogenous promoter in order for the encoded sequences to be expressed. Further, in such cases, the cassettes or template nucleic acids may comprise elements (e.g., splice acceptor sequences, 2A or IRES sequences, and the like) necessary for the nucleic acids to be operably linked to the endogenous promoter. In other embodiments, the cassettes or template nucleic acids of the invention comprise one or more exogenous promoters that are operably linked to the nucleic acid sequences and drive expression of the shRNAmiR, CAR or exogenous TCR, and/or HLA-E fusion protein.

Each of the coding sequences can be present in the genome in the same orientation or in different orientations from each other. For example, one coding sequence can be on the plus strand of the double-stranded DNA and another coding sequence on the minus strand. In some embodiments, the shRNAmiR-encoding nucleic acid sequence is 3' downstream of the nucleic acid sequence encoding the CAR or exogenous TCR and/or the nucleic acid sequence encoding the HLA-E fusion protein. In alternative embodiments, the shRNAmiR-encoding sequence is 5' upstream of the CAR/TCR-encoding sequence and/or the nucleic acid sequence encoding the HLA-E fusion protein.

In certain embodiments, nucleic acid sequences, such as those encoding a CAR or exogenous TCR, a shRNAmiR, and/or an HLA-E fusion protein, are operably linked to the same promoter and are separated by any element known in the art to allow for the translation of two or more genes (i.e., cistrons) from the same nucleic acid molecule. Such elements can include, but are not limited to, an IRES element, a T2A element, a P2A element (e.g., P2A/furin), an E2A element, and an F2A element.

In certain embodiments, the genetically-modified immune cell comprises a nucleic acid sequence encoding a cell-surface protein that protects the immune cell from NK cell killing. In some examples, the nucleic acid sequence encodes a non-classical MHC I protein. Non-classical MHC class I proteins can include, without limitation, HLA-E, HLA-F, HLA-G, and HLA-H. In particular examples, the nucleic acid sequence encodes an HLA-E protein. Examples of HLA-E proteins include, without limitation, an HLA-E-01:01 protein or an HLA-E-01:03 protein (e.g., SEQ ID NO: 118). In particular examples of the invention, the nucleic acid sequence encodes a fusion protein comprising a non-classical MHC class I protein (e.g., HLA-E) and at least one additional protein that enables expression of the MHC class I protein on the cell-surface of the immune cell. The fusion protein can comprise, for example, an MHC class I protein (e.g., HLA-E) fused to a beta-2 microglobulin protein (e.g., SEQ ID NO: 119), that enables expression of the MHC class I protein on the cell-surface. In order to inhibit expression of endogenous beta-2 microglobulin, and not expression of a fusion protein that comprises beta-2 microglobulin, the beta-2 microglobulin coding sequence in the fusion protein can be altered (e.g., codon optimized) such that the shRNAmiR does not have specificity for the altered sequence. In further examples, the fusion protein can comprise a non-classical MHC class I protein (e.g., HLA-E) fused to both a beta-2 microglobulin protein and an additional protein that is presented extracellularly by the non-classical MHC. Such additional proteins can include, for example, an HLA-G leader peptide (e.g., SEQ ID NO: 120). The individual proteins of the fusion protein can be fused by polypeptide linkers such as, for example, a linker comprising SEQ ID NO: 121 (i.e., a (GGGGS)3 linker) or SEQ ID NO: 122 (i.e., a (GGGGS)4 linker).

In specific embodiments, the fusion protein is an HLA-E fusion protein comprising an HLA-E protein, a beta-2 microglobulin protein, and an HLA-G leader peptide. In some such embodiments, the HLA-E protein is an HLA-E-01:01 protein or an HLA-E-01:03 protein, and in particular embodiments, the HLA-E protein is an HLA-E-01:03 protein having an amino acid sequence of SEQ ID NO: 118. In some such embodiments, the beta-2 microglobulin protein has an amino acid sequence of SEQ ID NO: 119, and the HLA-G leader peptide has an amino acid sequence of SEQ ID NO: 120. In further such embodiments, the HLA-E protein, the beta-2 microglobulin protein, and the HLA-G leader protein are fused by polypeptide linkers comprising SEQ ID NO: 121 (i.e., a (GGGGS)3 linker) or SEQ ID NO: 122 (i.e., a (GGGGS)4 linker). In a particular embodiment, the fusion protein comprises an amino acid sequence having at least 80%, at least 85%, at least 90%, at least 91%, at least 92%, at least 93%, at least 94%, at least 95%, at least 96%, at least 97%, at least 98%, or up to at least 99% sequence identity to SEQ ID NO: 66. In a specific embodiment, the fusion protein comprises an amino acid sequence of SEQ ID NO: 66.

In certain embodiments, the genetically-modified immune cells comprise a nucleic acid sequence encoding a chimeric antigen receptor (CAR). Generally, a CAR of the present disclosure will comprise at least an extracellular domain, a transmembrane domain, and an intracellular domain. In some embodiments, the extracellular domain comprises a target-specific binding element otherwise referred to as an extracellular ligand-binding domain or moiety. In some embodiments, the intracellular domain, or cytoplasmic domain, comprises at least one co-stimulatory domain and one or more signaling domains.

In some embodiments, a CAR useful in the invention comprises an extracellular ligand-binding domain. The choice of ligand-binding domain depends upon the type and number of ligands that define the surface of a target cell. For example, the ligand-binding domain may be chosen to recognize a ligand that acts as a cell surface marker on target cells associated with a particular disease state. Thus, some examples of cell surface markers that may act as ligands for the ligand-binding domain in a CAR can include those associated with viruses, bacterial and parasitic infections, autoimmune disease, and cancer cells. In some embodiments, a CAR is engineered to target a cancer-specific antigen of interest by way of engineering a desired ligand-binding moiety that specifically binds to an antigen on a cancer (i.e., tumor) cell. In the context of the present disclosure, "cancer antigen," tumor antigen," "cancer-specific antigen," or "tumor-specific antigen" refer to antigens that are common to specific hyperproliferative disorders such as cancer.

In some embodiments, the extracellular ligand-binding domain of the CAR is specific for any antigen or epitope of interest, particularly any tumor antigen or epitope of interest. As non-limiting examples, in some embodiments the antigen of the target is a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD22, CD30, CD40, CD79B, IL1RAP, glypican 3 (GPC3), CLL-1, disialoganglioside GD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-la, p53, prostein, PSMA, surviving and telomerase, prostate-carcinoma tumor antigen-1 (PCTA-1), MAGE, ELF2M, neutrophil elastase, ephrin B2, insulin growth factor (IGF1)-1, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the Al domain of tenascin-C (TnC Al) and fibroblast associated protein (fap); a lineage-specific or tissue specific antigen such as CD3, CD4, CD8, CD24, CD25, CD33, CD34, CD38, CD123, CD133, CD138, CTLA-4, B7-1 (CD80), B7-2 (CD86), endoglin, a major histocompatibility complex (MHC) molecule, BCMA (CD269, TNFRSF 17), CS1, or a virus-specific surface antigen such as an HIV-specific antigen (such as HIV gp120); an EBV-specific antigen, a CMV-specific antigen, a HPV-specific antigen such as the E6 or E7 oncoproteins, a Lasse Virus-specific antigen, an Influenza Virus-specific antigen, as well as any derivate or variant of these surface markers.

In some examples, the extracellular ligand-binding domain or moiety is an antibody, or antibody fragment. An antibody fragment can, for example, be at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some such embodiments, the scFv can comprise a heavy chain variable (VH) domain and a light chain variable (VL) domain from a monoclonal antibody having specificity for an antigen. In some embodiments, the scFv is attached via a linker sequence. In some embodiments, the scFv is murine, humanized, or fully human.

The extracellular ligand-binding domain of a chimeric antigen receptor can also comprise an autoantigen (see, Payne et al. (2016), Science 353 (6295): 179-184), that can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

In some embodiments, the extracellular domain of a chimeric antigen receptor can comprise a naturally-occurring ligand for an antigen of interest, or a fragment of a naturally-occurring ligand which retains the ability to bind the antigen of interest.

A CAR can comprise a transmembrane domain which links the extracellular ligand-binding domain with the intracellular signaling and co-stimulatory domains via a hinge region or spacer sequence. The transmembrane domain can be derived from any membrane-bound or transmembrane protein. For example, the transmembrane polypeptide can be a subunit of the T-cell receptor (e.g., an $\alpha$, $\beta$, $\gamma$ or $\zeta$, polypeptide constituting CD3 complex), IL2 receptor p55 (a chain), p75 ($\beta$ chain) or $\gamma$ chain, subunit chain of Fc receptors (e.g., Fc$\gamma$ receptor III) or CD proteins such as the CD8 alpha chain. In certain examples, the transmembrane domain is a CD8 alpha domain. Alternatively, the transmembrane domain can be synthetic and can comprise predominantly hydrophobic residues such as leucine and valine.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence or may be an entirely synthetic hinge sequence. In particular examples, a hinge domain can comprise a part of a human CD8 alpha chain, Fc$\gamma$RIIIa receptor or IgG1. In certain examples, the hinge region can be a CD8 alpha domain.

Intracellular signaling domains of a CAR are responsible for activation of at least one of the normal effector functions of the cell in which the CAR has been placed and/or activation of proliferative and cell survival pathways. The term "effector function" refers to a specialized function of a cell. Effector function of a T cell, for example, may be cytolytic activity or helper activity including the secretion of cytokines. The intracellular stimulatory domain can include one or more cytoplasmic signaling domains that transmit an activation signal to the T cell following antigen binding. Such cytoplasmic signaling domains can include, without limitation, a CD3 zeta signaling domain.

The intracellular stimulatory domain can also include one or more intracellular co-stimulatory domains that transmit a proliferative and/or cell-survival signal after ligand binding. In some cases, the co-stimulatory domain can comprise one or more TRAF-binding domains. Such intracellular co-stimulatory domains can be any of those known in the art and can include, without limitation, those co-stimulatory domains disclosed in WO 2018/067697 including, for example, Novel 6 ("N6"). Further examples of co-stimulatory domains can include 4-1BB (CD137), CD27, CD28, CD8, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In a particular embodiment, the co-stimulatory domain is an N6 domain. In another particular embodiment, the co-stimulatory domain is a 4-1BB co-stimulatory domain.

In other embodiments, the genetically-modified immune cell comprises a nucleic acid sequence encoding an exogenous T cell receptor (TCR). Such exogenous T cell receptors can comprise alpha and beta chains or, alternatively, may comprise gamma and delta chains. Exogenous TCRs useful in the invention may have specificity to any antigen or epitope of interest such as, without limitation, any antigen or epitope disclosed herein.

In particular embodiments, the CAR or the exogenous TCR can be specific for any type of cancer cell. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin lymphoma. In specific embodiments, cancers and disorders include but are not limited to pre-B ALL (pediatric indication), adult ALL, mantle cell lymphoma, diffuse large B cell lymphoma, salvage post allogenic bone marrow transplantation, and the like. These cancers can be treated using a combination of CARs that target, for example, CD19, CD20, CD22, and/or ROR1. In some non-limiting examples, a genetically-modified immune cell or population thereof of the present disclosure targets carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin lymphoma. In some examples, cancers can include, without limitation, cancers of B cell origin or multiple myeloma. In some examples, the cancer of B cell origin is acute lymphoblastic leukemia (ALL), chronic lymphocytic leukemia (CLL), small lymphocytic lymphoma (SLL), or non-Hodgkin lymphoma (NHL). In some examples, the cancer of B cell origin is mantle cell lymphoma (MCL) or diffuse large B cell lymphoma (DLBCL).

In some embodiments, genetically-modified immune cells of the invention comprise an inactivated TCR alpha gene and/or an inactivated TCR beta gene. Inactivation of the TCR alpha gene and/or TCR beta gene to generate the genetically-modified cells of the present invention occurs in at least one or both alleles where the TCR alpha gene and/or TCR beta gene is being expressed. Accordingly, inactivation of one or both genes prevents expression of the endogenous TCR alpha chain or the endogenous TCR beta chain protein. Expression of these proteins is required for assembly of the endogenous alpha/beta TCR on the cell surface. Thus, inactivation of the TCR alpha gene and/or the TCR beta gene results in genetically-modified immune that have no detectable cell surface expression of the endogenous alpha/beta TCR. The endogenous alpha/beta TCR incorporates CD3. Therefore, cells with an inactivated TCR alpha gene and/or TCR beta chain can have no detectable cell surface expression of CD3. In particular embodiments, the inactivated gene is a TCR alpha constant region (TRAC) gene.

In some examples, the TCR alpha gene, the TRAC gene, or the TCR beta gene is inactivated by insertion of a template nucleic acid into a cleavage site in the gene. Insertion of the template nucleic acid disrupts expression of the endogenous TCR alpha chain or TCR beta chain and, therefore, prevents assembly of an endogenous alpha/beta TCR on the T cell surface. In some examples, the template nucleic acid is inserted into the TRAC gene. In a particular example, a template nucleic acid is inserted into the TRAC gene at an engineered meganuclease recognition sequence comprising SEQ ID NO: 58 (i.e., the TRC 1-2 recognition sequence). In particular examples, the CAR transgene is inserted into SEQ ID NO: 58 between nucleotide positions 13 and 14.

In some of those embodiments wherein the genetically-modified immune cell expresses a CAR or exogenous TCR, such cells have no detectable cell-surface expression of an endogenous T cell receptor (e.g., an alpha/beta T cell receptor). Thus, the invention further provides a population of genetically-modified immune cells that express a shRNAmiR and have no detectable cell-surface expression of an endogenous T cell receptor (e.g., an alpha/beta T cell receptor), and in some embodiments also express a CAR or exogenous TCR. For example, the population can include a plurality of genetically-modified immune cells of the invention which express a CAR (i.e., are CAR+), or an exogenous T cell receptor (i.e., exoTCR+), and have no cell-surface expression of an endogenous T cell receptor (i.e., are TCR−).

As used herein, "detectable cell-surface expression of an endogenous TCR" refers to the ability to detect one or more components of the TCR complex (e.g., an alpha/beta TCR complex) on the cell surface of an immune cell using standard experimental methods. Such methods can include, for example, immunostaining and/or flow cytometry specific for components of the TCR itself, such as a TCR alpha or TCR beta chain, or for components of the assembled cell-surface TCR complex, such as CD3. Methods for detecting cell-surface expression of an endogenous TCR (e.g., an alpha/beta TCR) on an immune cell include those described in the examples herein, and, for example, those described in MacLeod et al. (2017) Molecular Therapy 25(4): 949-961.

2.4 shRNAmiR Target Proteins

The genetically-modified immune cells of the presently disclosed compositions and methods can comprise and express a shRNAmiR that reduces the expression of any endogenous protein. Non-limiting examples of endogenous proteins whose expression can be reduced with a shRNAmiR include beta-2 microglobulin (B2M), transforming growth factor beta receptor 2 (TGFBR2), Cbl proto-oncogene B (CBL-B), CS1, CD52, deoxycytidine kinase (DCK), glucocorticoid receptor (GR), a T cell receptor alpha gene, and a T cell receptor alpha constant region gene.

A. Beta-2 Microglobulin

In some embodiments, the endogenous protein with reduced expression levels as the result of the expression of a shRNAmiR molecule is B2M. B2M is a component of the major histocompatibility complex (MHC) class I molecule, which will not assemble on the cell surface without B2M present. MHC class I molecules are comprised of $\alpha 1$, $\alpha 2$, and $\alpha 3$ proteins, in addition to B2M. Within MHC class I molecules, the B2M protein is situated beside the $\alpha 3$ protein and below the α1 protein on the cell surface. B2M lacks a transmembrane region and is necessary for the stability of the peptide-binding groove of MHC class I molecules.

The shRNAmiR molecule may target any region of a B2M mRNA. Representative B2M mRNA and protein sequences are known in the art. A non-limiting example of a B2M mRNA sequence is NCBI Acc. No. NM_004048.3 and a B2M protein sequence is NCBI Acc. No. NP_004039.1.

In some of those embodiments wherein the expression of B2M is reduced by a shRNAmiR, the cell surface expression of B2M is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a B2M-targeted shRNAmiR).

Given that B2M is necessary for the assembly of the MHC class I molecule on the cell surface, cells with reduced expression of B2M also exhibit a reduction in MHC class I molecules on the cell surface. In some of these embodiments, the expression of MHC class I molecules is reduced on the cell surface by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a B2M-targeted shRNAmiR).

shRNAmiR molecules that target B2M may comprise any passenger and corresponding guide sequence that is complementary (fully or partially) to a sequence within the B2M gene. In some embodiments, the passenger and guide sequence of the shRNAmiR comprise the sequences set forth as SEQ ID NO: 17 and 18, respectively (e.g., B2M 7289 shRNAmiR). In particular embodiments, the passenger and guide sequence of the shRNAmiR comprise the sequences set forth as SEQ ID NO: 7 and 8, respectively (e.g., B2M 7282 shRNAmiR). In other embodiments, the passenger and guide sequence of the shRNAmiR comprise the sequences set forth as SEQ ID NO: 9 and 10, respectively (e.g., B2M 7285 shRNAmiR). In still other embodiments, the passenger and guide sequence of the shRNAmiR comprise the sequences set forth as SEQ ID NO: 11 and 12, respectively (e.g., B2M 7286 shRNAmiR). In yet other embodiments, the passenger and guide sequence of the shRNAmiR comprise the sequences set forth as SEQ ID NO: 13 and 14, respectively (e.g., B2M 7287 shRNAmiR). In particular embodiments, the passenger and guide sequence of the shRNAmiR comprise the sequences set forth as SEQ ID NO: 15 and 16, respectively (e.g., B2M 7288 shRNAmiR). In certain embodiments, the passenger and guide sequence of the shRNAmiR comprise the sequences set forth as SEQ ID NO: 19 and 20, respectively (e.g., B2M 7290 shRNAmiR).

The B2M-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth in any one of SEQ ID NOs: 41-47. In particular embodiments, the shRNAmiR comprises the sequence set forth in any one of SEQ ID NOs: 41-47. In some embodiments, the shRNAmiR comprises the sequence set forth in SEQ ID NO: 41. In some embodiments, the shRNAmiR comprises the sequence set forth in SEQ ID NO: 42. In some embodiments, the shRNAmiR comprises the sequence set forth in SEQ ID NO: 43. In some embodiments, the shRNAmiR comprises the sequence set forth in SEQ ID NO: 44.

In some embodiments, the shRNAmiR comprises the sequence set forth in SEQ ID NO: 45. In some embodiments, the shRNAmiR comprises the sequence set forth in SEQ ID NO: 46. In some embodiments, the shRNAmiR comprises the sequence set forth in SEQ ID NO: 47.

Cells with reduced levels of B2M and WIC class I molecules can exhibit reduced allogenicity compared to a control cell (e.g., a cell not expressing a B2M-targeted shRNAmiR). As used herein, the term "allogenicity" refers to the ability of a cell to be recognized and acted upon by the immune system as "other" or not autologous. Allogenicity can be measured using any method known in the art, including those methods described elsewhere herein wherein the percentage of living cells were quantitated after incubation with primed alloantigen-specific CTLs or NK cells.

B. CS1

In some embodiments, the endogenous protein with reduced expression levels as the result of the expression of a shRNAmiR molecule is CS1 (also known as CCND3 subset 1, CRACC, CD319, and SLAMF7). CS1 is a member of the signaling lymphocyte activating-molecule (SLAM)-related receptor family and is expressed on the surface of normal NK cells, B cells, T cells, dendritic cells, NK-T cells, and monocytes. CS1 is overexpressed by multiple myeloma cells and can serve as an immunotherapeutic target for multiple myeloma.

The shRNAmiR molecule may target any region of a CS1 mRNA. Representative CS1 mRNA and protein sequences are known in the art. A non-limiting example of a CS1 mRNA sequence is NCBI Acc. No. NM_021181 and a CS1 protein sequence is NCBI Acc. No. NP_067004.3.

In some of those embodiments wherein the expression of CS1 is reduced by a shRNAmiR, the cell surface expression of CS1 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a CS1-targeted shRNAmiR).

shRNAmiR molecules that target CS1 may comprise any passenger and corresponding guide sequence that is complementary (fully or partially) to a sequence within the CS1 gene. In some embodiments, the passenger and guide sequence of the shRNAmiR comprise the sequences set forth as SEQ ID NO: 21 and 22, respectively. In some embodiments, the passenger and guide sequence of the shRNAmiR comprise the sequences set forth as SEQ ID NO: 23 and 24, respectively. In some embodiments, the passenger and guide sequence of the shRNAmiR comprise the sequences set forth as SEQ ID NO: 25 and 26, respectively.

The CS1-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth in any one of SEQ ID NOs: 48-50. In particular embodiments, the shRNAmiR comprises the sequence set forth in any one of SEQ ID NOs: 48-50. In some embodiments, the shRNAmiR comprises the sequence set forth in SEQ ID NO: 48. In some embodiments, the shRNAmiR comprises the sequence set forth in SEQ ID NO: 49. In some embodiments, the shRNAmiR comprises the sequence set forth in SEQ ID NO: 50.

In some of the embodiments wherein the genetically-modified cell expresses a shRNAmiR that reduces the expression of CS1, the genetically-modified immune cell comprises a CAR having specificity for CS1. Non-limiting examples of CARs having specificity for CS1 include, without limitation, those described in WO 2014/179759, WO2015121454, and WO 2016/090369.

Cells having the expression of CS1 knocked down via shRNAmiR expression can be less susceptible to fratricide by a genetically-modified immune cell expressing a CAR having specificity for CS1 as compared to a control cell (e.g., a cell not expressing a CS1-targeted shRNAmiR). This is useful when using CAR-expressing cells with specificity for CS1 for the treatment of a disease, such as multiple myeloma, wherein prolonged presence of the CAR-expressing cell and thus, killing of the diseased cells (e.g., multiple myeloma cell) is desired. As used herein, the term "fratricide" refers to the killing of cells by cells of like genotype and/or phenotype. Fratricide by a genetically-modified immune cell expressing a CS1-specific CAR can be measured using any method known in the art, including but not limited to incubation of immune cells expressing the CS1-specific shRNAmiR with immune cells expressing a CS1-specific CAR and quantitating the number of living shRNAmiR-expressing cells.

C. TGFBR2

In some embodiments, the endogenous protein with reduced expression levels as the result of the expression of a shRNAmiR molecule is transforming growth factor beta receptor 2 (TGFBR2). TGFBR2 is a transmembrane receptor that binds transforming growth factor-beta (TGFB). TGFBR2 comprises a serine/threonine protein kinase domain and heterodimerizes with other TGFB receptors.

The shRNAmiR molecule may target any region of a TGFBR2 mRNA. Representative B2M mRNA and protein sequences are known in the art. A non-limiting example of a TGFBR2 mRNA sequence is NM_001024847.2 and a TGFBR2 protein sequence is NCBI Acc. No. NP_001020018.1.

In some of those embodiments wherein the expression of TGFBR2 is reduced by a shRNAmiR, the cell surface expression of TGFBR2 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a TGFBR2-targeted shRNAmiR).

shRNAmiR molecules that target TGFBR2 may comprise any passenger and corresponding guide sequence that is complementary (fully or partially) to a sequence within the TGFBR2 gene. In some embodiments, the passenger and guide sequence of the shRNAmiR comprise the sequences set forth as SEQ ID NO: 27 and 28, respectively (e.g., TGFBR2 721110 shRNAmiR). In other embodiments, the passenger and guide sequence of the shRNAmiR comprise the sequences set forth as SEQ ID NO: 29 and 30, respectively (e.g., TGFBR2 721111 shRNAmiR). In still other embodiments, the passenger and guide sequence of the shRNAmiR comprise the sequences set forth as SEQ ID NO: 31 and 32, respectively (e.g., TGFBR2 721112 shRNAmiR). In yet other embodiments, the passenger and guide sequence of the shRNAmiR comprise the sequences set forth as SEQ ID NO: 33 and 34, respectively (e.g., TGFBR2 721113 shRNAmiR). In particular embodiments, the passenger and guide sequence of the shRNAmiR comprise the sequences set forth as SEQ ID NO: 35 and 36, respectively (e.g., TGFBR2 721114 shRNAmiR).

The TGFBR2-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth in any one of SEQ ID NOs: 51-55. In particular embodiments, the shRNAmiR comprises the sequence set forth in any one of SEQ ID NOs: 51-55. In some embodiments, the shRNAmiR comprises the sequence set forth in SEQ ID NO: 51. In some embodiments, the shRNAmiR comprises the sequence set forth in SEQ ID NO: 52. In some embodiments, the shRNAmiR comprises the sequence set forth in SEQ ID NO: 53. In some embodiments, the shRNAmiR comprises the sequence set forth in SEQ ID NO: 54. In some embodiments, the shRNAmiR comprises the sequence set forth in SEQ ID NO: 55.

In some of the embodiments wherein the genetically-modified immune cell expresses a shRNAmiR that reduces the expression of TGFBR2, the genetically-modified immune cell is less susceptible to immunosuppression by transforming growth factor B1 (TGFB1) compared to a control cell (e.g., an immune cell not expressing a TGFBR2-targeted shRNAmiR). As used herein, the term "immunosuppression" refers to the reduction of the activation or efficacy of the immune system. Immunosuppression by TGFB1 can be measured using any method known in the art, including but not limited to measuring the effects of TGFB1 on T cell differentiation and/or cytokine production.

D. CBL-B

In some embodiments, the endogenous protein with reduced expression levels as the result of the expression of a shRNAmiR molecule is Cbl proto-oncogene B (CBL-B). CBL-B is an E3 ubiquitin ligase that catalyzes the attachment of ubiquitin to a protein, thus targeting the protein for degradation.

The shRNAmiR molecule may target any region of a CBL-B mRNA. Representative CBL-B mRNA and protein sequences are known in the art. A non-limiting example of a CBL-B mRNA sequence is NCBI Acc. No. NM_170662.5 and a CBL-B protein sequence is NCBI Acc. No. NP_733762.2.

In some of those embodiments wherein the expression of CBL-B is reduced by a shRNAmiR, the cell surface expression of CBL-B is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a CBL-B-targeted shRNAmiR).

shRNAmiR molecules that target CBL-B may comprise any passenger and corresponding guide sequence that is complementary (fully or partially) to a sequence within the CBL-B gene.

In some of the embodiments wherein the genetically-modified immune cell expresses a shRNAmiR that reduces the expression of CBL-B, the genetically-modified immune cell is less susceptible to suppression of T cell receptor (TCR) signaling by degradation of downstream signaling proteins compared to a control cell (e.g., an immune cell not expressing a CBL-B-targeted shRNAmiR). CBL proteins regulates the turnover of p85 (a regulatory subunit of PI3K), phospholipase C-g, and tyrosine kinases, such as Lck, Fyn, and ZAP70, all of which are involved in TCR signaling (Lee et al. (2003) Science 302:1218-1222). Susceptibility to suppression of TCR signaling by degradation of downstream signaling proteins can be measured using any method known in the art, including but not limited to ELISA, flow cytometry, Western blot, immunocytochemistry, and immunoprecipitation.

E. CD52

In some embodiments, the endogenous protein with reduced expression levels as the result of the expression of a shRNAmiR molecule is CD52 (cluster of differentiation 52), which is also known as CAmPATH-1 antigen. CD52 is a glycoprotein present on the surface of mature lymphocytes and on monocytes and dendritic cells. Soluble CD52 molecules interact with sialic acid-binding immunoglobulin-like lectin 10 (Siglec10) to inhibit T cell proliferation and activation (Zhao et al. (2017) *Inflamm Res* 66(7):571-578).

The shRNAmiR molecule may target any region of a CD52 mRNA. Representative CD52 mRNA and protein sequences are known in the art. A non-limiting example of a CD52 mRNA sequence is NCBI Acc. No. NM_001803.3 and a CD52 protein sequence is NCBI Acc. No. NP_001794.2.

In some of those embodiments wherein the expression of CD52 is reduced by a shRNAmiR, the cell surface expression of CD52 is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a CD52-targeted shRNAmiR).

shRNAmiR molecules that target CD52 may comprise any passenger and corresponding guide sequence that is complementary (fully or partially) to a sequence within the CD52 gene. In some embodiments, the passenger and guide sequence of the shRNAmiR comprise the sequences set forth as SEQ ID NO: 37 and 38, respectively (e.g., CD52 72123 shRNAmiR). In other embodiments, the passenger and guide sequence of the shRNAmiR comprise the sequences set forth as SEQ ID NO: 39 and 40, respectively (e.g., CD52 72124 shRNAmiR).

The CD52-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth as SEQ ID NO: 56 or 57. In particular embodiments, the shRNAmiR comprises the sequence set forth as SEQ ID NO: 56 or 57. In some embodiments, the shRNAmiR comprises the sequence set forth in SEQ ID NO: 56. In some embodiments, the shRNAmiR comprises the sequence set forth in SEQ ID NO: 57.

In some of the embodiments wherein the genetically-modified immune cell expresses a shRNAmiR that reduces the expression of CD52, the genetically-modified immune cell is less susceptible to CD52 antibody-induced cell death.

F. Deoxycytidine Kinase (DCK)

In some embodiments, the endogenous protein with reduced expression levels as the result of the expression of a shRNAmiR molecule is deoxycytidine kinase (DCK). DCK predominantly phosphorylates deoxycytidine and converts it into deoxycytidine monophosphate.

The shRNAmiR molecule may target any region of a DCK mRNA. Representative DCK mRNA and protein sequences are known in the art. A non-limiting example of a DCK mRNA sequence is NCBI Acc. No. NM_000788.3 and a DCK protein sequence is NCBI Acc. No. NP_000779.1.

In some of those embodiments wherein the expression of DCK is reduced by a shRNAmiR, the cell surface expression of DCK is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a DCK-targeted shRNAmiR).

shRNAmiR molecules that target DCK may comprise any passenger and corresponding guide sequence that is complementary (fully or partially) to a sequence within the DCK gene. In some embodiments, the passenger and guide sequence of the shRNAmiR comprise the sequences set forth as SEQ ID NO: 76 and 77, respectively (e.g., DCK 72136 shRNAmiR). In other embodiments, the passenger and guide sequence of the shRNAmiR comprise the sequences set forth as SEQ ID NO: 78 and 79, respectively (e.g., DCK 72137 shRNAmiR). In other embodiments, the passenger and guide sequence of the shRNAmiR comprise the sequences set forth as SEQ ID NO: 80 and 81, respectively (e.g., DCK 72138 shRNAmiR). In other embodiments, the passenger and guide sequence of the shRNAmiR comprise the sequences set forth as SEQ ID NO: 82 and 83, respectively (e.g., DCK 72139 shRNAmiR). In other embodiments, the passenger and guide sequence of the shRNAmiR comprise the sequences set forth as SEQ ID NO: 84 and 85, respectively (e.g., DCK 72140 shRNAmiR).

The DCK-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth in any one of SEQ ID NOs: 86-90. In particular embodiments, the shRNAmiR comprises the sequence set forth in any one of SEQ ID NOs: 86-90. In some embodiments, the shRNAmiR comprises the sequence set forth in SEQ ID NO: 86. In some embodiments, the shRNAmiR comprises the sequence set forth in SEQ ID NO: 87. In some embodiments, the shRNAmiR comprises the sequence set forth in SEQ ID NO: 88. In some embodiments, the shRNAmiR comprises the sequence set forth in SEQ ID NO: 89. In some embodiments, the shRNAmiR comprises the sequence set forth in SEQ ID NO: 90.

In some of the embodiments wherein the genetically-modified immune cell expresses a shRNAmiR that reduces the expression of DCK, the genetically-modified immune cell is less susceptible to effects of purine nucleoside analogs (e.g., fludarabine) on cell proliferation. Indeed, genetically-modified immune cells having reduced expression of DCK can be enriched by incubation of a cell population with a purine nucleoside analog such as fludarabine. Further, genetically-modified immune cells (e.g., CAR T cells) having reduced expression of DCK may have greater persistence in vivo during immunotherapy when a purine nucleoside analog such as fludarabine is administered during the course of therapy.

G. Glucocorticoid Receptor (GR)

In some embodiments, the endogenous protein with reduced expression levels as the result of the expression of a shRNAmiR molecule is glucocorticoid receptor (GR). Binding of glucocorticoids, such as cortisol or dexamethasone, can induce the release of protein, such as heat shock proteins, that can lead to transactivation or transrepression in the cell.

The shRNAmiR molecule may target any region of a GR mRNA. Representative GR mRNA and protein sequences are known in the art. A non-limiting example of a GR mRNA sequence is NCBI Acc. No. AM183262.1.

In some of those embodiments wherein the expression of GR is reduced by a shRNAmiR, the expression of GR is reduced by at least about 10%, about 20%, about 30%, about 40%, about 50%, about 55%, about 60%, about 65%, about 70%, about 75%, about 80%, about 85%, about 90%, about 95%, or up to about 99% compared to a control cell (e.g., a cell not expressing a GR-targeted shRNAmiR).

shRNAmiR molecules that target GR may comprise any passenger and corresponding guide sequence that is complementary (fully or partially) to a sequence within the GR gene. In some embodiments, the passenger and guide sequence of the shRNAmiR comprise the sequences set forth as SEQ ID NO: 91 and 92, respectively (e.g., GR 72142 shRNAmiR). In other embodiments, the passenger and guide sequence of the shRNAmiR comprise the sequences set forth as SEQ ID NO: 93 and 94, respectively (e.g., GR 72143 shRNAmiR). In other embodiments, the passenger and guide sequence of the shRNAmiR comprise the sequences set forth as SEQ ID NO: 95 and 96, respectively (e.g., GR 72145 shRNAmiR). In other embodiments, the passenger and guide sequence of the shRNAmiR comprise the sequences set forth as SEQ ID NO: 97 and 98, respectively (e.g., GR 72146 shRNAmiR). In other embodiments, the passenger and guide sequence of the shRNAmiR comprise the sequences set forth as SEQ ID NO: 99 and 100, respectively (e.g., GR 72148 shRNAmiR). In other embodiments, the passenger and guide sequence of the shRNAmiR comprise the sequences set forth as SEQ ID NO: 101 and 102, respectively (e.g., GR 72149 shRNAmiR). In other embodiments, the passenger and guide sequence of the shRNAmiR comprise the sequences set forth as SEQ ID NO: 103 and 104, respectively (e.g., GR 72150 shRNAmiR). In other embodiments, the passenger and guide sequence of the shRNAmiR comprise the sequences set forth as SEQ ID NO: 105 and 106, respectively (e.g., GR 72151 shRNAmiR). In other embodiments, the passenger and guide sequence of the shRNAmiR comprise the sequences set forth as SEQ ID NO: 107 and 108, respectively (e.g., GR 72152 shRNAmiR).

The GR-targeted shRNAmiR may comprise a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more sequence identity to the nucleic acid sequence set forth in any one of SEQ ID NOs: 109-117. In particular embodiments, the shRNAmiR comprises the sequence set forth in any one of SEQ ID NOs: 109-117. In some embodiments, the shRNAmiR comprises the sequence set forth in SEQ ID NO: 109. In some embodiments, the shRNAmiR comprises the sequence set forth in SEQ ID NO: 110. In some embodiments, the shRNAmiR comprises the sequence set forth in SEQ ID NO: 111. In some embodiments, the shRNAmiR comprises the sequence set forth in SEQ ID NO: 112. In some embodiments, the shRNAmiR comprises the sequence set forth in SEQ ID NO: 113. In some embodiments, the shRNAmiR comprises the sequence set forth in SEQ ID NO: 114. In some embodiments, the shRNAmiR comprises the sequence set forth in SEQ ID NO: 115. In some embodiments, the shRNAmiR comprises the sequence set forth in SEQ ID NO: 116. In some embodiments, the shRNAmiR comprises the sequence set forth in SEQ ID NO: 117.

In some of the embodiments wherein the genetically-modified immune cell expresses a shRNAmiR that reduces the expression of GR, the genetically-modified immune cell is less susceptible to effects of glucocorticoids, such as cortisol or dexamethasone, such as reduced proliferation. Indeed, genetically-modified immune cells having reduced expression of GR can be enriched by incubation of a cell population with a glucocorticoid. Further, genetically-modified immune cells (e.g., CAR T cells) having reduced expression of GR may have greater persistence in vivo during immunotherapy when a glucocorticoid (e.g., steroid) is administered during the course of therapy.

2.5 Methods for Reducing Expression of Endogenous Proteins

The present invention provides methods for reducing the expression of an endogenous protein in an immune cell by introducing into the cell a template nucleic acid comprising a nucleic acid sequence encoding a shRNAmiR, whereby the template nucleic acid is inserted into the genome and expressed.

The template nucleic acid can be inserted into the genome of the immune cell by random integration. Alternatively, the template nucleic acid can be inserted into a target gene by nuclease-mediated targeted insertion, wherein an engineered nuclease has specificity for a recognition sequence in the genome of the immune cell and generates a cleavage site at the recognition sequence, allowing for the insertion of the template nucleic acid into the genome of the immune cell at the cleavage site.

Any engineered nuclease can be used for targeted insertion of the template nucleic acid, including an engineered meganuclease, a zinc finger nuclease, a TALEN, a compact TALEN, a CRISPR system nuclease, or a megaTAL.

For example, zinc-finger nucleases (ZFNs) can be engineered to recognize and cut pre-determined sites in a genome. ZFNs are chimeric proteins comprising a zinc finger DNA-binding domain fused to a nuclease domain from an endonuclease or exonuclease (e.g., Type IIs restriction endonuclease, such as the FokI restriction enzyme). The zinc finger domain can be a native sequence or can be redesigned through rational or experimental means to produce a protein which binds to a pre-determined DNA sequence ~18 basepairs in length. By fusing this engineered protein domain to the nuclease domain, it is possible to target DNA breaks with genome-level specificity. ZFNs have been used extensively to target gene addition, removal, and substitution in a wide range of eukaryotic organisms (reviewed in S. Durai et al., *Nucleic Acids Res* 33, 5978 (2005)).

Likewise, TAL-effector nucleases (TALEN5) can be generated to cleave specific sites in genomic DNA. Like a ZFN, a TALEN comprises an engineered, site-specific DNA-binding domain fused to an endonuclease or exonuclease (e.g., Type IIs restriction endonuclease, such as the FokI restriction enzyme) (reviewed in Mak, et al. (2013) *Curr Opin Struct Biol.* 23:93-9). In this case, however, the DNA binding domain comprises a tandem array of TAL-effector domains, each of which specifically recognizes a single DNA basepair.

Compact TALENs are an alternative endonuclease architecture that avoids the need for dimerization (Beurdeley, et al. (2013) *Nat Commun.* 4:1762). A Compact TALEN comprises an engineered, site-specific TAL-effector DNA-binding domain fused to the nuclease domain from the I-TeeI homing endonuclease or any of the endonucleases listed in Table 2 in U.S. Application No. 20130117869. Compact TALENs do not require dimerization for DNA processing activity, so a Compact TALEN is functional as a monomer.

Engineered endonucleases based on the CRISPR/Cas system are also known in the art (Ran, et al. (2013) *Nat Protoc.* 8:2281-2308; Mali et al. (2013) *Nat Methods.* 10:957-63). A CRISPR system comprises two components: (1) a CRISPR nuclease; and (2) a short "guide RNA" comprising a ~20 nucleotide targeting sequence that directs the nuclease to a location of interest in the genome. The CRISPR system may also comprise a tracrRNA. By expressing multiple guide RNAs in the same cell, each having a different targeting sequence, it is possible to target DNA breaks simultaneously to multiple sites in the genome.

Engineered meganucleases that bind double-stranded DNA at a recognition sequence that is greater than 12 base pairs can be used for the presently disclosed methods. A meganuclease can be an endonuclease that is derived from I-CreI and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker.

Nucleases referred to as megaTALs are single-chain endonucleases comprising a transcription activator-like effector (TALE) DNA binding domain with an engineered, sequence-specific homing endonuclease.

In particular embodiments, the recognition sequence of the engineered nuclease is within a target gene. The target gene can be any gene in which the sequence is desired to be altered (e.g., addition or subtraction of nucleotide, substitution of nucleotide, or insertion of a heterologous or exogenous sequence). For example, knockout of a target gene by genetic inactivation may be desired. In some embodiments, the target gene is a TCR alpha gene or a TCR beta gene. In particular embodiments, the target gene can be the TCR alpha constant region (TRAC) gene. In some specific embodiments, the target gene is the TRAC gene and the recognition sequence is the TRC 1-2 recognition sequence set forth in SEQ ID NO: 58.

In some of these embodiments, the insertion of the template nucleic acid into the target gene leads to disruption of expression of the full-length endogenous protein encoded by the target gene. Thus, in some of those embodiments wherein the target gene is a TCR alpha gene, TRAC gene, or TCR beta gene, the genetically-modified immune cell does not have detectable cell-surface expression of an endogenous TCR, such as an alpha/beta TCR, because the endogenous TCR will not properly assemble at the cell surface in the absence of the endogenous proteins encoded by these genes.

In particular embodiments in which the genetically-modified immune cell does not have detectable cell-surface expression of an endogenous TCR (e.g., an alpha/beta TCR) due to inactivation of a gene encoding a component of an alpha/beta TCR, the genetically-modified immune cell further expresses a CAR or exogenous TCR and/or an HLA-E fusion protein. The CAR or exogenous TCR and/or the HLA-E fusion protein can be encoded by sequences comprised within the template nucleic acid. In some of these embodiments, the CAR/TCR-encoding sequence and/or the HLA-E fusion protein-encoding sequence is operably linked to a different promoter than the shRNAmiR-encoding sequence. In alternative embodiments, the CAR/TCR-encoding sequence and/or the HLA-E fusion protein-encoding sequence is operably linked to the same promoter, or to a different promoter, as the shRNAmiR-encoding sequence. The CAR/TCR-encoding sequence and/or the HLA-E fusion protein-encoding sequence can be 5' or 3' of the shRNAmiR-encoding sequence, and the coding sequences can be in the same or different orientation, such as 5' to 3' or 3' to 5'. Further, the coding sequences may be separated by an element known in the art to allow for the translation of two or more genes (i.e., cistrons) from the same nucleic acid molecule including, but not limited to, an IRES element, a T2A element, a P2A element (e.g., a P2A/furin), an E2A element, and an F2A element.

The use of nucleases for disrupting expression of an endogenous TCR has been disclosed, including the use of zinc finger nucleases (ZFNs), transcription activator-like effector nucleases (TALEN5), megaTALs, and CRISPR systems (e.g., Osborn et al. (2016), Molecular Therapy 24(3): 570-581; Eyquem et al. (2017), Nature 543: 113-117; U.S. Pat. No. 8,956,828; U.S. Publication No. US2014/0301990; U.S. Publication No. US2012/0321667). The specific use of engineered meganucleases for cleaving DNA targets in the human TRAC gene has also been previously disclosed. For example, International Publication No. WO 2014/191527, which disclosed variants of the I-OnuI meganuclease that were engineered to target a recognition sequence within exon 1 of the TCR alpha constant region gene.

Moreover, in International Publication Nos. WO 2017/062439 and WO 2017/062451, Applicants disclosed engineered meganucleases which have specificity for recognition sequences in exon 1 of the TCR alpha constant region (TRAC) gene. These included "TRC 1-2 meganucleases" which have specificity for the TRC 1-2 recognition sequence (SEQ ID NO: 58) in exon 1 of the TRAC gene. The '439 and '451 publications also disclosed methods for targeted insertion of a CAR coding sequence or an exogenous TCR coding sequence into the TRC 1-2 meganuclease cleavage site.

In particular embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

Engineered nucleases can be delivered into a cell in the form of protein or, preferably, as a nucleic acid encoding the engineered nuclease. Such nucleic acids can be DNA (e.g., circular or linearized plasmid DNA or PCR products) or RNA (e.g., mRNA). For embodiments in which the engineered nuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804):304-10) as well as inducible promoters such as the tetracycline-inducible promoter (Dingermann et al. (1992), Mol Cell Biol. 12(9):4038-45). A nucleic acid encoding an engineered nuclease can also be operably linked to a synthetic promoter. Synthetic promoters can include, without limitation, the JeT promoter (WO 2002/012514).

In certain embodiments, a nucleic acid sequence encoding an engineered nuclease is delivered on a recombinant DNA construct or expression cassette. For example, the recombinant DNA construct can comprise an expression cassette (i.e., "cassette") comprising a promoter and a nucleic acid sequence encoding an engineered nuclease described herein.

In some embodiments, mRNA encoding the engineered nuclease is delivered to the cell because this reduces the likelihood that the gene encoding the engineered nuclease will integrate into the genome of the cell.

The mRNA encoding an engineered nuclease can be produced using methods known in the art such as in vitro transcription. In some embodiments, the mRNA comprises a modified 5' cap. Such modified 5' caps are known in the art and can include, without limitation, an anti-reverse cap analogs (ARCA) (U57074596), 7-methyl-guanosine, CLEANCAP reverse cap analogs, such as Cap 1 analogs (Trilink; San Diego, CA), or enzymatically capped using, for example, a vaccinia capping enzyme or the like. In some embodiments, the mRNA may be polyadenylated. The mRNA may contain various 5' and 3' untranslated sequence elements to enhance expression of the encoded engineered nuclease and/or stability of the mRNA itself. Such elements can include, for example, posttranslational regulatory elements such as a woodchuck hepatitis virus posttranslational regulatory element.

The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In another particular embodiment, a nucleic acid encoding an engineered nuclease can be introduced into the cell using a single-stranded DNA template. The single-stranded DNA can further comprise a 5' and/or a 3' AAV inverted terminal repeat (ITR) upstream and/or downstream of the sequence encoding the engineered nuclease. In other embodiments, the single-stranded DNA can further comprise a 5' and/or a 3' homology arm upstream and/or downstream of the sequence encoding the engineered nuclease.

In another particular embodiment, genes encoding a nuclease can be introduced into a cell using a linearized DNA template. In some examples, a plasmid DNA encoding a nuclease can be digested by one or more restriction enzymes such that the circular plasmid DNA is linearized prior to being introduced into a cell.

Purified nuclease proteins can be delivered into cells to cleave genomic DNA, which allows for homologous recombination or non-homologous end-joining at the cleavage site with a sequence of interest, by a variety of different mechanisms known in the art, including those further detailed herein below.

In some embodiments, nuclease proteins, or DNA/mRNA encoding the nuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706), and HSV-1 VP-22 (Deshayes et al. (2005) Cell Mol Life Sci. 62:1839-49). In an alternative embodiment, nuclease proteins, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, nuclease protein/DNA/mRNA can be coupled covalently or non-covalently to the natural ligand (or a portion of the natural ligand) for such a cell-surface receptor. (McCall, et al. (2014) Tissue Barriers. 2(4):e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, nuclease proteins, or DNA/mRNA encoding nucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 µm, preferably <100 nm. Such nanoparticles may be designed using a core composed of metal, lipid, polymer, or biological macromolecule, and multiple copies of the nuclease proteins, mRNA, or DNA can be attached to or encapsulated with the nanoparticle core. This increases the copy number of the protein/mRNA/DNA that is delivered to each cell and, so, increases the intracellular expression of each nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the nuclease proteins or DNA/mRNA encoding the nucleases are encapsulated within liposomes or complexed using cationic lipids (see, e.g., Lipofectamine™, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, and facilitate cellular uptake and delivery efficiency through fusion with and/or disruption of the cellular membranes of the target cells.

In some embodiments, nuclease proteins, or DNA/mRNA encoding nucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, nuclease proteins, or DNA/mRNA encoding recombinant nucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, nuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-inwater-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, nuclease proteins, or DNA/mRNA encoding nucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding a nuclease are delivered using a viral vector (i.e., a recombinant virus). Such vectors are known in the art and include retroviral vectors, lentiviral vectors, adenoviral vectors, and adeno-associated virus (AAV) vectors (reviewed in Vannucci, et al. (2013 New Microbiol. 36:1-22). Recombinant AAV vectors useful in the invention can have any serotype that allows for transduction of the virus into the cell and insertion of the nuclease gene into the cell genome. In particular embodiments, recombinant AAV vectors have a serotype of AAV2 or AAV6. AAV vectors can also be self-complementary such that they do not require second-strand DNA synthesis in the host cell (McCarty, et al. (2001) Gene Ther. 8:1248-54). Polynucleotides delivered by recombinant AAV vectors, including those that deliver a template nucleic acid disclosed herein, can include left (5') and right (3') inverted terminal repeats.

If the nuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, nuclease genes are operably linked to a promoter that drives gene expression preferentially in the target cell (e.g., a T cell).

The CAR/TCR coding sequence and/or the HLA-E fusion protein coding sequence can further comprise additional control sequences. For example, the sequence can include homologous recombination enhancer sequences, Kozak sequences, polyadenylation sequences, transcriptional termination sequences, selectable marker sequences (e.g., antibiotic resistance genes), origins of replication, and the like. Sequences encoding engineered nucleases can also include at least one nuclear localization signal. Examples of nuclear localization signals are known in the art (see, e.g., Lange et al., *J. Biol. Chem.*, 2007, 282:5101-5105).

The invention further provides for the introduction of a template nucleic acid into a target gene. In some embodiments, the template nucleic acid comprises a 5' homology arm and a 3' homology arm flanking the elements of the insert. Such homology arms have sequence homology to corresponding sequences 5' upstream and 3' downstream of the nuclease recognition sequence where a cleavage site is produced. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

A template nucleic acid disclosed herein (e.g., encoding a shRNAmiR, a nucleic acid encoding a CAR or exogenous TCR, and/or an HLA-E fusion protein), can be introduced into the cell by any of the means previously discussed. In a particular embodiment, the template nucleic acid is introduced by way of a viral vector (i.e., a recombinant virus), such as a recombinant lentivirus, a recombinant retrovirus, a recombinant adenovirus, or preferably a recombinant AAV vector (i.e., a recombinant AAV). Recombinant AAV vectors useful for introducing an exogenous nucleic acid (e.g., a template nucleic acid) can have any serotype that allows for transduction of the virus into the cell and insertion of the exogenous nucleic acid sequence into the cell genome. In particular embodiments, the recombinant AAV vectors have a serotype of AAV2 or AAV6. The recombinant AAV vectors can also be self-complementary such that they do not require second-strand DNA synthesis in the host cell.

In another particular embodiment, the template nucleic acid disclosed herein (e.g., encoding a shRNAmiR, a nucleic acid encoding a CAR or exogenous TCR, and/or an HLA-E fusion protein), can be introduced into the cell using a single-stranded DNA template. The single-stranded DNA can comprise the exogenous sequence of interest and, in preferred embodiments, can comprise 5' and 3' homology arms to promote insertion of the nucleic acid sequence into the meganuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, the template nucleic acid disclosed herein (e.g., encoding a shRNAmiR, a nucleic acid encoding a CAR or exogenous TCR, and/or an HLA-E fusion protein) can be introduced into the cell by transfection with a linearized DNA template. In some examples, a plasmid DNA can be digested by one or more restriction enzymes such that the circular plasmid DNA is linearized prior to transfection into the cell.

Immune cells (e.g., T cells) modified by the present invention may require activation prior to introduction of a nuclease and/or an exogenous sequence of interest. For example, T cells can be contacted with anti-CD3 and anti-CD28 antibodies that are soluble or conjugated to a support (i.e., beads) for a period of time sufficient to activate the cells.

Genetically-modified immune cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic pro-drug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEnd10-binding epitope. For such a gene, Rituximab can be administered to a subject to induce cell depletion when needed. In further examples, a suicide gene may include a QBEnd10-binding epitope expressed in combination with a truncated EGFR polypeptide.

Variants of naturally-occurring nucleases and microRNA sequences (including pre-miRNA and pri-miRNA sequences) can be used in the presently disclosed compositions and methods. As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein. Such variants may result, for example, from human manipulation. Biologically active variants of a native polypeptide will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, as determined by sequence alignment programs and parameters described elsewhere herein. A biologically active variant of a polypeptide may differ from that polypeptide or subunit by as few as about 1-40 amino acid residues, as few as about 1-20, as few as about 1-10, as few as about 5, as few as 4, 3, 2, or even 1 amino acid residue.

The polypeptides may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a polypeptide or RNA. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its biological activity.

2.6 Pharmaceutical Compositions

In some embodiments, the invention provides a pharmaceutical composition comprising a genetically-modified immune cell of the invention, or a population of genetically-modified immune cells of the invention, and a pharmaceutically-acceptable carrier. Such pharmaceutical compositions can be prepared in accordance with known techniques. See, e.g., Remington, The Science and Practice of Pharmacy (21st ed. 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, pharmaceutical compositions of the invention can further include biological molecules, such as cytokines (e.g., IL-2, IL-7, IL-15, and/or IL-21), which promote in vivo cell proliferation and engraftment of genetically-modified T cells. Pharmaceutical compositions comprising genetically-modified immune cells of the invention can be administered in the same composition as an additional agent or biological molecule or, alternatively, can be co-administered in separate compositions.

The present disclosure also provides genetically-modified immune cells, or populations thereof, described herein for use as a medicament. The present disclosure further provides the use of genetically-modified immune cells or populations thereof described herein in the manufacture of a medicament for treating a disease in a subject in need thereof. In one such aspect, the medicament is useful for cancer immunotherapy in subjects in need thereof.

Pharmaceutical compositions of the invention can be useful for treating any disease state that can be targeted by adoptive immunotherapy, and particularly T cell adoptive immunotherapy. In a particular embodiment, the pharmaceutical compositions and medicaments of the invention are useful in the treatment of cancer. Non-limiting examples of cancers which may be treated with the pharmaceutical compositions and medicaments of the present disclosure include, without limitation, various types of cancers described herein that can be targeted by a CAR or exogenous TCR.

In some of these embodiments wherein cancer is treated with the presently disclosed genetically-modified immune cells or populations thereof, the subject administered the genetically-modified immune cells or populations thereof is further administered an additional therapeutic, such as radiation, surgery, or a chemotherapeutic agent.

The invention further provides a population of genetically-modified immune cells comprising a plurality of genetically-modified immune cells described herein, which comprise in their genome a nucleic acid sequence encoding a shRNAmiR, wherein the exogenous nucleic acid molecule encoding the shRNAmiR can be inserted into a target gene, such as the TCR alpha gene or the TRAC gene, such that the cell has no detectable cell-surface expression of an endogenous TCR (e.g., an alpha/beta TCR). Thus, in various embodiments of the invention, a population of immune cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified immune cell described herein. In some embodiments of the invention, a population of immune cells is provided wherein about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or up to 100%, of cells in the population are a genetically-modified immune cell described herein. In further embodiments of the invention, a population of immune cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified immune cell described herein which further expresses a CAR or exogenous TCR and/or further expresses an HLA-E fusion protein. In certain embodiments of the invention, a population of immune cells is provided wherein about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or up to 100%, of cells in the population are a genetically-modified immune cell described herein which further expresses a CAR or exogenous TCR and/or an HLA-E fusion protein.

2.7 Methods of Administering Genetically-Modified Immune Cells

Another aspect disclosed herein is the administration of an effective amount of the genetically-modified immune cells, or populations thereof, of the present disclosure to a subject in need thereof. In particular embodiments, the pharmaceutical compositions described herein are administered to a subject in need thereof. For example, an effective amount of a population of cells can be administered to a subject having a disease. In particular embodiments, the disease can be cancer, and administration of the genetically-modified immune cells of the invention represent an immunotherapy. The administered cells are able to reduce the proliferation, reduce the number, or kill target cells in the recipient. Unlike antibody therapies, genetically-modified immune cells of the present disclosure are able to replicate and expand in vivo, resulting in long-term persistence that can lead to sustained control of a disease.

Examples of possible routes of administration include parenteral, (e.g., intravenous (IV), intramuscular (IM), intradermal, subcutaneous (SC), or infusion) administration. Moreover, the administration may be by continuous infusion or by single or multiple boluses. In specific embodiments, the agent is infused over a period of less than about 12 hours, 6 hours, 4 hours, 3 hours, 2 hours, or 1 hour. In still other embodiments, the infusion occurs slowly at first and then is increased over time.

In some embodiments, a genetically-modified immune cell or population thereof of the present disclosure targets a tumor antigen for the purposes of treating cancer. Such cancers can include, without limitation, various types of cancers described herein that can be targeted by a CAR or exogenous TCR.

When an "effective amount" or "therapeutic amount" is indicated, the precise amount to be administered can be determined by a physician with consideration of individual differences in age, weight, tumor size (if present), extent of infection or metastasis, and condition of the patient (subject). In some embodiments, a pharmaceutical composition comprising the genetically-modified immune cells or populations thereof described herein is administered at a dosage of $10^4$ to $10^9$ cells/kg body weight, including all integer values within those ranges. In further embodiments, the dosage is $10^5$ to $10^6$ cells/kg body weight, including all integer values within those ranges. In some embodiments, cell compositions are administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In some embodiments, administration of genetically-modified immune cells or populations thereof of the present disclosure reduce at least one symptom of a target disease or condition. For example, administration of genetically-modified T cells or populations thereof of the present disclosure can reduce at least one symptom of a cancer. Symptoms of cancers are well known in the art and can be determined by known techniques.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Transient Knockdown of Beta-2 Microglobulin when shRNA Cassette is Inserted into the Genome of Anti-CD19 CAR T Cells In these experiments, it was assessed whether beta-2 microglobulin (B2M) can be efficiently knocked down using a single copy of an shRNA that is co-delivered to the T cell receptor alpha constant (TRAC) locus with the CAR gene. An apheresis sample was drawn from a healthy donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml (Gibco). After 3 days of stimulation, cells were collected and samples of $1 \times 10^6$ cells were electroporated with 1 µg of RNA encoding the TRC 1-2L.1592 meganuclease, which recognizes and cleaves the TRC 1-2 recognition sequence (SEQ ID NO: 58) in the TRAC gene, and were transduced with AAV packaged with construct 7056 at an MOI of 25,000 viral genomes/cell. AAV 7056 encodes a CAR (composed of the anti-CD19 FMC63 scFv, CD8 hinge and transmembrane domains, a Novel 6 (N6) co-stimulatory domain, and a CD3 zeta intracellular signaling domain) oriented opposite of the TRAC open reading frame. Transcription is initiated by the JeT promoter and terminated by a bi-directional poly-A sequence. Upstream of the JeT promoter controlling CAR expression is situated an shRNA expression cassette also in opposite transcriptional orientation relative to the TRAC ORF. Transcription of the shRNA is initiated by a U6 promoter and terminated by a central poly-pyrimidine tract. Several shRNA sequences were evaluated for knockdown potency of B2M expression. AAV 7056 contains shRNA sequence TRCN0000381472, abbreviated as shRNA472, the sequence of which is set forth as SEQ ID NO: 6.

Cell cultures were maintained for up to 10 additional days in X-VIVO™ 15 medium supplemented with 5% FBS and 30 ng/ml of IL-2. On days 4, 7, and/or 10 post-nucleofection, the cultures were sampled and analyzed for surface expression of CD3 (anti-CD3-PE, BioLegend), CAR (anti-FMC63 anti-CAR, clone VM16 conjugated to AlexaFluor488), B2M (anti-B2M-APC, or PE, clone TU-99 BD Biosciences), and HLA-A, B, and C (clone W6/32, BV605, BioLegend). Flow cytometry data were acquired on a Beckman-Coulter CytoFLEX-LX. The detection of cell-surface CD3 is an indicator of the endogenous T cell receptor on the cell surface. Accordingly, it is understood that genetically-modified cells which are CD3+ or CD3− are TCR+ and TCR−, respectively.

B2M and HLA-ABC levels were measured in samples expressing construct 7056 and control populations. FIG. 1A shows the B2M surface levels in CD3−/CAR+ cells compared to TRAC-edited cells expressing no shRNA from a control culture. FIG. 1B shows B2M levels on CD3−/CAR+ versus CD3+/CAR− populations in the same culture. FIGS. 1C and 1D make the same respective comparisons in displays of HLA-ABC surface levels. The CD3−/CAR+ fraction of cells transduced with AAV-7056 displayed levels of B2M and HLA-ABC that are reduced by greater than 90% compared to control populations.

At the earliest time points following transgene delivery, CAR+ cells display a 90-95% reduction in surface levels of HLA-ABC and B2M, dependent on the marker and the comparison. As the culture is carried out for longer periods of time, there is a reduction in the frequency of CAR+ events and there is a recovery of B2M surface expression to near normal levels (FIGS. 2A-2F).

To determine the root cause of this loss of knockdown efficacy, the transgenic insert in the genomes of surviving CAR+ cells were sequenced ten days post-transduction (d10). Sequencing reactions were primed using oligonucleotides that hybridize in the TRAC homology arms in the 7056 sequence. The sequence of the self-complimentary hairpin structure intended to target the B2M transcript was not recovered in d10 genomes. However, this sequence was recovered from reactions in which the AAV preparation or the packaging plasmid was used as templates. Sequence loss appeared to be restricted to the hairpin sequence, as adjacent sequences, including the U6 promoter and the cPPT were not perturbed.

These studies show that a pre-screened B2M-targeted shRNA can knock down B2M expression levels on the surface of cells into which the construct has been delivered (via targeted insertion into the T cell receptor alpha constant region locus). This effect is specific to CAR+ populations (i.e., cells in which targeted integration into the TRAC locus has occurred). This experiment demonstrates that B2M can be efficiently knocked down using a single copy of shRNA472 co-delivered to the TRAC locus with the CAR gene on the same AAV template. Although results appeared promising at early time points, the knockdown effect was determined to be transient and associated with toxicity or growth arrest in the CAR+ population. As the knockdown effect waned, a loss of the shRNA sequence from the genome of surviving T cells was observed. This suggested that shRNA472 was excised from genomes and is not suitable for single integrated copy-mediated knockdown of B2M or potentially other endogenous proteins.

Example 2

Design, Construction, and Characterization of Beta-2 Microglobulin shRNAmiR

Targeting B2M expression using shRNA was hindered by transient knockdown effects and toxicity in the CAR T product, owing perhaps to the loss of the hairpin sequence from the genome. The guide and passenger strand sequences comprising the short hairpin were adapted into a larger, more highly structured micro-RNA scaffold (miR). This amalgam of shRNA and miRNA technology is referred to herein as a microRNA-adapted shRNA or shRNAmiR.

The miR scaffold selected to generate the shRNAmiR is called miR-E, which is an engineered derivative of a naturally-occurring miR in the human genome called miR-30 (see International Publication No. WO 2014/117050, which is herein incorporated by reference in its entirety). MicroRNAs enter the cell's RNAi pathway in the nucleus, where they are processed by Drosha and exported into the cytosol by exportin complexes before interacting with Dicer and Argonaut, and loading into the RNA-induced silencing complex (RISC).

The sequences of the miR-E scaffold used in this study are set forth as SEQ ID NO: 1 (5' miR-E scaffold domain), SEQ ID NO: 2 (5' miR-E basal stem domain), SEQ ID NO: 3 (mir-30a loop domain), SEQ ID NO: 4 (3' miR-E basal stem domain, and SEQ ID NO: 5 (3' miR-E scaffold domain).

89

B2M-targeting passenger and guide strand sequences, which are set forth as SEQ ID NOs: 7 and 8, respectively, were cloned into an anti-CD19 CAR (same as described in Example 1) vector downstream of the stop codon, but upstream of the poly-A transcriptional terminator. This vector (7282) was packaged into AAV6 capsids and used in a study to determine the magnitude and duration of B2M knockdown.

In this study, an apheresis sample was drawn from a healthy donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of 1×10$^6$ cells were electroporated with 1 μg of RNA encoding the TRC 1-2L.1592 meganuclease, which recognizes and cleaves the TRC 1-2 recognition sequence in the TRAC gene, and were transduced with AAV packaged with construct 7282 at an MOI of 25,000 viral genomes/cell. CAR T cells with no RNAi feature (7206) or with shRNA-472 (7056) were included as controls.

At 3, 7, and 11 days after editing and AAV transduction, cells from these cultures were analyzed for TCR knockout (using anti-CD3-BB515 clone SK7, BD Biosciences), CAR transgene knock-in (using anti-FMC63-AlexaFluor647, clone VM16, produced in-house), and B2M knockdown, using anti-B2M-PE (clone TU-99, BD Biosciences). B2M levels (measured by mean fluorescence intensity in the PE channel) were compared between CD3−/CAR+ populations and CD3+/CAR− populations of cells from the same culture.

At 3 days post-editing/transduction, CAR T cells produced using AAV 7282 compared favorably with AAV 7206 in terms of CAR+ frequency, while cultures produced using AAV 7056 contain a smaller frequency of CAR+ cells. The frequency of CD3−/CAR+ cells increased or stayed the same in cultures produced with AAV 7206 or AAV 7282, but were reduced to less than 5% of total cells in cultures transduced with AAV 7056.

Figure 2:
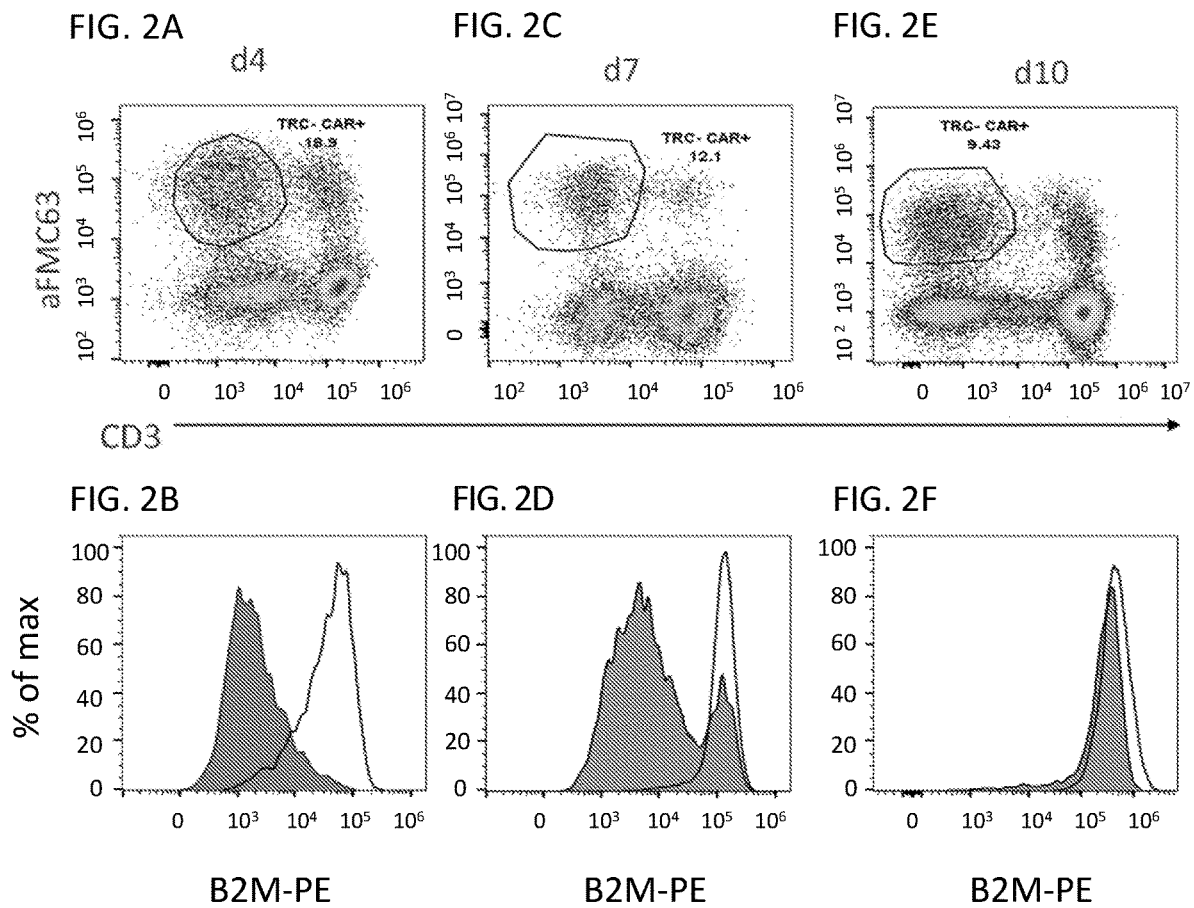
FIG. 2 shows the frequency of CD3−/CAR+ cells, and the knockdown of B2M, in cultures produced with AAV 7056.
Figure 3:
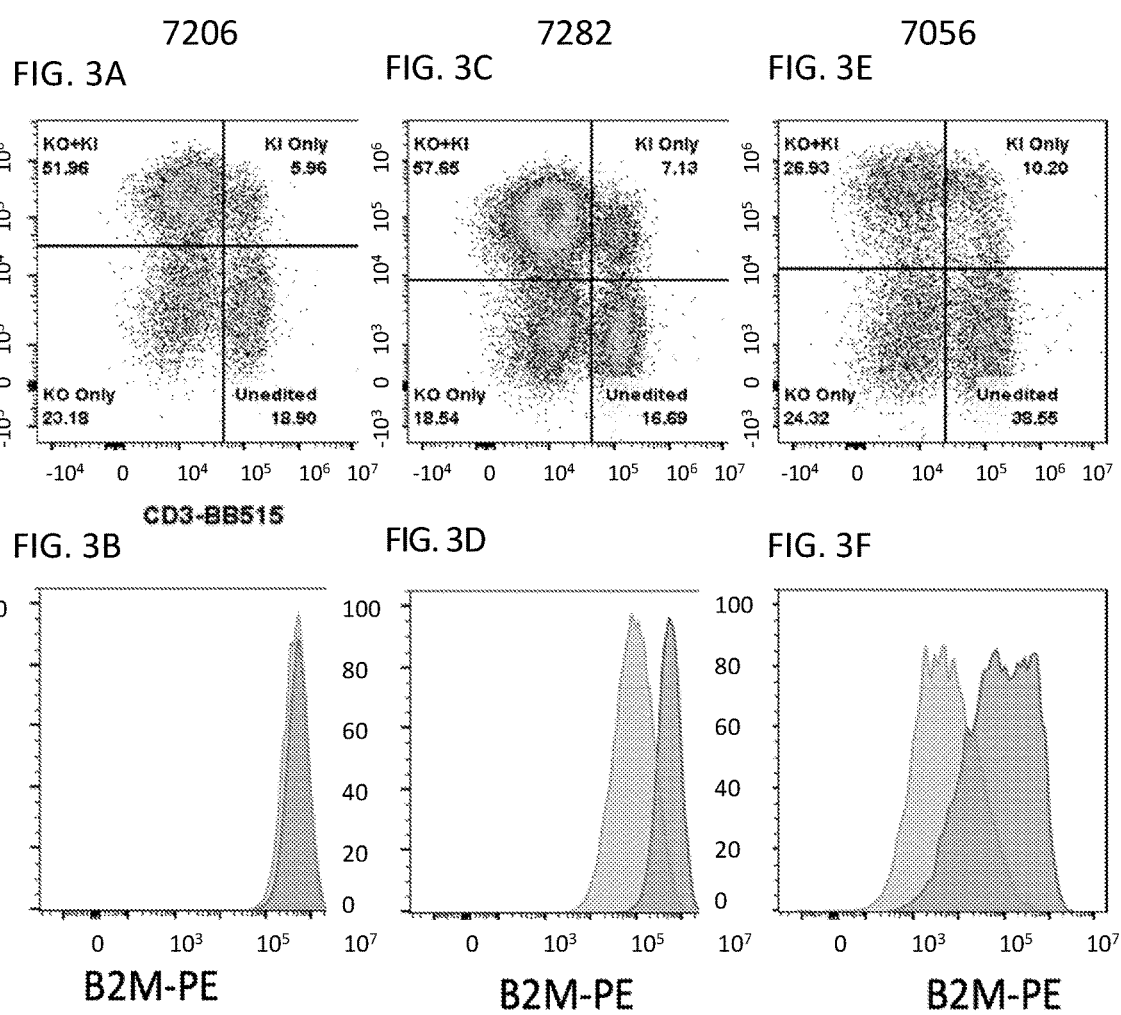
FIG. 3 shows the frequency of CD3−/CAR+ cells, and the knockdown of B2M, in cultures produced with AAV 7206, AAV 7056, or AAV 7282 three days post-transduction.
Figure 4:
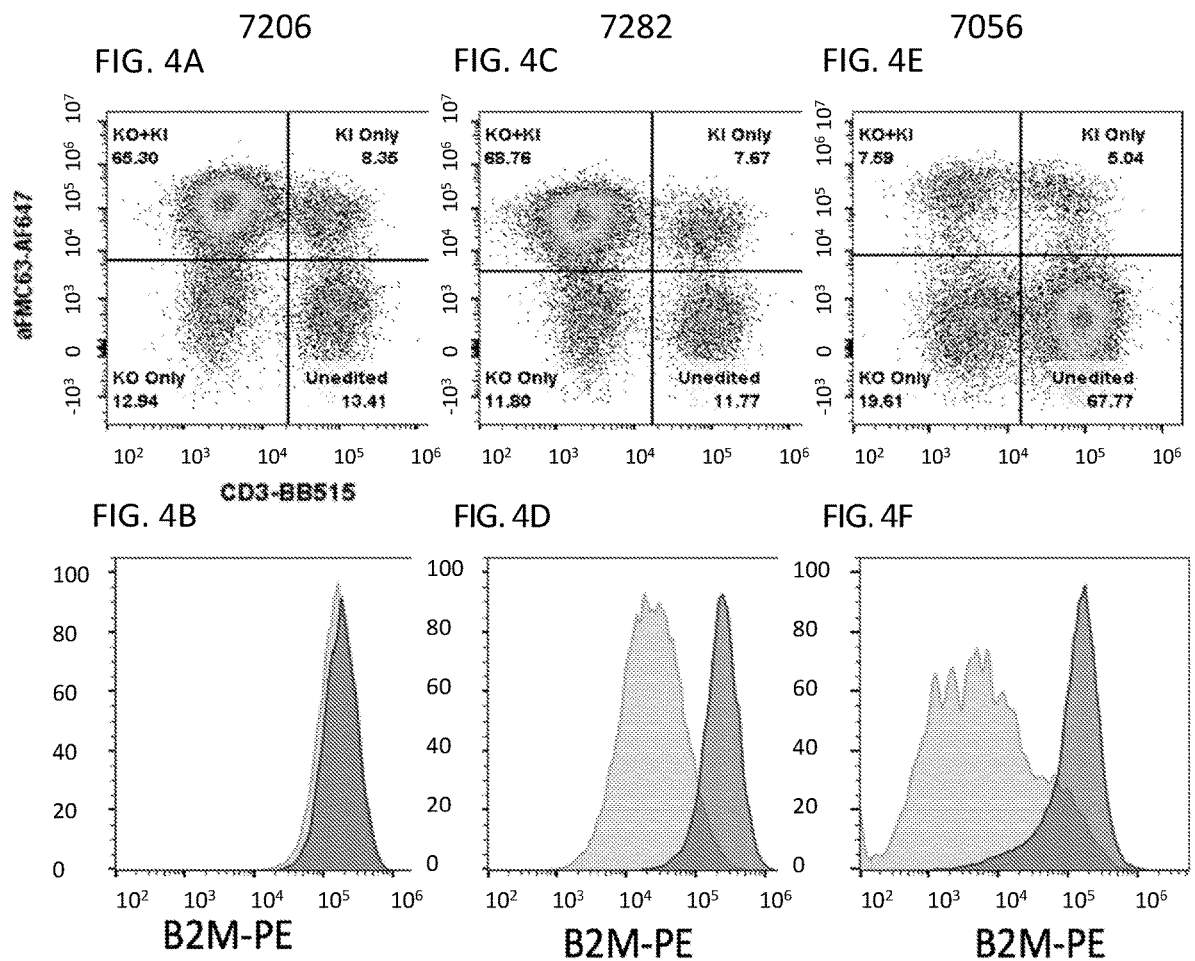
FIG. 4 shows the frequency of CD3−/CAR+ cells, and the knockdown of B2M, in cultures produced with AAV 7206, AAV 7056, or AAV 7282 seven days post-transduction.

CAR T cells expressing an shRNA (AAV 7056) rapidly downregulated surface levels of B2M by 91.9% on day 3. The B2M shRNAmiR downregulated B2M surface levels by 77.4% at this time point (FIG. 3). As the cultures were carried for additional days, the magnitude of knockdown mediated by shRNA decreased to 84.3% and 65.1% at days 7 and 11, respectively (FIGS. 4 and 5). Furthermore, at these time points, there were CAR+ events in the AAV 7056-transduced cultures that began to re-express normal or near normal levels of B2M. By comparison, the magnitude of knockdown mediated by shRNAmiR surprisingly increased on days 7 and 11 to approximately 85% at both time points, with no upregulations in B2M expression observed.

Thus, the use of a shRNAmiR to interfere with B2M expression advantageously resulted in slower knockdown kinetics and a slightly lower knockdown magnitude, but a more stable phenotype and greatly reduced toxicity when compared to the previously evaluated shRNA described in Example 1. The superior results observed in this study provide an initial proof-of-concept for the use of shRNAmiRs to downregulate endogenous protein expression in CAR T cells, which may be advantageous over gene knockout in certain situations.

90

Example 3

Design and Characterization of Additional B2M shRNAmiR Constructs

Six additional B2M guide and passenger strand sequences were identified and cloned into the miR-E backbone and inserted into the anti-CD19 CAR construct described in Example 2 between the stop codon of the CAR and the poly-A transcriptional terminator. The passenger and guide strands of the B2M 7285 shRNAmiR are set forth as SEQ ID NOs: 9 and 10, respectively. The passenger and guide strands of the B2M 7286 shRNAmiR are set forth as SEQ ID NOs: 11 and 12, respectively. The passenger and guide strands of the B2M 7287 shRNAmiR are set forth as SEQ ID NOs: 13 and 14, respectively. The passenger and guide strands of the B2M 7288 shRNAmiR are set forth as SEQ ID NOs: 15 and 16, respectively. The passenger and guide strands of the B2M 7289 shRNAmiR are set forth as SEQ ID NOs: 17 and 18, respectively. The passenger and guide strands of the B2M 7290 shRNAmiR are set forth as SEQ ID NOs: 19 and 20, respectively. These additional B2M shRNAmiR sequences were tested for their ability to knockdown B2M expression.

In this study, an apheresis sample was drawn from a donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of 1×10$^6$ cells were electroporated with 1 μg of RNA encoding the TRC 1-2L.1592 meganuclease, which recognizes and cleaves the TRC 1-2 recognition sequence in the T cell receptor alpha constant locus. The six CAR-shRNAmiR constructs (constructs 7285-7290) were delivered to T cells as linearized DNA (2 μg/sample), simultaneously with the TRC1-2 RNA during nucleofection. Alternatively, T cells were nucleofected with the B2M 13-14x.479 nuclease, which recognizes and cleaves the B2M 13-14 recognition sequence (SEQ ID NO: 60) in the human B2M gene (see, WO 2017112859). This was included to contextualize the amount of B2M surface signal present in the shRNAmiR knockdowns by defining the background signal present on a B2M knockout cell.

At days 4 and 11 following nucleofection, samples of the cultures were stained with anti-CD3-BB515 (clone SK7, BD Biosciences), anti-FMC63-AlexaFluor647 (clone VM16, produced in-house), anti-B2M-PE (using clone TU-99, BD Biosciences). B2M levels (measured by mean fluorescence intensity in the PE channel) were compared between CD3−/CAR+ populations and CD3+/CAR− populations of cells from the same culture.

The mean fluorescence intensity (MFI) of the CD3−/CAR+ population, as well as the CD3+ CAR-population is listed beside the corresponding shRNAmiR in Table 1 below. Percent knockdown is defined as: (MFI of the shRNAmiR+ population/MFI of reference population)×100. Tabulated data were acquired at day 11 post-nucleofection. Constructs 7289 and 7290 exhibited the highest magnitude of B2M interference of the 7 constructs tested. The background signal present on B2M knockout cells is less than 2% of the reference population (not listed).

TABLE 1

Knockdown of B2M by candidate sequences.

| Construct | B2M MFI CD3−/CAR+ | B2M MFI Control population | % knockdown |
|---|---|---|---|
| 7002 | 208469 | 219415 | 5 |
| 7282 | 41478 | 218647 | 81 |
| 7285 | 125840 | 199812 | 37 |
| 7286 | 76390 | 228482 | 67 |
| 7287 | 90590 | 222648 | 60 |
| 7288 | 31937 | 222326 | 86 |
| 7289 | 23676 | 228838 | 89 |
| 7290 | 23190 | 213868 | 89 |

All seven constructs tested in this study exhibited some degree of stable B2M knockdown and CAR expression. Interestingly, this study demonstrated that the degree of endogenous protein knockdown can be modulated by the selection of different guide and passenger strands. This flexibility provided by the shRNAmiR approach can be advantageous when various degrees of endogenous protein knockdown may be preferable to a nearly complete knockout. Candidate sequences encoded in 7282, 7288, 7289, and 7290 were investigated in further experiments.

Example 4

Allogenicity of shRNAmiR B2M CAR T Cells and Susceptibility to Natural Killer (NK) Cell Killing These studies assessed the effects of a knockout of B2M via genetic ablation in comparison to an incomplete, but stable knockdown using shRNAmiR on the sensitivity of the cells to cytolysis by alloantigen-specific cytotoxic lymphocytes (CTLs) or NK cells. CTLs were primed using monocyte-derived dendritic cells from an unrelated healthy donor to activate and expand alloantigen-specific CD8+ T cell populations.

Apheresis samples were drawn from two unrelated healthy donors, and the T cells were enriched using the CD3 positive selection kit II in accordance with the manufacturer's instructions (Stem Cell Technologies). To prepare dendritic cells, unfractionated mononuclear cells from the apheresis samples were plated in polystyrene cell culture flasks and allowed to adhere for 1-2 hours. Nonadherent cells were discarded and adherent cells were cultured for 6 days in a cytokine mixture that differentiates monocytes into dendritic cell-like cells (800 U/ml GM-CSF and 500 U/ml IL-4, both sourced from PeproTech). Dendritic cells (DCs) were collected and plated at various ratios with T cells from unrelated donors. The first 24 h of co-culture were carried out in the absence of exogenous cytokines. IL-2 was added to the cultures thereafter at 10 ng/ml.

Co-cultures were carried out for 5 days, and the CD8+ T cells were enriched by depleting CD4+ T cells using Miltenyi CliniMACS CD4 microbeads and an LS column. Purity was assessed using CD3-PE (Clone UCHT1, BioLegend) and CD8-BV421 (Clone RPA-T8, BioLegend). Primed CTLs were then co-cultured with target T cells from the same donor from which the DCs were made. The target T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, target T cells were either edited at the B2M locus using the meganuclease B2M13-14x.479 (B2M KO) or edited at the TRAC locus using TRC1-2L.1592. TRAC-edited target T cells were transduced with either AAV 7206 (control CAR T) or AAV 7289 (B2M shRNAmiR) at an MOI of 25,000 viral genomes/cell.

B2M− or CAR+ fractions were FACS-sorted to >99% purity using a FACSMelody cell sorter (Becton-Dickinson) and anti-B2M-PE (clone TU-99, BD Biosciences), CD3-PE (clone UCHT1, BioLegend), and anti-FMC63-BV421 (clone VM16 produced in house). Sorted target cells were labeled with 1 µM Cell Trace Violet (ThermoFisher) and placed into culture with alloantigen-sensitized CTLs at effector:target (E:T) ratios ranging from 1:5 through 5:1. 18 hours following culture setup, samples were analyzed for live dye-positive target cells and percent killing was calculated by comparing the number of surviving target cells to a "no effector" control.

Natural Killer (NK) responses were also measured. NK cells were magnetically enriched from PBMC samples using a CD56 positive selection kit (Stem Cell Technologies). Enriched NK cells were co-cultured for 18 h with Cell Trace Violet labeled CAR-T cells (produced with AAV6-7206), B2M knockdown CAR-T cells (produced with AAV6-7289 containing a B2M shRNAmiR), or B2M knockout T cells. After 18 h of co-culture, surviving dye-positive target cells were enumerated and percent killing was calculated.

CAR T cells with normal levels of B2M surface expression were killed by primed alloantigen-specific CTLs (FIG. 6A). As the E:T ratio increased, the percent killing increased accordingly, with a maximum of 74% killing at a 2:1 E:T ratio. T cells that were genetically edited at the B2M locus, and totally lacked surface expression of B2M protein were killed less efficiently than B2M+ controls at each E:T ratio. The levels of killing observed in the CAR T cells encoding a B2M shRNAmiR, and expressing 5-10% of normal B2M surface levels, were likewise killed inefficiently by primed CTLs, and at a lower percentage than that observed by B2M KO.

It was further observed that B2M knockout cells were killed by NK cells in correlation to E:T ratio, reaching a maximum of 50% killing at 5:1 E:T ratio (FIG. 6B). CART cells with unmanipulated levels of B2M expression were not efficiently killed by NK cells, although some background killing was observed at the highest E:T ratio. Notably, B2M knockdown cells were inefficiently killed by NK cells, although some killing (28%) is observed at the highest E:T ratio.

Genetic ablation of B2M expression with a meganuclease resulted in cells that were highly resistant to killing by primed alloantigen-specific CTLs; however, they were readily killed by NK cells. Producing a stable knockdown of endogenous B2M to 5-10% of normal level using the shRNAmiR approach resulted in cells that were similarly resistant to CTLs, but substantially less sensitive to NK cytolysis. This suggests that these cells would be more likely to evade NK cell killing in vivo than allogeneic CAR T cells having a complete knockout of B2M.

In addition to shRNAmiR-mediated knockdown of B2M, a second gene editing approach was evaluated for NK cell evasion. The second approach involved the use of an engineered meganuclease to generate a cleavage site with the B2M gene, and the introduction of a donor template into the cleavage site. This donor template encoded an HLA class I histocompatibility antigen, alpha chain E (HLA-E) polypeptide (SEQ ID NO: 66). When expressed on the cell surface, HLA-E is known to bind to the CD94/NKG2A inhibitory receptor on NK cells, and has been shown to shield HLA-E+ cells from NK cell-mediated lysis. Here, it was examined whether targeted insertion of an HLA-E coding sequence into the B2M gene could simultaneously knockout B2M expression, and thus reduce CAR T cell allogenicity, and express HLA-E to inhibit NK cell killing.

In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with 1 ug of RNA encoding the B2M13-14x.479 meganuclease, which recognizes and cleaves the B2M 13-14 recognition sequence (SEQ ID NO: 60) in the B2M locus.

Immediately following electroporation, cells were transduced with AAV7346, which encodes an HLA-E fusion protein comprising three polypeptides joined by glycine-serine linkers (SEQ ID NO: 66). The first polypeptide is a nonamer comprising an HLA-G leader peptide (SEQ ID NO: 120) followed by a (GGGGS)3 linker (SEQ ID NO: 121). The second polypeptide is a full-length codon-optimized human B2M gene (encoding SEQ ID NO: 119) followed by a (GGGGS)4 linker (SEQ ID NO: 122). The third polypeptide is the human HLA-E-01:03 sequence (SEQ ID NO: 118). The transgene is under the control of the JeT promoter and is terminated by a bi-directional poly-A sequence. The transgene is flanked by homology arms directing the transgene to insert at the B2M13-14 cut site.

Following at least 6 days of culture in complete X-VIVO15 medium containing 30 ng/ml IL-2, cells were stained with anti-HLA-ABC-PE (BioLegend, clone W6/32—to detect B2M-edited cells) and anti-HLA-E-BV421 (BioLegend clone 3D12). Cells were analyzed for knockout/knock-in frequencies using a Beckman-Coulter CytoFLEX-S or LX. HLA-ABC$^-$HLAE$^+$ cells were purified by FACS using a Beckton-Dickinson FACSMelody. Non-transduced HLA-ABC$^-$ (B2M-edited, no AAV) were sorted as a control. Sorted cells were measured for susceptibility to killing by CTLs and NK cells as described previously in this example.

T cells transfected with B2M13-14x.479 RNA developed a population that lacks display of the canonical WIC I proteins HLA-A, B, and C as well as HLA-E (FIG. 7A). When B2M-edited cells are transduced with AAV7346, a population of HLA-ABC– cells that expresses high levels of the HLA-E transgene are visible (FIG. 7B). These populations were sorted to >99% purity (FIG. 8).

Figures 9, 9A:
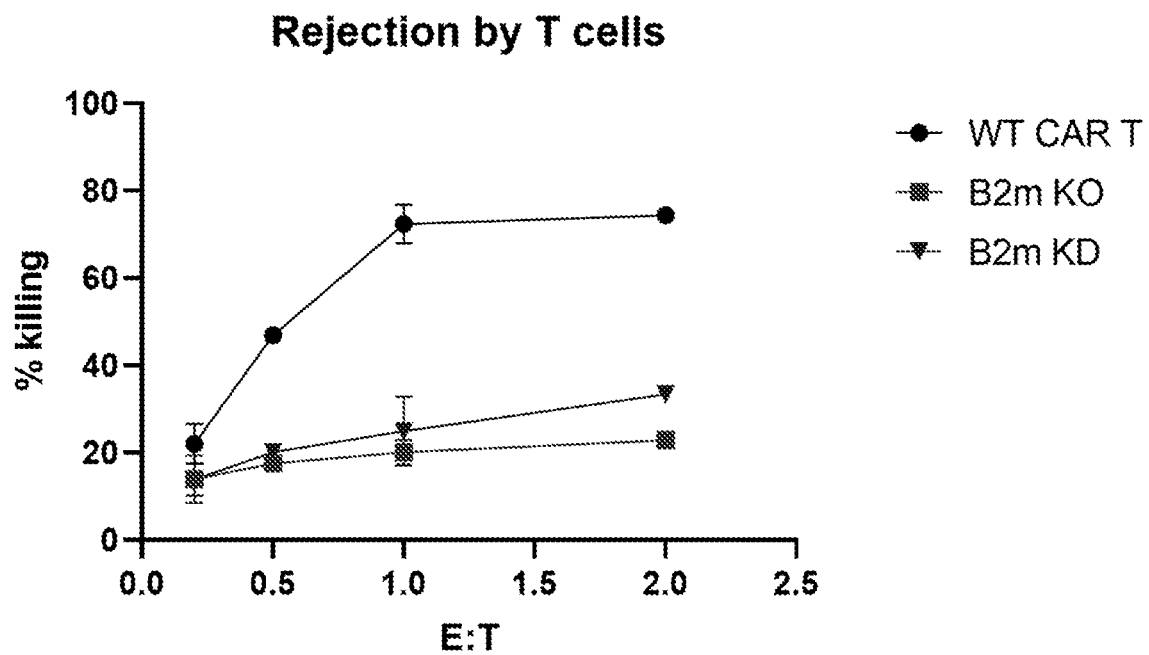
FIG. 9 shows CAR T cell killing by alloantigen-primed CTLs and cell killing by natural killer (NK) cells.
FIG. 9A shows killing of B2M-positive, B2M-knockout, and B2M-knockout/HLA-E knock in, CAR T cells by alloantigen-primed CTLs at increasing Effector:Target ratios.

As shown in FIG. 9A, CAR T cells with no B2M edits were killed by alloantigen-primed CTLs, and as E:T ratio increases, increased CAR T killing was observed (reaching a maximum of approximately 75%). In contrast, both B2M knockout cells and B2M knockout cells expressing the HLA-E transgene were not killed efficiently (10% or less), and there was no increase in killing observed as E:T ratio was increased.

Figures 9, 9B:
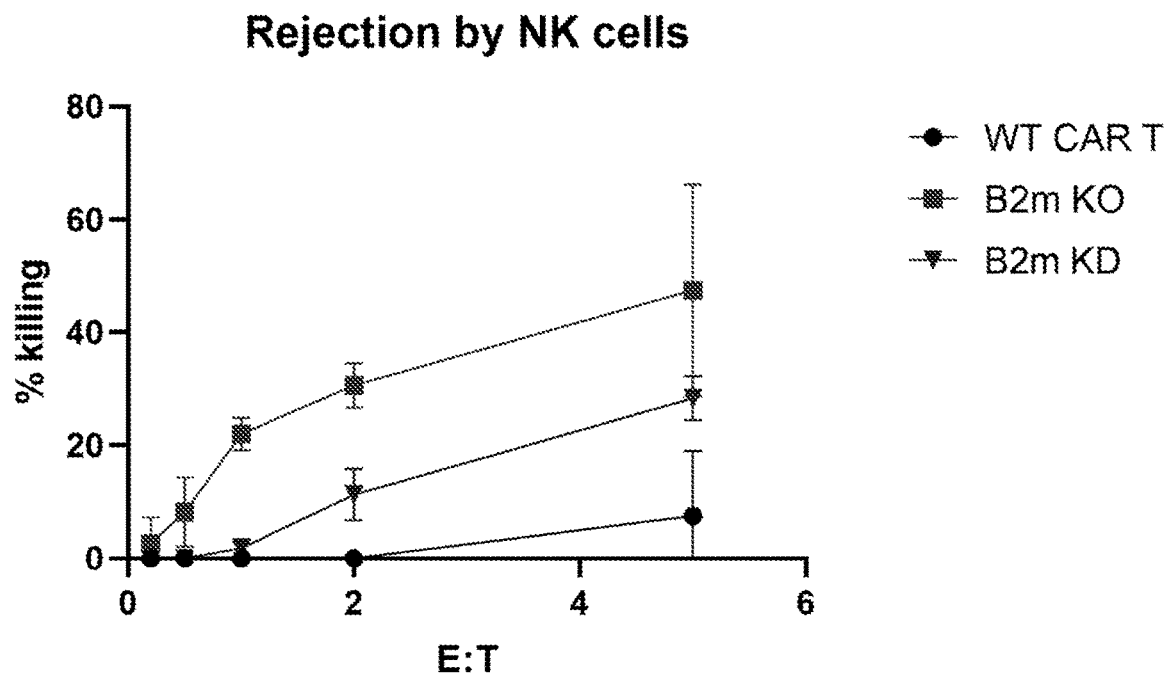
FIG. 9B shows NK cell killing of B2M-positive, B2M-knockout, and B2M-knockout/HLA-E knock in, CAR T cells at increasing Effector:Target ratios.

As shown in FIG. 9B, when killing by NK cells was measured, B2M-sufficient CAR T cells were not efficiently targeted by NK cells, but B2M knockout T cells were killed efficiently (with a maximum of approximately 50%). HLA-E$^+$ cells, despite lacking HLA-ABC expression were protected from NK cytolysis to an extent comparable to that observed in B2M-sufficient cells. These data indicate that genetic disruption of the endogenous B2M gene protects T cells against cytolysis by alloantigen-primed CTLs, and an HLA-E transgene prevents the missing-self mechanism of NK cytolysis.

Example 5

In Vivo Efficacy of CAR T Cells Having Knockdown of B2M by shRNAmiR and Stability of B2M Knockdown These studies were conducted to evaluate the efficacy of CD19 CAR T cells having a knockdown of B2M by a shRNAmiR, and to determine the stability of the B2M knockdown in vivo in comparison to control CD19 CAR T cells after the cells were exposed to target cells and activated in vivo.

Cryopreserved CD3+ T cells were thawed, rested, and activated as previously described. On day 3 post-activation, cells were electroporated with mRNA encoding the TRAC-specific nuclease (TRC1-2L.1592) and immediately transduced with the 7206 AAV vector carrying the CD19-directed CAR sequence or the 7289 AAV vector carrying the CD19 CAR with a B2M-targeting shRNAmiR encoded in between the stop codon for the CAR and the polyadenylation sequence. Residual CD3+(unedited) CAR T cells from both groups were depleted using a CD3 magnetic enrichment kit and discarded, and cells from both groups were cryopreserved after expansion post-depletion as previously described.

Female NSG mice were inoculated with a NALM-6 human acute lymphoblastic leukemia cell line expressing firefly luciferase one week before being injected intravenously (i.v.) with either vehicle control, CD19-directed CAR T cells, or CD19 CAR–B2M shRNAmiR cells at a dose of 5e6 CAR T cells per mouse (n=5 animals per group).

Luciferase activity was measured in live animals using IVIS Spectrum (Perkin Elmer, MA) imaging system equipped with a CCD camera mounted on a light-tight specimen chamber. On the day of imaging, animals were injected with Luciferin substrate and placed in anesthesia induction chamber. Upon sedation, animals were placed in the dorsal position in the imaging chamber, equipped with stage heated at physiological temperature, for image acquisition at regular intervals post-luciferin substrate. The acquisition time was automatically determined by LivingImage software. Regions of interest were drawn around each mouse, and flux was quantified and reported as photons per second (p/s). Data was analyzed and exported using Living Image software 4.5.2. (Perkin Elmer, MA).

For analysis of B2M expression on human T cells present in the mouse blood, blood samples were taken from individual mice at day 14 post-administration of CART cells. Red blood cells were lysed, and samples were then washed and stained for the presence of human CD45 and B2M, and analyzed by flow cytometry, as previously described.

As shown in FIG. 10A, mice engrafted with NALM-6 cells and treated with vehicle (black line with triangles) demonstrated increasing tumor growth over the course of the study with a steady increase in total flux over time as measured by bioluminescence imaging. In contrast, mice treated with either CD19-directed CAR T cells (dark gray line with circles) or CD19-directed CAR T cells with an integrated B2M-targeting shRNAmiR (light gray line with triangles) mediated rapid and durable anti-tumor activity over the course of the study, as observed by decreased total flux compared to the vehicle treated animals.

At 14 days post-CAR T administration, blood samples were taken to evaluate the expression of B2M on human CD45+ cells. As shown in FIG. 10B, the MFI of B2M expression was more than 90% reduced on CD19-directed CAR T cells with an integrated B2M-targeting shRNAmiR compared to control CD19-directed CAR T cells, indicating that B2M shRNAmiR bearing cells, which have been activated and have mediated clearance of target cells, still have reduced levels of B2M expression relative to control cells that do not have the B2M shRNAmiR integrated into the genome.

Two groups of CD19-directed CART cells were produced, differing only by the inclusion of a shRNAmiR vector in one of the constructs to enable targeted knockdown of B2M expression in the cells that express the CAR. CAR T cells from both groups were able to reduce tumor burden in a xenograft model of leukemia. Blood samples taken from the mice confirmed that the human T cells with the B2M shRNAmiR included had lower levels of B2M expression on the cell surface than T cells in the blood of mice from the control CD19 CAR T cell group, indicating that the knockdown of B2M is stable even in cells that have been activated and have mediated killing of target cells in a relevant mouse model of human leukemia.

Example 6

Stable Knockdown of CS1 in CART Cells

These studies were initiated to determine if CS1 could be stably knocked down using shRNAmiR sequences. Three candidate guide and passenger strand sequences for a CS1/SLAMF7 shRNAmiR were built into the miR-E scaffold and positioned after the stop codon of a BCMA-specific CAR (comprising a BCMA-specific scFv, CD8 hinge and transmembrane domains, an N6 co-stimulatory domain, and a CD3 zeta intracellular signaling domain). These were designated constructs 72101, 72102, and 72103.

In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with 1 ug of RNA encoding the TRC 1-2L.1592 meganuclease, which recognizes and cleaves the TRC 1-2 recognition sequence in the TRAC gene. Nucleofection was carried out in the presence of 2 ug/1e6 cells of linearized DNA encoding the CAR and one of the candidate CS1/SLAMF7 shRNAmiRs. In this experiment a separate sample was nucleofected with TRC1-2L.1592 as above, and a BCMA CAR construct that does not encode an RNAi feature. Seven days following nucleofection, cultures were stained with anti-CD3 (clone UCHT1, BD Biosciences), anti-CS1 (clone 162.1, BioLegend) and biotinylated BCMA (ACRO Biosystems) to detect the CAR (counterstained using streptavidin-APC or BV421, BioLegend).

Figure 11:
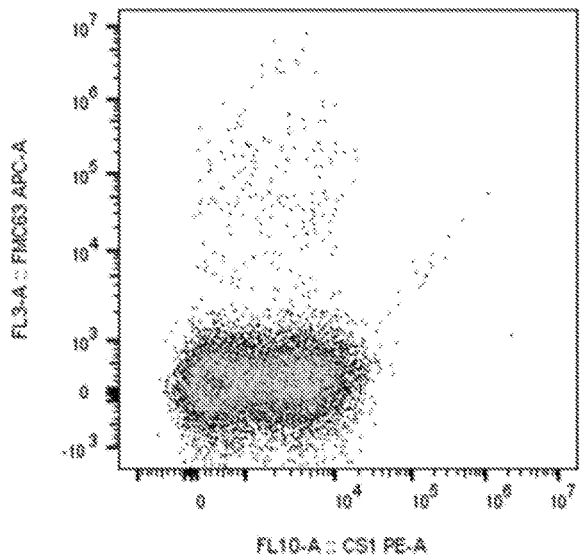
FIG. 11 shows shRNAmiR-induced stable knockdown of CS1 in CAR T cells. Three candidate guide and passenger strand sequences for a CS1/SLAMF7 shRNAmiR were built into a miR-E scaffold and positioned after the stop codon of a BCMA-specific CAR. Constructs were designated AAV72101-72103 and were used for transduction of donor T cells.
Figure 11:
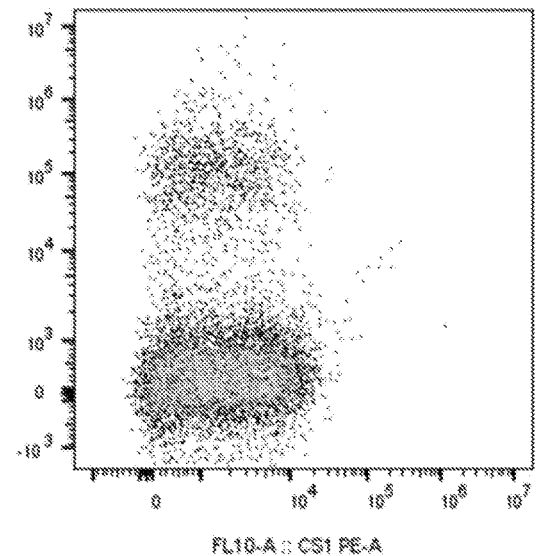
Figure 11:
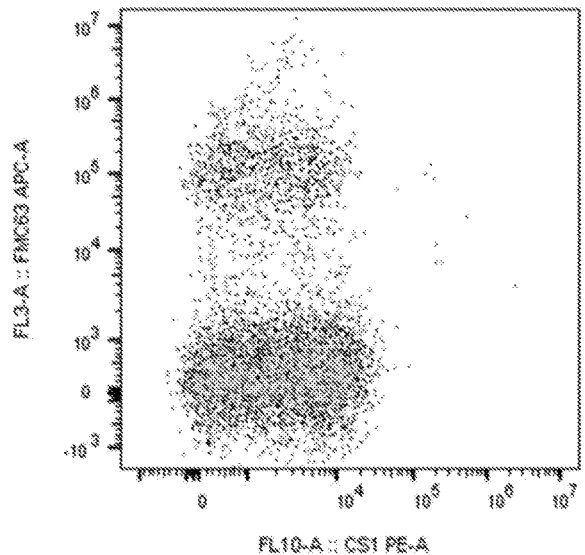
Figure 11:
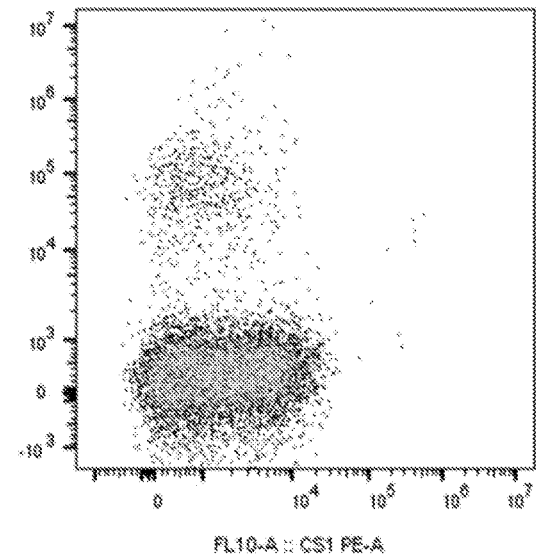

By comparing the CS1 surface expression levels on CAR+ cells to levels displayed on CAR-cells in the same culture, relative knockdown magnitudes could be measured. Constructs 72101 and 72102 did not visibly alter CS1 expression, although mean fluorescence intensities suggested knockdown of 26% and 30% respectively. CAR T cells produced using 72103 did display visibly lower levels of CS-1, with few high expressors and a calculated 36% knockdown (FIG. 11).

These experiments demonstrated that expression of endogenous CS1 could be stably reduced in CAR T cells. The 72103 candidate will be examined further with the goal of knocking down CS1 on CS1-specific CAR T cells in order to prevent fratricidal activity during production.

Example 7

Stable Knockdown of Transforming Growth Factor Beta Receptor 2 (TGFBR2) in CAR T Cells These studies were initiated in order to determine if an additional endogenous gene, TGFBR2, could be stably knocked down using shRNAmiR sequences. Candidate guide and passenger strand sequences for a TGFBR2 shRNAmiR were identified and incorporated into the miR-E scaffold, and positioned after the stop codon of the FMC63-based anti-CD19 CAR (as described in Example 1). The passenger and guide strands of the TGFBR2 72110 shRNAmiR are set forth as SEQ ID NOs: 27 and 28, respectively. The passenger and guide strands of the TGFBR2 72111 shRNAmiR are set forth as SEQ ID NOs: 29 and 30, respectively. The passenger and guide strands of the TGFBR2 72112 shRNAmiR are set forth as SEQ ID NOs: 31 and 32, respectively. The passenger and guide strands of the TGFBR2 72113 shRNAmiR are set forth as SEQ ID NOs: 33 and 34, respectively. The passenger and guide strands of the TGFBR2 72114 shRNAmiR are set forth as SEQ ID NOs: 35 and 36, respectively.

An apheresis sample was drawn from a healthy donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco).

After 3 days of stimulation, cells were collected and samples of $1 \times 10^6$ cells were electroporated with 1 µg of RNA encoding the TRC 1-2L.1592 meganuclease, which recognizes and cleaves the TRC 1-2 recognition sequence in the TRAC gene. Nucleofection was carried out in the presence of 2 µg/$1 \times 10^6$ cells of linearized DNA encoding the CAR and one of the candidate TGFBR2 shRNAmiRs. In this experiment, a separate sample was nucleofected with TRC1-2L.1592 as above, and transduced with AAV 7206, which encodes the FMC63 anti-CD19 CAR, but does not contain an RNAi feature.

Figures 12, 12A:
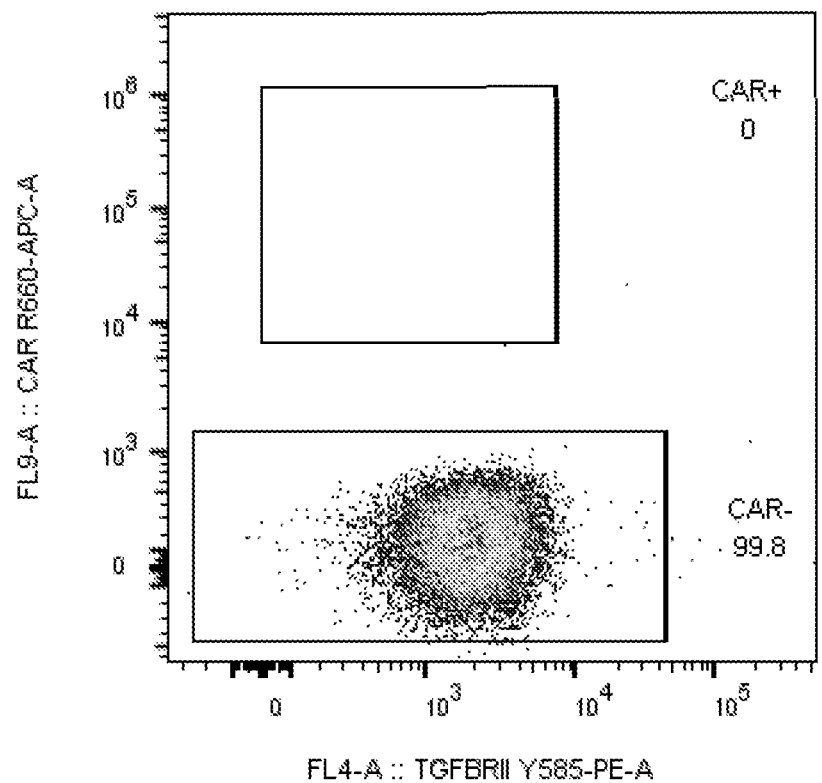
FIG. 12 shows shRNAmiR-induced stable knockdown of TGFRB2 in CAR T cells. Multiple candidate guide and passenger strand sequences for a TGFBR2 shRNAmiR were built into a miR-E scaffold and positioned after the stop codon of a CD19-specific CAR. Constructs were designated AAV 72110-72114 and were used for transduction of donor T cells.
FIG. 12A shows CAR and TGFBR2 staining after mock transduction.
Figures 12, 12B:
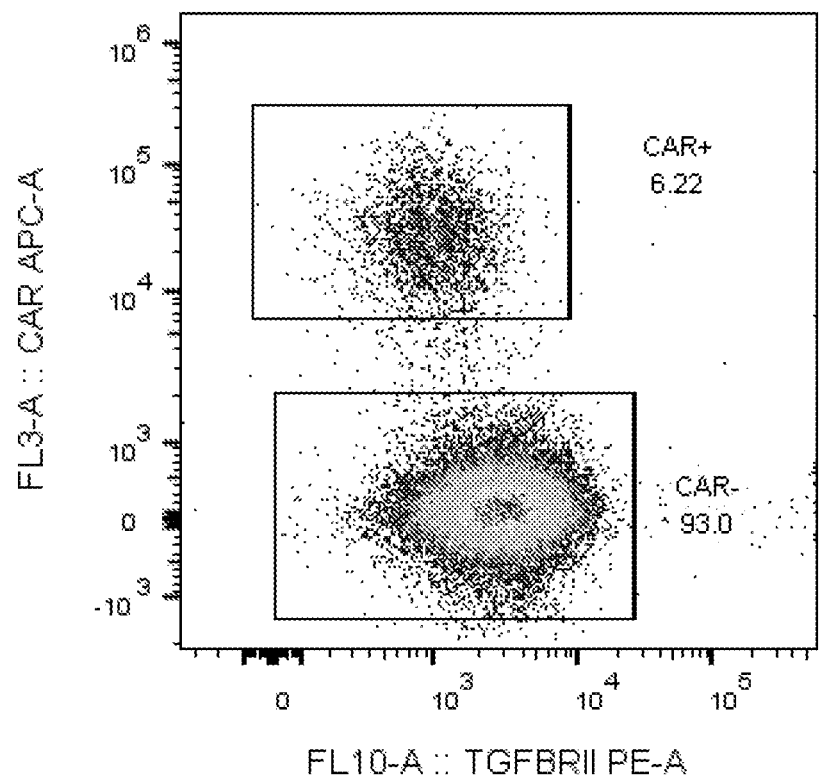
FIG. 12B shows CAR and TGFBR2 staining at day 14 post-transduction with AAV 72110.
Figures 12, 12C:
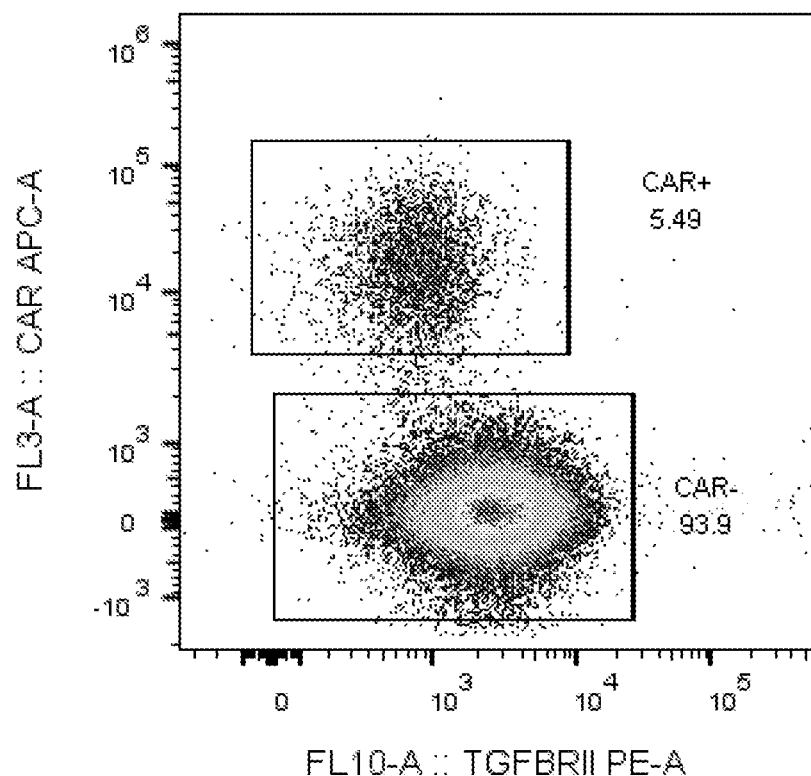
FIG. 12C shows CAR and TGFBR2 staining at day 14 post-transduction with AAV 72111.
Figures 12, 12D:
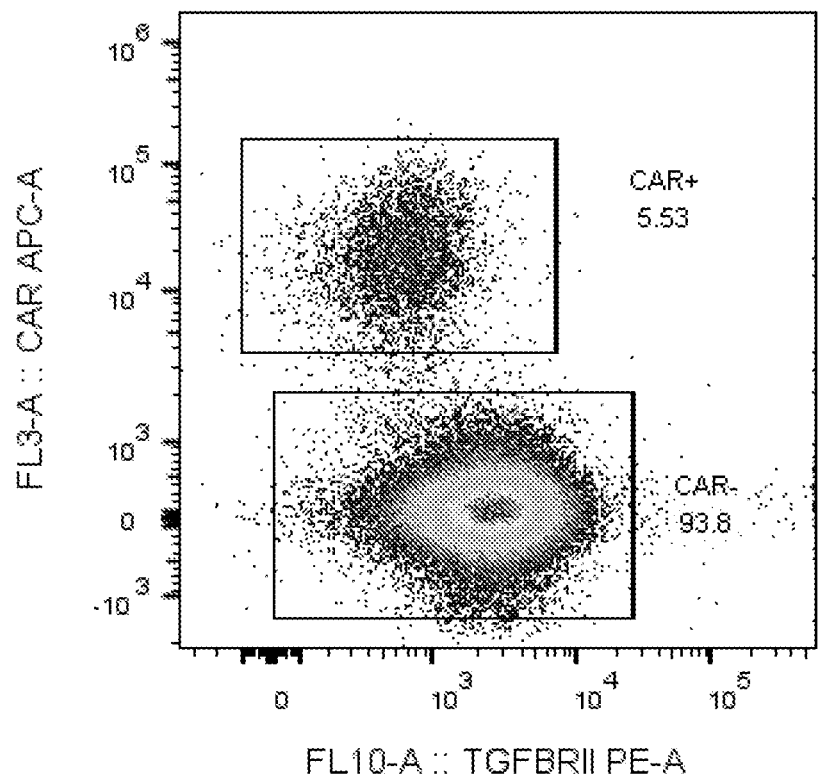
FIG. 12D shows CAR and TGFBR2 staining at day 14 post-transduction with AAV 72112.
Figures 12, 12E:
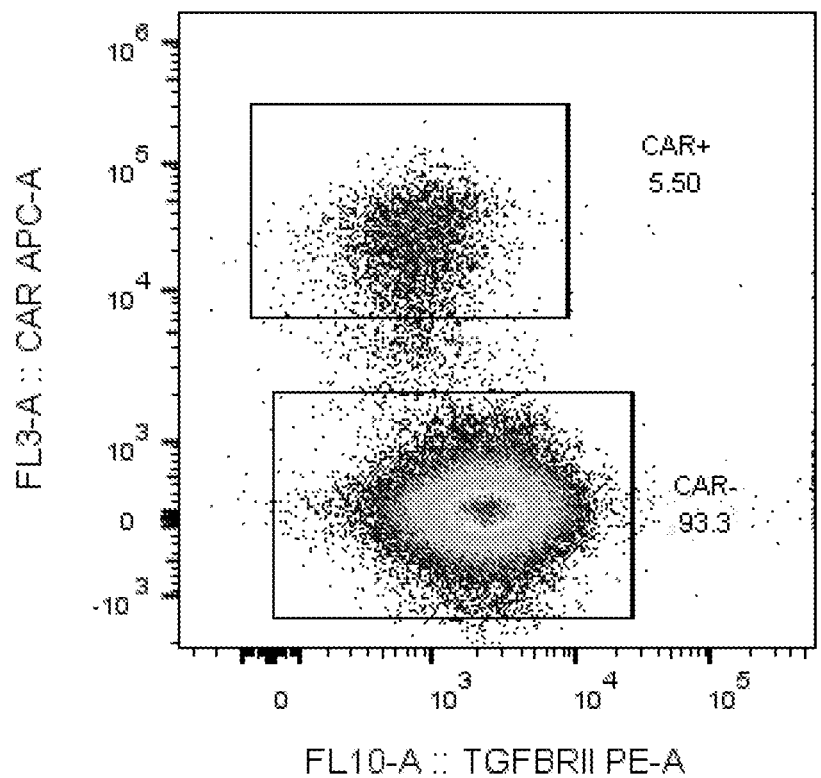
FIG. 12E shows CAR and TGFBR2 staining at day 14 post-transduction with AAV 72113.
Figures 12, 12F:
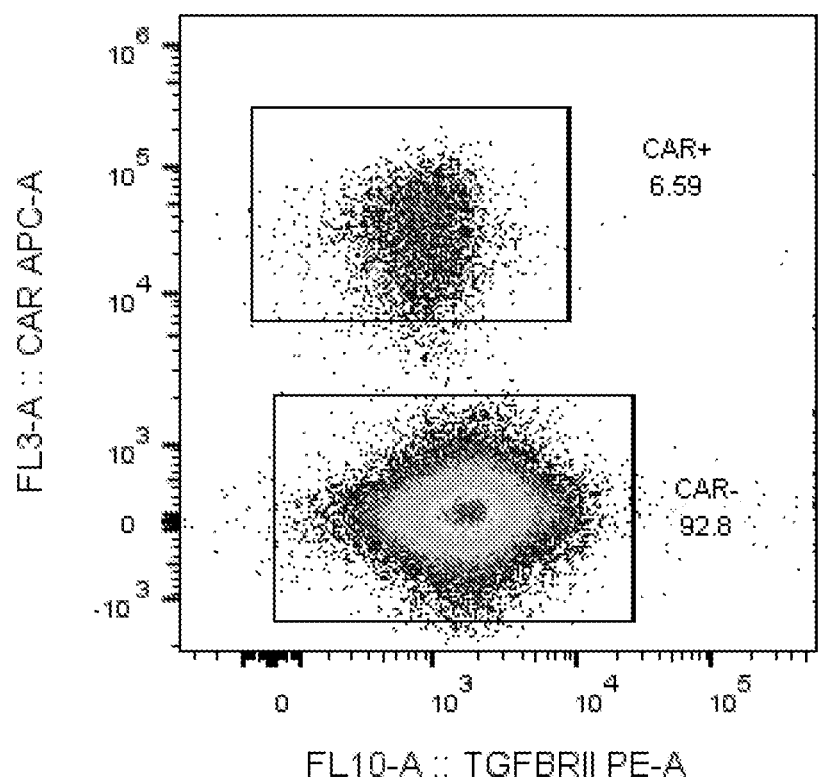
FIG. 12F shows CAR and TGFBR2 staining at day 14 post-transduction with AAV 72114.

Cells were analyzed for TGFBR2 expression at d7, 10, and 14 post-nucleofection using the anti-TGFBR2 antibody MM0056-4F14 (Abcam), and an anti-mouse kappa light chain secondary antibody conjugated to PE (BioLegend). CAR+ cells were identified using anti-FMC63-Alx647, produced in house. The mean fluorescence intensity (MFI) of TGFBR2 signal on the CAR+ was compared to that on the CAR− cells and a percent knockdown was calculated. The frequency of CAR+ events was consistent across the different constructs, ranging from 4.9% to 6.7% (FIG. 12).

TGFBR2 surface levels varied from sample to sample in the CAR+ population, but were relatively consistent in the CAR− population, which did not have the CAR-shRNAmiR construct incorporated into the TRAC locus. Sequences 72111, 72112, and 72113 appeared to support the most robust knockdown throughout the experiment (measured by TGFBR2 MFI and summarized below in Table 2). These three sequences were selected for further study.

TABLE 2

Knockdown of TGFBR2 by candidate sequences.

| Construct | % knockdown (d 7) | % knockdown (d 14) |
|---|---|---|
| 7206 | 0 | 0 |
| 72110 | 55 | 63 |
| 72111 | 64 | 67 |
| 72112 | 64 | 75 |
| 72113 | 65 | 63 |
| 72114 | 10 | 52 |

This screen of TGFBR2-specific shRNAmiR sequences demonstrated that CAR T cells could be prepared having a stable knockdown of TGFBR2 at various levels. Particularly, constructs 72111, 72112, and 72113 supported robust reduction of surface TGFBR2 in the cells into which the CAR-shRNAmiR sequence was successfully incorporated.

Additional studies were performed to compare the shRNAmir-mediated knockdown approach described herein with nuclease-mediated knockout of the TGFBR2 gene.

In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with 1 ug of RNA encoding TRC1-2L.1592, or with one of two nuclease candidates targeting the TGFBR2 gene: TGF1-2x.5 (SEQ ID NO: 64) or TGF1-2L.296 (SEQ ID NO: 65). Electroporated cells were cultured for 6 days in complete X-VIVO15 medium supplemented with 30 ng/ml IL-2 prior to an analysis of editing efficiency. This was achieved by staining cells with an anti-TGFβRII antibody (Abcam clone MM0056-4F14) followed by anti-mouse IgG κ light chain conjugated to PE (BioLegend clone RMK45). Data were acquired on a Beckman-Coulter CytoFLEX-S or LX.

T cells electroporated with TRC1-2L.1592 were immediately transduced with AAV72112 (encoding the anti-CD19 FMC63 CAR described in Example 1 and a TGFBR2-specific shRNAmiR inserted after the CAR stop codon and before a polyA sequence) or AAV7206 (encoding a control FMC63 CAR with no RNAi). Following six days of culture, CD3-CAR+ cells were purified by FACS using methods described above. In addition, TGFβRII-cells from TGF1-2L.296-edited cultures were sorted in this manner. Sorted cells were rested in serum free medium overnight before being stimulated with 500 ng/ml of recombinant human TGFβ1, the ligand for TGFBR2 (PeproTech). Thirty minutes following TGFβ1 addition, cells were harvested and immediately prepared for staining using Phos-Flow lyse-fix buffer and Phos-Flow Fix-Perm buffer III (BD Biosciences) according to the manufacturer's instructions. Fixed cells were stained with anti-pSMAD2/3-PE (BD Biosciences) and data were acquired on a Beckman-Coulter CytoFLEX-LX.

Mock nucleofected T cells were stained with the anti-TGFβRII antibody and the secondary antibody or the secondary antibody alone to serve as positive and negative controls, respectively, for surface detection of TGFβRII.

Compared to mock nucleofected cells, introduction of TGF1-2x.5 resulted in TGFBR2 knockout in 38.6% of cells in the culture, while introduction of TGF1-2L.296 resulted in a higher knockout frequency of 69% (FIG. 13).

Figure 14:
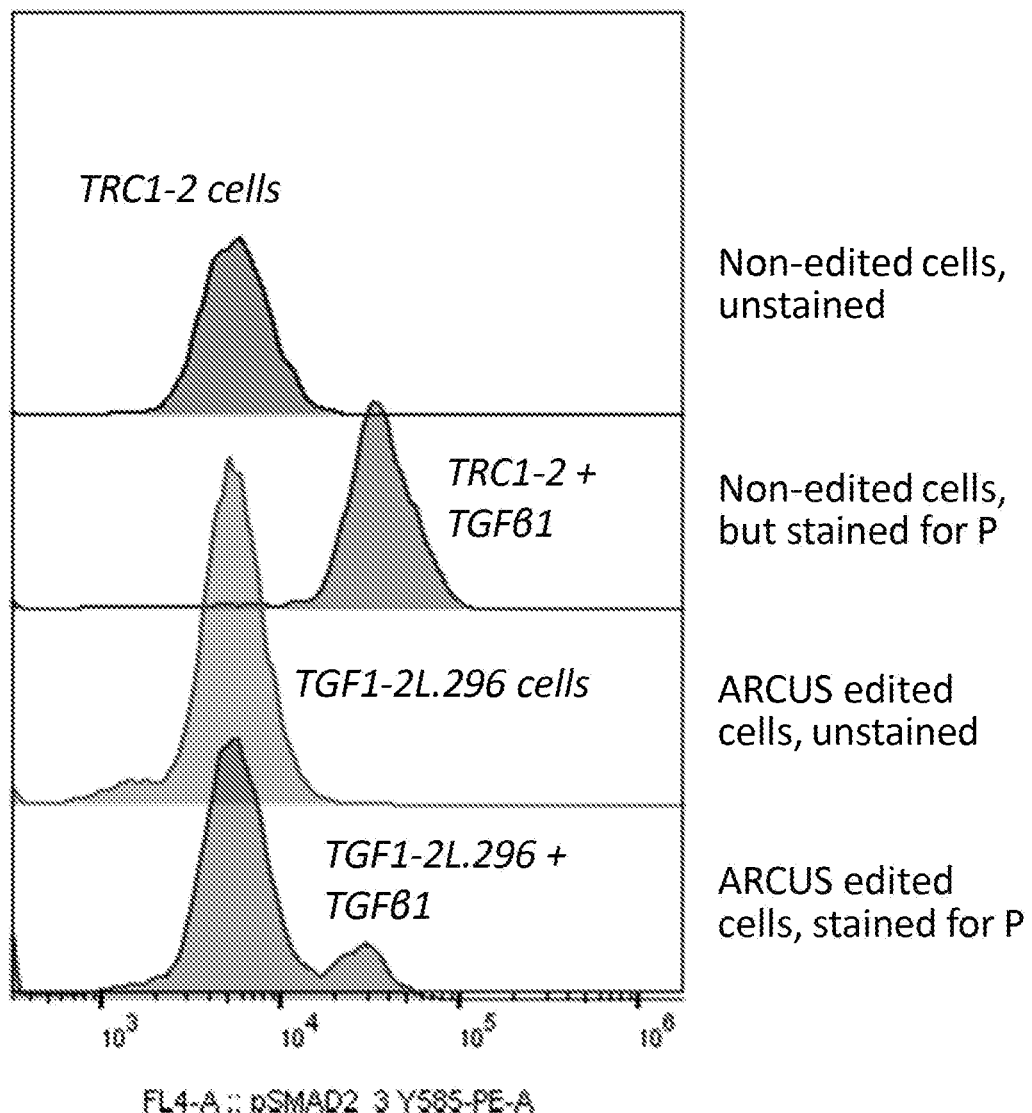
FIG. 14 shows flow cytometry staining for phosphorylated SMAD 2/3 in TGFBR2-positive and negative T cells treated with TGFB1.
Figure 15:
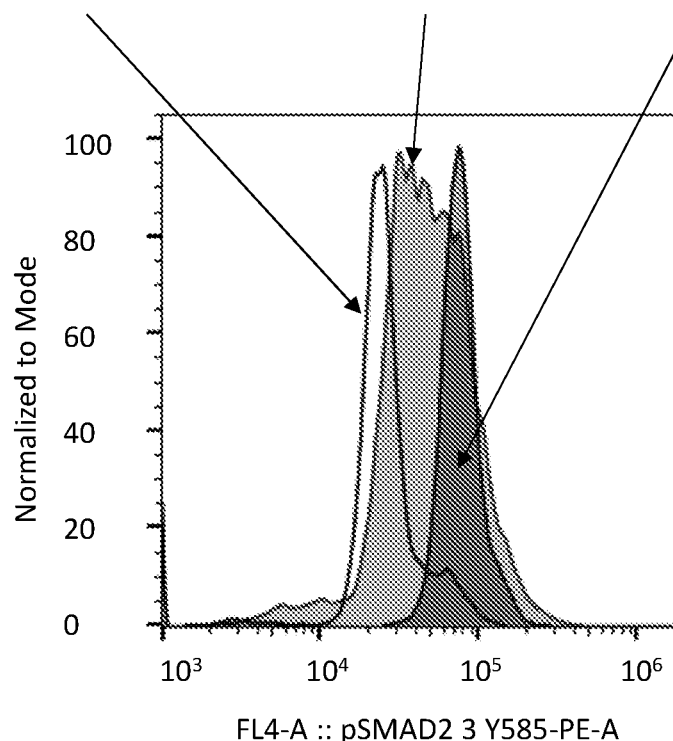
FIG. 15 shows flow cytometry for phosphorylated SMAD 2/3 in TGFBR2-positive CAR T cells, CAR T cells expressing an anti-TGFBR2 shRNAmiR to knockdown protein expression, and T cells treated with an engineered meganuclease to knockout TGFBR2 expression.

T cells with disruptions in TGFβRII expression (meganuclease versus RNAi) were sorted and stimulated with TGFβ1 to assess phosphorylation of SMAD2/3, which are downstream signal transducers of the TGFβR. Compared to TRAC-edited T cells, which exhibit low pSMAD2/3 signal in the absence of TGFβ1 and higher pSMAD signal after TGFβ1 exposure, TGFBR2 KO cells largely fail to respond to ligand exposure (FIG. 14). A small population of events in the TGFBR2-edited sample exhibits SMAD2/3 phosphorylation following cytokine exposure, although this likely represents a sort impurity. Compared to sorted TGFβRII-sufficient T cells (7206 CAR T), which phosphorylate SMAD2/3 in response to TGFβ1, and to sorted TGFBR2 KO cells, which do not, CAR T cells expressing a TGFBR2-directed shRNAmiR phosphorylate SMAD2/3 to a level that spans the range delineated by the positive and negative controls (FIG. 15).

A further experiment was carried out to determine whether meganuclease mediated knock out and shRNAmiR mediated knock down of TGFBR2 could reduce pSMAD 2/3 signaling in BCMA-specific CAR T cells (expressing the BCMA-specific CAR described in Example 6). Four experimental groups of BCMA CAR T cells were prepared and tested for pSMAD2/3 levels. The first and second groups included untreated control and TGFβ1 treated BCMA CAR T cells, respectively. The third and fourth groups included BCMA CAR T cells treated with TGFβ1 having either TGFBR2 knocked out with the TGF 1-2L.296 meganuclease or TGFBR2 knocked down with the 72112 TGFBR2 shRNAmiR, respectively.

Each of the groups of CART cells were prepared using the TRC1-2L.1592 meganuclease, which recognizes and cleaves the TRC 1-2 recognition sequence, and a DNA construct encoding a BCMA-specific CAR was inserted into this recognition sequence as described above. BCMA CAR T cells having knock out of TGFBR2 were prepared with the TGF 1-2L.296 meganuclease and cells having knock down of TGFBR2 were prepared with the 72112 TGFBR2 shRNAmiR as described above. The respective BCMA CAR T cell groups were treated with TGFβ1 (500 ng/ml) and all cell groups were harvested and analyzed as described above. For the TGFBR2 knock out cells, flow cytometry was gated on the TGFBR2-negative cell population.

Figure 16:
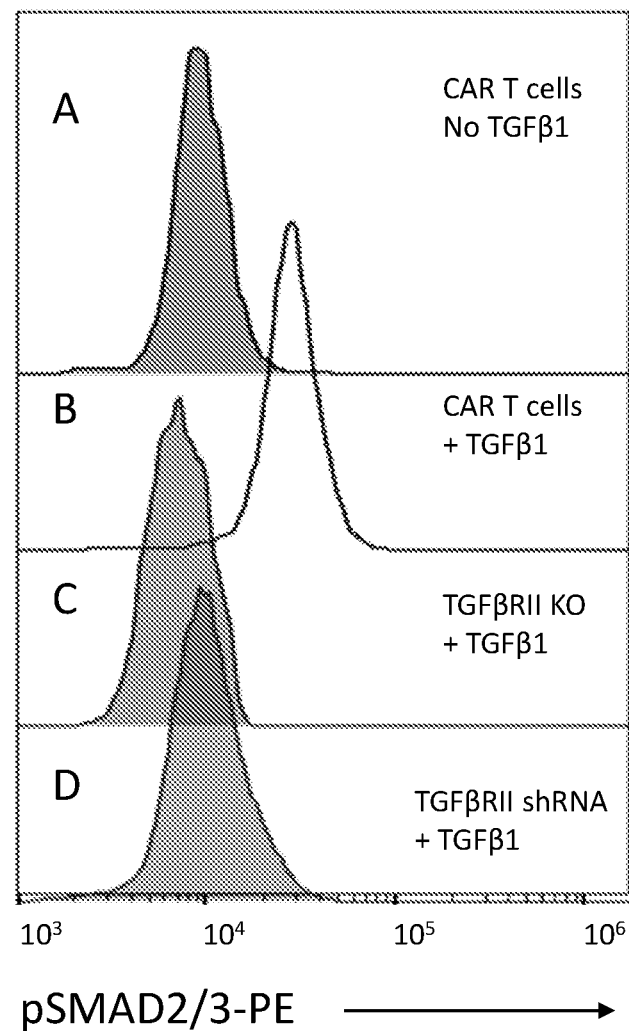
FIG. 16 shows flow cytometry for phosphorylated SMAD 2/3 in untreated control BCMA CAR T cells (A), BCMA CAR T cells treated with TGFβ1 (B), BCMA CAR T cells treated with TGFβ1 having either TGFBR2 knocked out with the TGF 1-2L.296 meganuclease (C) or TGFBR2 knocked down with the 72112 TGFBR2 shRNAmiR (D).

As shown in FIG. 16, untreated BCMA CART cells had low levels of pSMAD2/3, whereas treatment with TGFβ1 increased these levels. Knock out of TGFBR2 in BCMA CAR T cells with the TGF 1-2L.296 meganuclease decreased pSMAD2/3 to levels comparable to, or lower than, the untreated BCMA CAR T cell control. Knock down of TGFBR2 in BCMA CAR T cells with the 72112 TGFBR2 shRNAmiR also decreased pSMAD2/3 to levels comparable to the untreated BCMA CAR T cell control.

Thus, these studies demonstrated that TGFBR2 disruptions, either by gene editing or shRNAmiR, result in reduced ability of CAR T cells to phosphorylate SMAD2/3. No SMAD phosphorylation was detected in CAR T cells with a disabled TGFBR2 gene, while cells expressing a shRNAmiR are heterogeneous, with cells phosphorylating SMAD2/3 to varying degrees.

Example 8

Comparison of TGFBR2 Knockdown Versus Knockout in CAR T Cells

A further study was conducted in which the activity of CAR T cells was assessed following various alterations to the TGFβ pathway. CAR T cells were produced from healthy compensated donor T cells using a BCMA-specific CAR (as described in Example 6) inserted into the TRC 1-2 site in the TRAC gene (as described elsewhere). In some variants, a sequence encoding a shRNAmiR was also introduced at the TRC 1-2 site in the same cassette as the CAR (positioned between the CAR stop codon and a polyA sequence). In one variant, the shRNAmiR was a TGFBR2-specific shRNAmiR (construct 72154) while in another variant a shRNAmiR that is irrelevant to TGFβ function (targeting B2M—construct 72155) was introduced. A third variant of CAR T cells was produced using construct 72155, but they were edited at the TGFBR2 locus using the TGF1-2L296 nuclease described above in order to knockout the TGFBR2 gene. CAR T cells in the TGFBR2 KO group contained 60% KO.

Figure 17:
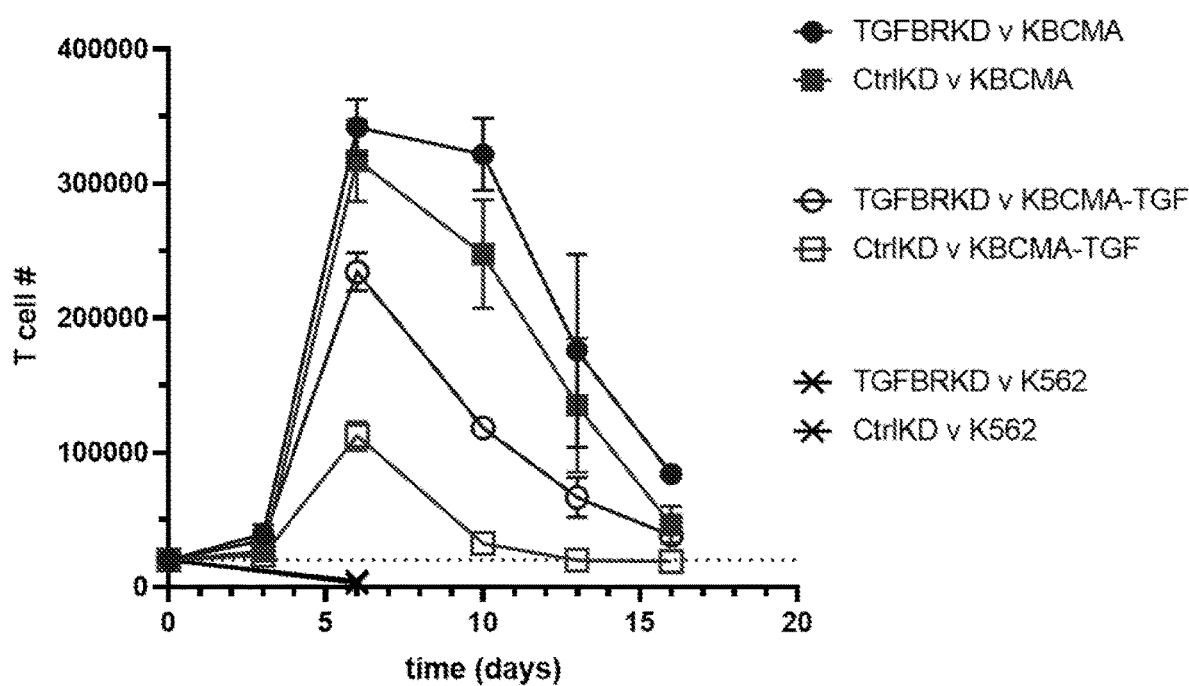
FIG. 17 shows BCMA CAR T cell numbers over time following co-culture with normal K562 cells, K562 cells transfected to stably express BCMA (KBCMA), or K562 cells stably expressing BCMA and constitutively secreting active TGFβ1 (KBCMA-TGF). BCMA CAR T cells were modified to knock down TGFBR2 using a shRNAmiR (TGFBRKD) or modified to knock down B2M with a shRNAmiR (CtrlKD).

Each group of CAR T cells was challenged with a variety of tumor targets: K562 negative control cells, K562 cells transfected to stably express BCMA, and K562 cells stably expressing BCMA and constitutively secreting active TGFβ1 (C223S C225S point mutations). In one experiment, CAR T cells and targets were plated at a 1:1 ratio. At the time points indicated in FIG. 17, T cells and any surviving targets were enumerated, and fresh targets were added to the culture so that a 1:1 ratio was re-established at each time point. The number of T cells in culture with respect to time are shown in FIG. 17. CAR T cells were not observed expanding in response to negative control K562 cells.

Figure 18:
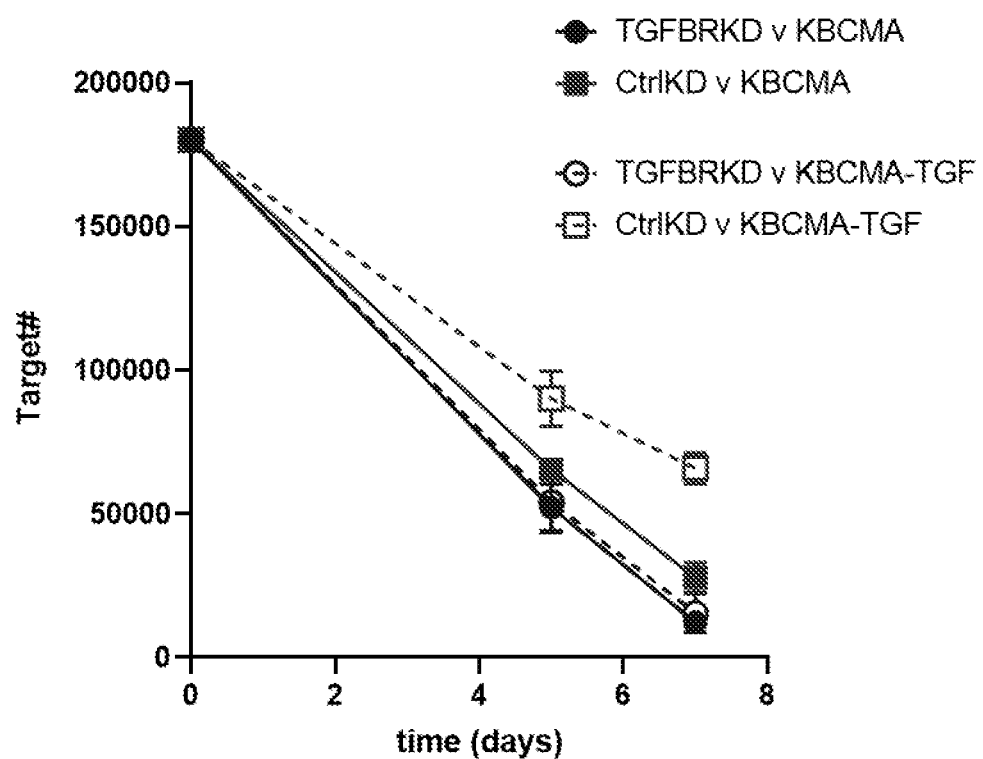
FIG. 18 shows target cell numbers over time following co-culture of BCMA CAR T cells with K562 cells transfected to stably express BCMA (KBCMA), or K562 cells stably expressing BCMA and constitutively secreting active TGFβ1 (KBCMA-TGF). BCMA CAR T cells were modified to knock down TGFBR2 using a shRNAmiR (TGFBRKD) or modified to knock down B2M with a shRNAmiR (CtrlKD).

CART cells with normal levels of TGFBR2 expression expanded >15-fold by day 6 of co-culture when challenged with BCMA+ targets, but only 5-fold in the presence of TGFB-secreting target cells. By comparison, TGFBR2 knockdown cells expand similarly in response to BCMA+ targets, but are less inhibited by TGFB-secreting targets (15-fold vs. 10-fold). In a separate experiment, CAR T cells were plated with targets at a 1:9 E:T ratio, and surviving target cells were enumerated on day 5 and day 7. By day 7, TGFBR2 knockdown cells had virtually eradicated BCMA+ target cells, regardless of their TGFb-secretion capacity. Control CAR T cells only eradicated control BCMA+ targets and did not eliminate TGFb-secreting BCMA+ targets (FIG. 18).

Figure 19:
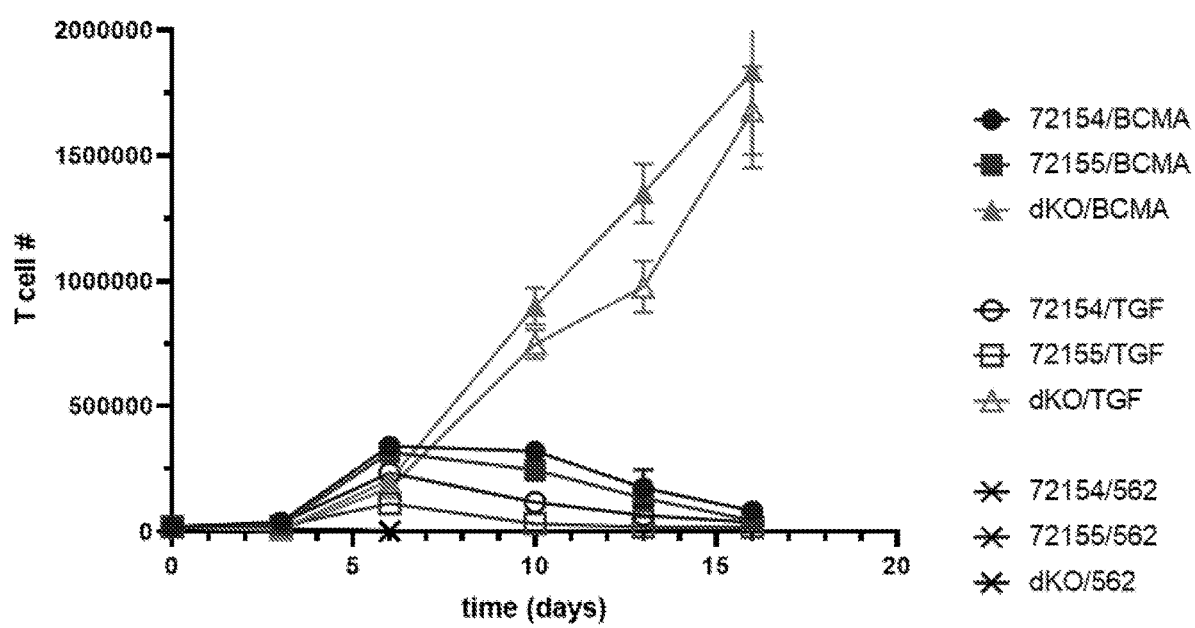
FIG. 19 shows BCMA CAR T cell numbers over time following co-culture with normal K562 cells, K562 cells transfected to stably express BCMA, and K562 cells stably expressing BCMA and constitutively secreting active TGFβ1. BCMA CAR T cells were modified to knock down TGFBR2 using a shRNAmiR (72154), modified to knock down B2M with a shRNAmiR (72155), or modified to knockout TGFBR2 with an engineered meganuclease (dKO).
Figure 20:
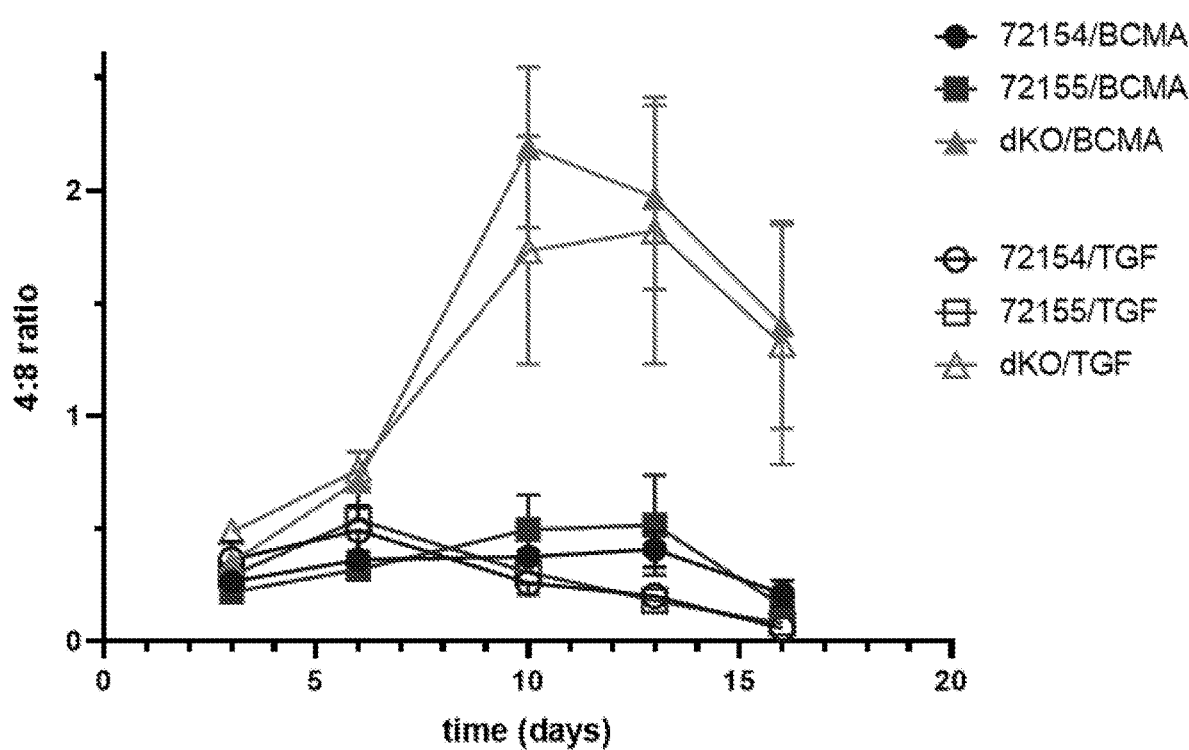
FIG. 20 shows the CD4:CD8 ratio of BCMA CAR T cells over time following co-culture with K562 cells transfected to stably express BCMA, and K562 cells stably expressing BCMA and constitutively secreting active TGFβ1. BCMA CAR T cells were modified to knock down TGFBR2 using a shRNAmiR (72154), modified to knock down B2M with a shRNAmiR (72155), or modified to knockout TGFBR2 with an engineered meganuclease (dKO).

CAR T cells that were edited with TGF1-2L296 nuclease to knockout TGFBR2 displayed a functional advantage over control or TGBFRII knockdown CAR T cells that was not related to TGFb secretion by the target cells. As shown in FIG. 19, cultures containing TGFBR2 knockout CAR T cells exhibited continuous expansion for the 17-day duration of the experiment. This was associated with an elevated and sustained CD4:CD8 ratio in the cultures containing TGFBR2 knockout CAR T cells (FIG. 20).

Together, these data indicate that editing with TGF1-2L296, or the inclusion of a TGFBR2-specific shRNAmiR, allow CAR T cells to maintain and carry out effector functions in the presence of suppressive amounts of TGFb 1.

Example 9

Comparison of TGFBR2 Knockdown Versus Knockout in CAR T Cells

Figure 21:
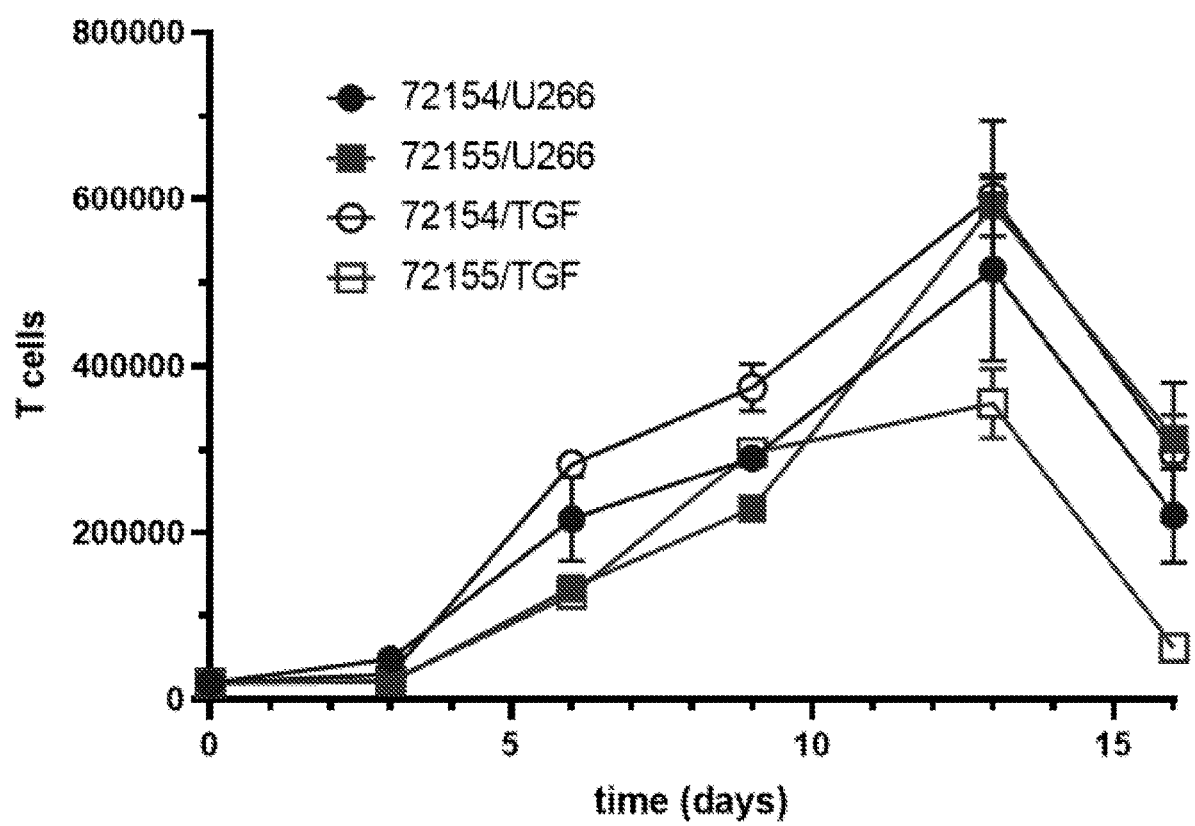
FIG. 21 shows BCMA CAR T cell numbers over time following co-culture with normal U266 cells, or U266 cells constitutively secreting active TGFβ1. BCMA CAR T cells were modified to knock down TGFBR2 using a shRNAmiR (72154), modified to knock down B2M with a shRNAmiR (72155), or modified to knockout TGFBR2 with an engineered meganuclease (dKO).
Figure 22:
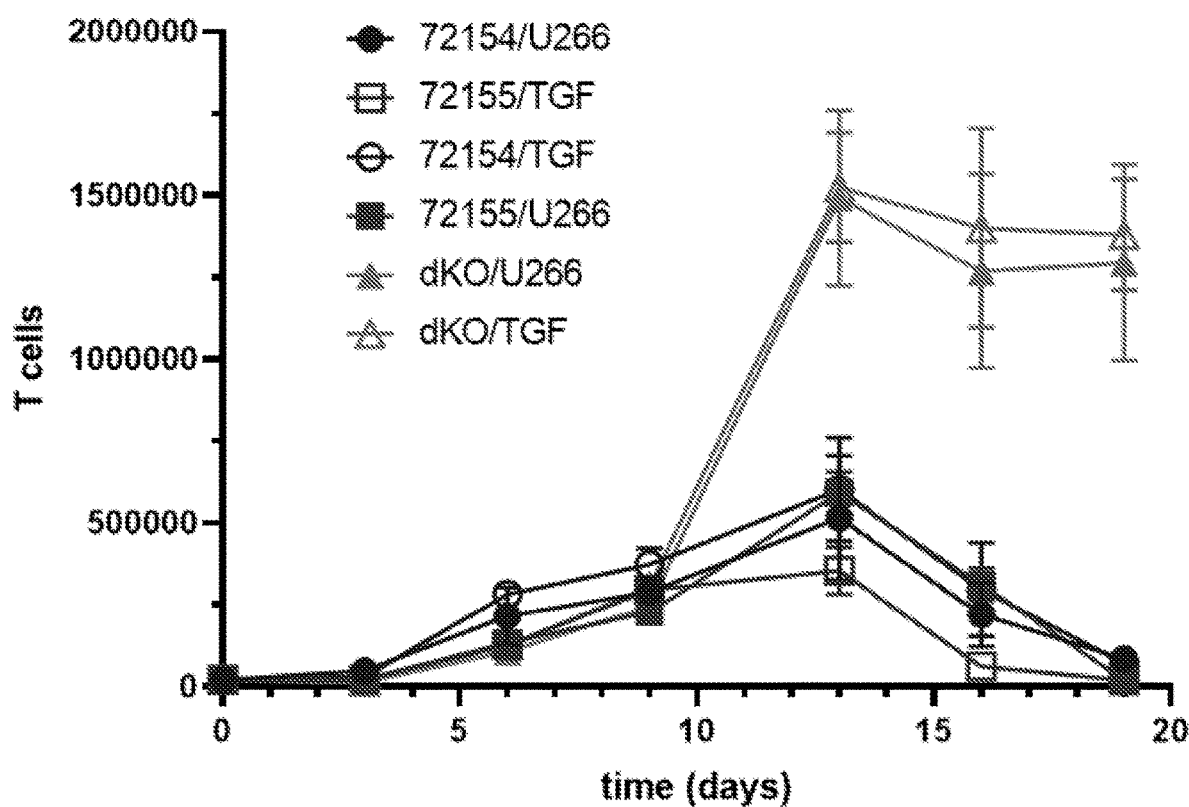
FIG. 22 shows BCMA CAR T cell numbers over time following co-culture with U266 cells, or U266 cells constitutively secreting active TGFβ1. BCMA CART cells were modified to knock down TGFBR2 using a shRNAmiR (72154), modified to knock down B2M with a shRNAmiR (72155), or modified to knockout TGFBR2 with an engineered meganuclease (dKO).

The CAR T variants described in Example 8 were also challenged repeatedly (as above) with the multiple myeloma cell line U266, or with U266 cells engineered to secrete active TGFb 1. Consistent with the findings from the K562 experiments, the peak expansion of control CAR T cells was approximately 50% reduced in response to TGFb-secreting U266 targets compared to control U266 targets (FIG. 21). CAR T cells expressing a TGFBR2-specific shRNAmiR were not inhibited by TGFb1-secreting U266 targets. CAR T cells edited with the TGF1-2L296 nuclease to knockout TGFBR2 expanded to higher numbers than other CAR T variants and maintained high numbers for the 19-day duration of this experiment (FIG. 22). This was also accompanied by an elevated frequency of CD4+ T cells (FIG. 23). The histograms in FIG. 23 were obtained at day 16 of co-culture and show that relative to control CAR T cultures (72154 at approximately 16% CD4+), TGFBR2 knockdown CAR T cultures had slightly elevated CD4 frequencies (23%) while dual-edited CAR T cultured contained 63% CD4+ cells.

Additional observations were made regarding the ability of CAR T cells to eradicate target cells in culture after their peak of expansion. Dot plots showing surviving target cells expressing BCMA (y-axes) or the TGFb-GFP transgene (x-axes) at the day 16 time point appear in FIG. 24. Despite observing a reduction in T cell numbers on day 16 following the re-challenge at day 13, both control and TGFBR2 knockdown CAR T cells were able to eradicate U266 targets. Dual edited CAR T cells, which did not exhibit a decrease in T cell number, also eradicated U266 targets between day 13 and day 16. Importantly, only CAR T cells with TGFb resistance (expressing the TGFBR2 shRNAmiR or edited with the TGF1-2L296 nuclease) were able to eliminate TGFb-secreting U266 targets. Control CAR T cells became unable to kill TGFb-secreting U266 targets and they grew to represent over 90% of the co-culture from day 13 to day 16.

These data support the conclusion in Example 8 that CAR T cells with perturbed expression of TGFBR2, through either shRNAmiR knockdown or by gene knockout, can proliferate and eliminate target cells in the presence of suppressive levels of TGFb cytokine.

Example 10

Stable Knockdown of CD52 in CAR T Cells

These studies were initiated in order to determine if an additional endogenous gene, CD52, could be stably knocked down using shRNAmiR sequences. The passenger and guide strands of the CD52 72123 shRNAmiR are set forth as SEQ ID NOs: 37 and 38, respectively. The passenger and guide strands of the CD52 72124 shRNAmiR are set forth as SEQ ID NOs: 39 and 40, respectively.

An apheresis sample was drawn from a healthy donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of $1\times10^6$ cells were electroporated with 1 µg of RNA encoding the TRC 1-2L.1592 meganuclease, which recognizes and cleaves the TRC 1-2 recognition sequence in the TRAC gene. Samples of linearized DNA were also added to cells at the time of nucleofection to a final concentration of 2 µg/$1\times10^6$ cells. Two different linearized constructs were used in this experiment, each one a variant of 7206 and each one encoding a different CD52-specific shRNAmiR downstream of the FMC63 CAR gene's stop codon but upstream of the poly-A transcriptional terminator.

At 10 days following nucleofection, cultures of cells were stained with anti-CD3-BV711 (Clone UCHT1, BD Biosciences), anti-FMC63-Alx647 (clone VM16, produced in-house), and anti-CD52-PE (Clone 4C8 BD BioSciences). The CD52 intensity was compared between CD3-CAR+ cells and unedited CD3+/CAR− cells.

At 10 days post-nucleofection, CD52 intensity on TRAC-edited CAR+ cells was plotted against CD52 intensity on non-edited (CD3+ CAR−) cells in the same culture. The CAR+ populations (unshaded histograms) from cultures nucleofected with constructs 72123 and 72124 expressed approximately one log lower CD52 signal than corresponding reference populations (shaded histograms), representing a stable reduction of approximately 90% in the CAR+ populations (FIG. 25).

This study demonstrates that the shRNAmiR approach can be leveraged to efficiently and stably knock down the endogenous CD52 protein in a CAR T cell population by approximately 90%.

Example 11

Multiplex Knockdown of Proteins by shRNAmiRs in CAR T Cells

Further studies were conducted to determine the feasibility of using shRNAmiR-mediated knockdown in CAR T cells in a multiplex approach. In these studies, both B2M and CD52 were targeted for knockdown in the same T cells by different shRNAmiRs that were stably expressed from the genome.

For these experiments, an apheresis sample was drawn from a healthy donor, and the T cells were enriched using the CD3 positive selection kit II in accordance with the manufacturer's instructions (Stem Cell Technologies). T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of 1×10⁶ cells were electroporated with 1 µg of RNA encoding the TRC 1-2L.1592 meganuclease, which recognizes and cleaves the TRC 1-2 recognition sequence in the TRAC gene.

Samples of linearized DNA were also added to cells at the time of nucleofection to a final concentration of 1 µg/1×10⁶ cells. Three different linearized constructs were used in this experiment, each one a variant of 7206, expressing a JeT-driven anti-CD19 CAR. One sequence referred to as clone 7290 contains a B2M-specific shRNAmiR in the 3' untranslated region (UTR) of the CAR. A second construct referred to as 72124 contains a CD52-specific shRNAmiR at the same location, and a third construct referred to as 72156 contains the CD52 shRNAmiR followed directly by the B2M shRNAmiR in the 3' UTR of the CAR.

After electroporation, cells were incubated for 7 days in complete X-VIVO15 supplemented with 30 ng/ml IL-2. At this time, T cells were analyzed for TRAC editing and CAR insertion, as well as CD52 and B2M expression as detailed above.

Figure 26:
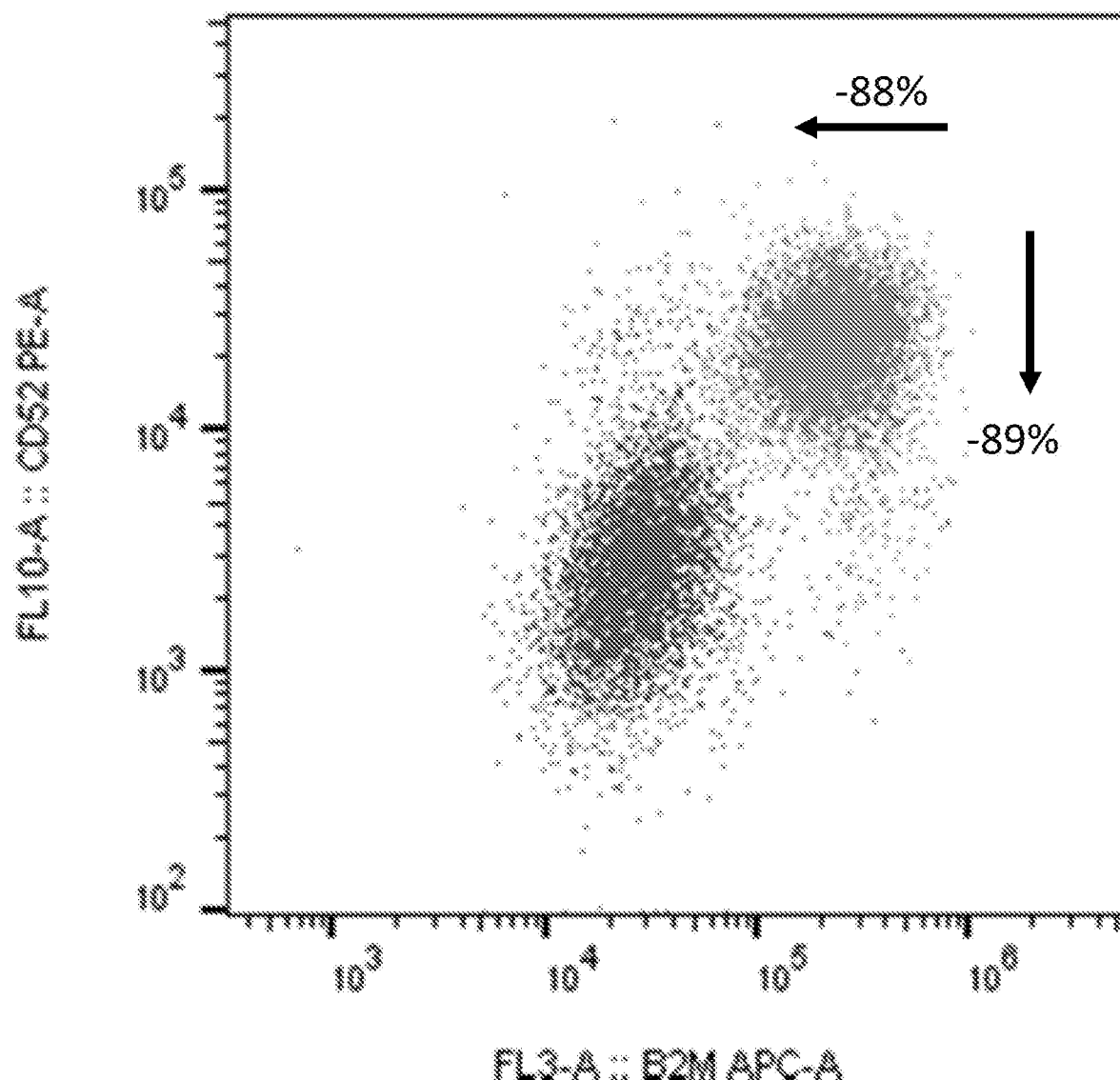
FIG. 26 shows flow cytometry staining for B2M and CD52 in T cells expressing a B2M-targeting shRNAmiR and a CD52-targeting shRNAmiR.
Figure 27:
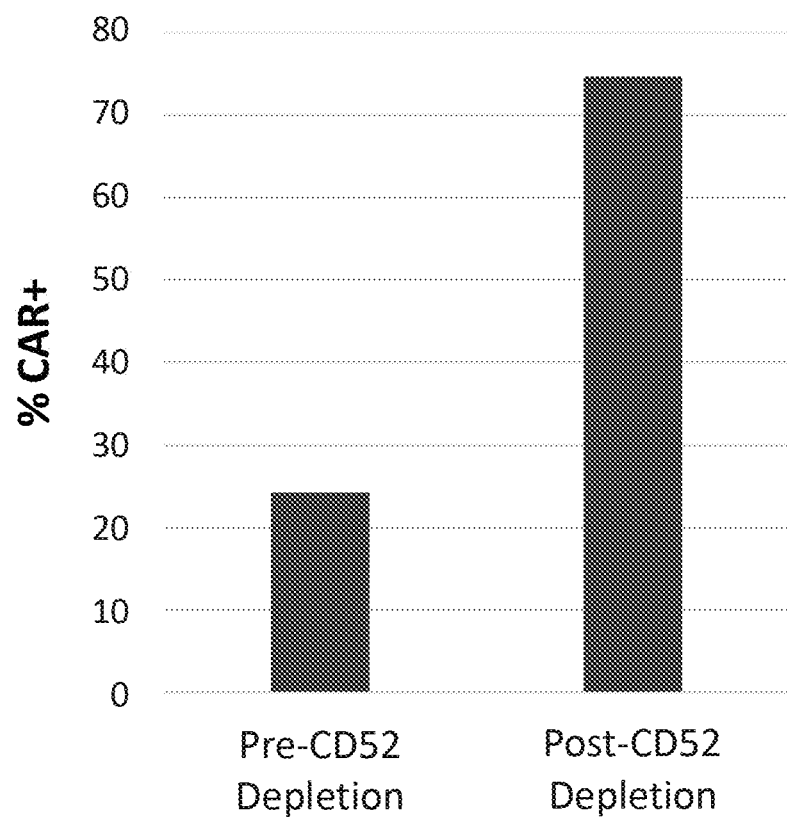
FIG. 27 shows the percentage of CAR+ T cells recovered following CD52 depletion of CAR T populations expressing a B2M-targeting shRNAmiR and a CD52-targeting shRNAmiR.

Populations of CAR⁺CD3⁻ cells were compared against non-edited CD3⁺CAR⁻ cells in each sample for CD52 and B2M expression. In samples receiving 7290 DNA, CAR T cells exhibited a 91% reduction in B2M surface levels (measured by mean fluorescence intensity) compared to CD3+ CAR− cells. Both populations displayed equivalent levels of surface CD52. In samples receiving 72124 DNA, the CAR+ population exhibited a 90% reduction in CD52 levels compared to the nonedited population but did not exhibit decreased B2M levels. CAR⁺ cells containing 72156 DNA demonstrated reduced levels of both CD52 (89%) and B2M (88%) relative to the reference population (FIG. 26). Further, it was demonstrated that a biotinylated anti-CD52 reagent could be used in a negative selection approach to deplete CAR− cells which still express high levels of CD52, and enrich the population of CAR+ cells which have reduced CD52 expression (FIG. 27).

These findings illustrate that two engineered shRNAmiRs, directed against two different transcripts, can be delivered to T cells via single-copy targeted insertion, and that both shRNAmiR genes can function simultaneously with little to no difference in performance relative to controls expressing only one shRNAmiR gene.

Example 12

Targeted Insertion of Constructs Encoding a CAR, HLA-E, and a shRNAmiR into a Single Genomic Locus Studies were conducted to further evaluate the use of shRNAmiR constructs in approaches for improving allogeneic CAR T cell persistence and reducing their susceptibility to potential NK cell killing. In these studies, four candidate constructs were inserted into T cells at the TRC 1-2 recognition site using the TRC 1-2L.1592 meganuclease previously described. Each construct contained a CD19-specific CAR gene (as described in Example 1, but modified to comprise the signal peptide of SEQ ID NO: 73) for tumor antigen targeting, a B2M-specific shRNAmiR (same used in the 7289 construct, previously described) optimized to reduce MHC I expression and evade alloreactive T cells, and an HLA-E fusion protein gene for inhibiting NK cytolysis. Constructs 73161-73164, shown in FIG. 28, incorporate these three elements in different configurations that vary in terms of promoter usage, and transcriptional termination.

Construct 73161 (FIG. 28A) uses a JeT promoter (SEQ ID NO: 67) to drive expression of the CAR, HLA-E fusion protein (SEQ ID NO: 66), and shRNAmiR genes as a single transcript that is terminated with a bidirectional SV40 polyA signal (labeled BipA; SEQ ID NO: 68). The shRNAmiR has been encoded in a synthetic intron (SEQ ID NO: 69) inserted at an exon junction in the HLA-E 03-01 allele. The intron will be spliced out and processed by nuclear microRNA biogenesis machinery while the remainder of the CAR-HLA-E transcript will be exported to the cytosol and translated into proteins. A P2A/furin site (SEQ ID NO: 70) enables the separation of the CAR and HLA-E fusion polypeptides.

Constructs 73162-164 (FIGS. 28B-28D) do not use a P2A/furin cleavage site but rely on separate promoters to drive CAR and HLA-E expression. In 73162, the shRNAmiR intron has been moved into the CAR gene, both of which are controlled by a JeT promoter and terminated by BipA, while HLA-E is controlled by a separate JeT promoter and terminated by a bovine growth hormone (BGH) polyA signal (SEQ ID NO: 71). In the 73163 and 73164 constructs, the shRNAmiR intron is again encoded in HLA-E, with CAR and HLA-E expression controlled by separate promoters and terminators. In 73163, the CAR gene is controlled by the JeT promoter and terminated by BipA, while HLA-E expression is controlled by the EF1α core promoter (SEQ ID NO: 72) and the BGH terminator. In 73164, both genes are controlled by separate JeT promoters and either BipA (CAR) or BGH (HLA-E) terminators. In all four of constructs, the CAR gene contains a signal peptide (SEQ ID NO: 73) that was optimized to increase CAR density on the surface of edited T cells.

Cryopreserved CD3+ T cells were thawed, rested, and activated as previously described. On day 3 post-activation, cells were electroporated with mRNA encoding the TRAC-specific nuclease (TRC 1-2L.1592) and immediately transduced with an AAV vector at an MOI of 25000 viral genomes/cell. Cells received AAV7206, or one of 73161-73164. Additionally, other samples of stimulated T cells were electroporated with mRNA encoding both TRC 1-2L.1592 and nuclease B2M 13-14x.479, which targets the endogenous B2M locus. These cells were transduced with AAV7206 and an AAV7346 (previously described), which encodes a JeT-driven HLA-E gene and directs insertion with homology to regions flanking the B2M13-14 site. These cells are referred to as double knockout, double knock-in (dKO dKI).

At 6 days following editing and AAV transduction, cells were analyzed by flow cytometry for surface expression of CAR, HLA-ABC, HLA-E, and CD3 using reagents, hardware, software, and procedures previously described.

The frequency of TRAC-edited CAR T cells, as well as the intensity of CAR staining, was assessed and is tabulated in the table of FIG. 29. Compared to the 7206 control, which only expresses a CD19-specific CAR, constructs 73161 and 73163 compared favorably, while constructs 73162 and 73164 produced CD3−/CAR+ populations but not as efficiently. All experimental constructs supported a higher expression level of CAR on the surface than 7206 (MFI listed in arbitrary fluorescence units as well as a percentage of the 7206 signal). This is potentially ascribable to improvements made to the leader peptide sequence.

All experimental constructs supported equally efficient knockdown of HLA-ABC (89-90%, FIG. 30), resulting from expression of the B2M shRNAmiR, and variable levels of HLA-E expression. Notably, the 73162 and 73164 constructs gave rise to populations of CD3−/CAR-populations that expressed HLA-E. This observation, coupled with the lower relative frequencies of CD3−/CAR+ cells in these samples, indicate that incomplete inserts missing either the left half (encoding the CAR) or the right half (HLA-E) of the vector were produced and packaged into AAV capsids. Sequence analysis (not shown) confirms that recombination events were driven by identical sequences that may be present in the vector. Fragmentation was observed in vectors 73162 and 73164, which contain two JeT promoters, while only intact inserts are detected from similarly-sized vectors, such as 73163, which did not contain any repeated identical sequences. Efficient knockdown of HLA-ABC also suggests that positioning the shRNAmiR in an intron is permissible and does not impair RNAi function.

In summary, these studies demonstrate the efficacy of several constructs that support three different functions in a CART cell (i.e., high expression of a CAR, high expression of HLA-E, and efficient knockdown of HLA-ABC). Both expression of HLA-E and knockdown of B2M (and therefore, HLA-ABC), can both potentially act to shield the CAR T cells from NK cell killing. Importantly, each of these multi-component constructs can be inserted into a single locus in the genome using a single nuclease, and avoids the need for multiplex gene editing to insert a CAR gene into the TRAC locus using a first nuclease, and to separately insert an HLA-E gene into the B2M locus with a second nuclease. Moreover, the signal intensity of HLA-E staining was found to be greater in the multigenic experimental samples (constructs 73161-73164) than with our previously described dKO dKI cells, where the HLA-E gene is inserted at the B2M13-14 site (see, WI reported in table of FIG. 30, 5th column). Knowing that we can achieve protection from NK cytolysis with the HLA-E expression level observed in dKO/dKI cells, we expect that the HLA-E expression levels supported by constructs 73161 and 73163 will confer protection as well.

Finally, these experiments further show that, in order to achieve a homogeneous vector, AAV preparation, and cell phenotype, intro-molecular homology-driven recombination events that result in partial vector loss must be minimized by avoiding the use of identical, repeated sequences in the transgene.

Example 13

Evaluation of CAR/HLA-E/B2M shRNAmiR Constructs

In this study, CAR T cells were prepared and assessed for surface expression of CAR, HLA-ABC, and HLA-E as described in Example 12. Here, constructs 7206, 73161, or 73163 were inserted into the TRC 1-2 site in the TRAC gene. Additional control cells (dKO/dKI) were included as a comparison for HLA-ABC and HLA-E expression levels. These control dKO/dKI cells had the CD19-CAR 7206 construct inserted at the TRC1-2 site in the TRAC gene and the HLA-E construct inserted at the B2M 13-14 site in the B2M gene.

Tabulated flow cytometry data appear in FIG. 31. The frequencies of CD3-CAR+ cells in cultures prepared with 73161 and 73163 compared favorably to the control (7206), as did the frequencies of TRAC-edited cells expressing transgene (KI of KO). The MFI of the CAR signal appeared to be approximately 2.5 times higher on samples generated with 73161 and 73163 than on 7206 or dKO/dKI samples. CAR+ cells generated with 73161 and 73163 exhibited greater than 90% reduction in HLA-ABC MFI and the majority of them also express HLA-E. Both the frequency and MFI of HLA-E+ CAR T cells was higher from the 73161 preparations. Taken together, these results indicate that vectors 73161 and 73163 support higher CAR expression than 7206, a high degree of HLA-ABC knockdown, and higher HLA-E levels than dKO/dKI approaches, which may confer greater avoidance from NK cell killing in vivo.

Example 14

In Vitro Assessment of Protection Against Alloreactive T Cells

This study assessed the ability of CAR T cells to escape natural killer (NK) and cytotoxic lymphocyte (CTL) killing when equipped with a B2M shRNAmiR and an HLA-E transgene. First, CART cells were produced using vectors 7206, 7289, 73161, or 73163 as described elsewhere. B2M KO T cells and B2M KO/HLA-E KI cells were produced using a B2M-specific meganuclease and a B2M-specific repair vector encoding the HLA-E fusion protein driven by a JeT promoter. All CAR T variants were produced from cells collected from the same donor (HC6366).

Next, naïve T cells from two unrelated donors (K2916 and K3212) were sensitized against H6366 alloantigens. Briefly, monocytes from HC6366 were cultured in the presence of recombinant human GM-CSF (800 U/ml—PeproTech) and IL-4 (400 U/ml—PeproTech) for 6 days to differentiate them into dendritic cell-like APCs. APCs were collected and co-cultured with naïve T cells from K3212 and K2916 at a T:APC ratio of 5:1. IL-2 (Gibco) was added to the culture after 24 h to a final concentration of 10 ng/ml. One week after plating, alloantigen-sensitized T cells were collected, and CTLs were enriched by CD4 depletion (CliniMACS CD4 microbeads, Miltenyi). CAR T variants were labeled with 1 uM CellTrace Violet (Thermo-Fisher) and then plated with alloantigen-primed CTLs from each donor at the ratios indicated in FIG. 32. This co-culture was carried out for 20-24 hours at which time the samples were labeled with 1 ug/ml of propidium iodide (Sigma) and the number of live dye-positive cells in each sample were enumerated using a Beckman-Coulter CytoFLEX-S. Percent killing was determined using a zero-effector control.

In FIG. 32, killing of CAR T cells by K3212 (panel A) or K2916 (panel B) CTLs is shown. Extensive killing was observed against control (7206) CAR T cells. Low E:T ratios (less than 1:1) resulted in 25-50% killing while E:T above 1 supported maximal killing for this assay: 50-60%. CAR T cells expressing a B2M-specific shRNAmiR were less susceptible to CTL killing with a maximum of 20% in 73163 CAR T cells and 10% in 73161 CAR T cells.

To assess NK activity against CAR T variants, NK cells were magnetically enriched from PBMCs from the same donor (HC6366) and an unrelated donor (K799) using a CD56 positive selection kit (StemCell Technologies) and cultured for 48 h in 10 ng/ml IL-15 (Gibco). CAR T target cells were labeled with Cell Trace Violet (as above) and plated with NK cells at the ratios specified in FIG. 33. Co-cultures were carried out for 4 to 5 days in XVIVO15+ 5% FBS and 10 ng/ml IL-2. Four to five days after plating, cultures were labeled with 1 ug/ml propidium iodide and surviving CAR T targets were enumerated as above. B2M KO cells and 7289 CAR T cells (shRNAmiR alone) were nearly eradicated (>90% killing) by both donor-matched and mismatched NK cells, associating killing with the lack of either normal HLA-ABC levels or an HLA-E transgene. NK killing of CAR T cells with normal HLA-ABC expression (7206) was very low (<10%) or not detected. CAR T variants lacking HLA-ABC but expressing an HLA-E transgene varied in their susceptibility to NK cytolysis. When cultured with autologous NK cells, 73163 CAR T cells and B2MKO/HLA-E+ cells were moderately protected (30-40% killing) while 73161 CAR T cells were robustly protected (<10% killing). In the experiment conducted with allogeneic NK cells, killing of B2MKO/HLA-E+ cells and 73161 cells was not detected.

These observations indicate that constructs 73161 and 73163 confer protection against alloantigen-specific CTLs without sensitizing the cells to NK killing. Furthermore, this protection can be afforded by a single recombinant AAV vector which is inserted at the TRAC locus using a single gene edit.

Example 15

In Vivo Activity of B2M shRNAmiR/HLA-E CAR T Cells

In order to demonstrate that inclusion of a shRNAmiR and an HLA-E transgene does not impair tumoricidal activity of CAR T cells, we performed an in vivo experiment in which tumor killing was monitored over time in immuno-deficient mice engrafted with NALM/6 leukemia cells. NOD.Cg-Prkdc$^{scid}$Il2rg$^{tm1Wjl}$SzJ mice (NOD.scid.γ-chain KO or NSG) mice were purchased from the Jackson Laboratory and injected via the tail vein with $5 \times 10^5$ NALM/6 cells expressing firefly luciferace (Imanis). Six days after tumor implantation, animals were injected with d-luciferin and luminescence was measured using the IVIS imager (Perkin-Elmer). After confirming tumor engraftment, mice were treated with either $1 \times 10^6$ or $5 \times 10^6$ CAR T cells (produced as described elsewhere) carrying either the 7206 control transgene (CD19 CAR only), the 7289 transgene, the 73161 transgene, or the 73163 transgene. One group of animals received vehicle control (saline supplemented with 2% human serum albumin). Mice were monitored longitudinally for luminescence and body weight. IACUC-approved humane endpoints were used to determine survival times. Luminescence measurements appear in FIG. 34 and survival is plotted in FIG. 35. Animals receiving vehicle control exhibited increasing luminescence after treatment until end point was reached at approximately day 27 after NALM/6 engraftment. Mice receiving CAR T intervention exhibited temporarily reduced luminescence with a duration and magnitude that is proportional to the CAR T dose. This is accompanied by survival benefits, with mice receiving $1 \times 10^6$ CAR T cells surviving 35-42 days and mice receiving $5 \times 10^6$ cells surviving from 52 days to beyond 60 days. No significant contributions to luminescence or survival between treatment groups were observed other than due to dose size. This study indicates that CAR T cells produced using constructs 73161 and 73163 have comparable efficacy as 7206 CART cells.

Example 16

Screening of DCK shRNAmiRs with Non-Viral DNA Transfection of CAR/shRNAmiR Constructs These studies were initiated to evaluate different guide and passenger sequences as shRNAmiRs to stably knockdown DCK. The goal was to determine whether knockdown of DCK in CAR T cells would allow for enrichment of the CD3−/CAR+ population in the presence of purine nucleoside analogs, such as fludarabine, which is commonly used in CAR T lymphodepletion regimens.

The transgene utilized in this study comprised a JeT promoter driving the expression of a CD19 CAR (previously described in Example 1) and a shRNAmiR gene as a single transcript, that is terminated with a bidirectional SV40 polyA signal. The transgene was flanked on either side by homology arms directing the transgene to insert at the TRC1-2 cut site in the TRAC gene. For the shRNAmiRs, five DCK guide and passenger strand sequences were identified and cloned into a miR-E backbone and inserted into the CD19-CAR construct between the stop codon of the CAR and the bidirectional SV40 polyA transcriptional terminator. In separate experiments, the DCK shRNAmiRs evaluated in this study exhibited reductions of 70% (72136), 40% (72137), 35% (72138), 60% (72140), when compared to endogenous DCK levels of control cells expressing a CD19 CAR that did not comprise a DCK-targeting shRNAmiR (7206). These DCK shRNAmiR sequences were tested for their ability to enrich for CD3−/CAR+ population when treated with fludarabine.

Cryopreserved CD3+ T cells were thawed, rested. CD3+ T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of $1 \times 10^6$ cells were electroporated with 1 µg of RNA encoding the TRC 1-2L.1592 meganuclease, which recognizes and cleaves the TRC 1-2 recognition sequence in the TRAC gene. The five CAR-shRNAmiR constructs (constructs 72136-72140) were delivered to T cells as linearized DNA (1 μg/1×10$^6$ cells.), simultaneously with the TRC 1-2 nuclease RNA during nucleofection. Electroporated cells were cultured in X-VIVO™15 medium supplemented with 5% fetal bovine serum and 30 ng/ml IL-2.

At day 4 post nucleofection, 2.5e5 viable cells were treated with wide range of doses of fludarabine in a 96 round bottom plate; 50 uM, 5 uM, 0.5 uM, 0.05 uM 0.005 uM and an untreated control in complete XVIVO™15 medium supplemented with 10 ng/mL of IL-15, IL-21 (Gibco). Untreated control received DMSO at volume equal to highest dose of fludarabine. 2 days post treatment, the 96 well plate was spun down, media containing drug was discarded and the cells were moved from 96 well plate to 48 well plate and treated with fresh complete XVIVO™15 media, cytokines, and fludarabine (except untreated control which did not receive any drug). On day 6 post treatment with fludarabine, 200 uL of sample was taken from each well for staining and remaining cells were spun down and treated with fresh complete XVIVO™ 15 medium supplemented with 10 ng/mL of IL-15, IL-21 (Gibco) and fludarabine (except untreated control which did not receive any drug). Day 6 and 10 post treatment with fludarabine, 200 uL of samples of the cultures were stained with anti-CD3-PE (BioLegend Clone UCHT1), anti-FMC63-AlexaFluor647 (clone VM16, produced in-house).

FIG. 36 shows the percent KI of KO plotted at different doses of fludarabine tested by flow cytometry and is also listed below the corresponding shRNAmiR in Table 3. Percent KI of KO is defined as: (% CD3−/CAR+)/(% Total CD3−)×100. Tabulated data were acquired at day 10 post-treatment with fludarabine. With CAR expressing DCK shRNAmiRs, treatment with increasing doses of fludarabine resulted in enrichment of CD3−/CAR+ population and can be observed in Table 3 by an increase in Percent KI of KO. Except 72139, all DCK knockdown constructs showed more than 70% KI of KO at dose 5 uM of fludarabine. Dose 50 uM Fludarabine was too toxic to the cells. FIG. 37 shows events/uL of CD3−/CAR+ population versus concentration of fludarabine in uM and correlates with percent KI of KO. Highest percent KI of KO and events/uL were seen at dose 5 uM Fludarabine.

TABLE 3

Percent KI of KO seen by knockdown of DCK by candidate sequences, post treatment with fludarabine.

| | Dose of fludarabine (uM) | | | | | |
|---|---|---|---|---|---|---|
| | 7206 | 72136 | 72137 | 72138 | 72139 | 72140 |
| Untreated (DMSO) | 23.06 | 17.71 | 18.40 | 16.58 | 15.72 | 14.46 |
| 0.005 | 23.32 | 20.60 | 21.93 | 19.15 | 17.34 | 17.61 |
| 0.05 | 22.71 | 21.12 | 23.43 | 18.69 | 17.72 | 16.85 |
| 0.5 | 27.60 | 39.03 | 41.25 | 41.13 | 27.57 | 33.94 |
| 5 | 33.27 | 70.70 | 72.87 | 80.70 | 43.69 | 70.02 |
| 50 | 4.35 | 43.14 | 7.69 | 8.33 | 7.49 | 4.76 |

Candidate sequences encoded in 72136, 72138 were investigated in further experiments using AAV.

This experiment demonstrated that knocking down DCK using a shRNAmiR allowed for enrichment of CD3−/CAR+ cells in the presence of fludarabine. Four out of the five DCK shRNAmiR constructs tested by this non-viral approach showed that treatment with dose 5 uM of fludarabine for 10 days resulted in above 70% KI of KO. Fludarabine is commonly used along with cyclophosphamide to lymphodeplete patients prior to administration of CAR T. This study provides a proof-of-concept that knocking down DCK with a shRNAmiR makes CAR T cells resistant to fludarabine, allowing for their enrichment. Clinically, the inclusion of a DCK shRNAmiR could allow for the continued administration of fludarabine to a patient after administration of allogeneic fludarabine-resistant CAR Ts, thus suppressing the host immune response and allowing these drug resistant CAR T cells to have greater proliferation and persistence in vivo. Thus, a potential clinical benefit of knocking down DCK could allow for an extended therapeutic window of activity of allogeneic drug resistant CAR T cells, while also potentially allowing for synergistic anti-tumor activity of fludarabine and the CAR T therapy.

Example 17

Effects of DCK Knockdown by shRNAmiR on CAR T Cell Phenotype and Anti-Tumor Activity These studies were initiated to evaluate different guide and passenger sequences as shRNAmiRs (constructs 72136 and 72138) to stably knockdown DCK following AAV transduction. The goal was to determine the effect of DCK knockdown on CAR T cell phenotype and anti-tumor activity.

Cryopreserved CD3+ T cells were thawed, rested, and activated as previously described. On day 3 post-activation, cells were electroporated with mRNA encoding the TRAC-specific nuclease TRC 1-2L.1592 and immediately transduced with an AAV vector at an MOI of 20000 viral genomes/cell. Cells received AAV7206, or 72136 or 72138 or no AAV (only received TRC 1-2L.1592). 3 days post transduction, CAR T phenotype was studied by staining with anti-CD3-PE (BioLegend, Clone UCHT1), anti-FMC63-AlexFluor647 (clone VM16, produced in-house), anti-CD4-BV711 (BioLegend, clone OKT4), anti-CD8a-BV785 (BioLegend, clone SK1), anti-CD62L-BS515 (BD Pharmingen, clone DREG-56), anti-CD45RO-PE/Cyanine7 (BioLegend, clone UCHL1), anti-CD27-BV421 (BioLegend, clone 0323). Samples were tested by flow cytometry and data was acquired on CytoFLEX-S.

2.5e5 viable cells were treated with the following doses of fludarabine in a 48 well plate; 12 uM, 6 uM, 3 uM and an untreated control in complete Xuri medium supplemented with 10 ng/mL of IL-15, IL-21 (Gibco). Note: Untreated control received DMSO at volume equal to highest dose of fludarabine. Day 4 post treatment, cell counts were taken (shown in FIG. 38) and 1e6 viable cells were spun down, supernatant was discarded (except samples TRC and 7206 treated with 6 uM and 12 uM fludarabine), and the cells were moved to a new 48 well plate and treated with fresh complete Xuri media, cytokines, +/−fludarabine. On Day 8 post treatment with fludarabine, samples were taken for CAR T phenotype staining as mentioned above. Remaining cells were CD3 depleted using EasySep Human Release CD3 positive selection kit. CD3− fractions were retained and cultured in complete Xuri media supplemented with 10 ng/mL of IL-15, IL-21 (Gibco) and no further treatment with fludarabine. Day 14 post transduction, samples were taken for CAR T phenotype staining prior to setting up ACEA assay (Refer panel as described above). This is because the % CD3-CAR+ is required to determine the exact number of CAR T to add as effectors. Day 15 post transduction, ACEA killing assay was setup using 72136 or 72138 (DCK knockdown CD19-CAR T) or 7206 (CD19 CAR T) untreated or treated with fludarabine at 3 or 6 uM as effector cells and HEK 293 expressing CD19 as target cells. Triton X-100 was used as a positive control for cytolysis and TRC was used as a negative control. Experiment was setup at Effector: Target (E:T) ratio of 2:1, 1:2 and 1:4.

CAR T phenotype on day 3 post-transduction (pretreatment with fludarabine) was tested via flow cytometry and is summarized in Table 4 below. Percent KI of KO is defined as (% CD3−/CAR+)/(% Total CD3−)*100. CD4:CD8 ratios and frequencies for T naïve (Tn), T central memory (Tcm)/T transition memory (Ttm), T effector memory (Tem) are reported in Table 4. Tn are CD62L+CD45RO− (low), whereas Tcm are CD62L+, CD45RO+ (mid), Ttm are CD62L+, CD45RO+ (high), Tem are CD62L−, CD45RO+. The CAR T phenotype before treatment with fludarabine remains unchanged between 7206 (CD19-CAR) and 72136, 72138 (CD19-CAR expressing DCK shRNAmiRs) as shown below.

CAR T phenotype on day 8 post treatment with fludarabine was tested via flow cytometry and is reported in Table 5 below. FIG. 39 shows viable cell counts/mL taken on day 8 post treatment with fludarabine. Due to DCK knockdown, the CAR T cells expressing DCK shRNAmiRs were more viable in the presence of fludarabine compared to TRC nuclease only (no AAV) and 7206 (CD19-CAR AAV). With CAR T expressing DCK shRNAmiRs, treatment with increasing doses of fludarabine resulted in enrichment of CD3−/CAR+ population and can be observed in Table 5 by an increase in Percent KI of KO. CD4:CD8 ratios and frequencies for T naïve (Tn), T central memory (Tcm)/T transition memory (Ttm), T effector memory (Tem) are also reported. No significant differences were observed in CAR T phenotype of CD19-CAR expressing DCK shRNAmiR's between untreated or samples treated with fludarabine.

TABLE 4

CAR T phenotype based on CD45RO and CD62L gating (pretreatment with fludarabine)

| | Percent | | T cell phenotype derived by staining and gating with CD62L, CD45RO | | | | | | | |
| | | | CD4 | | | | CD8 | | | |
| AAV | KI of KO | CD4:CD8 | Tn | Tcm | Ttm | Tem | Tn | Tcm | Ttm | Tem |
|---|---|---|---|---|---|---|---|---|---|---|
| 7206 | 67.87 | 1.1 | 0.74 | 83.56 | 11.55 | 2.88 | 2.01 | 94.74 | 3.22 | 0.55 |
| 72136 | 69.31 | 1.2 | 0.56 | 84.22 | 11.17 | 2.94 | 1.98 | 95.65 | 2.86 | 0.55 |
| 72138 | 68.25 | 1.19 | 0.7 | 84.66 | 10.98 | 2.53 | 2.65 | 95.76 | 2.92 | 0.38 |

FIG. 38 shows viable cell count/mL taken on day 4 post treatment with fludarabine. With TRC only (no AAV) or 7206 (CD19-CAR AAV) a 50% or higher decrease in cell count was seen post treatment with increasing dose of fludarabine compared to 72136 and 72138 (CD19-CAR AAV expressing DCK shRNAmiRs).

However, with the CD19 CAR (7206) the CD4 and CD8 phenotype upon treatment with fludarabine shifts from central memory to transition and effector memory phenotype. This shows that DCK knockdown and treatment with fludarabine did not have any significant effect on the CAR T cell phenotype.

TABLE 5

CAR T phenotype based on CD45RO and CD62L gating (D8 post treatment with fludarabine)

| | | | T cell phenotype derived by staining and gating with CD62L, CD45RO | | | | | | | |
| | Percent | | CD4 | | | | CD8 | | | |
| AAV | KI of KO | CD4:CD8 | Tn | Tcm | Ttm | Tem | Tn | Tcm | Ttm | Tem |
|---|---|---|---|---|---|---|---|---|---|---|
| 7206 untreated | 74.09 | 0.63 | 0.2 | 60.15 | 28.29 | 8.56 | 0.86 | 96.19 | 2.31 | 0.53 |
| 7206 3 uM Flu | 72.51 | 0.68 | 0.04 | 25.78 | 56.91 | 13.55 | 0.28 | 86.38 | 9.76 | 1.79 |
| 7206 6 uM Flu | 74.21 | 1.7 | 0.05 | 16.42 | 60.53 | 20.22 | 0.09 | 74.18 | 16.42 | 4.29 |
| 72136 untreated | 69.27 | 0.7 | 0.34 | 55.95 | 29.5 | 11.17 | 1.61 | 95.4 | 2.36 | 0.89 |
| 72136 3 uM Flu | 70.59 | 0.6 | 0.8 | 60.09 | 25.84 | 10.6 | 3.44 | 96.93 | 1.52 | 0.49 |
| 72136 6 uM Flu | 75.12 | 0.61 | 0.48 | 55.49 | 29.42 | 11.5 | 2.36 | 95.83 | 2.17 | 0.64 |
| 72138 untreated | 72.70 | 0.66 | 0.14 | 56.24 | 32.47 | 8.75 | 0.53 | 95.52 | 3.02 | 0.6 |
| 72138 3 uM Flu | 80.38 | 0.53 | 0.23 | 55.18 | 28.72 | 11.35 | 1.88 | 96.9 | 1.79 | 0.48 |

TABLE 5-continued

CAR T phenotype based on CD45RO and CD62L gating (D8 post treatment with fludarabine)

| | | | T cell phenotype derived by staining and gating with CD62L, CD45RO | | | | | | | |
|---|---|---|---|---|---|---|---|---|---|---|
| | Percent | | CD4 | | | | CD8 | | | |
| AAV | KI of KO | CD4:CD8 | Tn | Tcm | Ttm | Tem | Tn | Tcm | Ttm | Tem |
| 72138 6 uM Flu | 84.15 | 0.54 | 0.19 | 51.29 | 32.74 | 12.01 | 1.33 | 96.21 | 2.46 | 0.56 |

FIG. 40 shows % cytolysis (normalized to TRC) using 7206 (CD19-CAR), untreated or treated with 3 and 6 uM fludarabine, as effector cells in an ACEA assay. HEK 293 expressing CD19 were used as target cells. Experiment was setup at E:T ratio of 2:1, 1:2 and 1:4. Triton was used as a positive control for cytolysis and TRC was used as a negative control. Irrespective of +/−treatment with fludarabine, most efficient killing was seen at E:T ratio of 2:1. At E:T ratios of 1:2, 1:4, less efficient killing was seen in presence of increasing doses of fludarabine compared to untreated.

FIG. 41 shows % cytolysis (normalized to TRC) using 72138 (CD19-CAR expressing DCK shRNAmiR), untreated or treated with 3 uM or 6 uM fludarabine, as effector cells in an ACEA assay. HEK 293 expressing CD19 were used as target cells. Experiment was setup at E:T ratio of 2:1, 1:2 and 1:4. Triton was used as a positive control for cytolysis and TRC was used as a negative control. It was observed that irrespective of treatment with or without fludarabine, most efficient killing was seen at E:T ratio of 2:1 followed by 1:2 and then 1:4. FIG. 42 shows % cytolysis (normalized to TRC) using 72136 (CD19-CAR expressing DCK shRNAmiR), untreated or treated with 3 uM or 6 uM fludarabine, as effector cells in an ACEA assay. HEK 293 expressing CD19 were used as target cells. Experiment was setup at E:T ratio of 2:1, 1:2 and 1:4. Triton was used as a positive control for cytolysis and TRC was used as a negative control. It was observed that irrespective of treatment with or without fludarabine, most efficient killing was seen at E:T ratios of 2:1 followed by 1:2 and then 1:4.

Finally, the CD19-CAR expressing DCK shRNAmiRs (72136, 72138) showed more efficient killing at E:T ratio of 1:2 than CD19 CAR when treated with fludarabine. This demonstrated that DCK knockdown using a shRNAmiR and treatment with fludarabine had a synergistic effect on the anti-tumor activity of CD19-CAR.

Example 18

Screening of Glucocorticoid Receptor shRNAmiRs with Non-Viral DNA Transfection of CAR/shRNAmiR Constructs These studies were initiated to evaluate different guide and passenger sequences as shRNAmiRs to stably knockdown the glucocorticoid receptor (GR). The goal was to determine whether knockdown of GR in CAR T cells would allow for enrichment of the CD3−/CAR+ population in the presence of corticosteroids such as dexamethasone, which is commonly used in the treatment of cytokine release syndrome that can be associated with CAR T cell therapy.

The transgene utilized in this study comprised a JeT promoter driving the expression of a CD19-CAR and a shRNAmiR gene as a single transcript, that is terminated with a bidirectional SV40 polyA signal. The transgene was flanked on either side by homology arms directing the transgene to insert at the TRC1-2 cut site in the TRAC gene. For the shRNAmiRs, nine GR guide and passenger strand sequences were identified and cloned into a miR-E backbone and inserted into the CD19-CAR construct between the stop codon of the CAR and the bidirectional SV40 polyA transcriptional terminator. In separate experiments, the GR shRNAmiRs evaluated in this study exhibited reductions of 37% (72142), 45% (72143), 50% (72145), and 56% (72149), when compared to endogenous GR levels of control cells that expressed a CD19 CAR but did not comprise a GR-targeting shRNAmiR (7206). These GR shRNAmiR sequences were tested for their ability to enrich for CD3−/CAR+ population when treated with dexamethasone.

Cryopreserved CD3+ T cells were thawed, rested. T cells were activated using ImmunoCult™ T cell stimulator (anti-CD2/CD3/CD28, Stem Cell Technologies) in X-VIVO™ 15 medium (Lonza) supplemented with 5% fetal bovine serum and 10 ng/ml IL-2 (Gibco). After 3 days of stimulation, cells were collected and samples of $1\times10^6$ cells were electroporated with 1 μg of RNA encoding the TRC 1-2L.1592 meganuclease, which recognizes and cleaves the TRC 1-2 recognition sequence in the T cell receptor alpha constant gene. The nine CAR-shRNAmiR constructs (constructs 72142, 72143, 72145, 72146, 72148-72152) were delivered to T cells as linearized DNA (1 μg/$1\times10^6$ cells.), simultaneously with the TRC1-2 nuclease RNA during nucleofection. Electroporated cells were cultured in X-VIVO™15 medium supplemented with 5% fetal bovine serum and 30 ng/ml IL-2.

At day 8 post nucleofection, 2.5e5 viable cells were treated with wide range of doses of dexamethasone in a 96 round bottom plate; 100 uM, 10 uM, 1 uM, 0.1 uM, 0.01 uM and an untreated control in complete XVIVO™15 medium supplemented with 10 ng/mL of IL-15, IL-21 (Gibco). Note: Untreated control received 95% ethanol at a volume equal to highest dose of dexamethasone. 3 days post treatment, 96 well plate was spun down, media containing drug was discarded and the cells were moved from 96 well plate to 48 well plate and treated with fresh complete XVIVO™15 media, cytokines and dexamethasone (except untreated control which did not receive any drug). On day 7 post treatment with dexamethasone, 200 uL of sample was taken from each well for staining. Samples were stained with anti-CD3-PE (BioLegend, Clone UCHT1), anti-FMC63-AlexaFluor647 (clone VM16, produced in-house) and tested by flow cytometry on CytoFLEX-LX.

FIG. 43 shows percent KI of KO at different doses of dexamethasone tested by flow cytometry and is listed below the corresponding shRNAmiR in Table 6. Percent KI of KO is defined as: (% CD3−/CAR+)/(% Total CD3−)×100. Tabulated data were acquired at day 7 post-treatment with dexamethasone. With CAR expressing GR shRNAmiRs, treatment with increasing doses of dexamethasone resulted in enrichment of CD3−/CAR+ population and can be observed in Table 6 by an increase in percent KI of KO. Except for 72148, all GR knockdown constructs showed between 35-50% KI of KO at dose 1, 10 uM of dexamethasone. FIG. 44 shows events/uL of CD3−/CAR+ plotted versus concentration of dexamethasone in uM. Percent KI of KO correlates with the events/uL.

TABLE 6

Percent KI of KO seen by knockdown of GR by candidate sequences, post treatment with dexamethasone.

| | dexamethasone (uM) | | | | | | | | | |
| --- | --- | --- | --- | --- | --- | --- | --- | --- | --- | --- |
| | 7206 | 72142 | 72143 | 72145 | 72146 | 72148 | 72149 | 72150 | 72151 | 72152 |
| Untreated (ethanol) | 19.98 | 25.28 | 20.4 | 15.45 | 15.23 | 19.17 | 12.45 | 15.99 | 16.11 | 16.76 |
| 0.01 | 15.58 | 37.25 | 34.3 | 24.94 | 26.49 | 21.98 | 25.61 | 23.95 | 24.75 | 25.25 |
| 0.1 | 8.55 | 39.22 | 41.69 | 33.24 | 41.85 | 22.71 | 40.84 | 40.33 | 31.87 | 33.88 |
| 1 | 16.17 | 46.84 | 44.21 | 40.27 | 38.85 | 21.69 | 42.64 | 39.74 | 32.54 | 35.24 |
| 10 | 14.96 | 44.14 | 41.4 | 38.07 | 39.5 | 20.19 | 43.44 | 40.58 | 34.46 | 34.13 |
| 100 | 13.7 | 28.77 | 24.48 | 23.94 | 27.25 | 21.05 | 15.21 | 23.24 | 17.49 | 17.42 |

This experiment demonstrated that knocking down GR using a shRNAmiR allowed for enrichment of CD3−/CAR+ cells in the presence of a corticosteroid like dexamethasone. Eight out of the nine GR shRNAmiRs tested by non-viral approach showed that treatment with dose 1 uM or 10 uM of dexamethasone for 7 days resulted in 35-50% KI of KO.

Thus, these experiments confirm that knocking down GR with a shRNAmiR makes CAR T cells resistant to dexamethasone and allows for their enrichment. Clinically, corticosteroids are commonly used along with tocilizumab in the treatment of cytokine release syndrome (CRS), a potentially life-threatening toxicity sometimes seen following administration of adoptive T-cell therapies for cancer. Cytokine release syndrome is associated with elevated circulating levels of several cytokines. However, the administration of high doses of corticosteroids may reduce the clinical effectiveness of CAR T therapy. By making CAR T cells resistant to corticosteroids, HvG responses against the CAR T cells can be suppressed without affecting CAR T function, thereby increasing the potential window for activity and improving safety.

The invention claimed is:

1. A genetically-modified human T cell comprising in its genome a cassette comprising, from 5' to 3':

(a) a promoter;

(b) a nucleic acid sequence encoding a chimeric antigen receptor (CAR) or an exogenous T cell receptor TCR;

(c) a 2A or IRES sequence;

(d) a nucleic acid sequence encoding a HLA class I histocompatibility antigen, alpha chain E (HLA-E) fusion protein, wherein an intron sequence is positioned within said nucleic acid sequence encoding said HLA-E fusion protein, and wherein a nucleic acid sequence encoding a microRNA-adapted shRNA (shRNAmiR) is positioned within said intron sequence, wherein said nucleic acid sequence encoding said shRNAmiR comprises SEQ ID NO: 46; and (e) a termination signal;

wherein said nucleic acid sequence encoding said CAR or said exogenous TCR, said nucleic acid sequence encoding said HLA-E fusion protein, and said nucleic acid sequence encoding said shRNAmiR are operably linked to said promoter, and wherein said cassette is positioned within a T cell receptor (TCR) alpha constant region gene.

2. The genetically-modified human T cell of claim 1, wherein said cassette is positioned within a sequence consisting of SEQ ID NO: 58 within said TCR alpha constant region gene.

3. The genetically-modified human T cell of claim 2, wherein said cassette is positioned between nucleotide positions 13 and 14 of SEQ ID NO: 58.

* * * * *

SEQUENCE LISTING

```
Sequence total quantity: 123
SEQ ID NO: 1            moltype = DNA  length = 118
FEATURE                 Location/Qualifiers
misc_feature            1..118
                        note = Synthesized
source                  1..118
                        mol_type = other DNA
                        organism = synthetic construct
SEQUENCE: 1
ctgtttgaat gaggcttcag tactttacag aatcgttgcc tgcacatctt ggaaacactt   60
gctgggatta cttcgacttc ttaacccaac agaaggctcg agaaggtata ttgctgtt    118

SEQ ID NO: 2            moltype = DNA  length = 11
FEATURE                 Location/Qualifiers
misc_feature            1..11
                        note = Synthesized
source                  1..11
                        mol_type = other DNA
                        organism = synthetic construct
SEQUENCE: 2
gacagtgagc g                                                        11

SEQ ID NO: 3            moltype = DNA  length = 19
FEATURE                 Location/Qualifiers
misc_feature            1..19
                        note = Synthesized
source                  1..19
```

```
                            mol_type = other DNA
                            organism = synthetic construct
SEQUENCE: 3
tagtgaagcc acagatgta                                                    19

SEQ ID NO: 4               moltype = DNA   length = 11
FEATURE                    Location/Qualifiers
misc_feature               1..11
                           note = Synthesized
source                     1..11
                           mol_type = other DNA
                           organism = synthetic construct
SEQUENCE: 4
tgcctactgc c                                                            11

SEQ ID NO: 5               moltype = DNA   length = 121
FEATURE                    Location/Qualifiers
misc_feature               1..121
                           note = Synthesized
source                     1..121
                           mol_type = other DNA
                           organism = synthetic construct
SEQUENCE: 5
tcggacttca aggggctaga attcgagcaa ttatcttgtt tactaaaact gaatacccttg      60
ctatctcttt gatacatttt tacaaagctg aattaaaatg gtataaatta aatcactttg     120
c                                                                     121

SEQ ID NO: 6               moltype = DNA   length = 62
FEATURE                    Location/Qualifiers
misc_feature               1..62
                           note = Synthesized
source                     1..62
                           mol_type = other DNA
                           organism = synthetic construct
SEQUENCE: 6
gtaccggagg tttgaagatg ccgcatttct cgagaaatgc ggcatcttca aacctttttt      60
tg                                                                     62

SEQ ID NO: 7               moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 7
aaggtttgaa gatgccgcat tt                                                22

SEQ ID NO: 8               moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 8
aaatgcggca tcttcaaacc tc                                                22

SEQ ID NO: 9               moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 9
cgcaaggact ggtctttcta ta                                                22

SEQ ID NO: 10              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 10
tatagaaaga ccagtccttg ct                                                22

SEQ ID NO: 11              moltype = DNA   length = 22
```

-continued

```
FEATURE                 Location/Qualifiers
misc_feature            1..22
                        note = Synthesized
source                  1..22
                        mol_type = other DNA
                        organism = synthetic construct
SEQUENCE: 11
cggctatcca gcgtactcca aa                                                  22

SEQ ID NO: 12           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 12
tttggagtac gctggatagc ct                                                  22

SEQ ID NO: 13           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 13
cgcagagaat ggaaagtcaa at                                                  22

SEQ ID NO: 14           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 14
atttgacttt ccattctctg ct                                                  22

SEQ ID NO: 15           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 15
cgcttataca cttacacttt at                                                  22

SEQ ID NO: 16           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 16
ataaagtgta agtgtataag ca                                                  22

SEQ ID NO: 17           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 17
cggacatgat cttctttata at                                                  22

SEQ ID NO: 18           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 18
attataaaga agatcatgtc ca                                                  22
```

-continued

```
SEQ ID NO: 19            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 19
acgtgcataa gttaacttcc aa                                              22

SEQ ID NO: 20            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 20
ttggaagtta acttatgcac gc                                              22

SEQ ID NO: 21            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 21
ctgtattaat tggctctata aa                                              22

SEQ ID NO: 22            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 22
tttatagagc caattaatac at                                              22

SEQ ID NO: 23            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 23
acatgtttgg cagatactat aa                                              22

SEQ ID NO: 24            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 24
ttatagtatc tgccaaacat gg                                              22

SEQ ID NO: 25            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 25
agagtctgaa gtcacattgt aa                                              22

SEQ ID NO: 26            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 26
ttacaatgtg acttcagact cg                                              22
```

```
SEQ ID NO: 27              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 27
ggacctcaag agctccaata tc                                                  22

SEQ ID NO: 28              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 28
gatattggag ctcttgaggt ct                                                  22

SEQ ID NO: 29              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 29
agacctcaag agctccaata tc                                                  22

SEQ ID NO: 30              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 30
gatattggag ctcttgaggt cc                                                  22

SEQ ID NO: 31              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 31
ccctgacttg ttgctagtca ta                                                  22

SEQ ID NO: 32              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 32
tatgactagc aacaagtcag ga                                                  22

SEQ ID NO: 33              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 33
agcagtcaag atctttccct at                                                  22

SEQ ID NO: 34              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 34
```

```
atagggaaag atcttgactg cc                                                22

SEQ ID NO: 35           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 35
agcacgttca gaagtcggtt aa                                                22

SEQ ID NO: 36           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 36
ttaaccgact tctgaacgtg cg                                                22

SEQ ID NO: 37           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 37
accaccatca ctcgcaagag aa                                                22

SEQ ID NO: 38           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 38
ttctcttgcg agtgatggtg gc                                                22

SEQ ID NO: 39           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 39
acctcctggt tatggtacag at                                                22

SEQ ID NO: 40           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 40
atctgtacca taaccaggag gc                                                22

SEQ ID NO: 41           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 41
ctgtttgaat gaggcttcag tactttacag aatcgttgcc tgcacatctt ggaaacactt        60
gctgggatta cttcgacttc ttaacccaac agaaggctcg agaaggtata ttgctgttga       120
cagtgagcga aggtttgaag atgccgcatt ttagtgaagc cacagatgta aaatgcggca       180
tcttcaaacc tctgcctact gcctcggact tcaagggget agaattcgag caattatctt       240
gtttactaaa actgaatacc ttgctatctc tttgatacat ttttacaaag ctgaattaaa       300
atggtataaa ttaaatcact ttgc                                              324

SEQ ID NO: 42           moltype = DNA  length = 324
FEATURE                 Location/Qualifiers
```

```
misc_feature            1..324
                        note = Synthesized
source                  1..324
                        mol_type = other DNA
                        organism = synthetic construct
SEQUENCE: 42
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc gcaaggactg gtctttctat atagtgaagc cacagatgta tatagaaaga   180
ccagtccttg cttgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 43           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 43
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc ggctatccag cgtactccaa atagtgaagc cacagatgta tttggagtac   180
gctggatagc cttgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 44           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 44
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc gcagagaatg gaaagtcaaa ttagtgaagc cacagatgta atttgacttt   180
ccattctctg cttgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 45           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 45
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc gcttatacac ttcactttta ttagtgaagc cacagatgta ataaagtgta   180
agtgtataag catgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 46           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 46
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc ggacatgatc ttctttataa ttagtgaagc cacagatgta attataaaga   180
agatcatgtc catgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 47           moltype = DNA  length = 324
FEATURE                 Location/Qualifiers
misc_feature            1..324
                        note = Synthesized
source                  1..324
                        mol_type = other DNA
```

```
                        organism = synthetic construct
SEQUENCE: 47
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga cgtgcataag ttaacttcca atagtgaagc cacagatgta ttggaagtta   180
acttatgcac gctgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                           324

SEQ ID NO: 48           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 48
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc tgtattaatt ggctctataa atagtgaagc cacagatgta tttatagagc   180
caattaatac attgccctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                           324

SEQ ID NO: 49           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 49
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga catgtttggc agatactata atagtgaagc cacagatgta ttatagtatc   180
tgccaaacat ggtgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                           324

SEQ ID NO: 50           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 50
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga gagtctgaag tcacattgta atagtgaagc cacagatgta ttacaatgtg   180
acttcagact cgtgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                           324

SEQ ID NO: 51           moltype = DNA  length = 322
FEATURE                 Location/Qualifiers
misc_feature            1..322
                        note = Synthesized
source                  1..322
                        mol_type = other DNA
                        organism = synthetic construct
SEQUENCE: 51
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgg acctcaagag ctccaatatc tagtgaagcc acagatgtag atattggagc   180
tcttgaggtc tgcctactgc ctcggacttc aaggggctag aattcgagca attatctgt    240
ttactaaaac tgaataccct tgctatctct tgatacattt ttacaaagct gaattaaaat   300
ggtataaatt aaatcacttt gc                                             322

SEQ ID NO: 52           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 52
ctgtttgaat gaggcttcag tactttacag aatcgttgcc tgcacatctt ggaaacactt    60
gctgggatta cttcgacttc ttaacccaac agaaggctcg agaaggtata ttgctgttga   120
```

```
cagtgagcga gacctcaaga gctccaatat ctagtgaagc cacagatgta gatattggag    180
ctcttgaggt cctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 53              moltype = DNA   length = 324
FEATURE                    Location/Qualifiers
misc_feature               1..324
                           note = Synthesized
source                     1..324
                           mol_type = other DNA
                           organism = synthetic construct
SEQUENCE: 53
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcgc cctgacttgt tgctagtcat atagtgaagc cacagatgta tatgactagc    180
aacaagtcag gatgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 54              moltype = DNA   length = 324
FEATURE                    Location/Qualifiers
misc_feature               1..324
                           note = Synthesized
source                     1..324
                           mol_type = other DNA
                           organism = synthetic construct
SEQUENCE: 54
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga gcagtcaaga tcttccccta ttagtgaagc cacagatgta atagggaaag    180
atcttgactg cctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 55              moltype = DNA   length = 324
FEATURE                    Location/Qualifiers
misc_feature               1..324
                           note = Synthesized
source                     1..324
                           mol_type = other DNA
                           organism = synthetic construct
SEQUENCE: 55
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga gcacgttcag aagtcggtta atagtgaagc cacagatgta ttaaccgact    180
tctgaacgtg cgtgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 56              moltype = DNA   length = 324
FEATURE                    Location/Qualifiers
misc_feature               1..324
                           note = Synthesized
source                     1..324
                           mol_type = other DNA
                           organism = synthetic construct
SEQUENCE: 56
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga ccaccatcac tcgcaagaga atagtgaagc cacagatgta ttctcttgcg    180
agtgatggtg gctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 57              moltype = DNA   length = 324
FEATURE                    Location/Qualifiers
misc_feature               1..324
                           note = Synthesized
source                     1..324
                           mol_type = other DNA
                           organism = synthetic construct
SEQUENCE: 57
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga cctcctggtt atggtacaga ttagtgaagc cacagatgta atctgtacca    180
taaccaggag gctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324
```

```
SEQ ID NO: 58          moltype = DNA  length = 22
FEATURE                Location/Qualifiers
source                 1..22
                       mol_type = genomic DNA
                       organism = Homo sapiens
SEQUENCE: 58
tggcctggag caacaaatct ga                                                  22

SEQ ID NO: 59          moltype = DNA  length = 22
FEATURE                Location/Qualifiers
source                 1..22
                       mol_type = genomic DNA
                       organism = Homo sapiens
SEQUENCE: 59
accggacctc gttgtttaga ct                                                  22

SEQ ID NO: 60          moltype = DNA  length = 22
FEATURE                Location/Qualifiers
source                 1..22
                       mol_type = genomic DNA
                       organism = Homo sapiens
SEQUENCE: 60
ctatctcttg tactacactg aa                                                  22

SEQ ID NO: 61          moltype = DNA  length = 22
FEATURE                Location/Qualifiers
source                 1..22
                       mol_type = genomic DNA
                       organism = Homo sapiens
SEQUENCE: 61
gatagagaac atgatgtgac tt                                                  22

SEQ ID NO: 62          moltype = DNA  length = 22
FEATURE                Location/Qualifiers
source                 1..22
                       mol_type = genomic DNA
                       organism = Homo sapiens
SEQUENCE: 62
cccgggggat tgctcacctc ca                                                  22

SEQ ID NO: 63          moltype = DNA  length = 22
FEATURE                Location/Qualifiers
source                 1..22
                       mol_type = genomic DNA
                       organism = Homo sapiens
SEQUENCE: 63
gggcccccta acgagtggag gt                                                  22

SEQ ID NO: 64          moltype = AA  length = 354
FEATURE                Location/Qualifiers
REGION                 1..354
                       note = Synthesized
source                 1..354
                       mol_type = protein
                       organism = synthetic construct
SEQUENCE: 64
MNTKYNKEFL LYLAGFVDGD GSIYACIEPD QSRKFKHTLR LYFEVGQKTQ RRWFLDKLVD    60
EIGVGYVLDR GSVSNYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACITP SQTHKFKHRL FLRFTVGQKT   240
QRRWFLDKLV DEIGVGYVVD SGSVSEYRLS QIKPLHNFLT QLQPFLKLKQ KQANLVLKII   300
EQLPSAKESP DKFLEVCTWV DQIAALNDSK TRKTTSETVR AVLDSLSEKK KSSP          354

SEQ ID NO: 65          moltype = AA  length = 354
FEATURE                Location/Qualifiers
REGION                 1..354
                       note = Synthesized
source                 1..354
                       mol_type = protein
                       organism = synthetic construct
SEQUENCE: 65
MNTKYNKEFL LYLAGFVDGD GSIYACITPK QRSKFKHSLR LRFTVGQKTQ RRWFLDKLVD    60
EIGVGYVLDG GGVSEYRLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA TSSASSSPGS   180
GISEALRAGA GSGTGYNKEF LLYLAGFVDG DGSIYACIEP DQSRKFKHTL RLYFEVGQKT   240
QRRWFLDKLV DEIGVGYVYD RGSVSNYRLS EIKPLHNFLT QLQPFLKLKQ KQANLVLKII   300
EQLPSAKESP DKFLEVCTWV DQIAALNDSK TRKTTSETVR AVLDSLSEKK KSSP          354
```

```
SEQ ID NO: 66               moltype = AA   length = 325
FEATURE                     Location/Qualifiers
REGION                      1..325
                            note = Synthesized
source                      1..325
                            mol_type = protein
                            organism = synthetic construct
SEQUENCE: 66
VMAPRTLFLG GGGSGGGGSG GGGSIQRTPK IQVYSRHPAE NGKSNFLNCY VSGFHPSDIE    60
VDLLKNGERI EKVEHSDLSF SKDWSFYLLY YTEFTPTEKD EYACRVNHVT LSQPKIVKWD   120
RDMGGGGSGG GGSGGGGSGG GGSGSHSLKY FHTSVSRPGR GEPRFISVGY VDDTQFVRFD   180
NDAASPRMVP RAPWMEQEGS EYWDRETRSA RDTAQIFRVN LRTLRGYYNQ SEAGSHTLQW   240
MHGCELGPDG RFLRGYEQFA YDGKDYLTLN EDLRSWTAVD TAAQISEQKS NDASEAEHQR   300
AYLEDTCVEW LHKYLEKGKE TLLHL                                        325

SEQ ID NO: 67               moltype = DNA   length = 164
FEATURE                     Location/Qualifiers
misc_feature                1..164
                            note = Synthesized
source                      1..164
                            mol_type = other DNA
                            organism = synthetic construct
SEQUENCE: 67
gggcggagtt agggcggagc caatcagcgt gcgccgttcc gaaagttgcc ttttatggct    60
gggcggagaa tggcggtga acgccgatga ttatataagg acgcgccggg tgtggcacag   120
ctagttccgt cgcagccggg atttgggtcg cggttcttgt ttgt                   164

SEQ ID NO: 68               moltype = DNA   length = 207
FEATURE                     Location/Qualifiers
misc_feature                1..207
                            note = Synthesized
source                      1..207
                            mol_type = other DNA
                            organism = synthetic construct
SEQUENCE: 68
gatccagaca tgataagata cattgatgag tttggacaaa ccacaactag aatgcagtga    60
aaaaaatgct ttatttgtga aatttgtgat gctattgctt tatttgtaac cattataagc   120
tgcaataaac aagttaacaa caacaattgc attcatttta tgtttcaggt tcaggggag   180
gtgtgggagg ttttttaaag caagtaa                                      207

SEQ ID NO: 69               moltype = DNA   length = 133
FEATURE                     Location/Qualifiers
misc_feature                1..133
                            note = Synthesized
source                      1..133
                            mol_type = other DNA
                            organism = synthetic construct
SEQUENCE: 69
gtaagtatta atgttacaag acaggtttaa ggacaccaat agaaactggg cttgtcgaga    60
cagagaagac tcttgcgttt ctgataggca cctattggtc ttactgacat ccactttgcc   120
tttctctcca cag                                                     133

SEQ ID NO: 70               moltype = DNA   length = 81
FEATURE                     Location/Qualifiers
misc_feature                1..81
                            note = Synthesized
source                      1..81
                            mol_type = other DNA
                            organism = synthetic construct
SEQUENCE: 70
cgggccaaga gatctggaag cggcgccaca aatttctcac tgctgaaaca ggccggcgac    60
gtggaagaga accctggacc t                                             81

SEQ ID NO: 71               moltype = DNA   length = 225
FEATURE                     Location/Qualifiers
misc_feature                1..225
                            note = Synthesized
source                      1..225
                            mol_type = other DNA
                            organism = synthetic construct
SEQUENCE: 71
ctgtgccttc tagttgccag ccatctgttg tttgcccctc cccgtgcctt ccttgaccc    60
tggaaggtgc cactcccact gtcctttcct aataaaatga ggaaattgca tcgcattgtc   120
tgagtaggtg tcattctatt ctggggggtg gggtggggca ggacagcaag gggaggatt   180
gggaagacaa tagcaggcat gctggggatg cgtgggctc tatgg                   225

SEQ ID NO: 72               moltype = DNA   length = 212
FEATURE                     Location/Qualifiers
misc_feature                1..212
```

|  |  |  |
|---|---|---|
|  | note = Synthesized |  |
| source | 1..212 |  |
|  | mol_type = other DNA |  |
|  | organism = synthetic construct |  |

SEQUENCE: 72
```
gggcagagcg cacatcgccc acagtccccg agaagttggg gggaggggtc ggcaattgaa    60
cgggtgccta gagaaggtgg cgcggggtaa actgggaaag tgatgtcgtg tactggctcc   120
gccttttcc cgagggtggg ggagaaccgt atataagtgc agtagtcgcc gtgaacgttc   180
tttttcgcaa cgggtttgcc gccagaacac ag                                 212
```

|  |  |  |
|---|---|---|
| SEQ ID NO: 73 | moltype = AA length = 20 |  |
| FEATURE | Location/Qualifiers |  |
| REGION | 1..20 |  |
|  | note = Synthesized |  |
| source | 1..20 |  |
|  | mol_type = protein |  |
|  | organism = synthetic construct |  |

SEQUENCE: 73
```
MEAPAQLLFL LLLWLPSSRA                                                20
```

|  |  |  |
|---|---|---|
| SEQ ID NO: 74 | moltype = DNA length = 3885 |  |
| FEATURE | Location/Qualifiers |  |
| misc_feature | 1..3885 |  |
|  | note = Synthesized |  |
| source | 1..3885 |  |
|  | mol_type = other DNA |  |
|  | organism = synthetic construct |  |

SEQUENCE: 74
```
gggcggagtt agggcggagc caatcagcgt gcgccgttcc gaaagttgcc ttttatggct     60
gggcggagaa tgggcggtga acgccgatga ttatataagg acgcgcccgg tgtggcacag   120
ctagttccgt cgcagccggg atttgggtcg cggttcttgt ttgtgccacc atggaggctc   180
ctgctcagct gctgttcctg ctcctgctgt ggctgcccag cagcagagct gacatacaga   240
tgactcgac tacctcttcc ctatctgctt ctttaggcga ccgagtaaca atatcttgcc   300
gggccagcca ggacatctca aaatacttaa actggtatca gcagaagcca gacggaacag   360
ttaagttgct catttaccac acgtcgagat tactccagg cgttcctagc cgattttcgg    420
gttccggttc cggtacggac tacagcctga caatcagtaa ccttgagcag gaggacatcg   480
ccacctactt ctgtcagcag ggcaacacgc tcccgtacac attcggtggg ggaactaagc   540
tggagattac cggaggcggt ggcagcgtg gcggcggcag cgggggtggc ggctcggagg   600
tcaagttaca ggagagcgga ccggggcttgg tcgcacctag ccagagcctc tcagtcacgt   660
gcactgtgtc tggagtcagt ctcccagact acgggtatc atggatacga cagccgccta   720
gaaagggctt agagtggctg ggggttatct gggaagtga aaccacatac tacaactcag   780
ctctcaagag ccgcctcacc atcattaagg acaacagtaa gtcgcaggtt ttcttaaaga   840
tgaactctct ccagactgac gacaccgcta tttactactg cgcgaagcac tactactacg   900
gcgggagtta cgcaatggac tactgggtc agggcacttc tgtgaccgta tccagcacta   960
ctaccccagc cccacgtccc ccacgccag ctccaacgat agcaagtcag cccttatctc   1020
ttcgcctga ggcttgcagg cccgcggcgg gcggcgccgt tcacacgcga ggactagact   1080
tcgcctgcga catctacatc tgggcaccac tagccggac ttgcggagtg ttgttgttga   1140
gcttggtaat aacgctctac tgcaaagcga gccgcaaaaa agcggcgcg gcggcgaaaa   1200
gcccgttgc gagcccggcg agcagcgcgc aggaagaaga tgcgagcagc tgccgcgcgc   1260
cgagcgaaga agaaggcagc tgcgaactga gagtgaagtt ctctcgctcc gcggacgcac   1320
ccgcttacca gcagggtcag aaccagctat acaacgagtt aaacctgggg cgccgggagg   1380
agtacgacgt gttagacaag cgtagaggta gggaccccgg gatgggaggc aagcctcgga   1440
gaaagaaccc ccaggagggc ctgtacaacg aactccagaa ggacaagatg gctgagcgt   1500
actcggagat tggtatgaag ggcgagagac gtcgcgaaa gggacacgac ggcttatacc   1560
aggggcttt caccgcgacc aaggacacat acgacgcgt gacatgcaa gccttaccac   1620
ctcgacgggc caagagatct ggaagcggcc ccacaaattt ctcactgctg aaacaggccg   1680
gcgacgtgga agagaaccct ggacctatgt ctcgctccgt ggccttaget gtgctcgcgc   1740
tactctctct ttctggcctg gaggctgtga tggcgccgcg caccctgttt ctgggaggcg   1800
ggggtagcgg tgggggcgga agcggggag gcggcagcat ccagcgtact ccaaagattc   1860
aggttactc acgtcatcca gcagagaatg gaaagtcaaa ttccctgaat tgctatgtgt   1920
ctgggtttca tccatccgac attgaagtta acttactgaa gaatggagag agaattgaaa   1980
aagtggagca ttcagacttg tctttcagca aggactggtc tttctacctg ctctattata   2040
cggaattcac ccccactgaa aaagatgagt atgcctgccg tgtgaaccat gtgactttgt   2100
cacagcccaa gatagttaag tgggatcgaa acatgggtgg tggcgtgac ggaggtggag   2160
gtagcggtgg tggaggcagc ggtggaggcg gcagcggctc ccactccttg aagtatttcc   2220
acacttccgt gtcccggccc ggccgcgggg agccccgctt catctctgtg ggctacgtgg   2280
acgacaccca gttcgtgcgc ttcgacaacg acgccgcgag tccgaggatg gtgccgcggg   2340
cgccgtggat ggagcaggag gggtcagagt attgggaccg ggagacacgg agcgccaggg   2400
acaccgcaca gatttccga gtgaatctgc ggacgctact aatcagagcg ttcccaagca   2460
aggccggctc tcacaccctg cagtggatgc atggctgcga gctggggccc gacgggcgct   2520
tcctccgcgg gtatgaacag ttcgcctacg acggcaagga ttatctcacc ctgaatgagg   2580
acctgcgctc ctgaccgcg gtggacacgg cgctcagat ctccgagcaa aagtcaaatg   2640
atgcctctga ggcggagcac cagagagcct acctggaaga cacatgcgtg gagtggctcc   2700
acaaatacct ggagaagggg aaggacacgc tgcttcacct gggtaagtat taatgttaca   2760
agacaggttt aaggacacca atagaaactg gcttgtcga gacagagagt acctgtttga   2820
atgaggcttc agtactttac agaatcgttg cctgcacatc ttggaaacac ttgctgggat   2880
tacttcgact tcttaaccca acagaaggct cgagaaggta tattgctgtt gacagtgagc   2940
gcggacatga tcttcttat aattagtgaa gccacagatg taattataaa gaagatcatg   3000
tccatgccta ctgcctcgga cttcaagggg ctagaattcg agcaattatc ttgtttacta   3060
```

```
aaactgaata ccttgctatc tctttgatac attttacaa agctgaatta aaatggtata    3120
aattaaatca ctttgcggcc agactcttgc gtttctgata ggcacctatt ggtcttactg    3180
acatccactt tgcctttctc tccacagagc ccccaaagac acacgtgact caccaccca    3240
tctctgacca tgaggccacc ctgaggtgct gggcctggg cttctaccct gcggagatca    3300
cactgacctg gcagcaggat ggggagggcc atacccagca cacggagctc gtggaaacca    3360
ggcctgcagg ggatggaacc ttccagaagt gggcagctgt ggtggtgcct tctggagagg    3420
agcagagata cacgtgccat gtgcagcatg aggggctacc cgagcccgtc accctgagat    3480
ggaagccggc ttcccagccc accatcccca tcgtgggcat cattgctggc ctggttctcc    3540
ttggatctgt ggtatctgga gctgtggttg ctgctgtgat atggaggaag aagagctcag    3600
gtggaaaagg agggagctac tctaaggctg agtggagcga cagtgcccag gggtctgagt    3660
ctcacagctt gtaaggtaga tccagacatg ataagataca ttgatgagtt tggacaaacc    3720
acaactagaa tgcagtgaaa aaaatgcttt atttgtgaaa tttgtgatgc tattgcttta    3780
tttgtaacca ttataagctg caataaacaa gttaacaaca acaattgcat tcattttatg    3840
tttcaggttc aggggaggt gtgggaggtt ttttaaagca agtaa                    3885

SEQ ID NO: 75          moltype = DNA   length = 4262
FEATURE                Location/Qualifiers
misc_feature           1..4262
                       note = Synthesized
source                 1..4262
                       mol_type = other DNA
                       organism = synthetic construct
SEQUENCE: 75
gggcggagtt agggcggagc caatcagcgt gcgccgttcc gaaagttgcc ttttatggct      60
gggcggagaa tgggcggtga acgccgatga ttatataagg acgcgccggg tgtggcacag     120
ctagttccgt cgcagccggg atttgggtcg cggttcttgt ttgtgccaac atggaggctc     180
ctgctcagct gctgttcctg tcctgctgct ggctgcccag cagcagagct gacatacaga     240
tgactcagac tacctcttcc ctatctgctt ctttaggcga ccgagtaaca atatcttgcc     300
gggccagcca ggacatctca aaatacttaa actggtatca gcagaagccg gacggaacag     360
ttaagttgct catttaccac acgtcgagat tacactcggt cgttcctagc cgattttcgg     420
gttccggttc cggtacggac tacagcctga caatcagtaa ccttgagcag gaggacatcg     480
ccacctactt ctgtcagcag ggcaacacgc tcccgtacac attcggtggg ggaactaagc     540
tggagattac cggaggcggt ggcagcgtg cggcggcag cggggtggc ggctcggagg      600
tcaagttaca ggagagcgga ccgggcttgg tcgcacctag ccagagcctc tcagtcacgt     660
gcactgtgtc tggagtcagt ctcccagact acgggtatc atggatacga cagccgccta     720
gaaagggctt agagtggctg ggggttatct ggggaagtga aaccacatac tacaactcag     780
ctctcaagag ccgcctcacc atcattaagg acaacagtaa gtcgcaggtt ttcttaaaga     840
tgaactctct ccagactgac gacaccgcta tttactactg cgcgaagcac tactactacg     900
gcgggagtta cgcaatggac tactgggtc agggcactc tgtgaccgta tccagcacta     960
ctaccccagc cccacgtccc cccacgccag ctcaacgat agcaagtcag ccctatctc    1020
ttcgccctga ggcttgcagg ccccgcggcg gcggcgccgt tcacacgcga ggactagact    1080
tcgcctgcga catctacatc tgggcaccac tagccgggac ttgcggagtg ttgttgttga    1140
gcttggtaat aacgctctac tgcaaagcga gccgcaaaaa gacgggcggcg gcggcgaaaa    1200
gcccgtttgc gagcccggcg agcagcgcgc aggaagaaga tgcgagcagc tgccgcgcgc    1260
cgagcgaaga agaaggcagc tgcgaactga gagtgaagtt ctctcgctcc gcggacgcac    1320
ccgcttacca gcagggtcag aaccagctat acaacgagtt aaacctgggg cgccggggagg    1380
agtacgacgt gttagacaag cgtagaggta gggacccgga gatggaggc aagcctcgga    1440
gaaagaaccc ccaggagggc ctgtacaacg aactccagaa ggacaagatg ctgaggcgt    1500
actcggagat tggtatgaag ggcgagagac gtcgcggaaa gggacacgac ggcttatacc    1560
aggggctttc caccgcgacc aaggacacat acgacgcgct gcacatgcaa gccttaccac    1620
ctcgatgaag ccgatccaga catgataaga tacattgatg agtttggaca aaccacaact    1680
agaatgcagt gaaaaaaatg ctttatttgt gaaatttgtg atgctattgc tttatttgta    1740
accattataa gctgcaataa acaagttaac aacaacaatt gcattcattt tatgtttcag    1800
gttcaggggg aggtgtggga ggttttttaa agcaagtaat cgggcagaga gcgcacatcg    1860
cccacagtcc ccgagaagtt ggggggaggg gtcggcaatt gaacgggtgc ctagagaagg    1920
tggcgcgggg taaactggga aagtgatgtc gtgtactggc tccgcctttt tcccgagggt    1980
gggggagaac cgtatataag tgcagtagtc gccgtgaacg ttcttttttcg caacgggttt    2040
gccgccagaa cacagccatg ccaccatgtc tcgctccgtg gccttagctg tgctcgcgct    2100
actctctctt tctggcctgg aggctgtgat ggcgccgcgc accctgtttc tgggaggcgg    2160
gggtagcggt gggggcggaa gcgggggagg cggcagcatc cagcgtactc caaagattca    2220
ggtttactca cgtcatccag cagagaatgg aaagtcaaat ttcctgaatt gctatgtgtc    2280
tgggtttcat ccatccgaca ttgaagttga cttactgaag aatggagaga gaattgaaaa    2340
agtggagcat tcagacttgt cttcagcaa ggactggtct ttctacctgc tctattatac    2400
ggaattcacc cccactgaaa aagatgagta tgcctgcgca gtgaaccatg tgactttgtc    2460
acagccaag atagttaagt gggatcgaga catggcgcgt ggcggtagcg gaggtggagg    2520
tagcggtggt ggaggcagcg gtgaggcgg cagcggctcc cactccttga agtattccaa    2580
cacttccgtg tccggccccg gccgcgggga gcccgcttc atctctgtgg gctacgtgga    2640
cgacacccag ttcgtgcgct tcgacaacga cgccgcgagt ccgaggatgg tgccgcgggc    2700
gccgtggatg gagcaggagg ggtcagagta ttgggacgag gagacacgga gcgccaggga    2760
caccgcacag atttttccgag tgaatctgcg gacgctgcgc ggctactaca atcagagcga    2820
ggccggctct cacaccctgc agtgatgca tggctgcgag ctgggccccg acgggcgctt    2880
cctccgcggg tatgaacagt tcgcctacga cggcaaggat tatctcaccc tgaatgagga    2940
cctgcgctcc tggaccgcgg tggacacggc ggctcagatc tccagcaaa agtcaaatga    3000
tgcctctgag gcggaagcac agagaggcta cctggaagac acatggtgg agtggctcca    3060
caaatacctg gagaagggga aggagacgct gctcaccta ggtaagtatt aatgttacaa    3120
gacaggttta aggacaccaa tagaaactgg gcttgtcgag acagagagta cctgtttgaa    3180
tgaggcttca gtactttaca gaatcgttgc ctgcacatct tggaaacact tgctgggatt    3240
acttcgactt cttaacccaa cagaaggctc gagaaggtat attgctgttg acagtgagcg    3300
cggacatgat cttcttttata attagtgaag ccacagatgt aattataaag aagatcatgt    3360
```

```
ccatgcctac tgcctcggac ttcaaggggc tagaattcga gcaattatct tgtttactaa   3420
aactgaatac cttgctatct ctttgataca tttttacaaa gctgaattaa aatggtataa   3480
attaaatcac tttgcggcca gactcttgcg tttctgatag gcacctattg gtcttactga   3540
catccacttt gcctttctct ccacagagcc cccaaagaca cacgtgactc accaccccat   3600
ctctgaccat gaggccaccc tgaggtgctg ggccctggcc ttctaccctg cggagatcac   3660
actgacctgg cagcaggatg ggagggcca  tacccaggac acggagctcg tggaaaccag   3720
gcctgcaggg gatggaacct tccagaagtg ggcagctgtg gtggtgccctt ctggagagga  3780
gcagagatac acgtgccatg tgcagcatga ggggctaccc gagcccgtca ccctgagatg   3840
gaagccggct tcccagccca ccatccccat cgtgggcatc attgctggcc tggttctcct   3900
tggatctgtg gtatctggag ctgtggttgc tgctgtgata tggaggaaga agagctcagg   3960
tggaaaagga gggagctact ctaaggctga gtggagcgac agtgcccagg ggtctgagtc   4020
tcacagcttg taaatggctg tgccttctag ttgccagcca tctgttgttt gcccctcccc   4080
cgtgccttcc ttgaccctgg aaggtgccac tcccactgtc ctttcctaat aaaatgagga   4140
aattgcatcg cattgtctga gtaggtgtca ttctattctg gggggtgggg tggggcagga   4200
cagcaagggg gaggattggg aagacaatag caggcatgct ggggatgcgg tgggctctat   4260
gg                                                                  4262

SEQ ID NO: 76          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 76
cgcaaggcat tcctcttgaa ta                                            22

SEQ ID NO: 77          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 77
tattcaagag gaatgccttg ct                                            22

SEQ ID NO: 78          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 78
cggcattcct cttgaatatt ta                                            22

SEQ ID NO: 79          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 79
taaatattca agaggaatgc ct                                            22

SEQ ID NO: 80          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 80
cggtttctta ttcaaagatg at                                            22

SEQ ID NO: 81          moltype = DNA   length = 22
FEATURE                Location/Qualifiers
misc_feature           1..22
                       note = Synthesized
source                 1..22
                       mol_type = other DNA
                       organism = synthetic construct
SEQUENCE: 81
atcatctttg aataagaaac ca                                            22

SEQ ID NO: 82          moltype = DNA   length = 22
FEATURE                Location/Qualifiers
```

```
misc_feature            1..22
                        note = Synthesized
source                  1..22
                        mol_type = other DNA
                        organism = synthetic construct
SEQUENCE: 82
agctcctgca taggacactg aa                                                  22

SEQ ID NO: 83           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 83
ttcagtgtcc tatgcaggag cc                                                  22

SEQ ID NO: 84           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 84
cggctagaaa gcatccatta at                                                  22

SEQ ID NO: 85           moltype = DNA  length = 22
FEATURE                 Location/Qualifiers
misc_feature            1..22
                        note = Synthesized
source                  1..22
                        mol_type = other DNA
                        organism = synthetic construct
SEQUENCE: 85
attaatggat gctttctagc ct                                                  22

SEQ ID NO: 86           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 86
ctgtttgaat gaggcttcag tactttacag aatcgttgcc tgcacatctt ggaaacactt         60
gctgggatta cttcgacttc ttaacccaac agaaggctcg agaaggtata ttgctgttga        120
cagtgagcgc gcaaggcatt cctcttgaat atagtgaagc cacagatgta tattcaagag        180
gaatgccttg cttgcctact gcctcggact tcaaggggct agaattcgag caattatctt        240
gtttactaaa actgaatacc ttgctatctc tttgatacat ttttacaaag ctgaattaaa        300
atggtataaa ttaaatcact ttgc                                              324

SEQ ID NO: 87           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 87
ctgtttgaat gaggcttcag tactttacag aatcgttgcc tgcacatctt ggaaacactt         60
gctgggatta cttcgacttc ttaacccaac agaaggctcg agaaggtata ttgctgttga        120
cagtgagcgc ggcattcctc ttgaatattt atagtgaagc cacagatgta taaatattca        180
agaggaatgc cttgcctact gcctcggact tcaaggggct agaattcgag caattatctt        240
gtttactaaa actgaatacc ttgctatctc tttgatacat ttttacaaag ctgaattaaa        300
atggtataaa ttaaatcact ttgc                                              324

SEQ ID NO: 88           moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 88
ctgtttgaat gaggcttcag tactttacag aatcgttgcc tgcacatctt ggaaacactt         60
gctgggatta cttcgacttc ttaacccaac agaaggctcg agaaggtata ttgctgttga        120
cagtgagcgc ggtttcttat tcaaagatga ttagtgaagc cacagatgta atcatctttg        180
```

```
aataagaaac catgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                          324

SEQ ID NO: 89           moltype = DNA   length = 324
FEATURE                 Location/Qualifiers
misc_feature            1..324
                        note = Synthesized
source                  1..324
                        mol_type = other DNA
                        organism = synthetic construct
SEQUENCE: 89
ctgtttgaat gaggcttcag tactttacag aatcgttgcc tgcacatctt ggaaacactt     60
gctgggatta cttcgacttc ttaacccaac agaaggctcg agaaggtata ttgctgttga    120
cagtgagcga gctcctgcat aggacactga atagtgaagc cacagatgta ttcagtgtcc    180
tatgcaggag cctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                          324

SEQ ID NO: 90           moltype = DNA   length = 324
FEATURE                 Location/Qualifiers
misc_feature            1..324
                        note = Synthesized
source                  1..324
                        mol_type = other DNA
                        organism = synthetic construct
SEQUENCE: 90
ctgtttgaat gaggcttcag tactttacag aatcgttgcc tgcacatctt ggaaacactt     60
gctgggatta cttcgacttc ttaacccaac agaaggctcg agaaggtata ttgctgttga    120
cagtgagcga ggctagaaag catccattaa ttagtgaagc cacagatgta attaatggat    180
gctttctagc cttgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                          324

SEQ ID NO: 91           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 91
aagatgtgat ggacttctat aa                                             22

SEQ ID NO: 92           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 92
ttatagaagt ccatcacatc tc                                             22

SEQ ID NO: 93           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 93
aaccaacggt ggcaatgtga aa                                             22

SEQ ID NO: 94           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 94
tttcacattg ccaccgttgg tg                                             22

SEQ ID NO: 95           moltype = DNA   length = 22
FEATURE                 Location/Qualifiers
misc_feature            1..22
                        note = Synthesized
source                  1..22
```

```
                         mol_type = other DNA
                         organism = synthetic construct
SEQUENCE: 95
aggtggcaat gtgaaattgt at                                                 22

SEQ ID NO: 96            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 96
atacaatttc acattgccac cg                                                 22

SEQ ID NO: 97            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 97
agcaagcttt cctggagcaa at                                                 22

SEQ ID NO: 98            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 98
atttgctcca ggaaagcttg cc                                                 22

SEQ ID NO: 99            moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 99
cgctttcctg gagcaaatat aa                                                 22

SEQ ID NO: 100           moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 100
ttatatttgc tccaggaaag ct                                                 22

SEQ ID NO: 101           moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 101
cggagcaaat ataattggta at                                                 22

SEQ ID NO: 102           moltype = DNA   length = 22
FEATURE                  Location/Qualifiers
misc_feature             1..22
                         note = Synthesized
source                   1..22
                         mol_type = other DNA
                         organism = synthetic construct
SEQUENCE: 102
attaccaatt atatttgctc ca                                                 22

SEQ ID NO: 103           moltype = DNA   length = 22
FEATURE                  Location/Qualifiers
misc_feature             1..22
                         note = Synthesized
```

```
source                      1..22
                            mol_type = other DNA
                            organism = synthetic construct
SEQUENCE: 103
cgctcctgat ctgattatta at                                            22

SEQ ID NO: 104              moltype = DNA   length = 22
FEATURE                     Location/Qualifiers
misc_feature                1..22
                            note = Synthesized
source                      1..22
                            mol_type = other DNA
                            organism = synthetic construct
SEQUENCE: 104
attaataatc agatcaggag ca                                            22

SEQ ID NO: 105              moltype = DNA   length = 22
FEATURE                     Location/Qualifiers
misc_feature                1..22
                            note = Synthesized
source                      1..22
                            mol_type = other DNA
                            organism = synthetic construct
SEQUENCE: 105
accaagagct atttgatgaa at                                            22

SEQ ID NO: 106              moltype = DNA   length = 22
FEATURE                     Location/Qualifiers
misc_feature                1..22
                            note = Synthesized
source                      1..22
                            mol_type = other DNA
                            organism = synthetic construct
SEQUENCE: 106
atttcatcaa atagctcttg gc                                            22

SEQ ID NO: 107              moltype = DNA   length = 22
FEATURE                     Location/Qualifiers
misc_feature                1..22
                            note = Synthesized
source                      1..22
                            mol_type = other DNA
                            organism = synthetic construct
SEQUENCE: 107
acagctttac atgcaattta tt                                            22

SEQ ID NO: 108              moltype = DNA   length = 22
FEATURE                     Location/Qualifiers
misc_feature                1..22
                            note = Synthesized
source                      1..22
                            mol_type = other DNA
                            organism = synthetic construct
SEQUENCE: 108
aataaattgc atgtaaagct gc                                            22

SEQ ID NO: 109              moltype = DNA   length = 324
FEATURE                     Location/Qualifiers
misc_feature                1..324
                            note = Synthesized
source                      1..324
                            mol_type = other DNA
                            organism = synthetic construct
SEQUENCE: 109
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga agatgtgatg gacttctata atagtgaagc cacagatgta ttatagaagt   180
ccatcacatc tctgcctact gcctcggact tcaagggact agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 110              moltype = DNA   length = 324
FEATURE                     Location/Qualifiers
misc_feature                1..324
                            note = Synthesized
source                      1..324
                            mol_type = other DNA
                            organism = synthetic construct
SEQUENCE: 110
```

```
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga accaacggtg gcaatgtgaa atagtgaagc cacagatgta tttcacattg   180
ccaccgttgg tgtgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 111           moltype = DNA   length = 324
FEATURE                  Location/Qualifiers
misc_feature             1..324
                         note = Synthesized
source                   1..324
                         mol_type = other DNA
                         organism = synthetic construct
SEQUENCE: 111
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga ggtggcaatg tgaaattgta ttagtgaagc cacagatgta atacaatttc   180
acattgccac cgtgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 112           moltype = DNA   length = 324
FEATURE                  Location/Qualifiers
misc_feature             1..324
                         note = Synthesized
source                   1..324
                         mol_type = other DNA
                         organism = synthetic construct
SEQUENCE: 112
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcga gcaagctttc ctggagcaaa ttagtgaagc cacagatgta atttgctcca   180
ggaaagcttg cctgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 113           moltype = DNA   length = 324
FEATURE                  Location/Qualifiers
misc_feature             1..324
                         note = Synthesized
source                   1..324
                         mol_type = other DNA
                         organism = synthetic construct
SEQUENCE: 113
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc gctttcctgg agcaaatata atagtgaagc cacagatgta ttatatttgc   180
tccaggaaag cttgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 114           moltype = DNA   length = 324
FEATURE                  Location/Qualifiers
misc_feature             1..324
                         note = Synthesized
source                   1..324
                         mol_type = other DNA
                         organism = synthetic construct
SEQUENCE: 114
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc ggagcaaata taattggtaa ttagtgaagc cacagatgta attaccaatt   180
atatttgctc catgcctact gcctcggact tcaaggggct agaattcgag caattatctt   240
gtttactaaa actgaatacc ttgctatctc tttgatacat ttttacaaag ctgaattaaa   300
atggtataaa ttaaatcact ttgc                                          324

SEQ ID NO: 115           moltype = DNA   length = 324
FEATURE                  Location/Qualifiers
misc_feature             1..324
                         note = Synthesized
source                   1..324
                         mol_type = other DNA
                         organism = synthetic construct
SEQUENCE: 115
ctgtttgaat gaggcttcag tactttacag aatcgttgcc tgcacatctt ggaaacactt    60
gctgggatta cttcgacttc ttaacccaac agaaggctcg agaaggtata ttgctgttga   120
cagtgagcgc gctcctgatc tgattattaa ttagtgaagc cacagatgta attaataatc   180
agatcaggag catgcctact gcctcggact tcaaggggct agaattcgag caattatctt   240
```

```
gtttactaaa actgaatacc ttgctatctc tttgatacat ttttacaaag ctgaattaaa    300
atggtataaa ttaaatcact ttgc                                           324

SEQ ID NO: 116          moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 116
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga ccaagagcta tttgatgaaa ttagtgacac acagatgta atttcatcaa    180
atagctcttg gctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 117          moltype = DNA  length = 324
FEATURE                 Location/Qualifiers
misc_feature            1..324
                        note = Synthesized
source                  1..324
                        mol_type = other DNA
                        organism = synthetic construct
SEQUENCE: 117
ctgtttgaat gaggcttcag tactttacag aatcgttgcc tgcacatctt ggaaacactt    60
gctgggatta cttcgacttc ttaacccaac agaaggctcg agaaggtata ttgctgttga    120
cagtgagcga cagctttaca tgcaatttat ttagtgaagc cacagatgta aataaattgc    180
atgtaaagct gctgcctact gcctcggact tcaaggggct agaattcgag caattatctt    240
gtttactaaa actgaatacc ttgctatctc tttgatacat ttttacaaag ctgaattaaa    300
atggtataaa ttaaatcact ttgc                                           324

SEQ ID NO: 118          moltype = AA  length = 182
FEATURE                 Location/Qualifiers
source                  1..182
                        mol_type = protein
                        organism = Homo sapiens
SEQUENCE: 118
GSHSLKYFHT SVSRPGRGEP RFISVGYVDD TQFVRFDNDA ASPRMVPRAP WMEQEGSEYW    60
DRETRSARDT AQIFRVNLRT LRGYYNQSEA GSHTLQWMHG CELGPDGRFL RGYEQFAYDG    120
KDYLTLNEDL RSWTAVDTAA QISEQKSNDA SEAEHQRAYL EDTCVEWLHK YLEKGKETLL    180
HL                                                                   182

SEQ ID NO: 119          moltype = AA  length = 99
FEATURE                 Location/Qualifiers
source                  1..99
                        mol_type = protein
                        organism = Homo sapiens
SEQUENCE: 119
IQRTPKIQVY SRHPAENGKS NFLNCYVSGF HPSDIEVDLL KNGERIEKVE HSDLSFSKDW    60
SFYLLYYTEF TPTEKDEYAC RVNHVTLSQP KIVKWDRDM                           99

SEQ ID NO: 120          moltype = AA  length = 9
FEATURE                 Location/Qualifiers
source                  1..9
                        mol_type = protein
                        organism = Homo sapiens
SEQUENCE: 120
VMAPRTLFL                                                            9

SEQ ID NO: 121          moltype = DNA  length = 15
FEATURE                 Location/Qualifiers
misc_feature            1..15
                        note = Synthesized
source                  1..15
                        mol_type = other DNA
                        organism = synthetic construct
SEQUENCE: 121
ggggsggggs gggs                                                      15

SEQ ID NO: 122          moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 122
```

```
ggggsggggs ggggsggggs                                                          20

SEQ ID NO: 123         moltype = AA  length = 163
FEATURE                Location/Qualifiers
source                 1..163
                       mol_type = protein
                       organism = Chlamydomonas reinhardtii
SEQUENCE: 123
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLKLKQK QANLVLKIIW RLPSAKESPD   120
KFLEVCTWVD QIAALNDSKT RKTTSETVRA VLDSLSEKKK SSP                     163
```